US006127163A

United States Patent [19]
Cochran et al.

[11] Patent Number: 6,127,163
[45] Date of Patent: Oct. 3, 2000

[54] RECOMBINANT SWINEPOX VIRUS

[75] Inventors: Mark D. Cochran, Carlsbad; David E. Junker, San Diego, both of Calif.

[73] Assignee: Syntro Corporation, Lenexa, Kans.

[21] Appl. No.: 08/295,802

[22] PCT Filed: Jul. 22, 1994

[86] PCT No.: PCT/US94/08277

§ 371 Date: Jan. 19, 1996

§ 102(e) Date: Jan. 19, 1996

[87] PCT Pub. No.: WO95/03070

PCT Pub. Date: Feb. 2, 1995

Related U.S. Application Data

[63] Continuation-in-part of application No. 07/820,154, Jan. 13, 1992, Pat. No. 5,382,425, and application No. 08/097,554, Jul. 22, 1993, Pat. No. 5,869,312.

[51] Int. Cl.⁷ .............................. C12N 7/01; C12N 15/86; A61K 39/275

[52] U.S. Cl. ................... 435/235.1; 435/320.1; 435/69.1; 435/69.3; 424/199.1

[58] Field of Search ................. 435/235.1, 520.1; 424/199.1, 93.2, 85.1, 85.2

[56] References Cited

U.S. PATENT DOCUMENTS 5,382,425  1/1995  Cochran .

FOREIGN PATENT DOCUMENTS

| 0284416 | 9/1988 | European Pat. Off. . |
| WO8903429 | 4/1989 | WIPO . |
| WO8912684 | 12/1989 | WIPO . |

OTHER PUBLICATIONS

Bhat R.A. et al., (1989) Nucleic Acids Research 17: 1159–1176.

Esposito J.J. et al., (1988) Virology 165: 313–316.

Joshi S. et al., (1991) Journal Of Virology 65: 5524–5530.

Flexner C. et al., (1990) Vaccine 8: 17–21.

Kasza L. et al., (1981) Diseases of the Swine 254–260.

Massung R.F. and Moyer R.W. (1991) Virology 180: 347–354.

Massung R.F. and Moyer R.W. (1991) Virology 180: 355–364.

Taylor J. et al., (1991) Vaccine 9: 190–193.

Schinitzlein W.M. and Tripathy D.N. (1991) Virology 181:727–732.

Wachsman M. et al., (1989) Journal of General Virology 70: 2513–2520.

Williams P.P. et al., (1989) Veterinary Immunology and Immunopathology 23:149–159.

Riviere M. et al., (1992) Journal of Virology 66: 3423–3434.

Massung R.F. et al., (1993) Virology 197: 511–528.

Tuboly T. et al., (1993) Research in Veterinary Science 54: 345–350.

Foley P.L. et al., (1991) Annals New York Academy of Science 646: 220–222.

van der Leek M.L. et al., (1994) The Veterinary Record 134: 13–18.

*Primary Examiner*—Mary E. Mosher
*Attorney, Agent, or Firm*—John P. White; Cooper & Dunham LLP

[57] ABSTRACT

The present invention relates to a recombinant swinepox virus capable of replication comprising foreign DNA inserted into a site in the swinepox viral DNA which is not essential for replication of the swinepox virus. The invention further relates to homology vectors which produce recombinant swinepox viruses by inserting foreign DNA into swinepox viral DNA

48 Claims, 80 Drawing Sheets

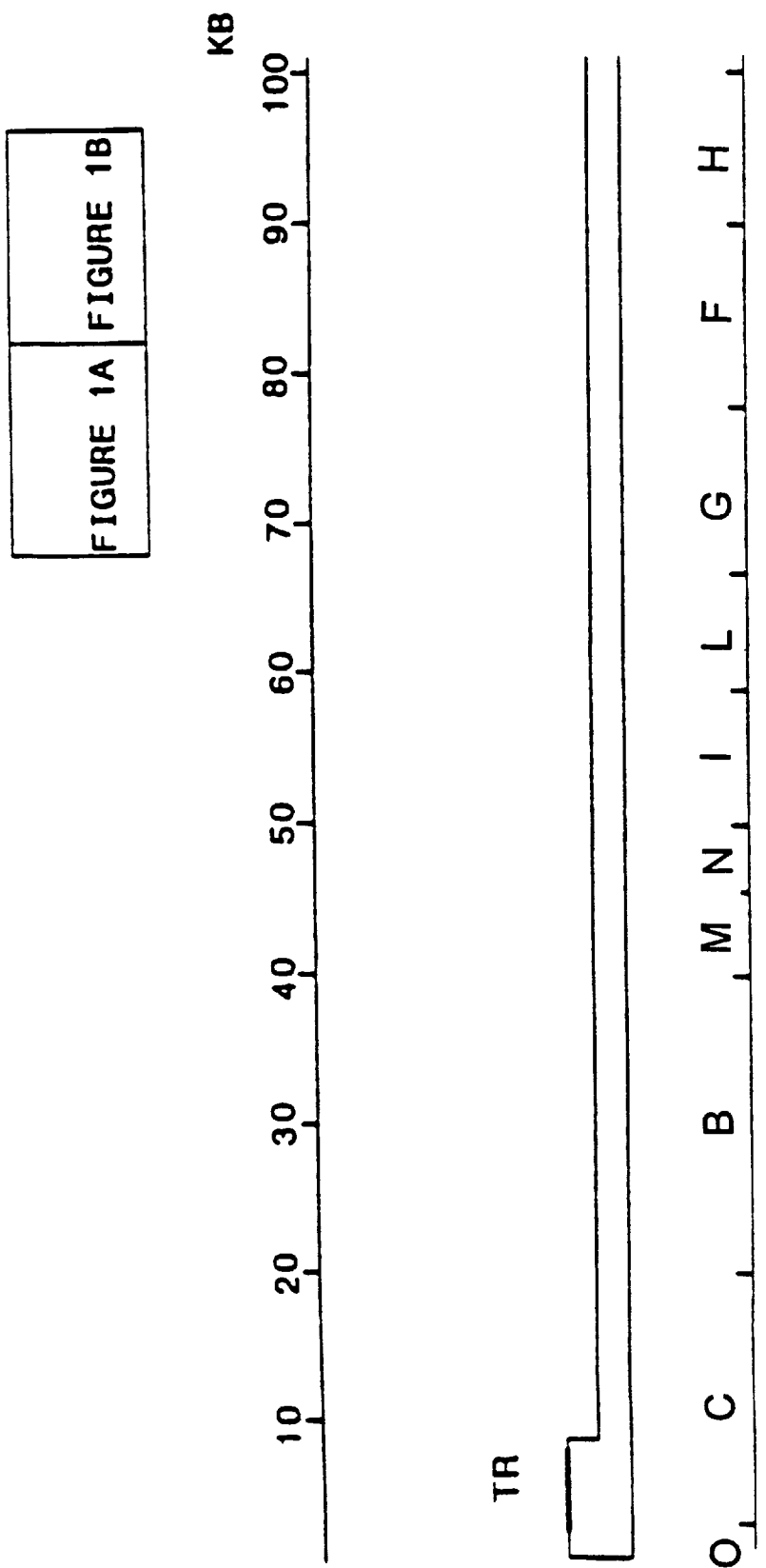

FIGURE 2A

```
AATGTATCCAGAGTTGTTGAATGCCTTATCGTACCTAATATATTAATTAATATAGAGTTATTAACT
GAATAAGTATATATAAATGATTGTTTTTATAATGTTTGTTATCGCCATTTAGTTTTGCTGT
ATGGTTATCATCATATACATTTTTAAGCCCGTATATGATAATGAAAATATATAAGCACTTAT
TTTTGTTAGTATAATAACACAATGCCCGTCGTATATCGTATATCCGAAGAACGCAAGAAAGTA
ATTTCAAAGATTATATCATTACAACTTGATATTAAAAACTTCCTAAAAATATATAAAT
ACCATGTTAGAATTTGGTCTCTACATGGAAATCTACCAGCTTGTATGTATAAAGATGCCGTA
                   MetProSer........
```

```
TCATATATGATATAAATAATATAAGATTTTTACCTTATAATTGTGTTATGGTTAAAGATTTA
ATAAATGTTATAAATCATCATCTGTAATAGATACTAGATTACATCAATCTGTATTAAAA
CATCGTAGAGCGTTAATAGATTACGGCCGATCAAGACATTATCACTTTAATGATCATTAAT
AAGTTACTACTATTAGATGATGATATATCCTATATATTAGATAAAAATAATTCATGTAAC
                                     ..IleHisVal
```

FIGURE 2B

```
GAGATATTAAATCATGTGTAAATGCTCCGATATGTTCCGACTCTATAACACATCATATATG
        AspIleLysSer.........
AACAACATCATGTATAAATTATAAATCTACCGATAATGATCTTATGATAGTATTGTTCA
ATCTAACTAGATATTTAATGCATGGATGATACATCCTAATCTTATAAGCGTAAAGGAT
GGGCTCCCCTTATTGGATTATTAACCGGGTGATATAGGTATTAATTAAAACTATATTCCA
CCATGAATATAAATGGGCTACGGTATGGAGAGATATTACGTTATCTTCATACGATATGAGTA
ATAAATTAGTCTCTATTATTAATACACCCATATGAGTTAATACCGTTTACTACATGTT
GTTCACTCAATGAATATTATTCAAAAATTGTGATTTTAATCGTAAAAAGATTTAATAACATTAAAGAAT
TGATATCTATTATATATAGAATACTGTAAATCGTACTAGAATCATCAGGCATATATTTTGTCAGATGC
TTATTTCAAAGTCGTACTAGAATCATCAGGCATATATTTTGTCAGATGC
GTGTACATGACAACAAATTGAATTGGAAATAGATGAGCTCATTATTAATGGATCTATGCCTG
TACAGCTTATGCATTTACTTCTAAAGGTAGCTACCATAATATTAGAGGAAATCAAAGAAA
                                ..... LysGluI
TATAAACGTATTTTTCTTTTAAATAAATAAAATACTTTTTTTTTAAACAAGGGGGTGCT
le---
ACCTTGTCTTAATTGTATCTTGTATTTTGGATCTGATGCAAGATTATTAAATAATCGTATG
AAAAGTAGTAGATATAGTTTATATCGTTACTGGACATGATATATGTTTAGTTAATTCT
TCTTTGGCATGAATTCTACACGTCGGANAAGGTAATGTATCTATAATGGTATAAAGCTT
```

FIGURE 3B

```
                      10         20         30         40         50         60         70
                       *          *          *          *          *          *          *
(A) VV       MFMYPEFARKALSKLISKKLNIEKVSSKHQLVLLDYGLHGLLPKSLYLEAINSDILNVRFFPPEIINVT
    orf 01L     :::        ::  :            ::  :       :   : :: ::   :: ::      ::
(B) SPV      MPSYMYPKNARKVISKIISLQLDIKKLPKKYINTMLEFGLHGNLPACMYKDAVSYDINNIRFLPYNCVMVK
    AccI-ClaI                                        ┴
                                                    AccI 80         90        100        110        120
                  *          *          *          *          *
(A) VV       DIVKALQNSCRVDEYLKAVSLYHKNSLMVSGPNVVK-LMIEYNLLTHSDLEWLINENVVKA
    orf 01L   :           :         :  :        ::: :: ::   :
(B) SPV      DLINVIKSSSVIDTRLH

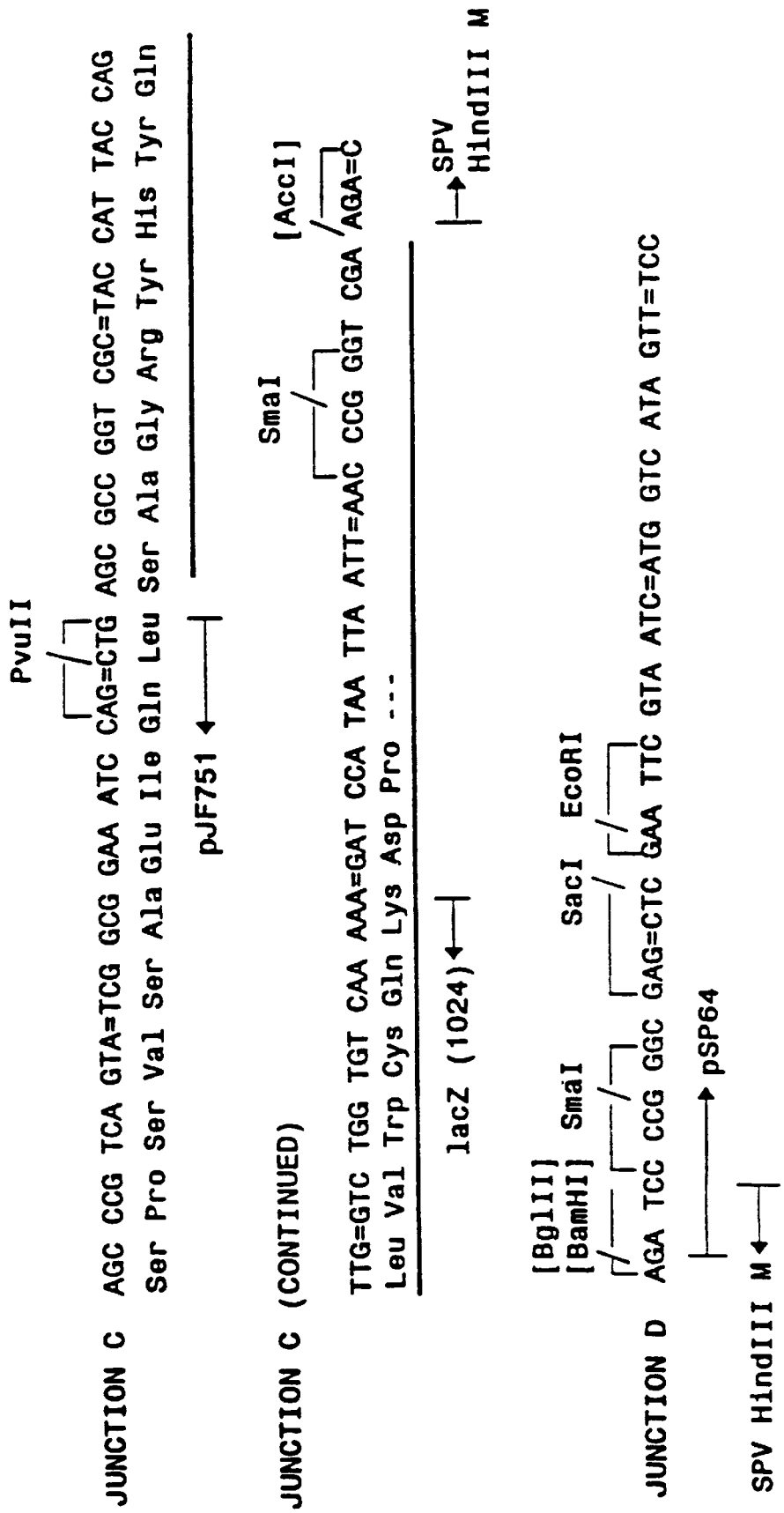

FIGURE 5A
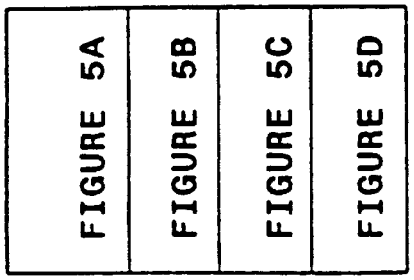
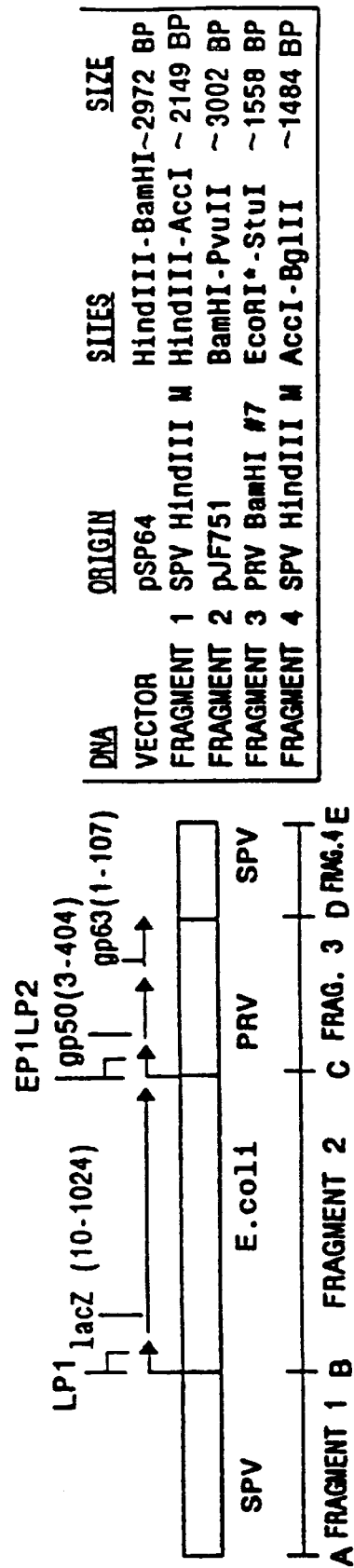

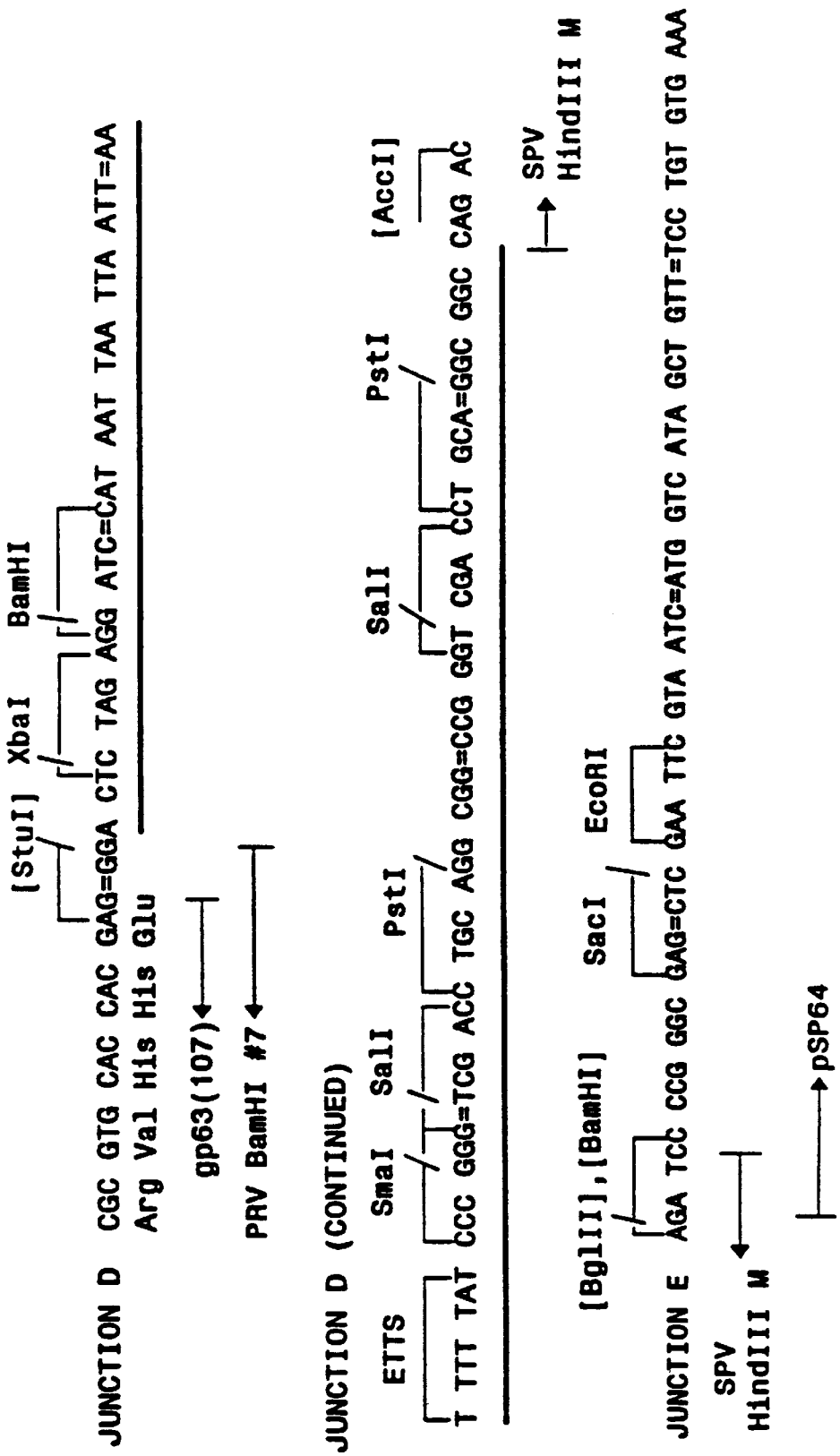

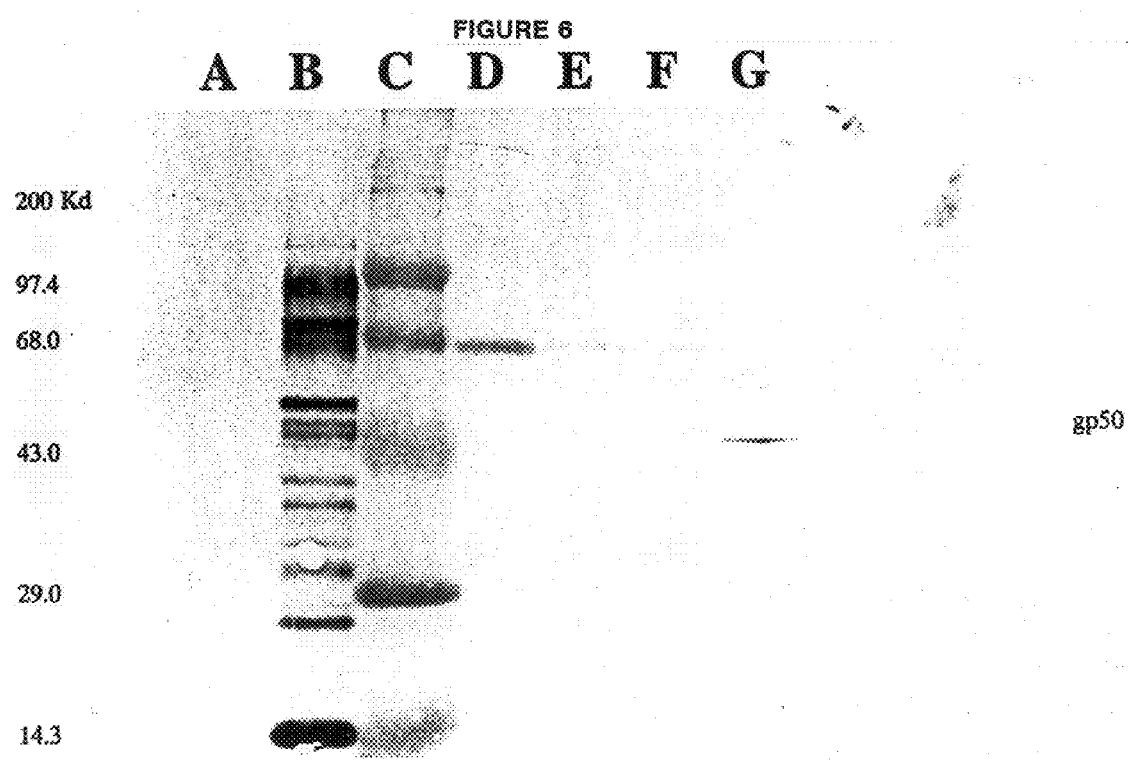

FIGURE 7

```
ACGGGTAGAACGGTAAGAGAGGCCGCCCCTCAATTGCGAGCCAGACTTCACAACCTCCGT
                                   AvaII
                                   r/―¬
TCTACCGCTTCACCGACAACAGTCCTCAATCATGGACCGCGCCGTTAGCCAAGTTGCGTT
                              MetAspGly.............
AGAGAATGATGAAAGAGAGGCAAAAAATACATGGCGCTTGATATTCCGGATTGCAATCTT
ATTCTTAACAGTAGTGACCTTGGCTATATCTGTAGCCTCCCTTTTATATAGCATGGGGGC
TAGCACACCTAGCGATCTTGTAGGCATACCGACTAGGATTTCCAGGGCAGAAGAAAAGAT
TACATCTACACTTGGTTCCAATCAAGATGTAGTAGATAGGATATATAAGCAAGTGGCCCT
TGAGTCTCCATTGGCATTGTTAAATACTGAGACCACAATTATGAACGCAATAACATCTCT
CTCTTATCAGATTAATGGAGCTGCAAACAACAGCGGGTGGGGGGCACCTATTCATGACCC
AGATTATATAGGGGGGATAGGCAAAGAACTCATTGTAGATGATGCTAGTGATGTCACATC
ATTCTATCCCTCTGCATTTCAAGAACATCTGAATTTTATCCCGGCGCCTACTACAGGATC
AGGTTGCACTCGAATACCCTCATTTGACATGAGTGCTACCCATTACTGCTACACCCATAA
TGTAATATTGTCTGGATGCAGAGATCACTCACACTCACATCAGTATTTAGCACTTGGTGT
GCTCCGGACATCTGCAACAGGGAGGGTATTCTTTTCTACTCTGCGTTCCATCAACCTGGA
CGACACCCAAAATCGGAAGTCTTGCAGTGTGAGTGCAACTCCCCTGGGTTGTGATATGCT
GTGCTCGAAAGCCACGGAGACAGAGGAAGAAGATTATAACTCAGCTGTCCCTACGCGGAT
GGTACATGGAGGTTAGGGTTCGACGGCCAATATCACGAAAAGGACCTAGATGTCACAAC
ATTATTCGGGGACTGGGTGGCCAACTACCCAGGAGTAGGGGGTGGATCTTTTATTGACAG
CCGCGTGTGGTTCTCAGTCTACGGAGGGTTAAAACCCAATACACCCAGTGACACTGTACA
GGAAGGGAAATATGTGATATACAAGCGATACAATGACACATGCCCAGATGAGCAAGACTA
CCAGATTCGAATGGCCAAGTCTTCGTATAAGCCTGGACGGTTTGGTGGGAAACGCATACA
GCAGGCTATCTTATCTATCAAAGTGTCAACATCCTTAGGCGAAGACCCGGTACTGACTGT
ACCGCCCAACACAGTCACACTCATGGGGGCCGAAGGCAGAATTCTCACAGTAGGGACATC
CCATTTCTTGTATCAGCGAGGGTCATCATACTTCTCTCCCGCGTTATTATATCCTATGAC
AGTCAGCAACAAAACAGCCACTCTTCATAGTCCTTATACATTCAATGCCTTCACTCGGCC
AGGTAGTATCCCTTGCCAGGCTTCAGCAAGATGCCCCAACTCATGTGTTACTGGAGTCTA
TACAGATCCATATCCCCTAATCTTCTATAGAAACCACACCTTGCGAGGGGTATTCGGGAC
AATGCTTGATGGTGAACAAGCAAGACTTAACCCTGCGTCTGCAGTATTCGATAGCACATC
CCGCAGTCGCATAACTCGAGTGAGTTCAAGCAGCATCAAAGCAGCATACACAACATCAAC
TTGTTTTAAAGTGGTCAAGACCAATAAGACCTATTGTCTCAGCATTGCTGAAATATCTAA
TACTCTCTTCGGAGAATTCAGAATCGTCCCGTTACTAGTTGAGATCCTCAAAGATGACGG
GGTTAGAGAAGCCAGGTCTGGCTAGTTGAGTCAACTATGAAAGAGTTGGAAAGATGGCAT
.............ArgSerGly---
                                                 NaeI
                                                 ―/―¬
TGTATCACCTATCTTCTGCGACATCAAGAATCAAACCGAATGCCGGC
```

FIGURE 8A
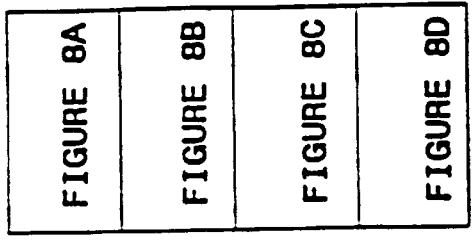
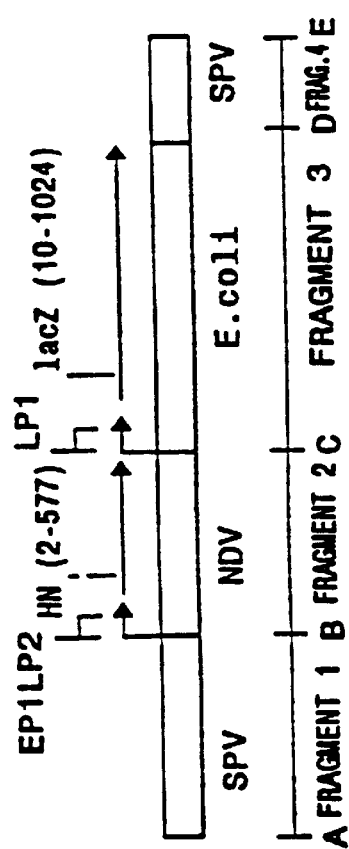

| DNA | Origin | Sites | Size |
|---|---|---|---|
| Vector | pSP64 | Bam HI—Hind III | ~2972 BP |
| Fragment 1 | SPV HindIII G | Hind III—Nde I | ~670 BP |
| Fragment 2 | pJF751 | Bam HI—Pvu II | ~3010 BP |
| Fragment 3 | SPV HindIII G | Nde I—Bam HI | ~1069 BP |

| FIGURE 9A |
| FIGURE 9B |
| FIGURE 9C |

| DNA | Origin | Sites | Size |
|---|---|---|---|
| Vector | pSP64 | Hind III—Bam HI | ~2972 BP |
| Fragment 1 | SPV HindIII M | Bgl II—Acc I | ~1484 BP |
| Fragment 2 | pJF751 | Bam HI—Pvu II | ~3002 BP |
| Fragment 3 | PRV BamHI 2 & 9 | Nco I—Nco I | ~2378 BP |
| Fragment 4 | SPV HindIII M | Acc I—Hind III | ~2149 BP |

FIGURE 10B

JUNCTION A

ACA GGA AAC AGC TAT GAC CAT GAT TAC GAA TTC GAG CTC GCC CGG GGA TCT
[Bam HI/Bgl II] → SPV Hind III M
← pSP64

JUNCTION B

AA ATA TAT AAA TAC CAT GTT AGA ATT TGG TCT GCT GCA GGT CGA CTC TAG AAT TTC ATT TTG
[Acc I] → SPV Hind III M
LP1

JUNCTION B (CONT.)

TTT TTT TCT ATG CTA TAA ATG AAT TCG GAT CCC GTC GTT TTA
LP1 | EcoRI BamHI | MET Asn Ser Asp Pro Val Val Leu
→ E. coli Lac Z (10)
← pJF 751

FIGURE 10D

JUNCTION D

```
     [Nco I]
  C CAT GCT CTA GAG GAT CCC CGG GCG AGC TCG AAT TCG GAT CCA TAA TTA ATT
         ────►                                      └──┘
         PRV Bam HI #9                              EcoRI
```

JUNCTION D (CONT.)

```
                                                           [Acc I]
  AAT TAA TTT TTA TCC CGG GTC GAC CGG GTC GAC CTG CAG CCT ACA TGG AAA TCT ACC
                                                          ────────►
                                                          SPV Hind III M
```

JUNCTION E

```
                                       HindIII
  TAA TGT ATC TAT AAT GGT ATA AAG CTT GTA TTC TAT AGT GTC ACC TAA ATC
                                  ────►      ◄────
                                  pSP64      SPV Hind III M
```

FIGURE 11B

JUNCTION A

ACA GGA AAC AGC TAT GAC CAT GAT TAC GAA TTC GAG CTC GCC CGG GGA TCT
[Bam HI/Bgl II]
SPV Hind III M
pSP64

JUNCTION B

AA ATA TAT AAA TAC CAT GTT AGA ATT TGG TCT GCT GCA GGT CGA CTC TAG AAT TTC ATT TTG
[Acc I]
SPV Hind III M
LP1

JUNCTION B (CONT.)

TTT TTT TCT ATG CTA TAA ATG AAT TCG GAT CCC GTC GTT TTA
                                MET Asn Ser Asp Pro Val Val Leu
LP1
EcoRI  BamHI
E. coli Lac Z (10)
pJF 751

FIGURE 11D

JUNCTION D

```
        [Nco I]
       ┌─────
     C CAT GCT CTA GAG GAT CCC CGG GCG AGC TCG AAT TCG GAT CCA TAA TTA ATT
            └──────►                                        └─────
            PRV Bam HI #9                                   EcoRI
```

JUNCTION D (CONT.)

```
                                                              [Acc I]
                                                             ┌─────
    AAT TAA TTT TTA TCC CGG GTC GAC CGG GTC GAC CTG CAG CCT ACA TGG AAA TCT ACC
                                                            └──────►
                                                            SPV Hind III M
```

JUNCTION E

```
                                              HindIII
                                             ┌──────┐
                                             │      │
    TAA TGT ATC TAT AAT GGT ATA AAG CTT GTA TTC TAT AGT GTC ACC TAA ATC
                                        ◄────────
                                        pSP64
    ◄─────
    SPV Hind III M
```

FIGURE 12C

JUNCTION C

```
        Pvu II
GAA ATC ⌐CAG┐CTG AGC GCC GGT CGC TAC CAT TAC CAG TTG GTC TGG TGT CAA AAA GAT
Glu Ile  Gln  Leu Ser Ala Gly Arg Tyr His Tyr Gln Leu Val Trp Cys Gln Lys Asp
         ↓                                                                    ↓
      pJF751                                              E. coli Lac Z (1024)
```

JUNCTION C (CONT.)

```
                       Sal I    Xba I                                    LP2
                       ⌐GTC GAC⌐TCT AGA⌐TTT TTT TTT TTT TTT TTG GCA TAT AAA
CCA TAA TTA ATT AAC CCG
Pro *
```

JUNCTION C (CONT.)

```
Bgl II                                                      Eco R I        [Nco I]
                                                                           ⌐GGC ATG GCC TCG
⌐AG ATC TGT ATC CTA AAA TTG AAT TGT AAT TAT CGA TAA ATG AAT TCC AAT TCG
                                                       MET Asn Ser Gly Met Ala Ser
                                   EP2                                     → PRV gpC (1)
```

FIGURE 12D
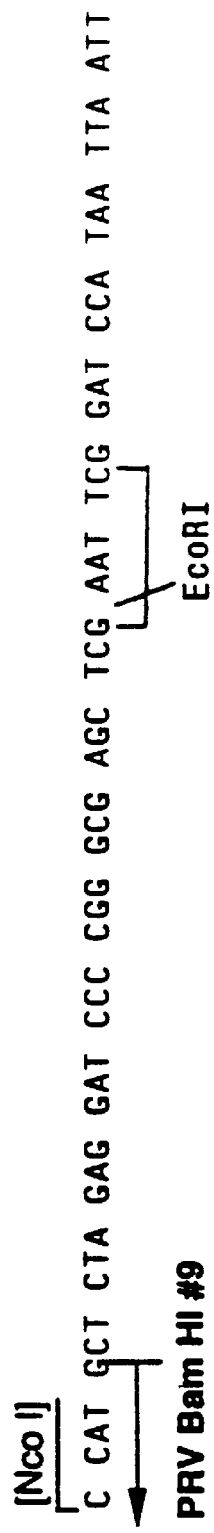
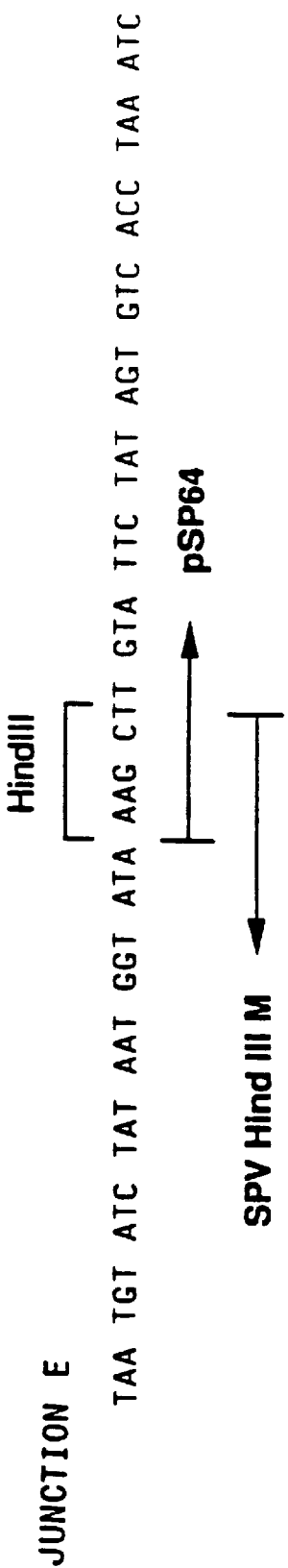

| DNA | Origin | Sites | Size |
|---|---|---|---|
| Vector | pSP64 | | |
| Fragment 1 | SPV HindIII M | Hind III–Bam HI | ~2972 BP |
| Fragment 2 | ILT Asp718I 5.1 kb | Bgl II–Acc I | ~1484 BP |
| | | Eco RI†–Mbo I | ~939 BP |
| Fragment 3 | pJF751 | Bam HI–Pvu II | ~3002 BP |
| Fragment 4 | SPV HindIII M | Acc I–Hind III | ~2149 BP |

† Restriction site introduced by PCR cloning

| FIGURE 13A |
| FIGURE 13B |
| FIGURE 13C |
| FIGURE 13D |

| DNA | Origin | Sites | Size |
|---|---|---|---|
| Vector | pSP64 | Hind III–Bam HI | ~2972 BP |
| Fragment 1 | SPV Hind III M | Bgl II–Acc I | ~1484 BP |
| Fragment 2 | ILT Asp 718I | Eco RI†–Bam HI† 8.0 kb | ~1090 BP |
| Fragment 3 | pJF751 | Bam HI–Pvu II | ~3010 BP |
| Fragment 4 | SPV Hind III M | Acc I–Hind III | ~2149 BP |

†Restriction sites introduced by PCR cloning

FIGURE 15B

Junction A

ACA GGA AAC AGC TAT GAC CAT GAT TAC GAA TTC GAG CTC GCC CGG GGA TCT → SPV Hind III M

[Bam HI/Bgl II]

← pSP64

Junction B

[Acc I] NotI — Sal I — Xba I
GTAT AGC GGC CGC CTG CAG GTC GAC TCT AGA TTT TTT TTT TTT TTG GCA TAT AAA
↓ SPV Hind III M
 — LP2 —

Junction B (Cont)

Bgl II — EP2 — EcoR I
TAG ATC TGT ATC CTA AAA TTG AAT TGT AAT TAT CGA TAA TAA ATG AAT TCC CCT GCC GCC CGG
                                                          MET Asn Ser Pro Ala Ala Arg
                                                                                  → IBR gpG (2)

FIGURE 15D

Junction D

```
                  Pvu II
GAA ATC  CAG CTG  AGC GCC GGT CGC TAC CAT TAC CAG TTG GTC TGG TGT CAA AAA GAT
Glu Ile  Gln Leu  Ser Ala Gly Arg Tyr His Tyr Gln Leu Val Trp Cys Gln Lys Asp
         ←──────
         pJF 751                                       ──────→
                                                       E. coli Lac Z (1024)
```

Junction D (Cont)

```
                     AscI                    SalI                  NotI       [AccI]
CCA TAA TTA ATT AAC CCG GGT CGA GGC GCG CCG  GGT CGA CCT GCA GGC GGC CGC  TAT AC
Pro *                                                                         ──────→
                                                                              SPV Hind III M
```

Junction E

```
                              Hind III
TAA TGT ATC TAT AAT GGT ATA  AAG CTT  GTA TTC TAT AGT GTC ACC TAA ATC
                             ──────
                             ←──────           ──────→
                                               pSP64
        ←──────
        SPV Hind III M
```

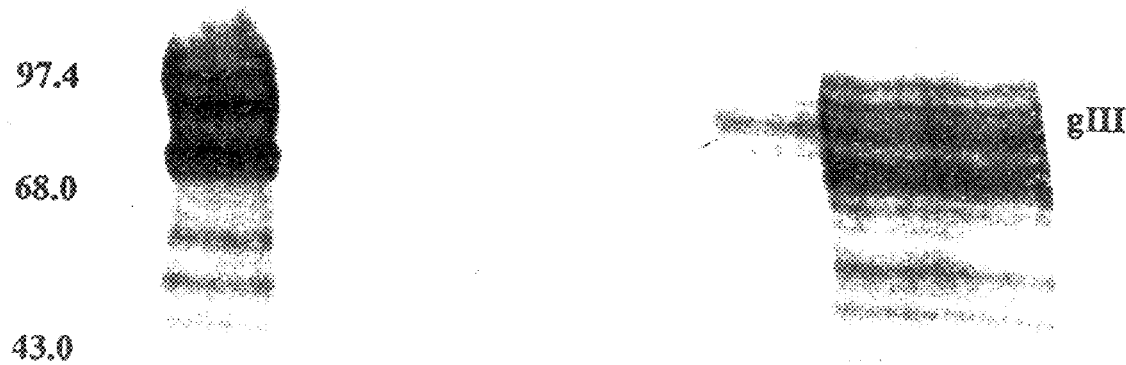

| FIGURE 18A |
|---|
| FIGURE 18B |
| FIGURE 18C |
| FIGURE 18D |

| DNA | Origin | Sites | Size |
|---|---|---|---|
| Vector | pSP64 | Hind III–Bam HI | ~2972 BP |
| Fragment 1 | SPV Hind III M | Bgl II–Acc I | ~1484 BP |
| Fragment 2 | EIVA PR/56 NA | BamH I†–BamH I† | ~1450 BP |
| Fragment 3 | pJF751 | Bam HI–Pvu II | ~3010 BP |
| Fragment 4 | SPV Hind III M | Acc I–Hind III | ~2149 BP |

†Restriction sites introduced by PCR cloning

| DNA | Origin | Sites | Size |
|---|---|---|---|
| Vector | pSP64 | Hind III–Bam HI | ~2972 BP |
| Fragment 1 | SPV Hind III M | Bgl II–Acc I | ~1484 BP |
| Fragment 2 | PRV Kpn I C | Sma I–Sac I | ~3500 BP |
| Fragment 3 | pJF751 | Bam HI–Pvu II | ~3010 BP |
| Fragment 4 | SPV Hind III M | Acc I–Hind III | ~2149 BP |

FIGURE 19B

Junction A

ACA GGA AAC AGC TAT GAC CAT GAT TAC GAA TTC GAG CTC GCC CGG GGA TCT [Bam HI/Bgl II]

→ SPV Hind III M

← pSP64

LP2

Junction B

[Acc I] NotI — SalI — XbaI

GTA T|GC GGC CGC CTG CAG GTC GAC TCT AGA TTT TTT TTT TTT TTG GCA TAT AAA

← SPV Hind III M

BglII

TAG ATC TGT ATC CTA AAA TTG AAT TGT AAT TAT CGA TAA TAA

EP2

Junction B Continued

TCT TTG GCG CGG GCC CCG TGG GCA TCG GTC GTC CGG GTA CCA CGG

SmaI → PRV KpnI C

Junction B Continued

EcoRI

A|TGAA T|C ACC CGC TGG

→ PRV gB (2-16) (Synthetic)

Synthetic N-terminal

FIGURE 19C
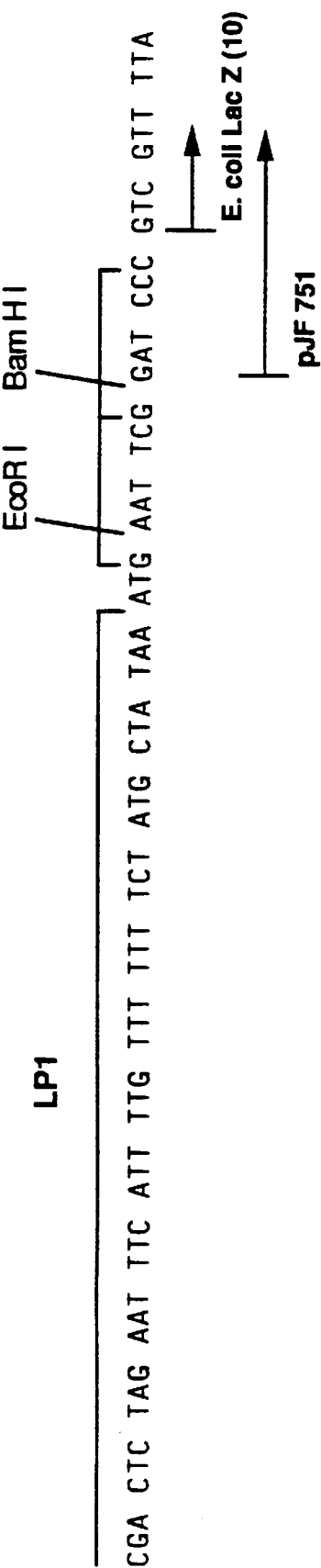

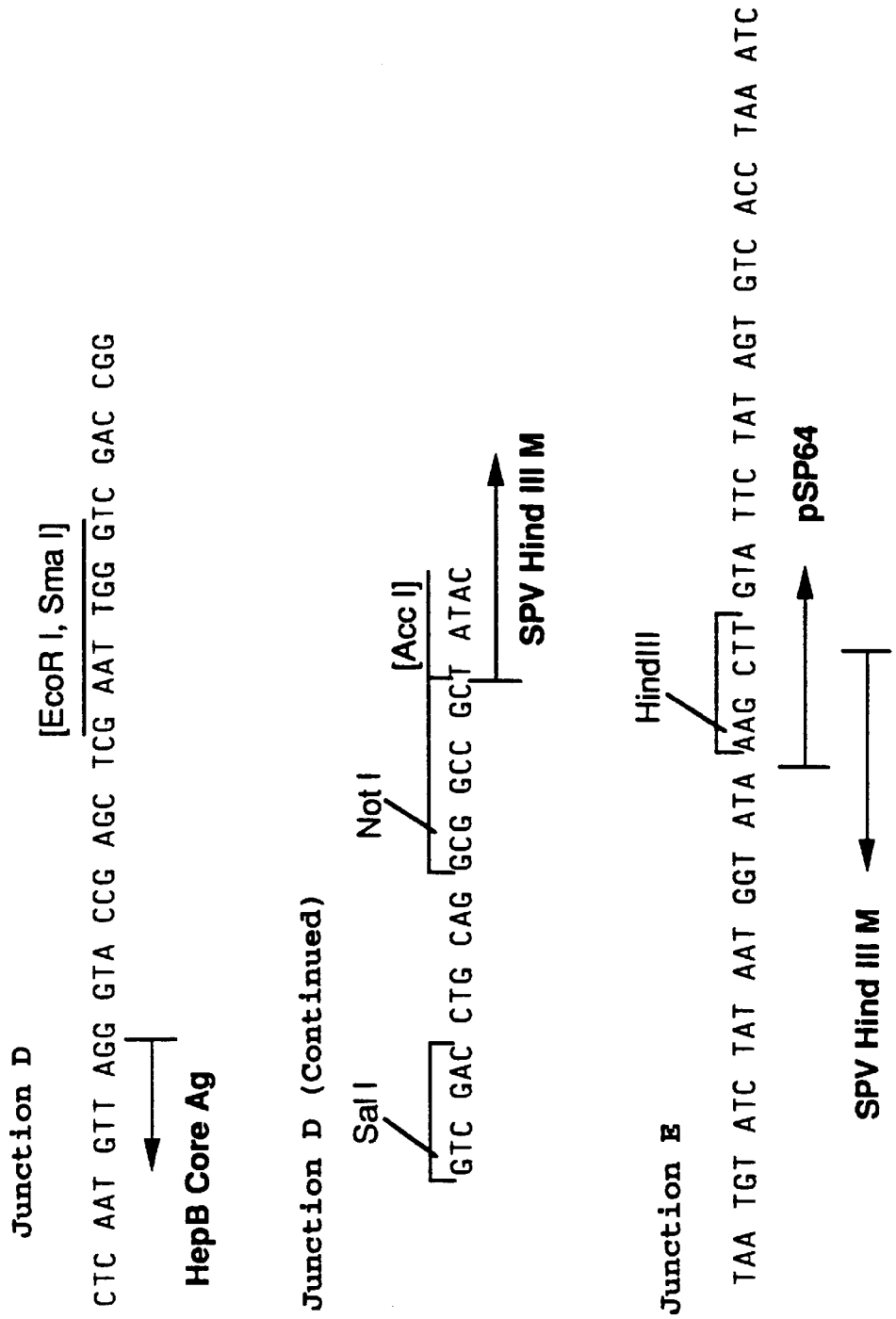

| FIGURE 21A |
| FIGURE 21B |
| FIGURE 21C |
| FIGURE 21D |

| DNA | Origin | Sites | Size |
| --- | --- | --- | --- |
| Vector | pSP64 | Hind III–Bam HI | ~2972 BP |
| Fragment 1 | SPV Hind III M | Bgl II–Acc I | ~1484 BP |
| Fragment 2 | EIVA NA AK/91 | Sal I†–Sal I† | ~1450 BP |
| Fragment 3 | pJF751 | Bam HI–Pvu II | ~3010 BP |
| Fragment 4 | SPV Hind III M | Acc I–Hind III | ~2149 BP |

†Restriction sites introduced by PCR cloning

| DNA | Origin | Sites | Size |
|---|---|---|---|
| Vector | pSP64 | | |
| Fragment 1 | SPV HindIII M | HindIII—BamHI | ~2972 BP |
| Fragment 2 | HCMV 2.1 kb PstI | BglII—AccI | ~1484 BP |
| Fragment 3 | pJF 751 | PstI—AvaII | ~1154 BP |
| Fragment 4 | PRV BamHI #7 | BamHI—PvuII | ~3010 BP |
| Fragment 5 | SPV HindIII M | NdeI—SalI | ~750 BP |
| | | AccI—HindIII | ~2149 BP |

| FIGURE 22A |
| FIGURE 22B |
| FIGURE 22C |

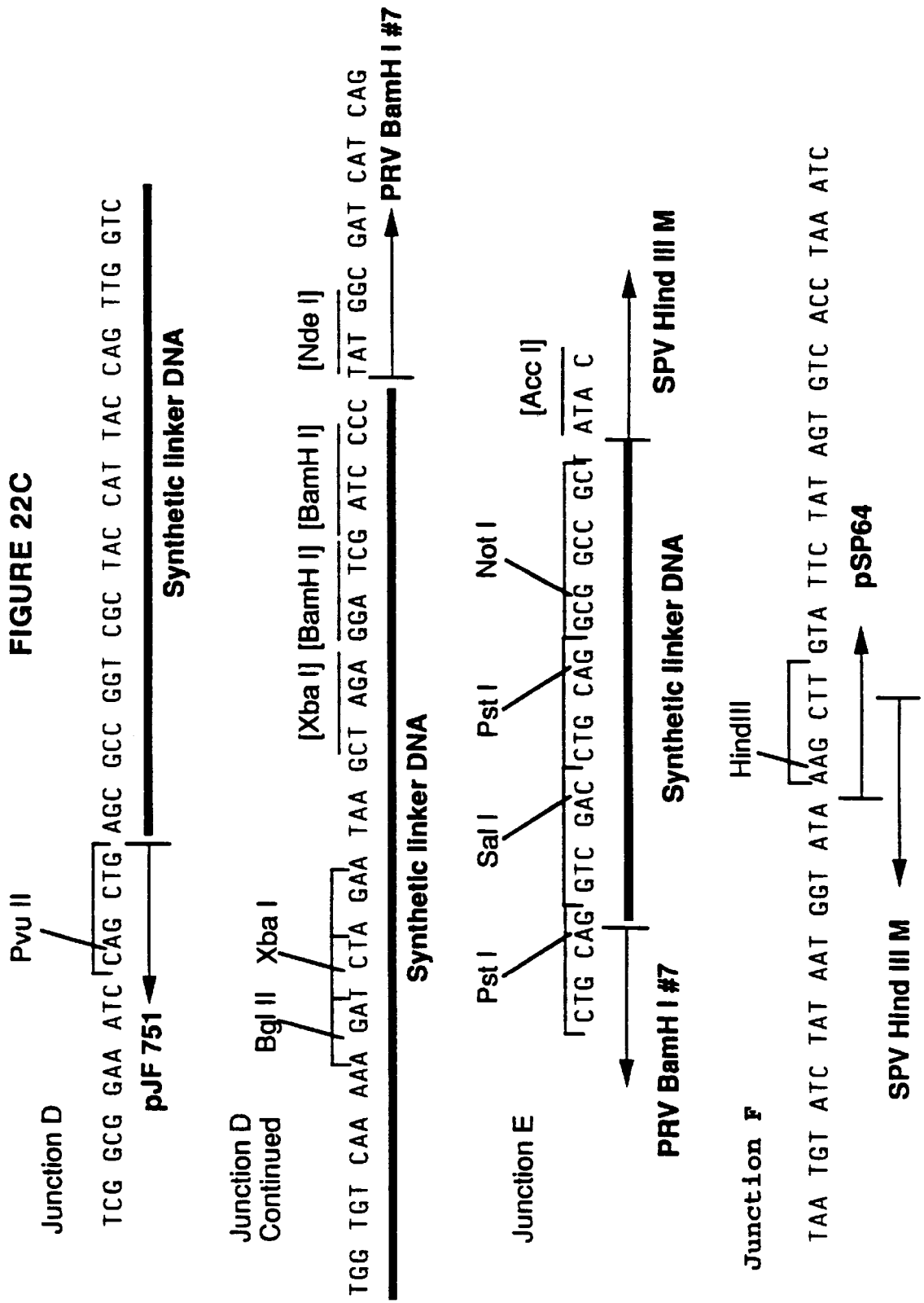

FIGURE 24C
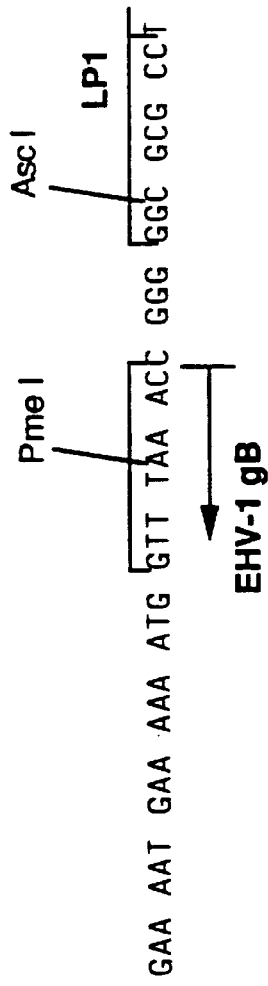
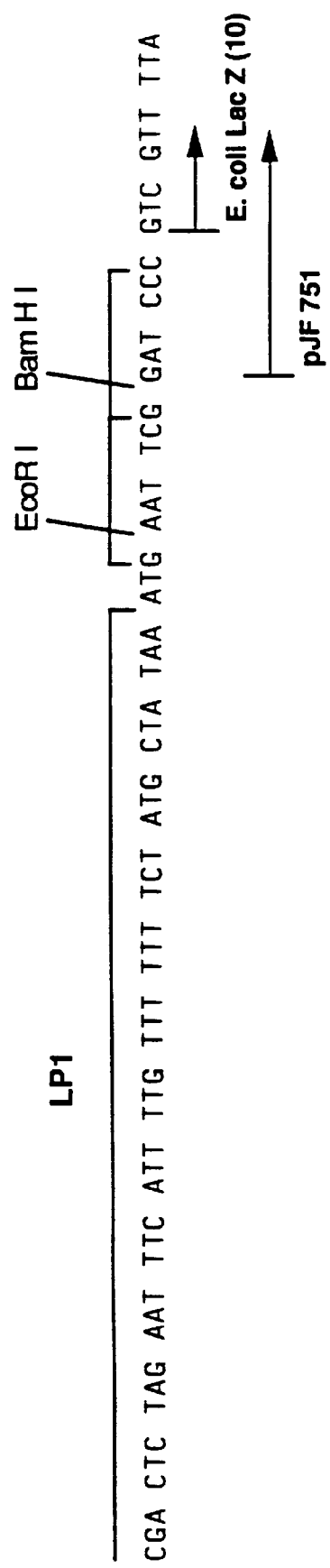

| DNA | Origin | Sites | Size |
| --- | --- | --- | --- |
| Vector | pSP64 | Hind III–Bam HI | ~2972 BP |
| Fragment 1 | SPV Hind III M | Bgl II–Acc I | ~1484 BP |
| Fragment 2 | EHV-1 BamH I "d" | Hind III–Hind III | ~1240 BP |
| Fragment 3 | pJF751 | Bam HI–Pvu II | ~3010 BP |
| Fragment 4 | SPV Hind III M | Acc I–Hind III | ~2149 BP |

FIGURE 25C
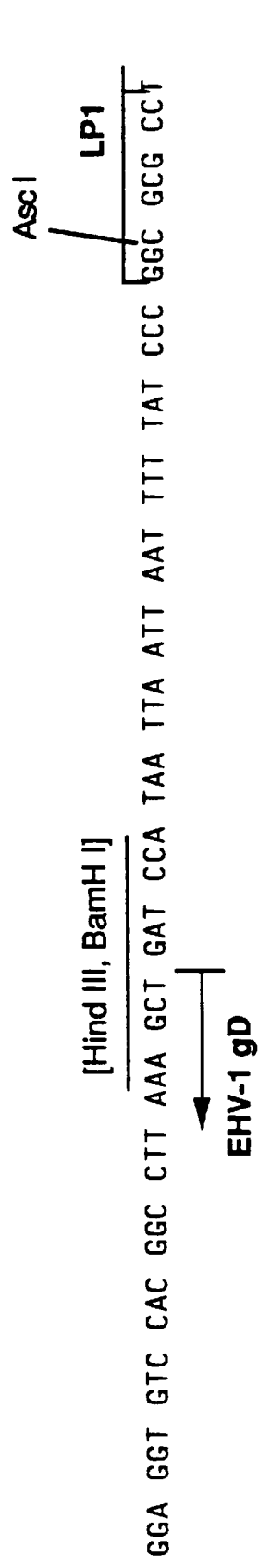
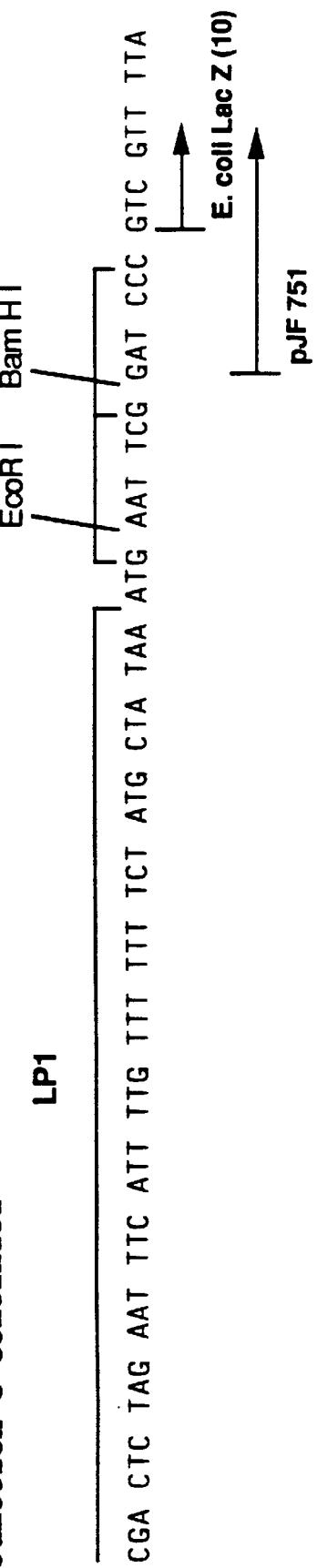

FIGURE 25D

Junction D

```
                    PvuII
GAA ATC  CAG CTG  AGC GCC GGT CGC TAC CAT TAC CAG TTG GTC TGG TGT CAA AAA GAT
         ───→                                                              ───→
         pJF 751                                                   E. coli Lac Z (1024)
```

Junction D Continued

```
              AscI                    SalI                  NotI
CCA TAA TTA ATT AAC CCG GGT CGA GGC GCG CCG GGT CGA CCT GCA GGC GGC CGC   TAT AC
                                                                    [AccI]
                                                                    ────→
                                                                   SPV HindIII M
```

Junction E

```
            HindIII
TAA TGT ATC TAT AAT GGT ATA AAG CTT GTA TTC TAT AGT GTC ACC TAA ATC
                              ───→
                             pSP64
        ←───
       SPV HindIII M
```

RECOMBINANT SWINEPOX VIRUS

This application is a U.S. national stage application under 35 USC 371 of international PCT/US94/08277, filed Jul. 22, 1994, which is a continuation-in-part of U.S. Ser. No. 07/820,154 filed Jan. 13, 1992, U.S. Pat. No. 5,382,425, and U.S. Ser. No. 08/097,554, filed Jul. 22, 1993, U.S. Pat. No. 5,869,312, the contents of which are incorporated by reference into the present application. Within this application several publications are referenced by arabic numerals within parentheses. Full citations for these publications may be found at the end of the specification immediately preceding the claims. The disclosures of these publications are hereby incorporated by reference into this application in order to more fully describe the state of the art to which this invention pertains.

BACKGROUND OF THE INVENTION

Swinepox virus (SPV) belongs to the family Poxviridae. Viruses belonging to this group are large, double-stranded DNA viruses that characteristically develop in the cytoplasm of the host cell. SPV is the only member of the genus Suipoxvirus. Several features distinguish SPV from other poxviruses. SPV exhibits species specificity (18) compared to other poxviruses such as vaccinia which exhibit a broad host range. SPV infection of tissue culture cell lines also differs dramatically from other poxviruses (24). It has also been demonstrated that SPV does not exhibit antigenic cross-reactivity with vaccinia virus and shows no gross detectable homology at the DNA level with the ortho, lepori, avi or entomopox virus groups (24). Accordingly, what is known and described in the prior art regarding other poxviruses does not pertain a priori to swinepox virus.

SPV is only mildly pathogenic, being characterized by a self-limiting infection with lesions detected only in the skin and regional lymph nodes. Although the SPV infection is quite limited, pigs which have recovered from SPV are refractory to challenge with SPV, indicating development of active immunity (18).

The present invention concerns the use of SPV as a vector for the delivery of vaccine antigens and therapeutic agents to swine. The following properties of SPV support this rationale: SPV is only mildly pathogenic in swine, SPV is species specific, and SPV elicits a protective immune response. Accordingly, SPV is an excellent candidate for a viral vector delivery system, having little intrinsic risk which must be balanced against the benefit contributed by the vector's vaccine and therapeutic properties.

The prior art for this invention stems first from the ability to clone and analyze DNA while in bacterial plasmids. The techniques that are available are detailed for the most part in Maniatis et al., 1983 and Sambrook et al., 1989. These publications teach state of the art general recombinant DNA techniques.

Among the poxviruses, five (vaccinia, fowlpox, canarypox, pigeon, and raccoon pox) have been engineered, previous to this disclosure, to contain foreign DNA sequences. Vaccinia virus has been used extensively to vector foreign genes (25) and is the subject of U.S. Pat. Nos. 4,603,112 and 4,722,848. Similarly, fowlpox has been used to vector foreign genes and is the subject of several patent applications EPA 0 284 416, PCT WO 89/03429, and PCT WO 89/12684. Raccoon pox (10) and Canarypox (31) have been utilized to express antigens from the rabies virus. These examples of insertions of foreign genes into poxviruses do not include an example from the genus Suipoxvirus. Thus, they do not teach methods to genetically engineer swinepox viruses, that is, where to make insertions and how to get expression in swinepox virus.

The idea of using live viruses as delivery systems for antigens has a very long history going back to the first live virus vaccines. The antigens delivered were not foreign but were naturally expressed by the live virus in the vaccines. The use of viruses to deliver foreign antigens in the modern sense became obvious with the recombinant vaccinia virus studies. The vaccinia virus was the vector and various antigens from other disease causing viruses were the foreign antigens, and the vaccine was created by genetic engineering. While the concept became obvious with these disclosures, what was not obvious was the answer to a more practical question of what makes the best candidate virus vector. In answering this question, details of the pathogenicity of the virus, its site of replication, the kind of immune response it elicits, the potential it has to express foreign antigens, its suitability for genetic engineering, its probability of being licensed by regulatory agencies, etc, are all factors in the selection. The prior art does not teach these questions of utility.

The prior art relating to the use of poxviruses to deliver therapeutic agents relates to the use of a vaccinia virus to deliver interleukin-2 (12). In this case, although the interleukin-2 had an attenuating effect on the vaccinia vector, the host did not demonstrate any therapeutic benefit.

The therapeutic agent that is delivered by a viral vector of the present invention must be a biological molecule that is a by-product of swinepox virus replication. This limits the therapeutic agent in the first analysis to either DNA, RNA or protein. There are examples of therapeutic agents from each of these classes of compounds in the form of anti-sense DNA, anti-sense RNA (16), ribozymes (34), suppressor tRNAs (2), interferon-inducing double stranded RNA and numerous examples of protein therapeutics, from hormones, e.g., insulin, to lymphokines, e.g., interferons and interleukins, to natural opiates. The discovery of these therapeutic agents and the elucidation of their structure and function does not make obvious the ability to use them in a viral vector delivery system.

SUMMARY OF THE INVENTION

The invention provides a recombinant swinepox virus capable of replication which comprises swinepox viral DNA and foreign DNA encoding RNA which does not naturally occur in an animal into which the recombinant swinepox virus is introduced. The foreign DNA is inserted into the swinepox viral DNA at a site which is not essential for replication of the swinepox virus and is under the control of a promoter.

This invention provides a homology vector for producing a recombinant swinepox virus by inserting foreign DNA into the genomic DNA of a swinepox virus which comprises a double-stranded DNA molecule. This molecule consists essentially of double-stranded foreign DNA encoding RNA which does not naturally occur in an animal into which the recombinant swinepox virus is introduced. At one end of this foreign DNA is double-stranded swinepox viral DNA homologous to genomic DNA located at one side of a site on the genomic DNA which is not essential for replication of the swinepox virus. At the other end of the foreign DNA is double-stranded swinepox viral DNA homologous to genomic DNA located at the other side of the same site on the genomic DNA.

BRIEF DESCRIPTION OF THE FIGURES

FIGS. 1A and 1B show a detailed diagram of SPV genomic DNA (Kasza strain) including the unique long and Terminal repeat (TR) regions. A restriction map for the enzyme HindIII is indicated (23). Fragments are lettered in order of decreasing size. Note that the terminal repeats are greater than 2.1 kb but less than 9.7 kb in size.

FIGS. 2A and 2B show the DNA sequence from homology vector 515-85.1. The sequence of two regions of the homology vector 515-85.1 are shown. The first region (FIG. 2A) (SEQ ID NO:1) covers a 599 base pair sequence which flanks the unique AccI site as indicated in FIG. 3. The beginning (Met) and end (Val) of a 115 amino acid ORF is indicated by the translation of amino acids below the DNA sequence. The second region (FIG. 2B) (SEQ ID NO:3) covers the 899 base pairs upstream of the unique HindIII site as indicated in FIG. 3. The beginning (Asp) and end (Ile) of a 220 amino acid ORF is indicated by the translation of amino acids below the DNA sequence.

FIGS. 3A, 3B, and 3C show the homology which exists between the 515.85.1 ORF and the Vaccinia virus 01L ORF. FIG. 3A shows two maps: The first line of FIG. 3A is a restriction map of the SPV HindIII M fragment and the second is a restriction map of the DNA insertion in plasmid 515 -85.1. The location of the 515-85.1 [VV 01L-like] ORF is also indicated on the map. The locations of the DNA sequences shown in FIGS. 3B and 3C are indicated below the map by heavy bars in FIG. 3A. FIG. 3B shows the homology between the VV 01L ORF (SEQ ID NO:5) and the 515-85.1 ORF (SEQ ID NO:6) at their respective N-termini. FIG. 3C shows the homology between the VV 01L ORF (SEQ ID NO:7) and the 515-85.1 ORF (SEQ ID NO:8) at their respective C-termini.

FIGS. 4A, 4B, and 4D show a description of the DNA insertion in Homology Vector 520-17.5. FIG. 4A contains a diagram showing the orientation of DNA fragments assembled in plasmid 520-17.5 and table indicating the origin of each fragment. FIG. 4B shows the sequences located at each of the junctions A and B between fragments, and FIG. 4C shows the sequences located at Junctions C and D (SEQ ID NO's: 9, 10, 13, and 16). FIGS. 4B and 4C further describe the restriction sites used to generate each fragment as well as the synthetic linker sequences which were used to join the fragments are described for each junction. The synthetic linker sequences are underlined by a heavy bar. The location of several gene coding regions and regulatory elements are also given. The following two conventions are used: numbers in parenthesis ( ) refer to amino acids, and restriction sites in brackets [ ] indicate the remnants of sites which were destroyed during construction. The following abbreviations are used, swinepox virus (SPV), early promoter 1 (EPI), late promoter 2 (LP2), lactose operon Z gene (lacZ), and *Escherichia coli* (*E. coli*).

FIGS. 5A, 5B, 5C, and 5D shows a detailed description of the DNA insertion in Homology Vector 538-46.16. FIG. 5A contains a diagram showing the orientation of DNA fragments assembled in plasmid 538-46.16 and a table indicating the origin of each fragment. FIG. 5B shows the sequences located at Junctions A and B between fragments, FIG. 5C shows sequences located at Junction C and FIG. 5D shows sequences located at Junctions D and E (SEQ ID NO's: 17, 18, 21, 26, and 28). FIGS. 5B to 5D also describe the restriction sites used to generate each fragment as well as the synthetic linker sequences which were used to join the fragments are described for each junction. The synthetic linker sequences are underlined by a heavy bar. The location of several gene coding regions and regulatory elements is also given. The following two conventions are used: numbers in parenthesis ( ) refer to amino acids, and restriction sites in brackets [ ] indicate the remnants of sites which were destroyed during construction. The following abbreviations are used, swinepox virus (SPV), pseudorabies virus (PRV), g50 (gpD), glycoprotein 63 (gp63), early promoter 1 (EP1), late promoter 1 (LP1) (SEQ ID NO: 46), late promoter 2 (LP2), lactose operon Z gene (lacZ), and *Escherichia coli* (*E. coli*).

FIG. 6

Western blot of lysates from recombinant SPV infected cells with anti-serum to PRV. Lanes (A) uninfected Vero cell lysate, (B) S-PRV-000 (pseudorabies virus S62/26) infected cell lysate, (C) pre-stained molecular weight markers, (D) uninfected EMSK cell lysate, (E) S-SPV- 000 infected cell lysate, (F) S-SPV-003 infected cell lysate, (G) S-SPV-008 infected cell lysate. Cell lysates were prepared as described in the PREPARATION OF INFECTED CELL LYSATES. Approximately ⅕ of the total lysate sample was loaded in each lane. FIG. 7

DNA sequence of NDV Hemagglutinin-Neuraminidase gene (HN) (SEQ ID NO: 29). The sequence of 1907 base pairs of the NDV HN cDNA clone are shown. The translational start and stop of the HN gene is indicated by the amino acid translation below the DNA sequence.

FIGS. 8A, 8B, 8C, and 8D show a detailed description of the DNA insertion in Homology Vector 538-46.26. FIG. 5A contains a diagram showing the orientation of DNA fragments assembled in plasmid 538-46.26 and table indicating the origin of each fragment. FIG. 8B shows the sequences located at Junctions A and B between fragments; FIG. 8C shows the sequences located at Junctions C and D, FIG. 8D shows the sequences located at Junction E (SEQ ID NO's: 31, 32, 34, 37, and 40). The restriction sites used to generate each fragment as well as the synthetic linker sequences which were used to join the fragments are described for each junction in FIGS. 8B and 8D. The synthetic linker sequences are underlined by a heavy bar. The location of several gene coding regions and regulatory elements is also given. The following two conventions are used: numbers in parenthesis ( ) refer to amino acids, and restriction sites in brackets [ ] indicate the remnants of sites which were destroyed during construction. The following abbreviations are used, swinepox virus (SPV), Newcastle Disease virus (NDV), hemagglutinin-neuraminidase (HN), early promoter 1 (EP1), late promoter 1 (LP1), late promoter 2 (LP2), lactose operon Z gene (lacZ), and *Escherichia coli* (*E. coli*).

FIGS. 9A, 9B, and 9C show a detailed description of Swinepox Virus S-SPV-010 and the DNA insertion in Homology Vector 561-36.26. FIG. 9A contains a diagram showing the orientation of DNA fragments assembled in plasmid 561-36.26 and a table indicating the origin of each fragment. FIG. 9B shows the sequences located at Junctions A and B between fragments and FIG. 9C show the sequences located at junction C and D (SEQ ID. NO: 47, 48, 49,50). The restriction sites used to generate each fragment as well as synthetic linker sequences which are used to join the fragments are described for each junction in FIGS. 9B and 9C. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), *Escherichia coli* (*E. coli*), thymidine kinase (TK), pox synthetic late promoter 1 (LP1), base pairs (BP).

FIGS. 10A, 10B, 10C, and 10D show a detailed description of Swinepox Virus S-SPV-011 and the DNA insertion in Homology Vector 570-91.21. FIG. 10A contains a diagram showing the orientation of DNA fragments assembled in plasmid 570-91.21 and a table indicating the origin of each fragment.

FIGS. 11, 11B, 11C and 11D show a detailed description of Swinepox Virus S-SPV-012 and the DNA insertion in Homology Vector 570-91.41. FIG. 11B shows the sequences located at Junctions A and B between fragements, FIG. 11C shows the sequences located at Junction C, and FIG. 11D shows the sequence located at Junctions D and E. (SEQ ID NO: 56, 57, 58, 59, 60). The restriction sites used to generate each fragment as well as synthetic linker sequences which are used to join the fragments are described for each junction in FIGS 11B to 11D. The location of several gene coding regions and regulatory elements is also given. The following two conventions are used: numbers in parentheses, ( ), refer to amino acids, and restriction sites brackets, [ ], indicate the remnants of sites which are destroyed during construction. The following abbreviations are used: swinepox virus (SPV), pseudorabies virus (PRV), Escherichia coli (*E. coli*), pox synthetic late promoter 1 (LP1), pox synthetic early promoter 1 late promoter 2 (EP1LP2) (SEQ ID NO: 43), gIII (gpC), base pairs (BP).

FIGS. 12, 12B, 12C and 12D show a detailed description of Swinepox Virus S-PRV-013 and the DNA insertion in Homology Vector 570-91.64. FIG. 12B shows the sequences located at Junctions A and B between fragments, FIG. 12C shows the sequences located at Junction C, and FIG. 12D shows the sequences located at Junctions D and E (SEQ ID NO: 61, 62, 63, 64, 65). The restriction sites used to generate each fragment as well as synthetic linker sequences which are used to join the fragments are described for each junction in FIGS. 12B to 12D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 1 (LP1), pox synthetic late promoter 2 early promoter 2 (LP2EP2) (SEQ ID NO: 44), gIII (gpC) base pairs (BP).

FIG. 13A contains a diagram showing the orientation of DNA fragments assembled in plasmid 599-65.25 and a table indicating the origin of each fragment. FIG. 13B shows sequences located at Junctions A and B between the fragments, FIG. 13C shows sequences located at Junction C, and FIG. 13D shows sequences located at Junctions D and E. (SEQ ID NO: 66, 67, 68, 69, 70). The restriction sites used to generate each fragment as well as synthetic linker sequences which are used to join the fragments are described for each junction in FIGS. 13B to 13D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used:

swinepox virus (SPV), infectious laryngotracheitis virus (ILT), *Escherichia coli* (*E. coli*), pox synthetic late promoter 1 (LP1), pox synthetic early promoter 1 late promoter 2 (EP1LP2), glycoprotein G (gpG), polymerase chain reaction (PCR), base pairs (BP).

Figure 14A:
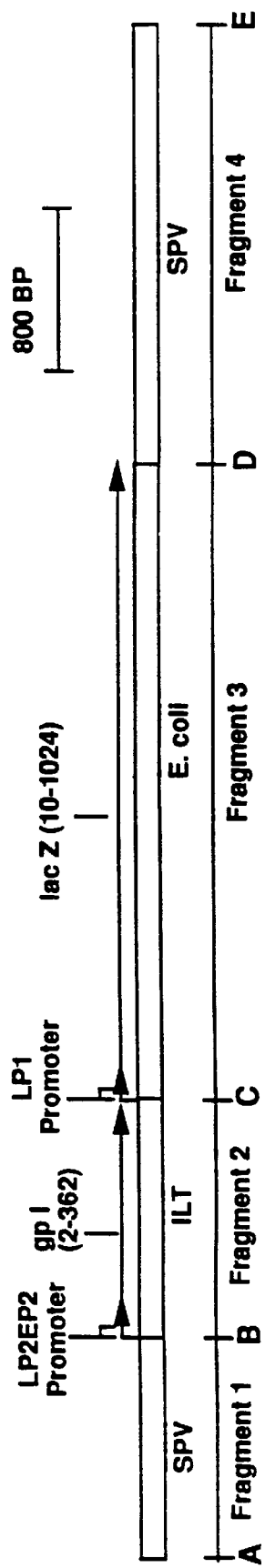
Figure 14B:
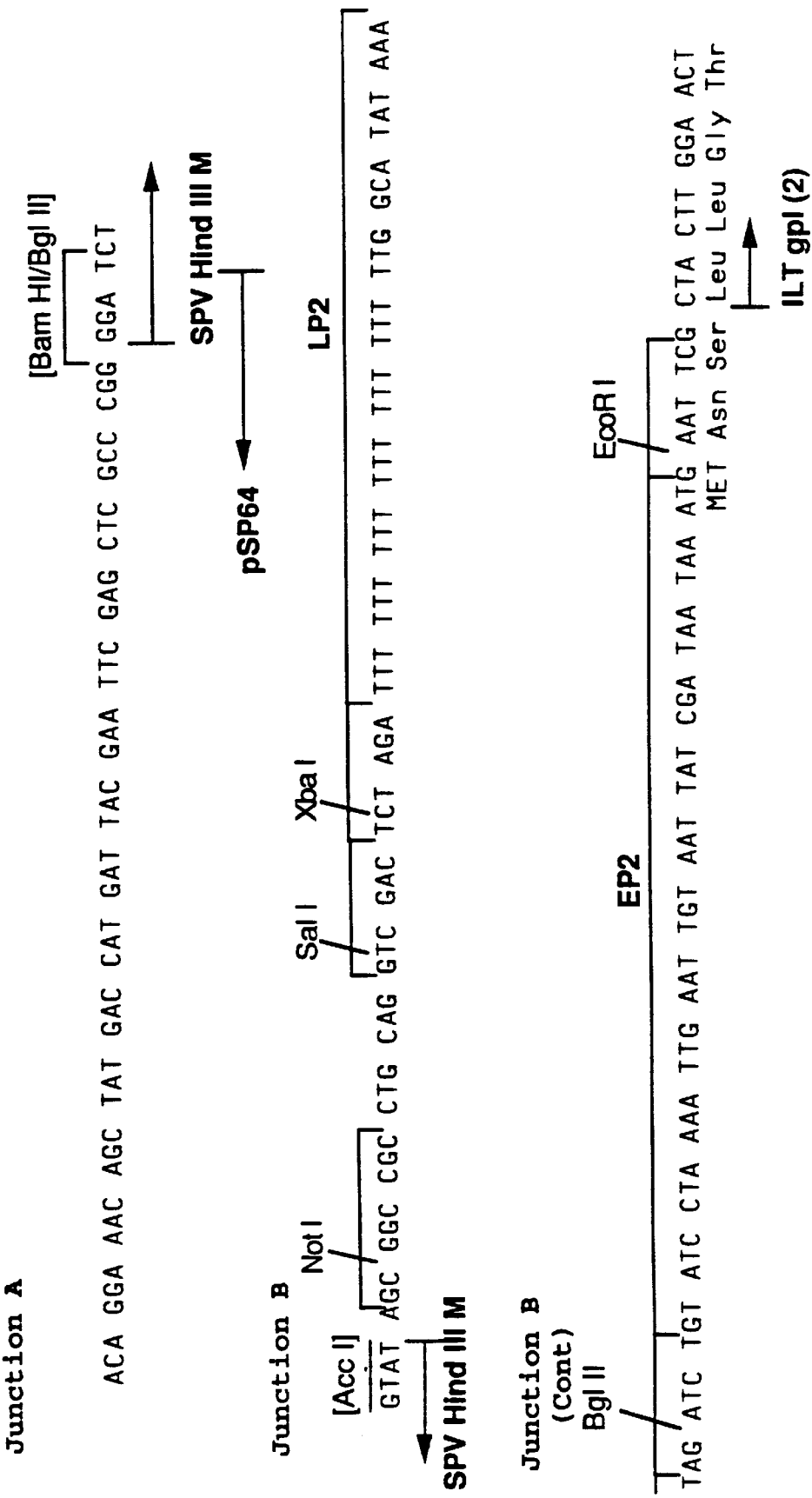
Figure 14C:
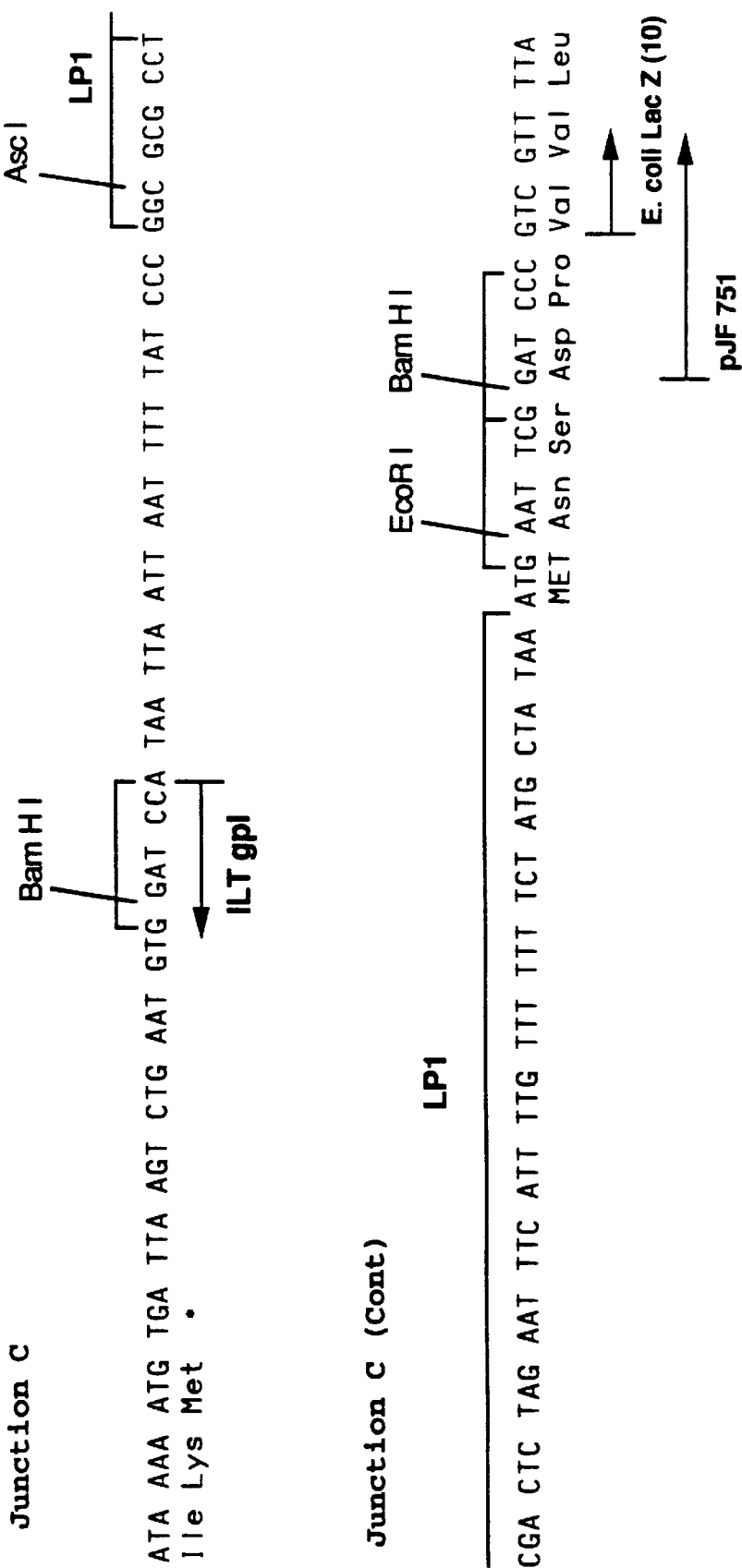
Figure 14D:
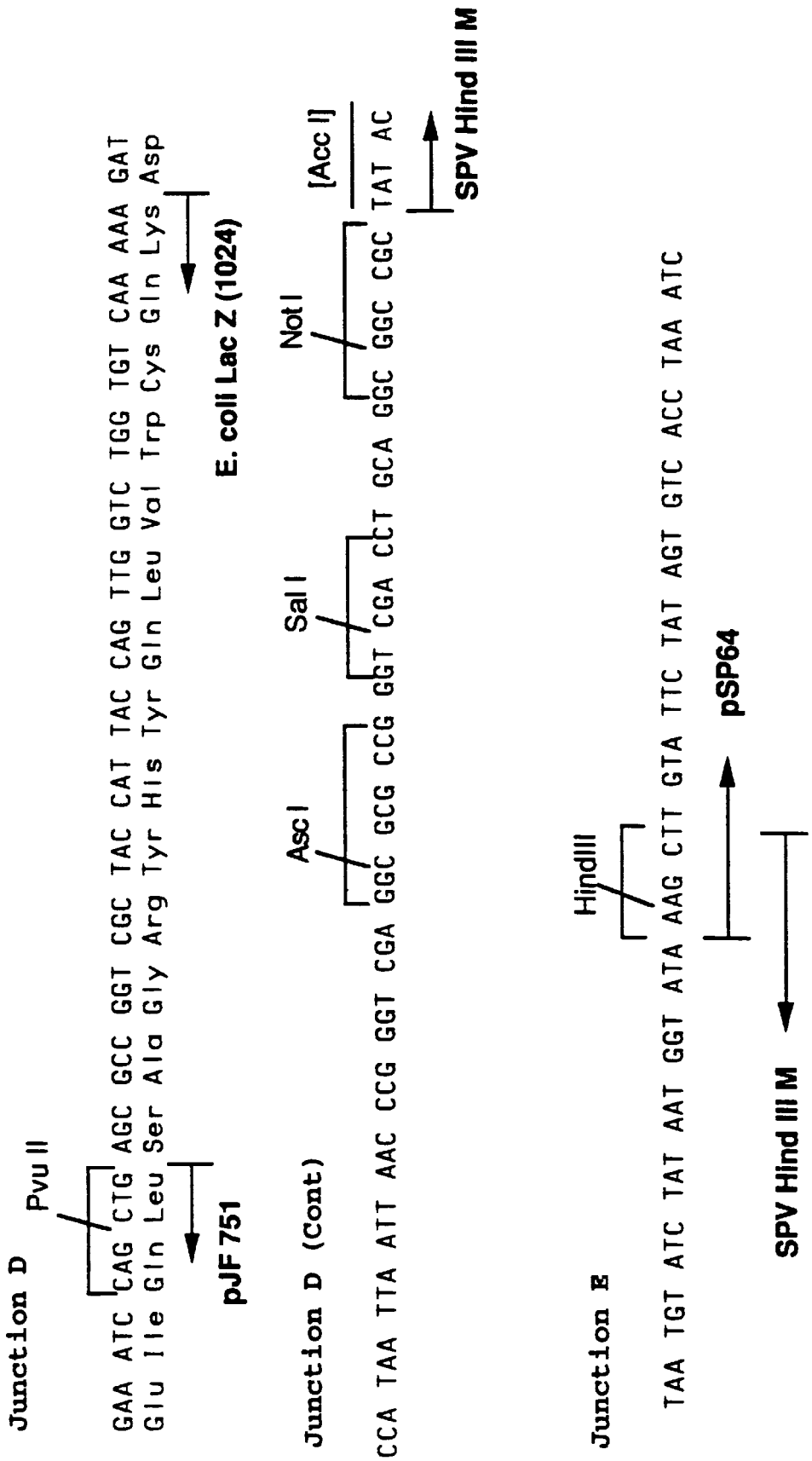

FIGS. 14A, 14B, 14C, and 14D show a derailed description of Swinepox Virus S-SPV-016 and the DNA insertion in Homology Vector 624-20.1C. FIG. 14A contains a diagram showing the orientation of DNA fragments assembled in plasmid 624-20.1C and a table indicating the origin of each fragment. FIG. 14B shows the sequences located at Junctions A and B betweeen fragments; FIG. 14C shows the sequences located at Junction C, and FIG. 14D shows the sequences at Junctions D and E. (SEQ ID NO: 71, 72, 73, 74, 75). The restriction sites are used to generate each fragment as well as synthetic linker sequences which are used to join the fragments are described for each junction in FIGS. 14B to 14D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), infectious laryngotracheitis virus (ILT), *Escherichia coli* (*E. coli*), pox synthetic late promoter 1 (LP1), pox synthetic late promoter 2 early promoter 2 (LP2EP2), glycoprotein I (gpI), polymerase chain reaction (PCR), base pairs (BP).

Figure 15A:
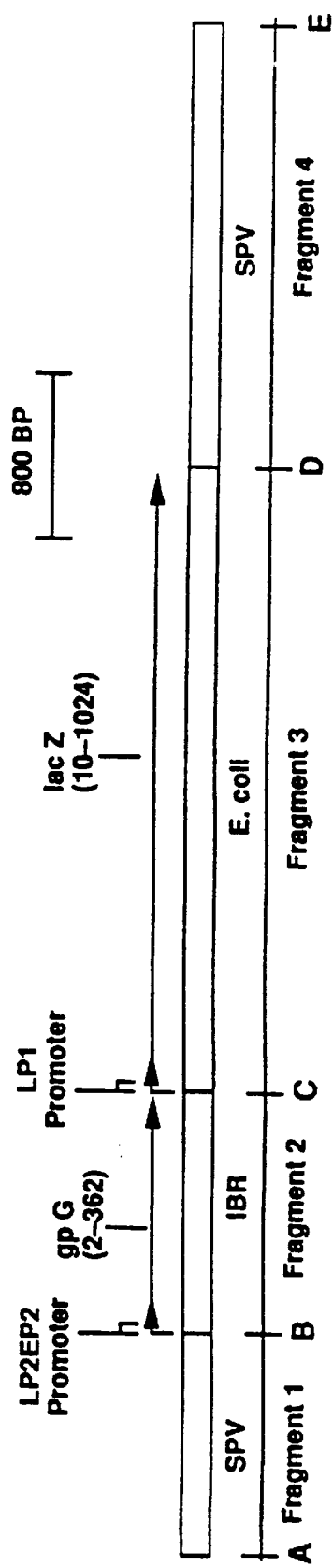
Figure 15C:
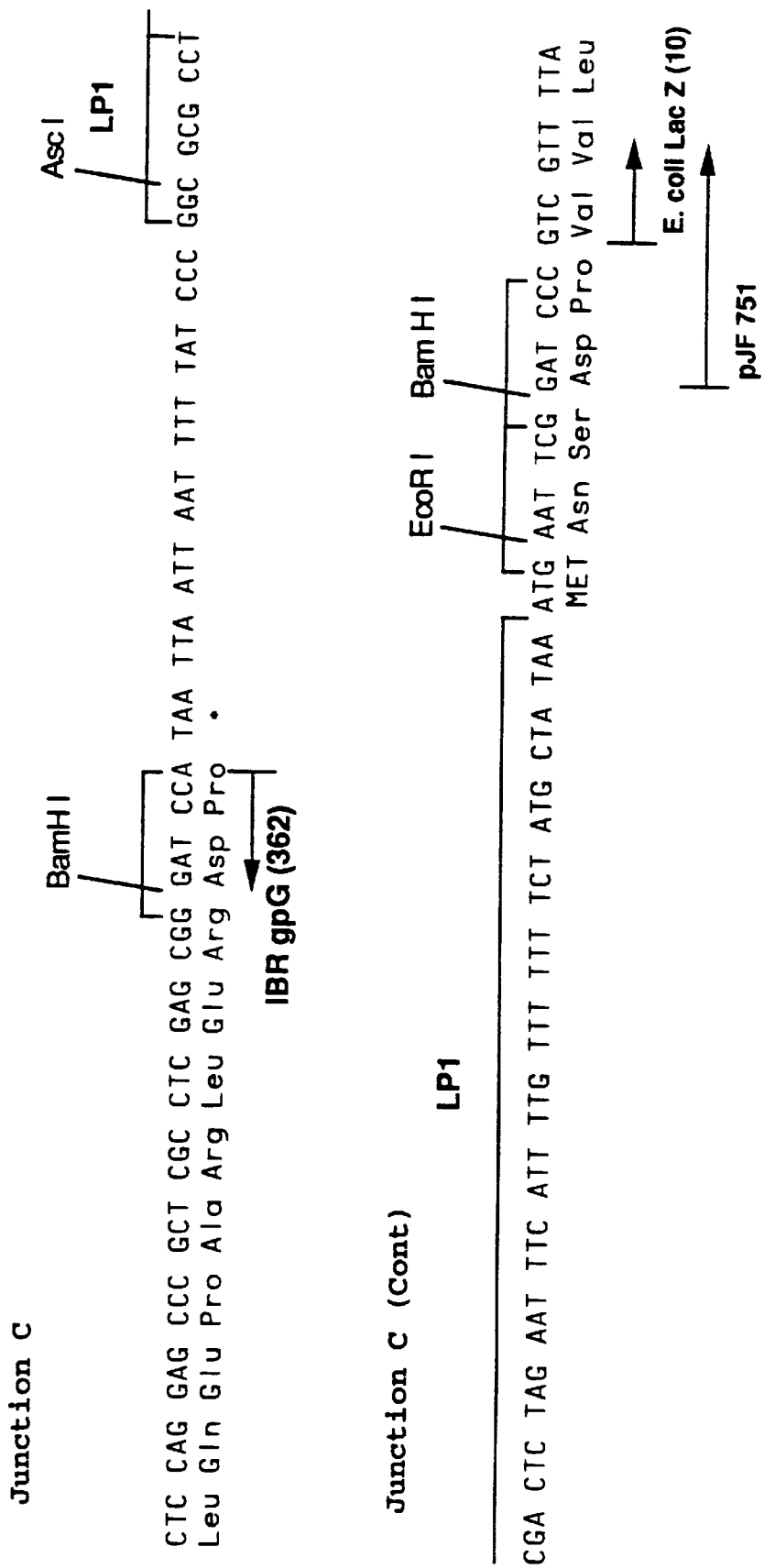

FIGS. 15A, 15B, 15C and 15D show a detailed description of Swinepox Virus S-SPV-017 and the DNA insertion in Homology Vector 614-83.18. FIG. 15A contains a diagram showing the orientation of DNA fragments assembled in plasmid 614-83.18 and a table showing the origin of each fragment. FIG. 15B shows the sequences located at Junctions A and B between fragments, FIG. 15C shows the sequences at Junction C, and FIG. 15D shows the sequences located at Junctions D and E. The restriction sites used tc generate each fragment as well as synthetic linker sequences which are used to join the fragments are described for each junction in FIGS. 15B to 15D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), infectious bovine rhinotracheitis virus (IBR), *Escherichia coli* (*E. coli*), pox synthetic late promoter 1 (LP1), pox synthetic late promoter 2 early promoter 2 (LP2EP2), glycoprotein G (gpG), polymerase chain reaction (PCR), base pairs (BP).

FIG. 16

Western blot of lysates from recombinant SPV infected cells with polyclonal goat anti-PRV gIII (gpC). Lanes (A)

S-PRV-002 (U.S. Pat. No. 4,877,737, issued Oct. 31, 1989) infected cell lysate, (B) molecular weight markers, (C) mock-infected EMSK cell lysate, (D) S-SPV-003 infected cell lysate, (E) S-SPV-008 infected cell lysate, (F) S-SPV-011 infected cell lysate, (G) S-SPV-012 infected cell lysate, (H) S-SPV-013 infected cell lysate. Cell lysates are prepared as described in the PREPARATION OF INFECTED CELL LYSATES. Approximately ⅕ of the total lysates sample is loaded in each lane.

FIG. 17

Map showing the 3,628 base pair BglII to HindIII swinepox virus DNA fragment inserted into homology vector 515-85.1.

Figure 23A:
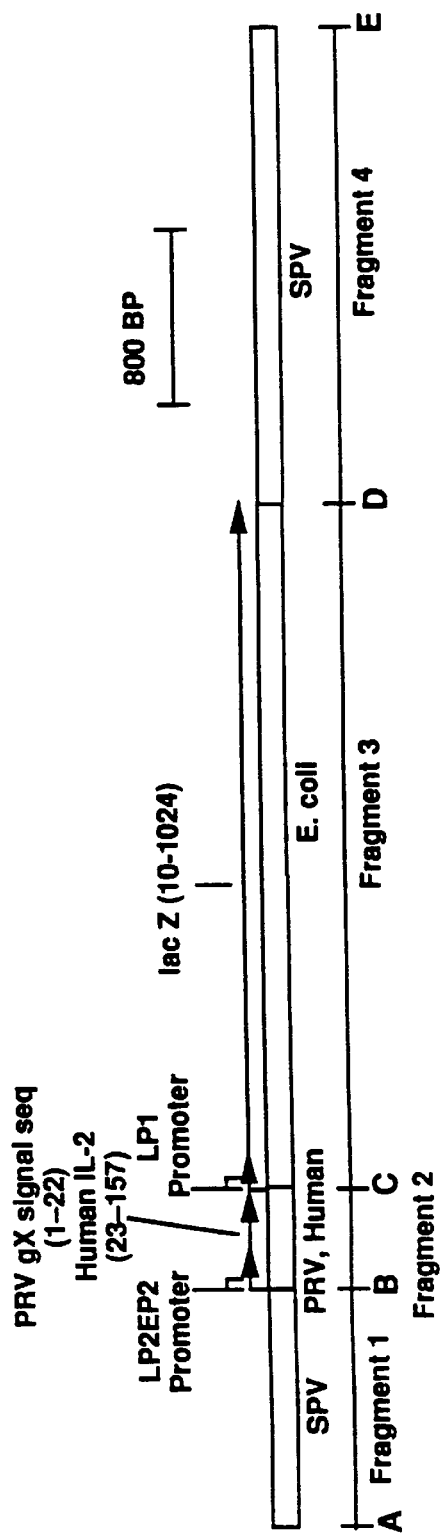
Figure 23B:
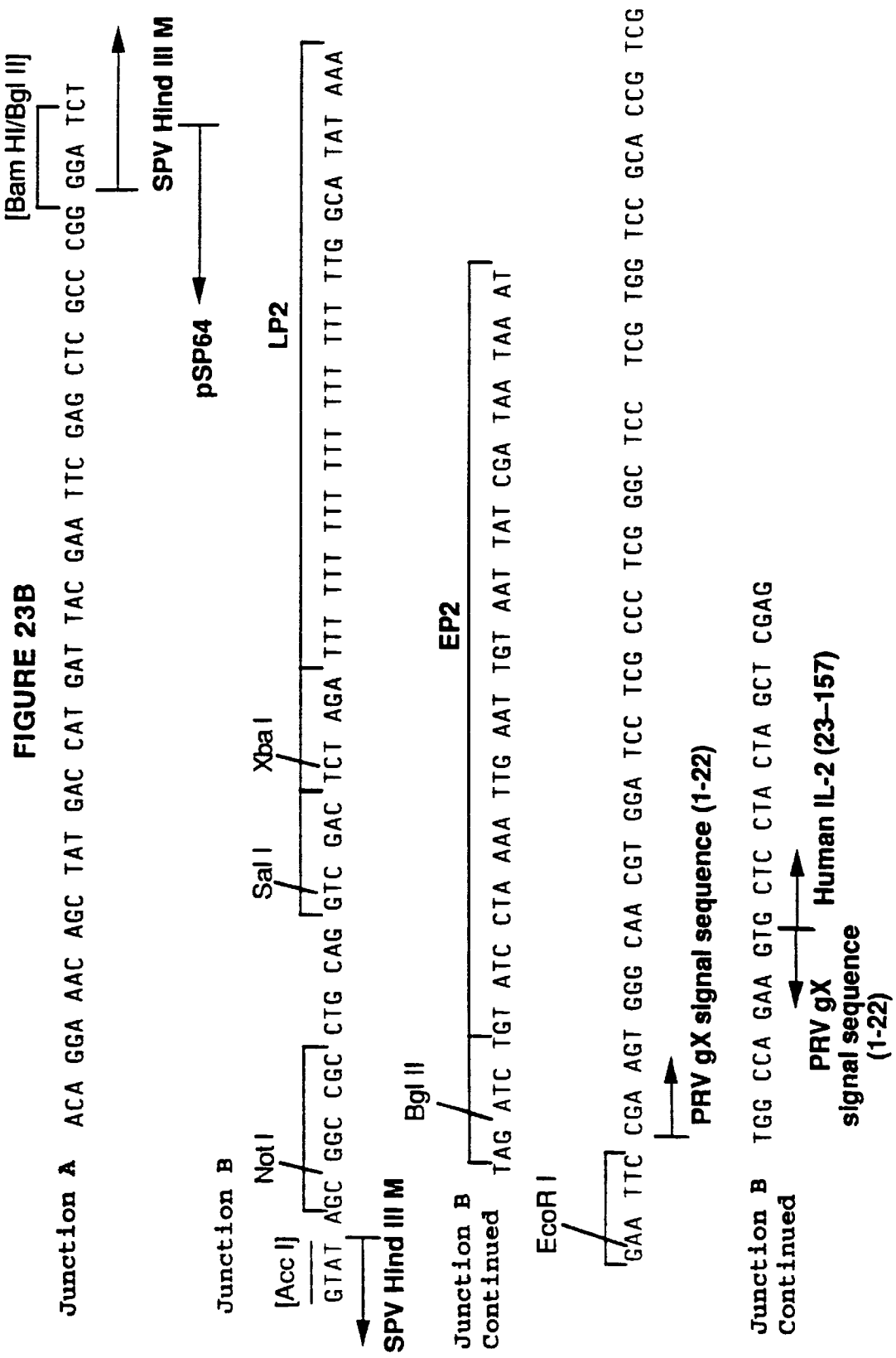
Figure 23C:
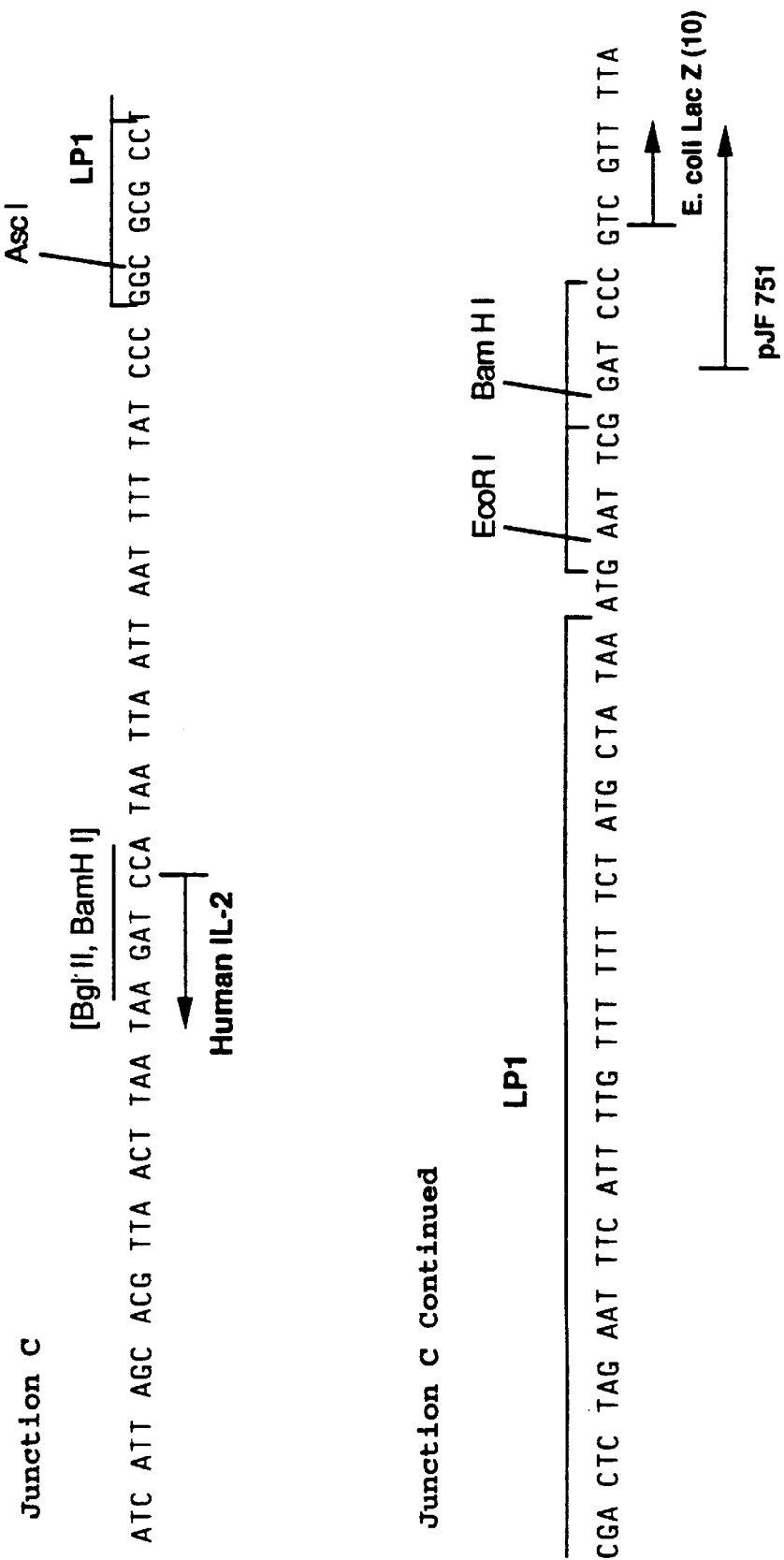
Figure 23D:
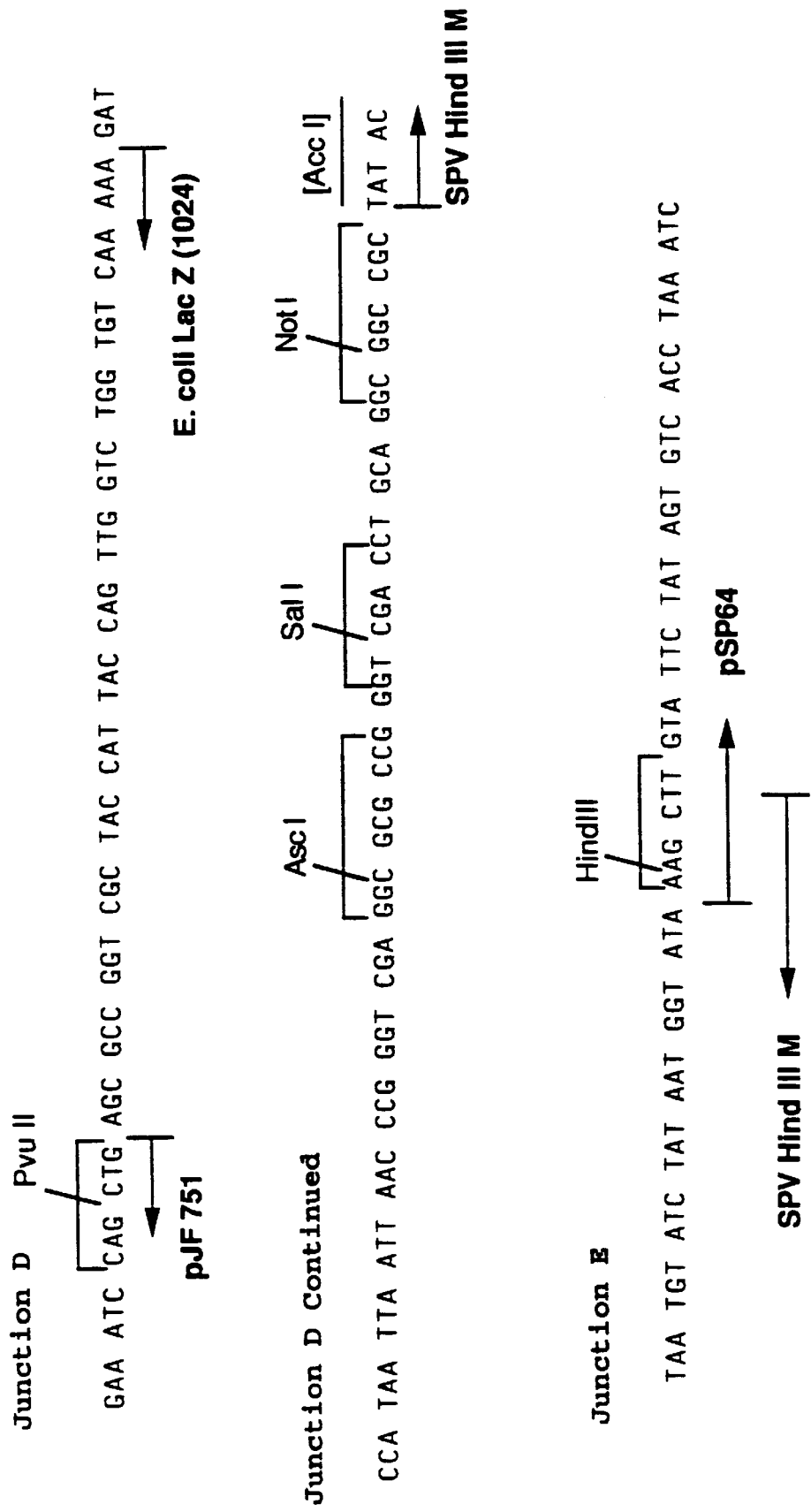

Two open reading frames, O2L and O1L, are shown with the number of amino acids coding in each open reading frame. The homology vector 738-94.5 contains a deletion of SPV DNA from nucleotides 1381 to 2133 (SEQ ID NO. 113). The lacZ gene has been inserted into this region and is expressed from the O1L promoter. Positions of restriction sites AccI, BglII, and HindIII are shown.

FIGS. 18A, 18B, 18C and 18D show a detailed description of Swinepox Virus S-SPV-034 and the DNA insertion in Homology Vector 723-59A9.22. FIG. 18A contains a diagram showing the orientation of DNA fragments assembled in plasmid 723-59A9.22 and a table indicating the origin of each fragment. FIG. 18B showns the sequences located at Junctions A and B between fragments, FIG. 18C shows the sequences located at Junction C, and FIG. 18D shows the sequences located at Junctions D and E. The restriction sites used to generate each fragment as well as synthetic linker sequences which are used to join the fragments are described for each junction in FIGS. 18B to 18D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), equine influenza virus (EIV), *Escherichia coli* (*E. coli*), pox synthetic late promoter 1 (LP1), pox synthetic late promoter 2 early promoter 2 (LP2EP2), neuraminidase (NA), Prague (PR), polymerase chain reaction (PCR), base pairs (BP).

FIGS. 19A, 19B, 19C and 19D show a detailed description of Swinepox Virus S-SPV-015 and the DNA insertion in Homology Vector 727-54.60. FIG. 19A contains a diagram showing the orientation of DNA fragments assembled in plasmid 727-54.60 and a table indicating the origin of each fragment. FIG. 19B shows the sequences located at Junctions A and B between fragments, FIG. 19C shows the sequences located at Junction C, and FIG. 19D shows the sequences located at Junctions D and E. The restriction sites used to generate each fragment as well as synthetic linker sequences which are used to join the fragments are described for each junction in FIGS. 19B to 19D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 1 (LP1), pox synthetic late promoter 2 early promoter 2 (LP2EP2), glycoprotein B (gB), base pairs (BP).

FIGS. 20A, 20B, 20C, and 20D show a detailed description of Swinepox Virus S-SPV-031 and the DNA insertion in Homology Vector 727-67.18. FIG. 20A contains a diagram showing the orientation of DNA fragments assembled in plasmid 727-67.18 and a table indicating the origin of each fragment. FIG. 20B shows the sequences located at Junctions A and B between fragments, FIG. 20C shows the sequences located at Junction C, and FIG. 20D shows the sequences located at Junctions D and E. The restriction sites used to generate each fragment as well as synthetic linker sequences which are used to join the fragments are described for each junction in FIGS. 20B to 20D. The location of several gene coding regions and regulatory elements is also given.

The following two conventions are used: numbers in parentheses, ( ), refer to amino acids, and restriction sites in brackets, [ ], indicate the remnants of sites which are destroyed during construction. The following abbreviations are used: swinepox virus (SPV), *Escherichia coli* (*E. coli*), pox synthetic late promoter 1 (LP1), pox synthetic early promoter 1 late promoter 2 (EP1LP2), antigen (Ag), base pairs (BP).

FIGS. 21A, 21B, 21C and 21D show a detailed description of Swinepox Virus S-SPV-033 and the DNA insertion in Homology Vector 732-18.4. FIG. 21A contains a diagram showing the orientation of DNA fragments assembled in plasmid 732-18.4 and a table indicating the origin of each fragment. FIG. 21B shows the sequences located at Junctions A and B between fragments, FIG. 21C shows the sequences located at Junction C, and FIG. 21D shows the sequences located at Junctions D and E. The restriction sites used to generate each fragment as well as synthetic linker sequences which are used to join the fragments are described for each junction in FIGS. 21B to 21D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), Escherichia coli (*E. coli*), pox synthetic late promoter 1 (LP1), pox synthetic late promoter 2 early promoter 2 (LP2EP2), equine influenza virus (EIV), neuraminidase (NA), Alaska (AK), polymerase chain reaction (PCR), base pairs (BP).

FIGS. 22A, 22B and 22C show a detailed description of Swinepox Virus S-SPV-036 and the DNA insertion in Homology Vector 741-80.3. FIG. 22A contains a diagram showing the orientation of DNA fragments assembled in plasmid 741-80.3 and a is table indicating the origin of each fragment. FIG. 22B shows the sequences located at Junctions A, B, and C between fragments and FIG. 22C shows the sequences located at Junctions D, E and F. The restriction sites used to generate each fragment as well as synthetic linker sequences which are used to join the fragments are described for each junction in FIGS. 22B and 22C. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), human cytomegalovirus immediate early (HCMV IE), pox synthetic late promoter 1 (LP1), pox synthetic late promoter 2 early promoter 2 (LP2EP2), polyadenylation site (poly A), base pairs (BP).

FIGS. 23A, 23B, 23C and 23D show a detailed description of Swinepox Virus S-SPV-035 and the DNA insertion in Homology Vector 741-84.14. FIG. 23A contains a diagram showing the orientation of DNA fragments assembled in plasmid 741-84.14 and a table indicating the origin of each fragment. FIG. 23B shows the sequences located at Junctions A and B between fragments, FIG. 23C shows the sequences located at Junction C, and FIG. 23D shows the sequences located at Junctions D and E. The restriction sites used to generate each fragment as well as synthetic linker sequences which are used to join the fragments are described for each junction in FIGS. 23B to 23D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), Escherichia coli (E. coli), pox synthetic late promoter 1 (LP1), pox synthetic late promoter 2 early promoter 2 (LP2EP2), interleukin-2 (IL-2), glycoprotein X (gX) polymerase chain reaction (PCR), sequence (seq), base pairs (BP).

Figure 24A:
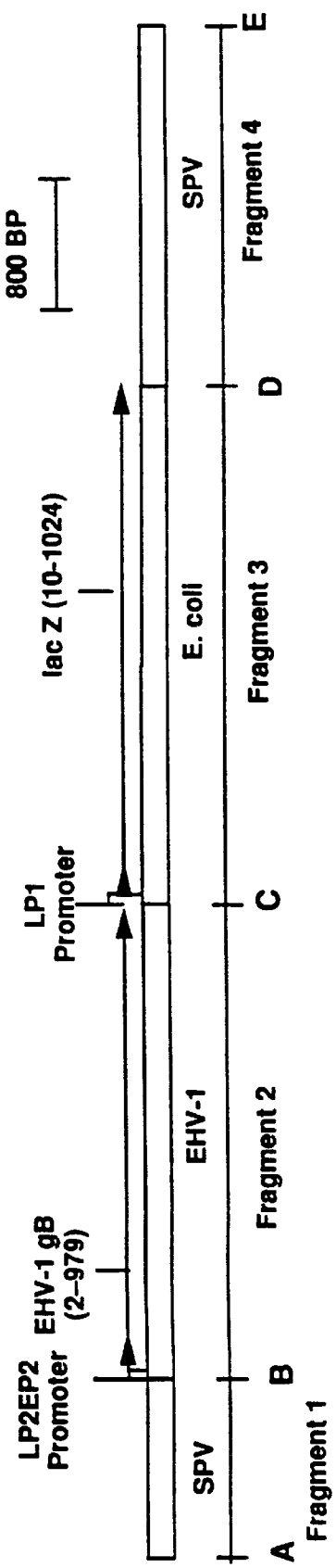
Figure 24B:
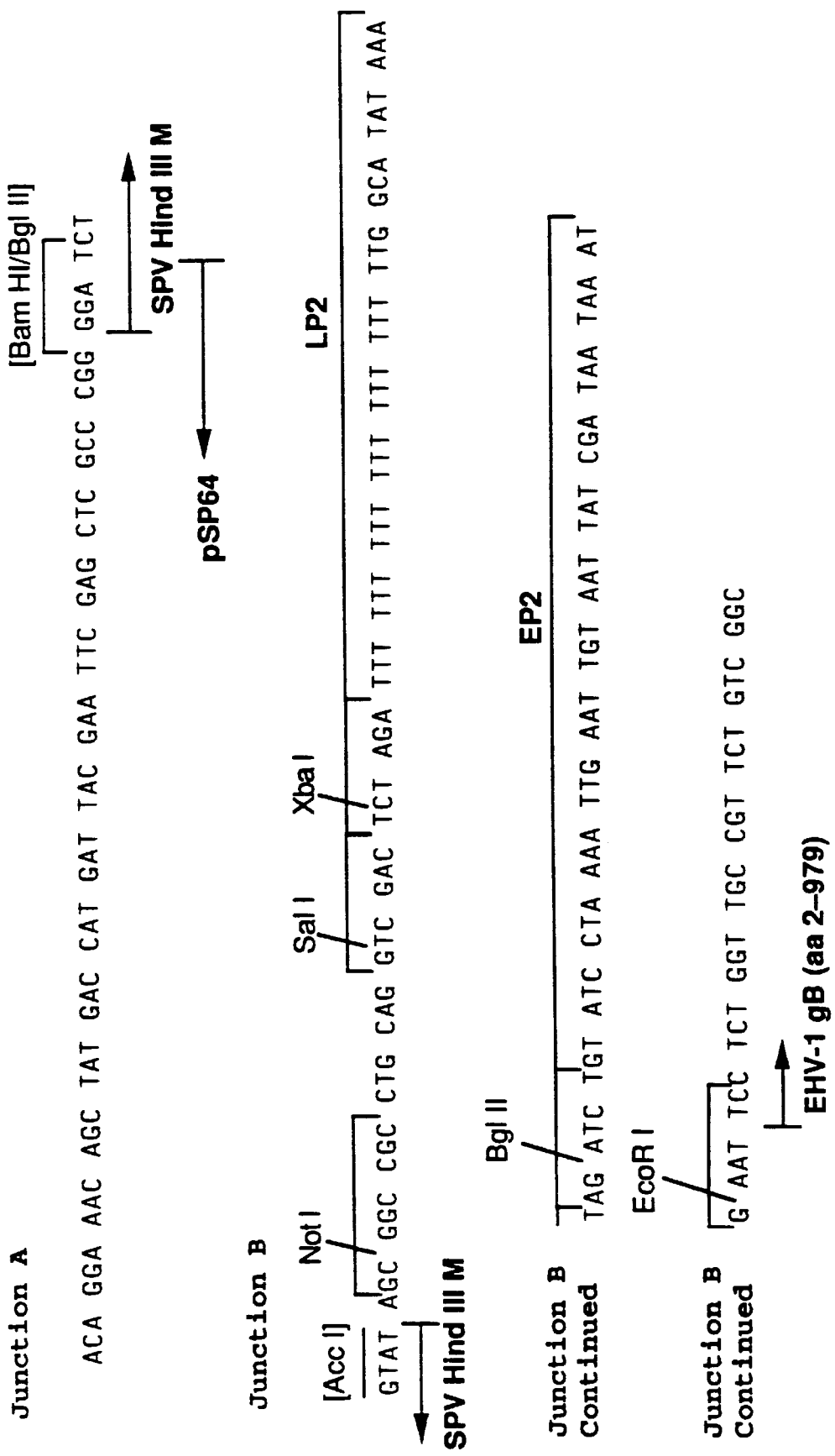
Figure 24D:
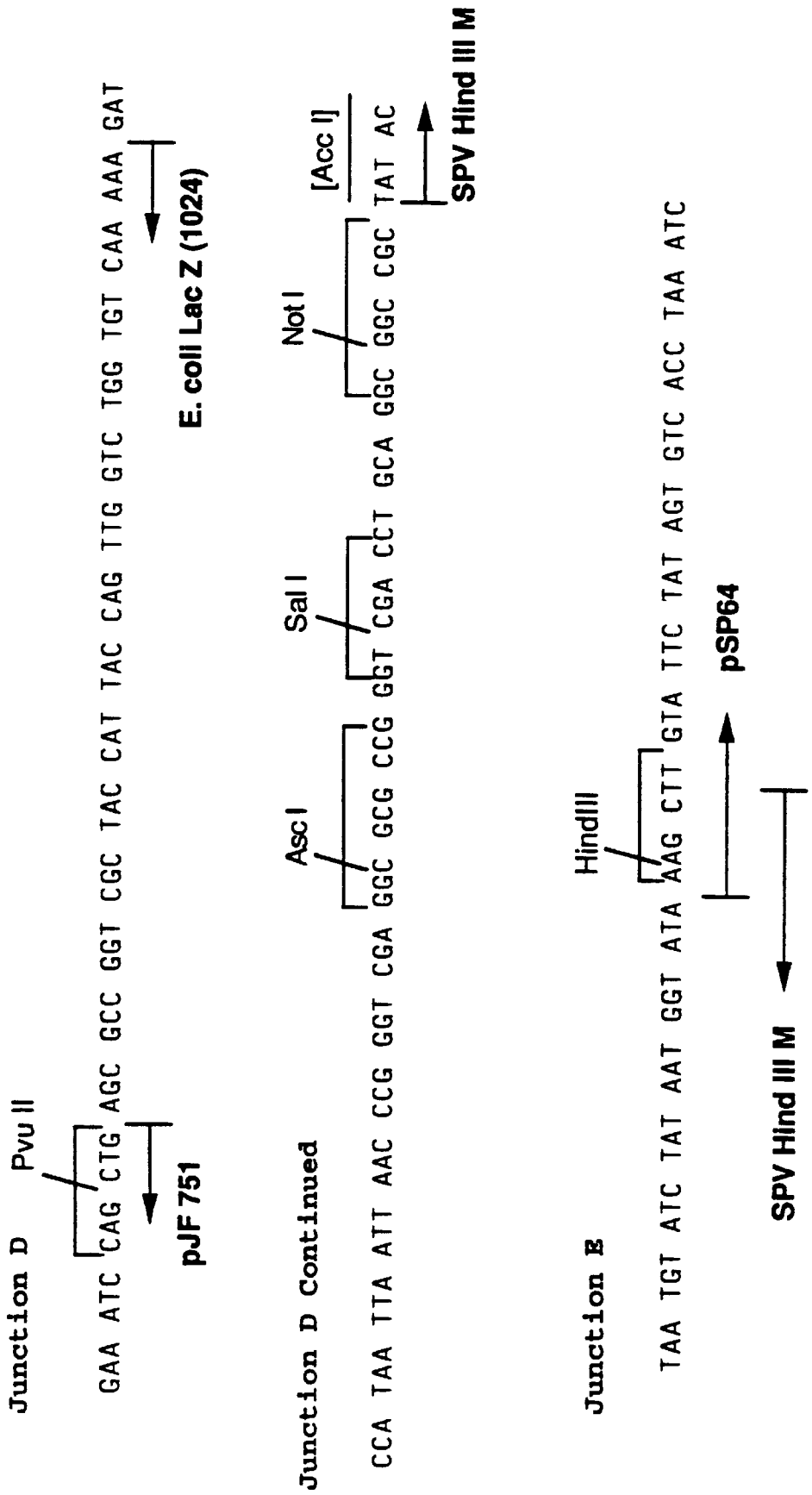

FIGS. 24A, 24B, 24C and 24D show a detailed description of Swinepox Virus S-SPV-038 and the DNA insertion in Homology Vector 744-34. FIG. 24A contains a diagram showing the orientation of DNA fragments assembled in plasmid 744-34 and a table indicating the origin of each fragment. FIG. 24B shows the sequences located at Junction A and B between fragments, FIG. 24C shows the sequences located at Junction C, and FIG. 24D shows the sequences located at Junctions D and E. The restriction sites used to generate each fragment as well as synthetic linker sequences which are used to join the fragments are described for each junction in FIGS. 24B and 24D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), equine herpesvirus type 1 (EHV-1), Escherichia coli (E. coli), pox synthetic late promoter 1 (LPs), pox synthetic late promoter 2 early promoter 2 (LP2EP2), glycoprotein B (gB), polymerase chain reaction (PCR), base pairs (BP).

Figure 25A:
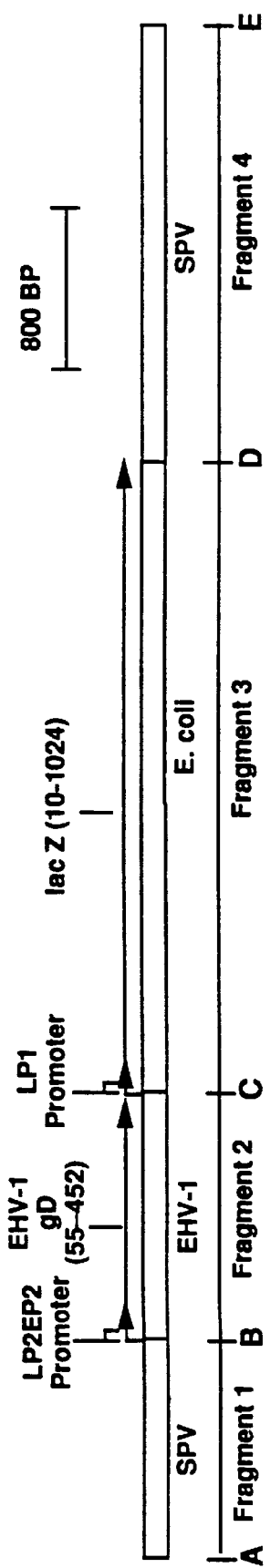
Figure 25B:
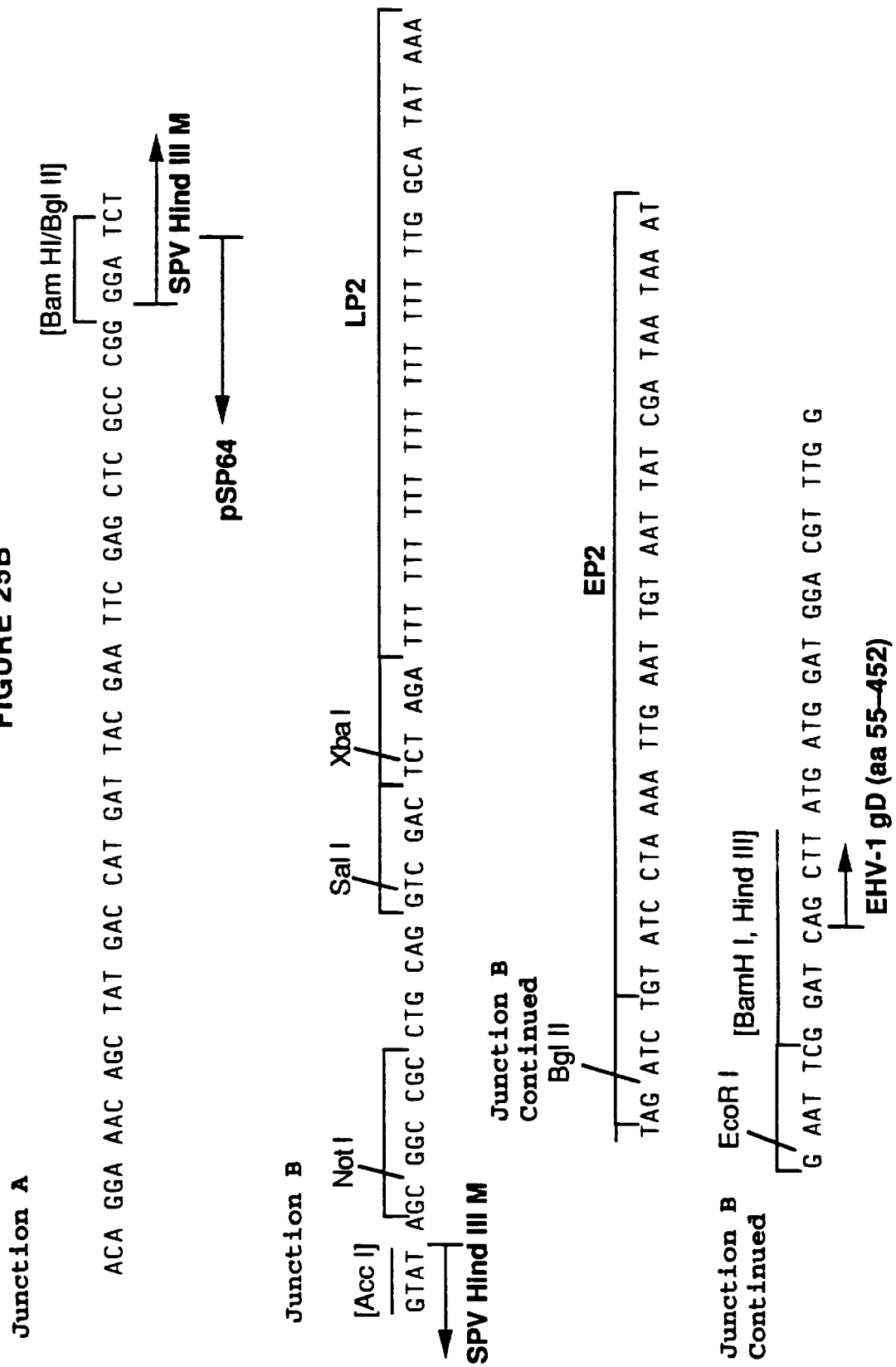

FIGS. 25A, 25B, 25C, and 25D show a detailed description of Swinepox Virus S-SPV-039 and the DNA insertion in Homology Vector 744-38. FIG. 25A contains a diagram showing the orientation of DNA fragments assembled in plasmid 744-38 and a table indicating the origin of each fragment. FIG. 25B shows the sequences located at Junction A and B between fragments. FIG. 25C shows the sequences located at Junction C and FIG. 25D shows the sequences located at Junctions D and E. The restriction sites used to generate each fragment as well as synthetic linker sequences which are used to join the fragments are described for each junction in FIGS. 25B to 25D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), equine herpesvirus type 1 (EHV-1), Escherichia coli (E. coli), pox synthetic late promoter 1 (LP1), pox synthetic late promoter 2 early promoter 2 (LP2EP2), glycoprotein D (gD), polymerase chain reaction (PCR), base pairs (BP).

DETAILED DESCRIPTION OF THE INVENTION

The present invention provides a recombinant swinepox virus (SPV) capable of replication in an animal into which the recombinant swinepox virus is introduced which comprises swinepox viral DNA and foreign DNA encoding RNA which does not naturally occur in the animal into which the recombinant swinepox virus is introduced, the foreign DNA being inserted into the swinepox viral DNA at an insertion site which is not essential for replication of the swinepox virus and being under the control of a promoter.

For purposes of this invention, "a recombinant swinepox virus capable of replication" is a live swinepox virus which has been generated by the recombinant methods well known to those of skill in the art, e.g., the methods set forth in HOMOLOGOUS RECOMBINATION PROCEDURE FOR GENERATING RECOMBINANT SPV in Materials and Methods and has not had genetic material essential for the replication of the recombinant swinepox virus deleted.

For purposes of this invention, "an insertion site which is not essential for replication of the swinepox virus" is a location in the swinepox viral genome where a sequence of DNA is not necessary for viral replication, for example, complex protein binding sequences, sequences which code for reverse transcriptase or an essential glycoprotein, DNA sequences necessary for packaging, etc.

For purposes of this invention, a "promoter" is a specific DNA sequence on the DNA molecule to which the foreign RNA polymerase attaches and at which transcription of the foreign RNA is initiated.

The invention further provides foreign RNA which encodes a polypeptide. Preferably, the polypeptide is antigenic in the animal. Preferably, this antigenic polypeptide is a linear polymer of more than 10 amino acids linked by peptide bonds which stimulates the animal to produce antibodies.

The invention further provides an insertion site present within the larger HindIII to BglII subfragment of the HindIII M fragment of swinepox viral DNA. Preferably, the insertion site is within an open reading frame contained in the HindIII to BctlII subfragment. Preferably, the insertion site is the AccI restriction endonuclease site located in the HindIII to BclII subfragment.

The invention further provides an insertion site within an open reading frame encoding swinepox thymidine kinase. Preferably, the insertion site is the NdeI restriction endonuclease site located within the swinepox virus thymidine kinase gene.

For purposes of this invention, an "open reading frame" is a segment of DNA which contains codons that can be transcribed into RNA which can be translated into an amino acid sequence and which does not contain a termination codon.

The invention further provides a recombinant swinepox virus capable of replication which contains a foreign DNA encoding a polypeptide which is a detectable marker. Preferably the detectable marker is the polypeptide E. coli β-galactosidase. Preferably, the insertion site for the foreign DNA encoding E. coli β-galactosidase is the AccI restriction endonuclease site located within the HindIII M fragment of the swinepox viral DNA. Preferably, this recombinant swinepox virus is designated S-SPV-003 (ATCC Accession No. VR 2335). The S-SPV-003 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2335.

For purposes of this invention, a "polypeptide which is a detectable marker" includes the bimer, trimer and tetramer form of the polypeptide. *E. coli* β-galactosidase is a tetramer composed of four polypeptides or monomer sub-units.

The invention further provides a recombinant swinepox virus capable of replication which contains foreign DNA encoding an antigenic polypeptide which is or is from pseudorabies virus (PRV) g50 (gpD), pseudorabies virus (PRV) II (gpB), Pseudorabies virus (PRV) gIII (gpC), pseudorabies virus (PRV) glycoprotein H, pseudorabies virus (PRV) glycoprotein E, Transmissible gastroenteritis (TGE) glycoprotein 195, Transmissible gastroenteritis (TGE) matrix protein, swine rotavirus glycoprotein 38, swine parvovirus capsid protein, *Serpulina hydodysenteriae* protective antigen, Bovine Viral Diarrhea (BVD) glycoprotein 55, Newcastle Disease Virus (NDV) hemagglutinin-neuraminidase, swine flu hemagglutinin or swine flu neuraminidase. Preferably, the antigenic polypeptide is Pseudorabies Virus (PRV) g50 (gpD). Preferably, the antigenic protein is Newcastle Disease Virus (NDV) hemagglutinin-neuraminidase.

The invention further provides a recombinant swinepox virus capable of replication which contains foreign DNA encoding an antigenic polypeptide which is or is from *Serpulina hyodysenteriae*, Foot and Mouth Disease Virus, Hog Cholera Virus, Swine Influenza Virus, African Swine Fever Virus or *Mycoplasma hyopneumoniae.*

The invention further provides for a recombinant swinepox virus capable of replication which contains foreign DNA encoding pseudorabies virus (PRV) g50 (gpD). This recombinant swinepox virus can be further engineered to contain foreign DNA encoding a detectable marker, such as *E. coli* B-galactosidase. A preferred site within the swinepox viral genome for insertion of the foreign DNA encoding PRV g50 (gpD) and *E. coli* B-galactosidase is the AccI site within the HindIII M fragment of the swinepox viral DNA. Preferably, this recombinant swinepox virus is designated S-SPV-008 (ATCC Accession No. VR 2339). The S-SPV-008 swinepox virus has been deposited pursuant to the Budapest Treaty on the International Deposit of Microorganisms for the Purposes of Patent Procedure with the Patent Culture is Depository of the American Type Culture Collection, 12301 Parklawn Drive, Rockville, Md. 20852 U.S.A. under ATCC Accession No. VR 2339.

The invention further provides for a recombinant swinepox virus capable of replication which contains foreign DNA encoding pseudorabies virus (PRV) gIII (gpC). This recombinant swinepox virus can also be further engineered to contain foreign DNA encoding a detectable marker, such as *E. coli* B-galactosidase. A preferred site within the swinepox viral DNA for insertion of the foreign DNA encoding PRV C gene and *E. coli* B-galactosidase is the AccI site within the HindIII M fragment of the swinepox viral DNA. Preferably, this recombinant swinepox virus is designated S-SPV-011, S-SPV-012, or S-SPV-013. The swinepox virus designated S-SPV-013 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

The invention further provides for a recombinant swinepox virus capable of replication which contains foreign DNA encoding pseudorabies virus (PRV) gII (gpB). This recombinant swinepox virus can also be further engineered to contain foreign DNA encoding a detectable marker, such as *E. coli* B-galactosidase. A preferred site within the swinepox viral DNA for insertion of the foreign DNA encoding PRV gII (gpB) and *E. coli* B-galactosidase is the AccI site within the HindIII M fragment of the swinepox viral DNA. Preferably, this recombinant swinepox virus is designated S-SPV-015. The S-SPV-015 swinepox virus has been deposited on Jul. 22, 1994 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

The invention further provides for a recombinant swinepox virus capable of replication which contains foreign DNA encoding pseudorabies virus (PRV) g50 (gpD) and foreign DNA encoding pseudorabies virus (PRV) gIII (gpC). This recombinant swinepox virus can also be further engineered to contain foreign DNA encoding a detectable marker, such as *E. coli* B-galactosidase. A preferred site within the swinepox viral DNA for insertion of the foreign DNA encoding PRV g50 (gpD), PRV gIII (gpC) and *E. coli* B-galactosidase is the AccI site within the HindIII M fragment of the swinepox viral DNA.

The invention further provides for a recombinant swinepox virus capable of replication which contains foreign DNA encoding pseudorabies virus (PRV) g50 (gpD) and foreign DNA encoding pseudorabies virus (PRV) gII (gpB). This recombinant swinepox virus can also be further engineered to contain Foreign DNA encoding a detectable marker, such as *E. coli* B-galactosidase. A preferred site within the swinepox viral genome for insertion of foreign DNA encoding PRV g50 (gpD), PRV gII (gpB) and *E. coli* B-galactosidase is the AccI site within the HindIII M fragment of the swinepox viral DNA.

The invention further provides for a recombinant swinepox virus capable of replication which contains foreign DNA encoding pseudorabies virus (PRV) gIII (gpC) and foreign DNA encoding pseudorabies virus (PRV) gII (gpB). This recombinant swinepox virus can also be further engineered to contain foreign DNA encoding a detectable marker, such as *E. coli* B-galactosidase. A preferred site within the swinepox viral genome for insertion of foreign DNA encoding PRV gIII (gpC), PRV gII (gpB) and *E. coli* B-galactosidase is the AccI site within the HindIII M fragment of the swinepox viral DNA.

The invention further provides for a recombinant swinepox virus capable of replication which contains foreign DNA encoding pseudorabies virus (PRV) g50 (gpD), foreign DNA encoding pseudorabies virus (PRV) gIII (gpC), and foreign DNA encoding pseudorabies virus (PRV) gII (gpB). This recombinant swinepox virus can also be further engineered to contain foreign DNA encoding a detectable marker, such as E. coli B-galactosidase.

A preferred site within the swinepox viral genome for insertion of foreign DNA encoding PRV g50 (gpD), PRV gIII (gpC), PRV gII (gpB) and *E. coli* B-galactosidase is the AccI site within the HindIII M fragment of the swinepox viral DNA.

The invention further provides for a recombinant swinepox virus capable of replication which contains foreign DNA encoding RNA encoding the antigenic polypeptide Newcastle Disease Virus (NDV) hemagglutinin-neuraminidase further comprising foreign DNA encoding a polypeptide which is a detectable marker. Preferably, this recombinant swinepox virus is designated S-SPV-009 (ATCC Accession No. VR 2344). The S-SPV-009 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2344.

The present invention further provides a recombinant swinepox virus which comprises a foreign DNA sequence inserted into a non-essential site of the swinepox genome, wherein the foreign DNA sequence encodes an antigenic polypeptide derived from infectious bovine rhinotracheitis virus and is capable of being expressed in a host infected by the recombinant swinepox virus. Examples of such antigenic polypeptide are infectious bovine rhinotracheitis virus glycoprotein E and glycoprotein G. Preferred embodiment of this invention are recombinant swinepox viruses designated S-SPV-017 and S-SPV-019.

The present invention further provides a recombinant swinepox virus which comprises a foreign DNA sequence inserted into a non-essential site of the swinepox genome, wherein the foreign DNA sequence encodes an antigenic polypeptide derived from infectious laryngotracheitis virus and is capable of being expressed in a host infected by the recombinant swinepox virus. Examples of such antigenic polypeptide are infectious laryngotracheitis virus glycoprotein G and glycoprotein I. Preferred embodiment of this invention are recombinant swinepox viruses designated S-SPV-014 and S-SPV-016.

The present invention further provides a recombinant swinepox virus which comprises a foreign DNA sequence inserted into a non-essential site of the swinepox genome, wherein the foreign DNA sequence encodes an antigenic polypeptide derived from a human pathogen and is capable of being expressed in a host infected by the recombinant swinepox virus.

For example, the antigenic polypeptide of a human pathogen is derived from human herpesvirus, herpes simplex virus-1, herpes simplex virus-2, human cytomegalovirus, Epstein-Barr virus, Varicell-Zoster virus, human herpesvirus-6, human herpesvirus-7, human influenza, human immunodeficiency virus, rabies virus, measles virus, hepatitis B virus and hepatitis C virus. Furthermore, the antigenic polypeptide of a human pathogen may be associated with malaria or malignant tumor from the group conisting of *Plasmodium falciparum, Bordetella pertusis*, and malignant tumor.

In one embodiment of the invention, a recombinant swinepox virus contains the foreign DNA sequence encoding hepatitis B virus core protein. Preferably, such virus recombinant virus is designated S-SPV-031.

The present invention further provides a recombinant swinepox virus which comprises a foreign DNA sequence inserted into a non-essential site of the swinepox genome, wherein the foreign DNA sequence encodes a cytokine capable of stimulating an immune in a host infected by the recombinant swinepox virus and is capable of being expressed in the host infected.

For example, the cytokine can be, but not limited to, interleukin-2, interleukin-6, interleukin-12, interferons, granulocyte-macrophage colony stimulating factors, and interleukin receptors.

In one embodiment of the invention, a recombinant swinepox virus contains a foreign DNA sequence encoding human interleukin-2. Preferably, such recombinant virus is designated S-SPV-035.

The present invention further provides a recombinant swinepox virus which comprises a foreign DNA sequence inserted into a non-essential site of the swinepox genome, wherein the foreign DNA sequence encodes an antigenic polypeptide derived from an equine pathogen and is capable of being expressed in a host infected by the recombinant swinepox virus.

The antigenic polypeptide of an equine pathogen can derived from equine influenza virus or equine herpesvirus. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidaseequine herpesvirus type 1 glycoprotein B, and equine herpesvirus type 1 glycoprotein D. Preferred embodiments of such recombinant virus are designated S-SPV-033, S-SPV-034, S-SPV-038, and S-SPV-039.

The present invention further provides a recombinant swinepox virus which comprises a foreign DNA sequence inserted into a non-essential site of the swinepox genome, wherein the foreign DNA sequence encodes an antigenic polypeptide derived from bovine respiratory syncytial virus or bovine parainfluenza virus, and is capable of being expressed in a host infected by the recombinant swinepox virus.

For example, the antigenic polypeptide of derived from bovine respiratory syncytial virus equine pathogen can derived from equine influenza virus is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

Preferred embodiments of a recombinant virus containing a foreign DNA encoding an antigenic polypeptide from a bovine respiratory syncytial virus are designated S-SPV-020, S-SPV-029, and S-SPV-030.

And a preferred embodiment of a recombinant virus containing a foreign DNA encoding an antigenic polypeptide from a bovine parainfluenza virus are designated S-SPV-028.

The present invention further provides a recombinant swinepox virus which comprises a foreign DNA sequence inserted into a non-essential site of the swinepox genome, wherein the foreign DNA sequence encodes bovine viral diarrhea virus glycoprotein 48 or glycoprotein 53, and wherein the foreign DNA sequence is capable of being expressed in a host infected by the recombinant swinepox virus. Preferred embodiments of such virus are designated S-SPV-032 and S-SPV-040.

The present invention further provides a recombinant swinepox virus which comprises a foreign DNA sequence inserted into a non-essential site of the swinepox genome, wherein the foreign DNA sequence encodes an antigenic polypeptide derived from infectious bursal disease virus and wherein the foreign DNA sequence is capable of being expressed in a host infected by the recombinant swinepox virus. Examples of such antigenic polypeptide are infectious bursal disease virus polyprotein and VP2. Preferred embodiments of such virus are designated S-SPV-026 and S-SPV-027.

The invention further provides that the inserted foreign DNA sequence is under the control of a promoter. Preferably, the promoter is a swinepox viral promoter. Preferably, the promoter is a synthetic pox viral promoter. For purposes of this invention, the promoters were generated by methods well known to those of skill in the art, for example, as set forth in the STRATEGY FOR THE CON- STRUCTION OF SYNTHETIC POX VIRAL PROMOTERS in Materials and Methods. For purposes of this invention, a synthetic pox promoter includes a synthetic late pox promoter, a synthetic early pox promoter or a synthetic early/late pox promoter.

The invention provides for a homology vector for producing a recombinant swinepox virus by inserting foreign DNA into the genomic DNA of a swinepox virus. The homology vector comprises a double-stranded DNA molecule consisting essentially of a double-stranded foreign DNA encoding RNA which does not naturally occur in an animal into which the recombinant swinepox virus is introduced, with at one end of the foreign DNA, double-stranded swinepox viral DNA homologous to genomic DNA located at one side of a site on the genomic DNA which is not essential for replication of the swinepox virus, and at the other end of the foreign DNA, double-stranded swinepox viral DNA homologous to genomic DNA located at the other side of the same site on the genomic DNA. Preferably, the RNA encodes a polypeptide.

In one embodiment, the polypeptide is a detectable marker. Preferably, the polypeptide which is a detectable marker is $E.$ $coli$ β-galactosidase.

In one embodiment, the polypeptide is antigenic in the animal. Preferably, the antigenic polypeptide is or is from pseudorabies virus (PRV) g50 (gpD), pseudorabies virus (PRV) gII (gpB), Pseudorabies virus (PRV) gIII (gpC), Pseudorabies virus (PRV) glycoprotein H, Transmissible gastroenteritis (TGE) glycoprotein 195, Transmissible gastroenteritis (TGE) matrix protein, swine rotavirus glycoprotein 38, swine parvovirus capsid protein, $Serpulina$ $hyodysenteriae$ protective antigen, Bovine Viral Diarrhea (BVD) glycoprotein 55, Newcastle Disease Virus (NDV) hemagglutinin-neuraminidase, swine flu hemagglutinin or swine flu neuraminidase. Preferably, the antigenic polypeptide is or is from $Serpulina$ $hyodesenteriae$, Foot and Mouth Disease Virus, Hog Cholera Virus, Swine Influenza Virus, African Swine Fever Virus or $Mycoplasma$ $hyopneumoniae$.

In an embodiment of the present invention, the double stranded foreign DNA sequence in the homology vector encodes an antigenic polypeptide derived from a human pathogen.

For example, the antigenic polypeptide of a human pathogen is derived from human herpesvirus, herpes simplex virus-1, herpes simplex virus-2, human cytomegalovirus, Epstein-Barr virus, Varicell-Zoster virus, human herpesvirus-6, human herpesvirus-7, human influenza, human immunodeficiency virus, rabies virus, measles virus, hepatitis B virus and hepatitis C virus. Furthermore, the antigenic polypeptide of a human pathogen may be associated with malaria or malignant tumor from the group conisting of Plasmodium falciparum, Bordetella pertusis, and malignant tumor.

In an embodiment of the present invention, the double stranded foreign DNA sequence in the homology vector encodes a cytokine capable of stimulating human immune response. For example, the cytokine can be, but not limited to, interleukin-2, interleukin-6, interleukin-12, interferons, granulocyte-macrophage colony stimulating factors, and interleukin receptors.

In an embodiment of the present invention, the double stranded foreign DNA sequence in the homology vector encodes an antigenic polypeptide derived from an equine pathogen.

The antigenic polypeptide of an equine pathogen can derived from equine influenza virus or equine herpesvirus. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidaseequine herpesvirus type 1 glycoprotein B, and equine herpesvirus type 1 glycoprotein D.

In an embodiment of the present invention, the double stranded foreign DNA sequence of the homology vector encodes an antigenic polypeptide derived from bovine respiratory syncytial virus or bovine parainfluenza virus.

For example, the antigenic polypeptide of derived from bovine respiratory syncytial virus equine pathogen can derived from equine influenza virus is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

In an embodiment of the present invention, the double stranded foreign DNA sequence of the homology vector encodes an antigenic polypeptide derived from infectious bursal disease virus. Examples of such antigenic polypeptide are infectious bursal disease virus polyprotein and infectious bursal disease virus VP2.

In another embodiment of the present invention, the double-stranded swinepox viral DNA of the homology vectors described above is homologous to genomic DNA present within the larger HindIII to BglII subfragment of the HindIII M fragment of swinepox virus. Preferably, the double-stranded swinepox viral DNA is homologous to genomic DNA present within the open reading frame contained in this HindIII to BclII subfragment. Preferably, the double-stranded swinepox viral DNA is homologous to genomic DNA present within the AccI restriction endonuclease site located in this HindIII to BclII subfragment.

For purposes of this invention, a "homology vector" is a plasmid constructed to insert foreign DNA in a specific site on the genome of a swinepox virus.

In one embodiment of the invention, the double-stranded swinepox viral DNA of the homology vectors described above is homologous to genomic DNA present within the open reading frame encoding swinepox thymidine kinase. Preferably, the double-stranded swinepox viral DNA is homologous to genomic DNA present within the NdeI restriction endonuclease site located in the open reading frame encoding swinepox thymidine kinase.

The invention further provides a homology vectors described above, the foreign DNA sequence of which is under control of a promoter located upstream of the foreign DNA sequence. The promoter can be an endogenous swinepox viral promoter or an exogenous promoter. The promoter can be a synthetic pox viral promoter or human cytomegalovrus immediate early gene promoter.

The invention further provides a vaccine which comprises an effective immunizing amount of a recombinant swinepox virus of the present invention and a suitable carrier.

Suitable carriers for the pseudorabies virus are well known in the art and include proteins, sugars, etc. One example of such a suitable carrier is a physiologically balanced culture medium containing one or more stabilizing agents such as stabilized, hydrolyzed proteins, lactose, etc.

For purposes of this invention, an "effective immunizing amount" of the recombinant swinepox virus of the present invention is within the range of $10^3$ to $10^9$ PFU/dose.

The present invention also provides a method of immunizing an animal, wherein the animal is a human, swine, bovine, equine, caprine or ovine. For purposes of this invention, this includes immunizing the animal against the virus or viruses which cause the disease or diseases pseudorabies, transmissible gastroenteritis, swine rotavirus, swine parvovirus, *Serpulina hyodysenteriae*, bovine viral diarrhea, Newcastle disease, swine flu, foot and mouth disease, hog cholera, African swine fever or *Mycoplasma hyopneumoniae*. For purposes of this invention, the method of immunizing also includes immunizing the animal against human pathogens, bovine pathogens, equine pathogens, avian pathogens described in the preceding part of this section.

The method comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

The present invention also provides a method for testing a swine to determine whether the swine has been vaccinated with the vaccine of the present invention, particularly the embodiment which contains the recombinant swinepox virus S-SPV-008 (ATCC Accession No. VR 2339), or is infected with a naturally-occurring, wild-type pseudorabies virus. This method comprises obtaining from the swine to be tested a sample of a suitable body fluid, detecting in the sample the presence of antibodies to pseudorabies virus, the absence of such antibodies indicating that the swine has been neither vaccinated nor infected, and for the swine in which antibodies to pseudorabies virus are present, detecting in the sample the absence of antibodies to pseudorabies virus antigens which are normally present in the body fluid of a swine infected by the naturally-occurring pseudorabies virus but which are not present in a vaccinated swine indicating that the swine was vaccinated and is not infected.

The present invention also provides a host cell infected with a recombinant swinepox virus capable of replication. In one embodiment, the host cell is a mammalian cell. Preferably, the mammalian cell is a Vero cell. Preferably, the mammalian cell is an ESK-4 cell, PK-15 cell or EMSK cell.

For purposes of this invention a "host cell" is a cell used to propagate a vector and its insert. Infecting the cells was accomplished by methods well known to those of skill in the art, for example, as set forth in INFECTION—TRANSFECTION PROCEDURE in Material and Methods.

Methods for constructing, selecting and purifying recombinant swinepox viruses described above are detailed below in Materials and Methods.

Materials and Methods

PREPARATION OF SWINEPOX VIRUS STOCK SAMPLES. Swinepox virus (SPV) samples were prepared by infecting embryonic swine kidney (EMSK) cells, ESK-4 cells, PK-15 cells or Vero cells at a multiplicity of infection of 0.01 PFU/cell in a 1:1 mixture of Iscove's Modified Dulbecco's Medium (IMDM) and RPMI 1640 medium containing 2 mM glutamine, 100 units/ml penicillin, 100 units/ml streptomycin (these components were obtained from Sigma or equivalent supplier, and hereafter are referred to as EMSK negative medium). Prior to infection, the cell monolayers were washed once with EMSK negative medium to remove traces of fetal bovine serum. The SPV contained in the initial inoculum (0.5 ml for 10 cm plate; 10 ml for T175 cm flask) was then allowed to absorb onto the cell monolayer for two hours, being redistributed every half hour. After this period, the original inoculum was brought up to the recommended volume with the addition of complete EMSK medium (EMSK negative medium plus 5% fetal bovine serum). The plates were incubated at 37° C. in 5% $CO_2$ until cytopathic effect was complete. The medium and cells were harvested and frozen in a 50 ml conical screw cap tube at −70° C. Upon thawing at 37° C., the virus stock was aliquoted into 1.0 ml vials and refrozen at −70° C. The titers were usually about $10^6$ PFU/ml.

PREPARATION OF SPV DNA. For swinepox virus DNA isolation, a confluent monolayer of EMSK cells in a T175 cm² flask was infected at a multiplicity of 0.1 and incubated 4–6 days until the cells were showing 100% cytopathic effect. The infected cells were then harvested by scraping the cells into the medium and centrifuging at 3000 rpm for 5 minutes in a clinical centrifuge. The medium was decanted, and the cell pellet was gently resuspended in 1.0 ml Phosphate Buffer Saline (PBS: 1.5 g $Na_2HPO_4$, 0.2 g $KH_2PO_4$, 0.8 g NaCL and 0.2 g KCl per liter $H_2O$) (per T175) and subjected to two successive freeze-thaws (−70° C. to 37° C.). Upon the last thaw, the cells (on ice) were sonicated two times for 30 seconds each with 45 seconds cooling time in between. Cellular debris was then removed by centrifuging (Sorvall RC-5B superspeed centrifuge) at 3000 rpm for 5 minutes in a HB4 rotor at 40° C. SPV virions, present in the supernatant, were then pelleted by centrifugation at 15,000 rpm for 20 minutes at 40° C. in a SS34 rotor (Sorvall) and resuspended in mM Tris (pH 7.5). This fraction was then layered onto a 36% sucrose gradient (w/v in 10 mM tris pH 7.5) and centrifuged (Beckman L8-70M Ultracentrifuge) at 18,000 rpm for 60 minutes in a SW41 rotor (Beckman) at 4° C. The virion pellet was resuspended in 1.0 ml of 10 mM tris pH 7.5 and sonicated on ice for 30 seconds. This fraction was layered onto a 20% to 50% continuous sucrose gradient and centrifuged 16,000 rpm for 60 minutes in a SW41 rotor at 4° C. The SPV virion band located about three quarters down the gradient was harvested, diluted with 20% sucrose and pelleted by centrifugation at 18,000 rpm for 60 minutes in a SW41 rotor at 4° C. The resultant pellet was then washed once with 10 mM Tris pH 7.5 to remove traces of sucrose and finally resuspended in 10 mM Tris pH 7.5. SPV DNA was then extracted from the purified virions by lysis (4 hours at 60° C.) induced by the addition of EDTA, SDS, and proteinase K to final concentrations of 20 mM, 0.5% and 0.5 mg/ml, respectively. After digestion, three phenol: chloroform (1:1) extractions were conducted and the sample precipitated by the addition of two volumes of absolute ethanol and incubation at −20° C. for 30 minutes. The sample was then centrifuged in an Eppendorf minifuge for 5 minutes at full speed. The supernatant was decanted, and the pellet air dried and rehydrated in 0.01 M Tris pH 7.5, 1 mM EDTA at 4° C.

PREPARATION OF INFECTED CELL LYSATES. For cell lysate preparation, serum free medium was used. A confluent monolayer of cells (EMSK, ESK-4, PK-15 or Vero for SPV or VERO for PRV) in a 25 $cm^2$ flask or a 60 mm petri dish was infected with 100 μl of virus sample. After cytopathic effect was complete, the medium and cells were harvested and the cells were pelleted at 3000 rpm for 5 minutes in a clinical centrifuge. The cell pellet was resuspended in 250 μl of disruption buffer (2% sodium dodecyl sulfate, 2% β-mercapto-ethanol). The samples were sonicated for 30 seconds on ice and stored at −20° C.

WESTERN BLOTTING PROCEDURE. Samples of lysates and protein standards were run on a polyacrylamide gel according to the procedure of Laemnli (1970). After gel electrophoresis the proteins were transferred and processed according to Sambrook et al. (1982). The primary antibody was a swine anti-PRV serum (Shope strain; lot370, PDV8201, NVSL, Ames, IA) diluted 1:100 with 5% non-fat dry milk in Tris-sodium chloride, and sodium Azide (TSA: 6.61 g Tris-HCl, 0.97 g Tris-base, 9.0 g NaCl and 2.0 g Sodium Azide per liter $H_2O$). The secondary antibody was a goat anti-swine alkaline phosphatase conjugate diluted 1:1000 with TSA.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al. (1982) and Sambrook et al. (1989). Except as noted, these were used with minor variation.

DNA SEQUENCING. Sequencing was performed using the USE Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence.

Sequence obtained was assembled and compared using Dnastar software. Manipulation and comparison of sequences obtained was performed with Superclone™ and Supersee™ programs from Coral Software.

CLONING WITH THE POLYMERASE CHAIN REACTION. The polymerase chain reaction (PCR) was used to introduce restriction sites convenient for the manipulation of various DNAs. The procedures used are described by Innis, et al. (1990). In general, amplified fragments were less than 500 base pairs in size and critical regions of amplified fragments were confirmed by DNA sequencing. The primers used in each case are detailed in the descriptions of the construction of homology vectors below.

Figure 4A:
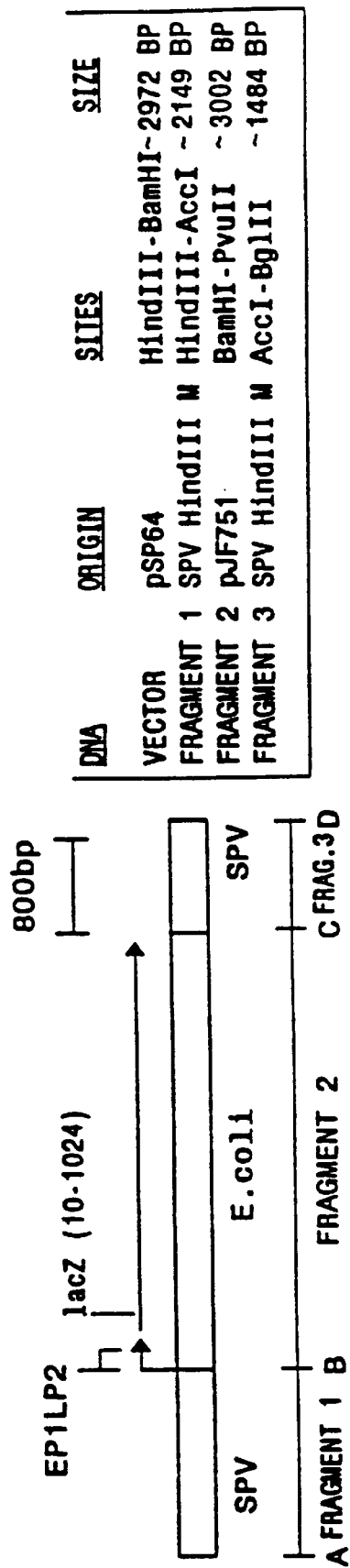
Figure 4B:
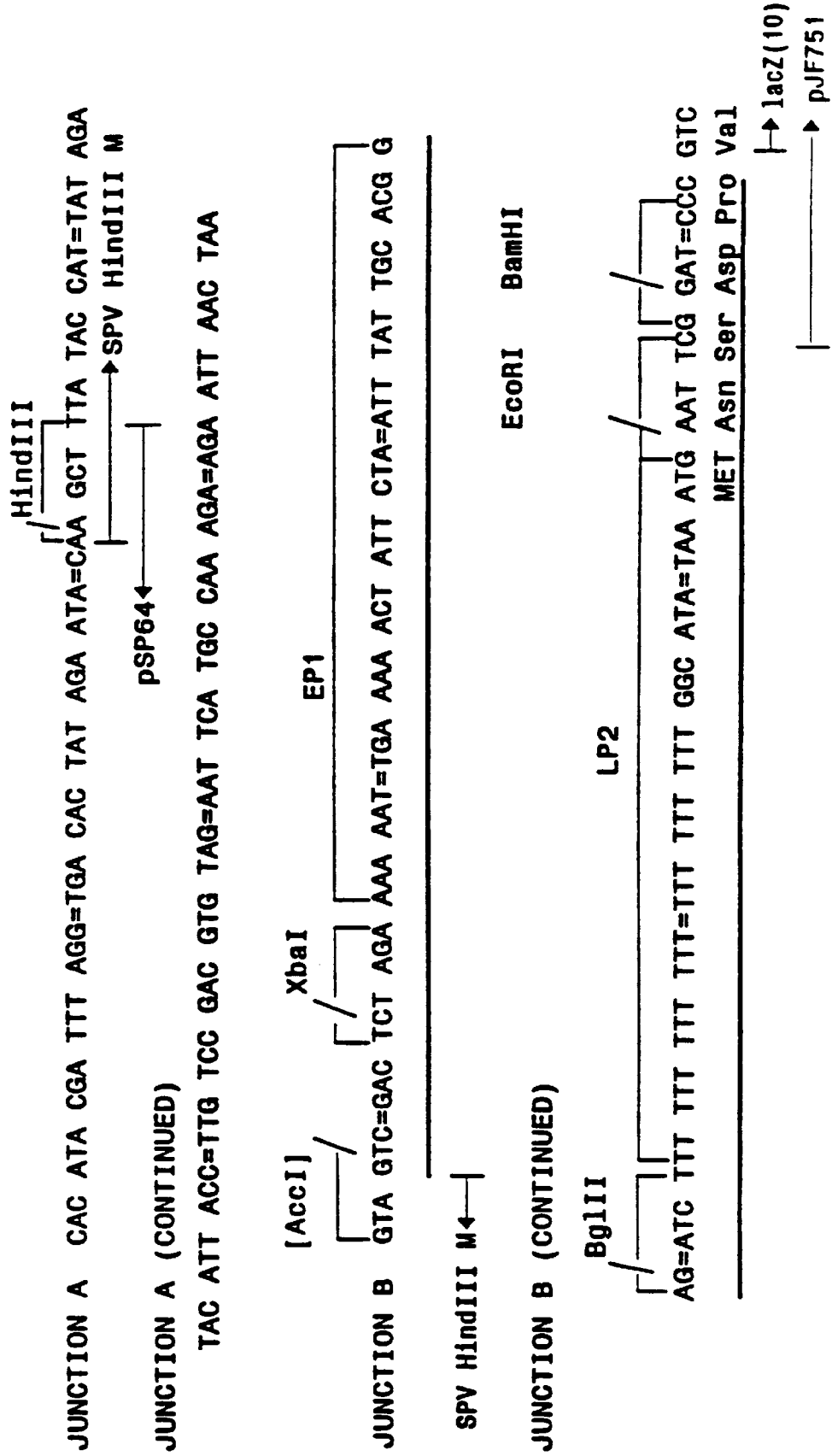

HOMOLOGOUS RECOMBINATION PROCEDURE FOR GENERATING RECOMBINANT SPV. This method relies upon the homologous recombination between the swinepox virus DNA and the plasmid homology vector DNA which occurs in the tissue culture cells containing both swinepox virus DNA and transfected plasmid homology vector. For homologous recombination to occur, the monolayers of EMSK cells are infected with S-SPV-001 (Kasza SPV strain, 17) at a multiplicity of infection of 0.01 PFU/cell to introduce replicating SPV (i.e. DNA synthesis) into the cells. The plasmid homology vector DNA is then transfected into these cells according to the INFECTION— TRANSFECTION PROCEDURE. The construction of homology vectors used in this procedure is described below INFECTION—TRANSFECTION PROCEDURE. 6 cm plates of EMSK cells (about 80% confluent) were infected with S-SPV-001 at a multiplicity of infection of 0.01 PFU/cell in EMSK negative medium and incubated at 37° C. in a humidified 5% $CO_2$ environment for 5 hours. The transfection procedure used is essentially that recommended for Lipofectin™ Reagent (BRL). Briefly, for each 6 cm plate, 15 $\mu$g of plasmid DNA was diluted up to 100 $\mu$l with $H_2O$. Separately, 50 micrograms of Lipofectin Reagent was diluted to 100 $\mu$l with $H_2O$. The 100 $\mu$l of diluted Lipofectin Reagent was then added dropwise to the diluted plasmid DNA contained in a polystyrene 5 ml snap cap tube and mixed gently. The mixture was then incubated for 15–20 minutes at room temperature. During this time, the virus inoculum was removed from the 6 cm plates and the cell monolayers washed once with EMSK negative medium. Three ml of EMSK negative medium was then added to the plasmid DNA/lipofectin mixture and the contents pipetted onto the cell monolayer. The cells were incubated overnight (about 16 hours) at 37° C. in a humidified 5% $CO_2$ environment. The next day the 3 ml of EMSK negative medium was removed and replaced with 5 ml EMSK complete medium. The cells were incubated at 37° C. in 5% $CO_2$ for 3–7 days until cytopathic effect from the virus was 80–100%. Virus was harvested as described above for the preparation of virus stocks. This stock was referred to as a transfection stock and was subsequently screened for recombinant virus by the BLUOGAL SCREEN FOR RECOMBINANT SWINEPOX VIRUS OR CPRG SCREEN FOR RECOMBINANT SWINEPOX VIRUS.

SCREEN FOR RECOMBINANT SPV EXPRESSING B-GALACTOSIDASE (BLUOGAL AND CPRG ASSAYS). When the *E. coli* β-galactosidase (lacZ) marker gene was incorporated into a recombinant virus the plaques containing the recombinants were visualized by one of two simple methods. In the first method, the chemical Bluogal™ (Bethesda Research Labs) was incorporated (200 $\mu$g/ml) into the agarose overlay during the plaque assay, and plaques expressing active β-galactosidase turned blue. The blue plaques were then picked onto fresh cells (EMSK) and purified by further blue plaque isolation. In the second method, CPRG (Boehringer Mannheim) was incorporated (400 $\mu$g/ml) into the agarose overlay during the plaque assay, and plaques expressing active β-galactosidase turned red. The red plaques were then picked onto fresh cells (EMSK) and purified by further red plaque isolation. In both cases viruses were typically purified with three rounds of plaque purification.

SCREEN FOR FOREIGN GENE EXPRESSION IN RECOMBINANT SPV USING BLACK PLAQUE ASSAYS. To analyze expression of foreign antigens expressed by recombinant swinepox viruses, monolayers of EMSK cells were infected with recombinant SPV, overlayed with nutrient agarose media and incubated for 6–7 days at 37° C. for plaque development to occur. The agarose overlay was then removed from the dish, the cells fixed with 100% methanol for 10 minutes at room temperature and the cells air dried. Fixation of the cells results in cytoplasmic antigen as well as surface antigen detection whereas specific surface antigen expression can be detected using non-fixed cells. The primary antibody was then diluted to the appropriate dilution with PBS and incubated on the cell monolayer for 2 hours at room temperature. To detect PRV g50 (gpD) expression from S-SPV-008, swine anti-PRV serum (Shope strain; lot370, PDV8201, NVSL, Ames, Iowa) was used (diluted 1:100). To detect NDV HN expression from S-SPV-009, a rabbit antiserum specific for the HN protein (rabbit anti-NDV#2) was used (diluted 1:1000). Unbound antibody was then removed by washing the cells three times with PBS at room temperature. The secondary antibody, either a goat anti-swine (PRV g50 (gpD); S-SPV-008) or goat anti-rabbit (NDV RN; S-SPV-009), horseradish peroxidase conjugate was diluted 1:250 with PBS and incubated with the cells for 2 hours at room temperature. Unbound secondary antibody was then removed by washing the cells three times with PBS at room temperature. The cells were then incubated 15–30 minutes at room temperature with freshly prepared substrate solution (100 $\mu$g/ml 4-chloro-1-naphthol, 0.003% $H_2O_2$ in PBS). Plaques expressing the correct antigen stain black.

PROCEDURE FOR PURIFICATION OF VIRAL GLYCOPROTEINS FOR USE AS DIAGNOSTICS. Viral glycoproteins are purified using antibody affinity columns. To produce monoclonal antibodies, 8 to 10 week old BALB/c female mice are vaccinated intraperitoneally seven times at two to four week intervals with $10^7$ PFU of S-SPV-009, -014, -016, -017, -018, or -019. Three weeks after the last vaccination, mice are injected intraperitoneally with 40 mg of the corresponding viral glycoprotein. Spleens are removed from the mice three days after the last antigen dose.

Splenocytes are fused with mouse NS1/Ag4 plasmacytoma cells by the procedure modified from Oi and Herzenberg, (41). Splenocytes and plasmacytoma cells are pelleted together by centrifugation at 300 × g for 10 minutes. One ml of a 50% solution of polyethylene glycol (m.w. 1300–1600) is added to the cell pellet with stirring over one minute. Dulbecco's modified Eagles's medium (5 ml) is added to the cells over three minutes. Cells are pelleted by centrifugation at 300 × g for 10 minutes and resuspended in medium with 10% fetal bovine serum and containing 100 mM hypoxanthine, 0.4 mM aminopterin and 16 mM thymidine (HAT). Cells (100 ml) are added to the wells of eight to ten 96-well tissue culture plates containing 100 ml of normal spleen feeder layer cells and incubated at 37° C. Cells are fed with fresh HAT medium every three to four days.

Hybridoma culture supernatants are tested by the ELISA ASSAY in 96-well microtiter plates coated with 100 ng of viral glycoprotein. Supernatants from reactive hybridomas are further analyzed by black-plaque assay and by Western Blot. Selected hybridomas are cloned twice by limiting dilution. Ascetic fluid is produced by intraperitoneal injection of $5\times10^6$ hybridoma cells into pristane-treated BALB/c mice.

Cell lysates from S-SPV-009, -014, -016, -017, -018, or -019 are obtained as described in PREPARATION OF INFECTED CELL LYSATES. The glycoprotein-containing cell lysates (100 mls) are passed through a 2-ml agarose affinity resin to which 20 mg of glycoprotein monoclonal antibody has been immobilized according to manufacturer's instructions (AFC Medium, New Brunswick Scientific, Edison, N.J.). The column is washed with 100 ml of 0.1% Nonidet P-40 in phosphate-buffered saline (PBS) to remove nonspecifically bound material. Bound glycoprotein is eluted with 100 mM carbonate buffer, pH 10.6 (40). Pre- and posteluted fractions are monitored for purity by reactivity to the SPV monoclonal antibodies in an ELISA system.

ELISA ASSAY. A standard enzyme-linked immunosorbent assay (ELISA) protocol is used to determine the immune status of cattle following vaccination and challenge.

A glycoprotein antigen solution (100 ml at ng/ml in PBS) is allowed to absorb to the wells of microtiter dishes for 18 hours at 4° C. The coated wells are rinsed one time with PBS. Wells are blocked by adding 250 ml of PBS containing 1% BSA (Sigma) and incubating 1 hour at 37° C. The blocked wells are rinsed one time with PBS containing 0.02% Tween 20. 50 ml of test serum (previously diluted 1:2 in PBS containing 1% BSA) are added to the wells and incubated 1 hour at 37° C. The antiserum is removed and the wells are washed 3 times with PBS containing 0.02% Tween 20. 50 ml of a solution containing anti-bovine IgG coupled to horseradish peroxidase (diluted 1:500 in PBS containing 1% BSA, Kirkegaard and Perry Laboratories, Inc.) is added to visualize the wells containing antibody against the specific antigen. The solution is incubated 1 hour at 37° C., then removed and the wells are washed 3 times with PBS containing 0.02% Tween 20. 100 ml of substrate solution (ATBS, Kirkegaard and Perry Laboratories, Inc.) are added to each well and color is allowed to develop for 15 minutes. The reaction is terminated by addition of 0.1M oxalic acid. The color is read at absorbance 410 nm on an automatic plate reader.

STRATEGY FOR THE CONSTRUCTION OF SYNTHETIC POX VIRAL PROMOTERS. For recombinant swinepox vectors synthetic pox promoters offer several advantages including the ability to control the strength and timing of foreign gene expression. We chose to design three promoter cassettes LP1, EP1 and LP2 based on promoters that have been defined in the vaccinia virus (1, 7 and 8). Each cassette was designed to contain the DNA sequences defined in vaccinia flanked by restriction sites which could be used to combine the cassettes in any order or combination. Initiator methionines were also designed into each cassette such that inframe fusions could be made at either EcoRI or BamHI sites. A set of translational stop codons in all three reading frames and an early transcriptional termination signal (9) were also engineered downstream of the inframe fusion site. DNA encoding each cassette was synthesized according to standard techniques and cloned into the appropriate homology vectors (see FIGS. 4, 5 and 8).

VACCINATION STUDIES IN SWINE USING RECOMBINANT SWINEPOX VIRUS CONTAINING PSEUDORABIES VIRUS GLYCOPROTEIN GENES: Young weaned pigs from pseudorabies-free herd are used to test the efficacy of the recombinant swinepox virus containing one or more of the pseudorabies virus glycoprotein genes (SPV/PRV). The piglets are inoculated intradermally or orally about $10^3$ to $10^7$ plaque forming units (PFU) of the recombinant SPV/PRV viruses.

Immunity is determined by measuring PRV serum antibody levels and by challenging the vaccinated pigs with virulent strain of pseudorabies virus. Three to four weeks post-vaccination, both vaccinated and non-vaccinated groups of pigs are challenged with virulent strain of pseudorabies virus (VDL4892). Post challenge, the pigs are observed daily for 14 days for clinical signs of pseudorabies.

Serum samples are obtained at the time of vaccination, challenge, and at weekly intervals for two to three weeks post-vaccination and assayed for serum neutralizing antibody.

HOMOLOGY VECTOR 515-85.1. The plasmid 515-85.1 was constructed for the purpose of inserting foreign DNA into SPV. It contains a unique AccI restriction enzyme site into which foreign DNA may be inserted. When a plasmid, containing a foreign DNA insert at the AccI site, is used according to the HOMOLOGOUS RECOMBINATION PROCEDURE FOR GENERATING RECOMBINANT SPV a virus containing the foreign DNA will result. A restriction map of the DNA insert in homology vector 515-85.1 is given in FIG. 4. It may be constructed utilizing standard recombinant DNA techniques (22 and 29), by joining two restriction fragments from the following sources. The first fragment is an approximately 2972 base pair HindIII to BamHI restriction fragment of pSP64 (Promega). The second fragment is an approximately 3628 base pair HindIII to BclII restriction sub-fragment of the SPV HindIII restriction fragment M (23).

HOMOLOGY VECTOR 520-17.5. The plasmid 520-17.5 was constructed for the purpose of inserting foreign DNA into SPV. It incorporates an *E. coli* β-galactosidase (lacZ) marker gene flanked by SPV DNA. Upstream of the marker gene is an approximately 2149 base pair fragment of SPV DNA. Downstream of the marker gene is an approximately 1484 base pair fragment of SPV DNA. When this plasmid is used according to the HOMOLOGOUS RECOMBINATION PROCEDURE FOR GENERATING RECOMBI- NANT SPV a virus containing DNA coding for the marker gene will result. Note that the β-galactosidase (lacZ) marker gene is under the control of a synthetic early/late pox promoter. A detailed description of the plasmid is given in FIG. 4. It may be constructed utilizing standard recombinant DNA techniques (22 and 30), by joining restriction fragments from the following sources with the synthetic DNA sequences indicated in FIG. 4. The plasmid vector is derived from an approximately 2972 base pair HindIII to BamHI restriction fragment of pSP64 (Promega). Fragment 1 is an approximately 2149 base pair HindIII to AccI restriction sub-fragment of the SPV HindIII restriction fragment M (23). Fragment 2 is an approximately 3006 base pair BamHI to PvuII restriction fragment of plasmid pJF751 (11). Fragment 3 is an approximately 1484 base pair AccI to BglII restriction sub-fragment of the SPV HindIII fragment M (23).

Figure 5B:
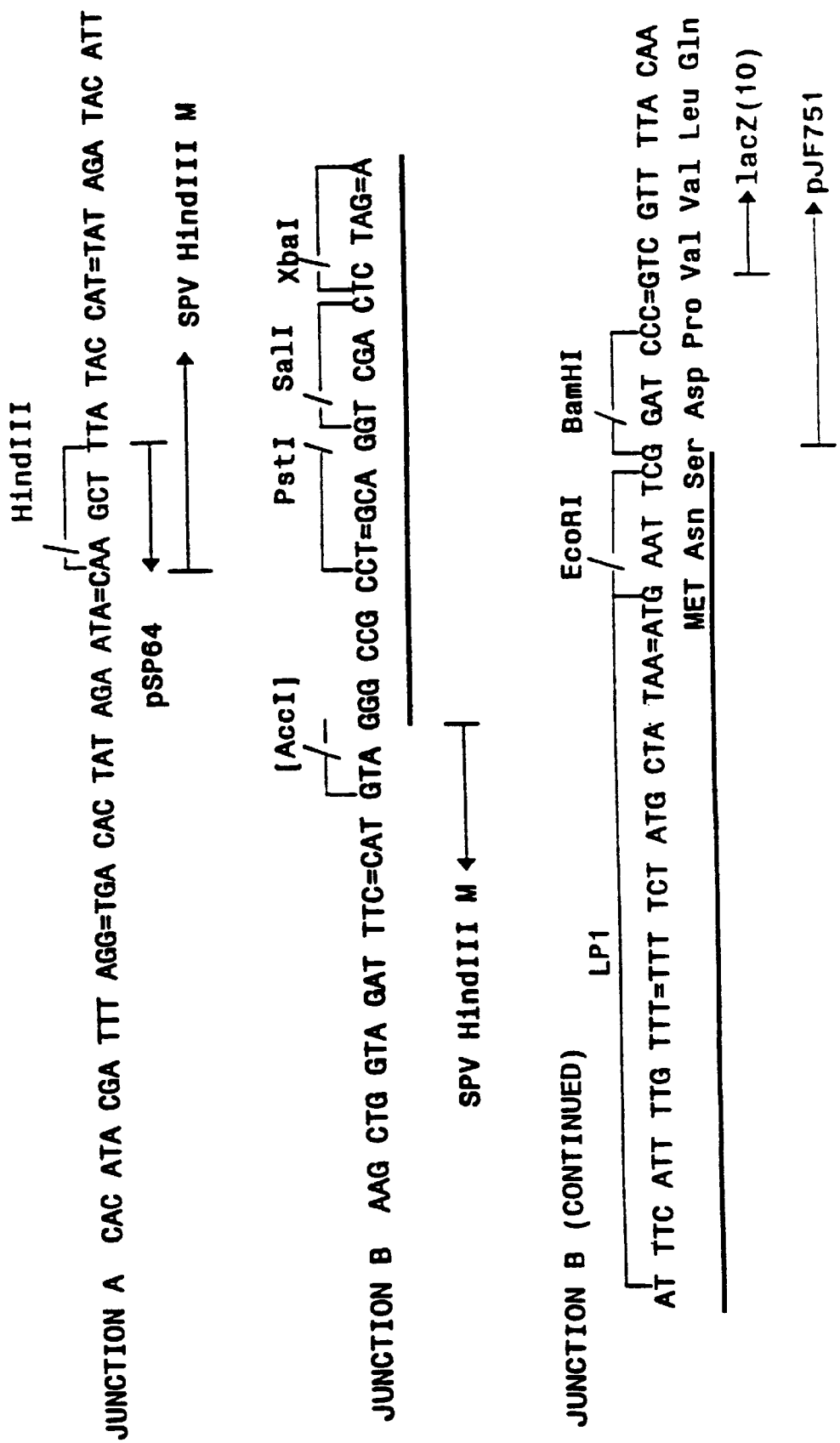
Figure 5C:
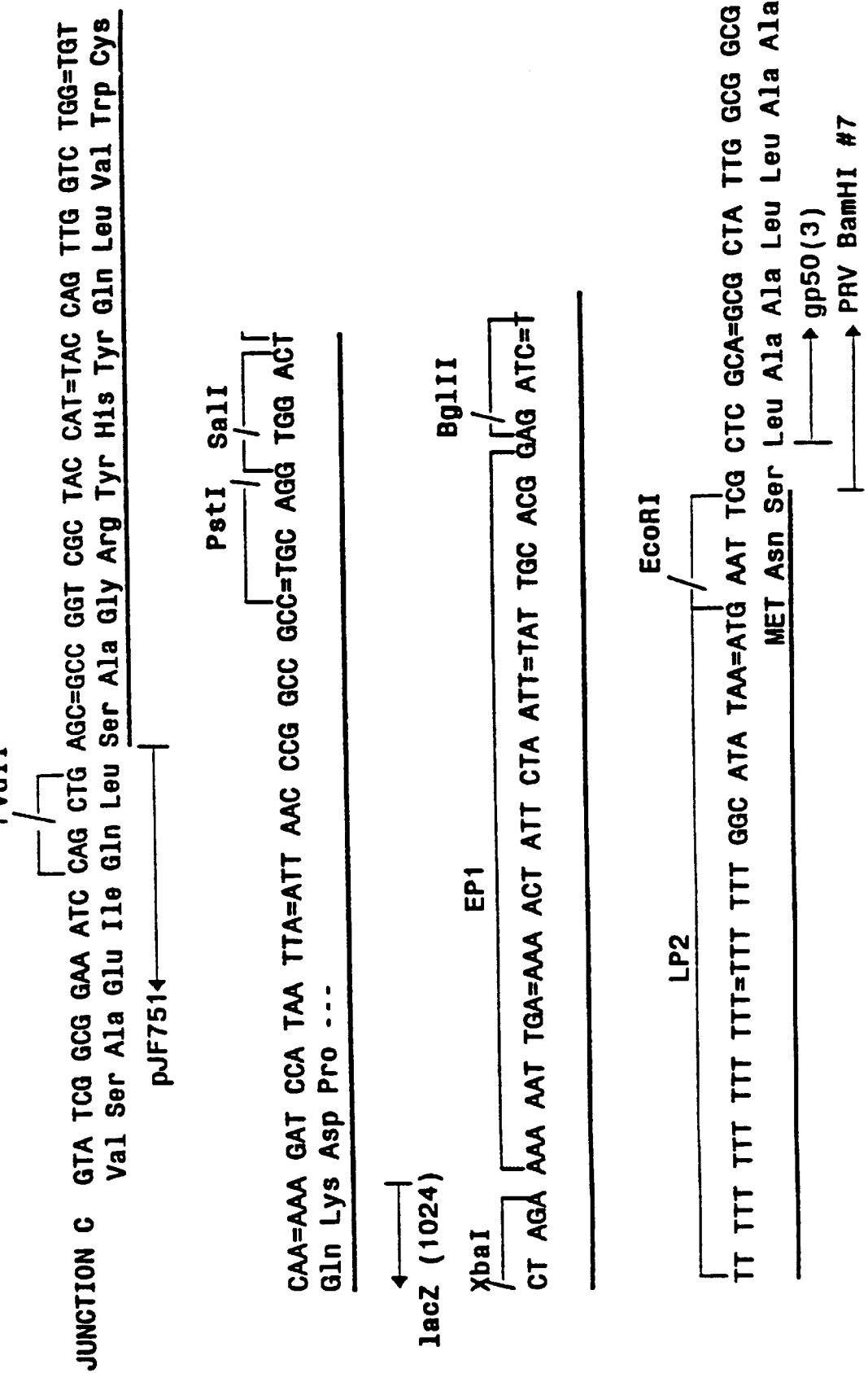
Figure 8B:
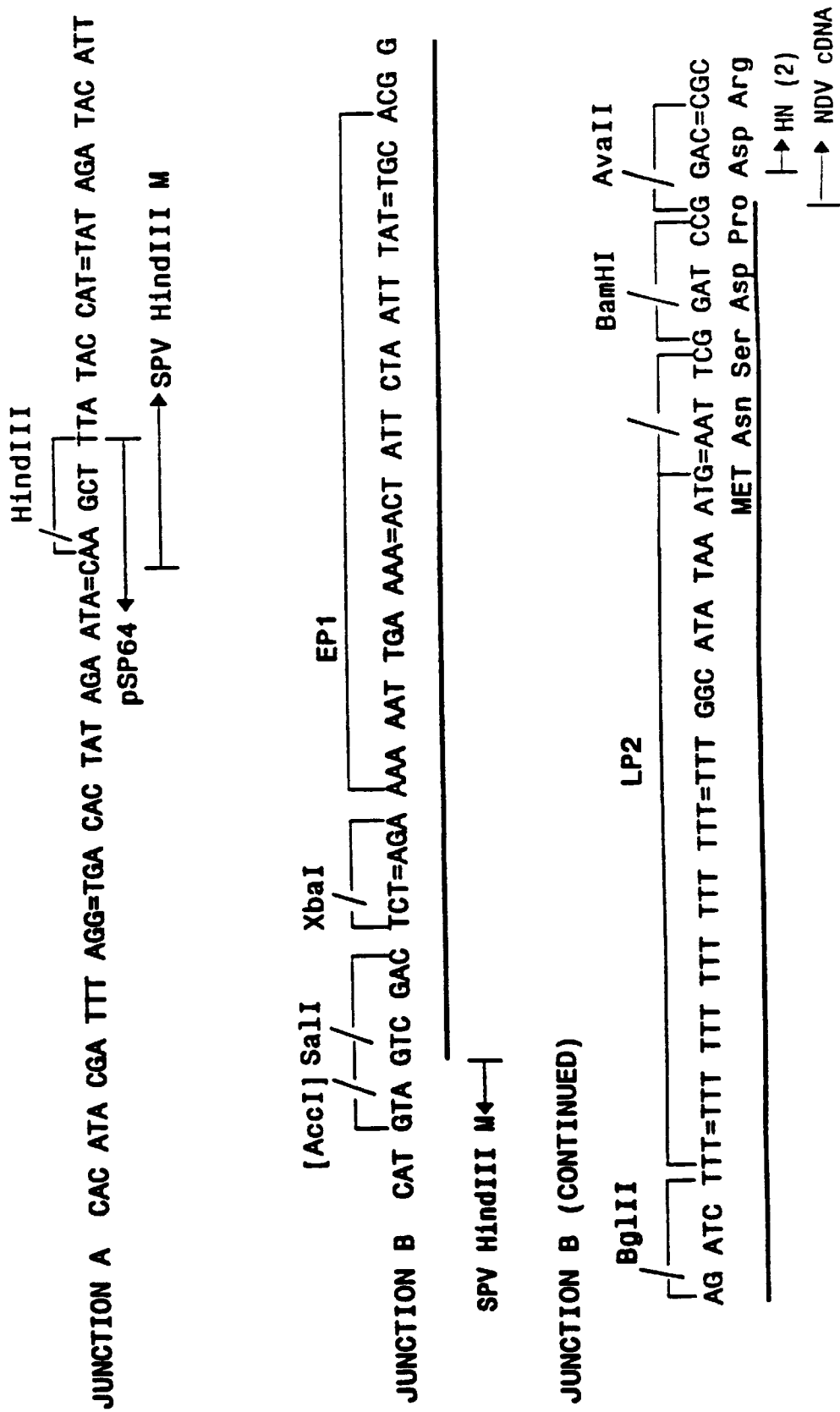
Figure 8C:
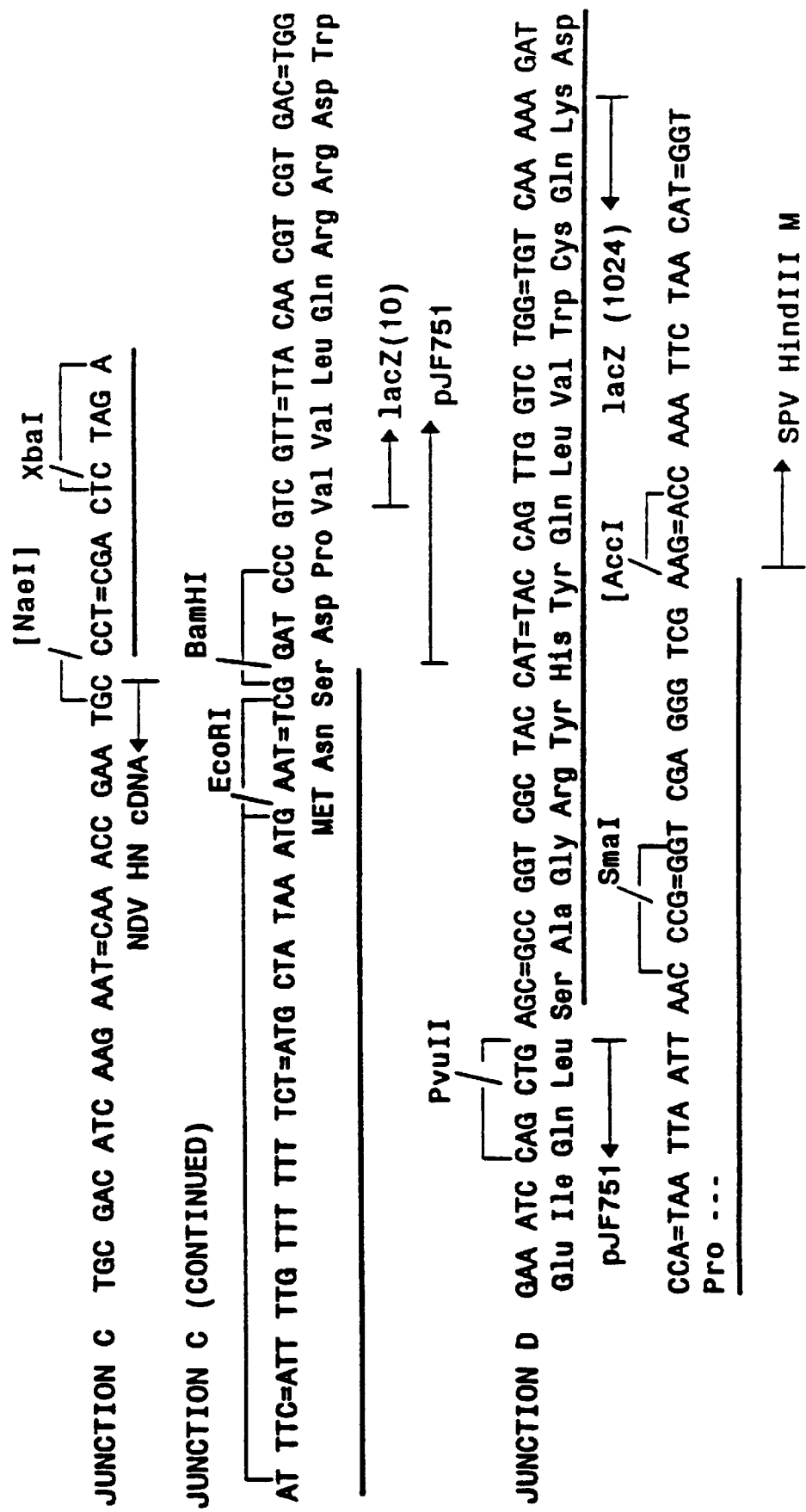
Figure 8D:
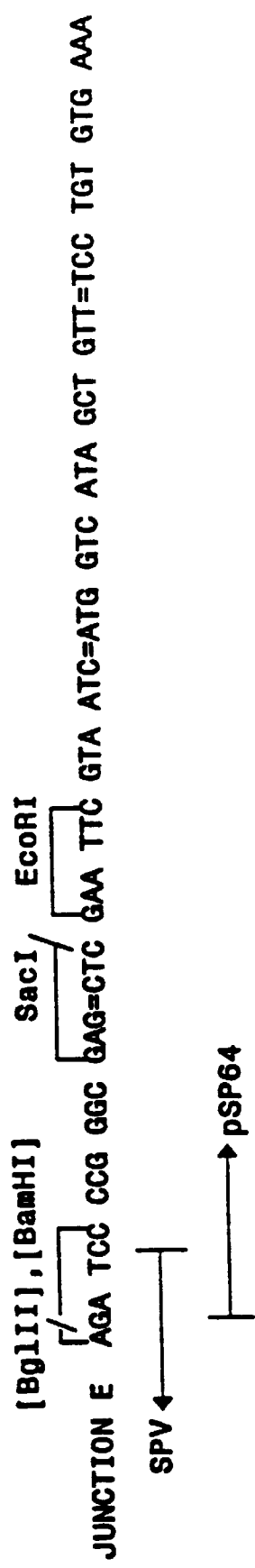
Figure 9A:
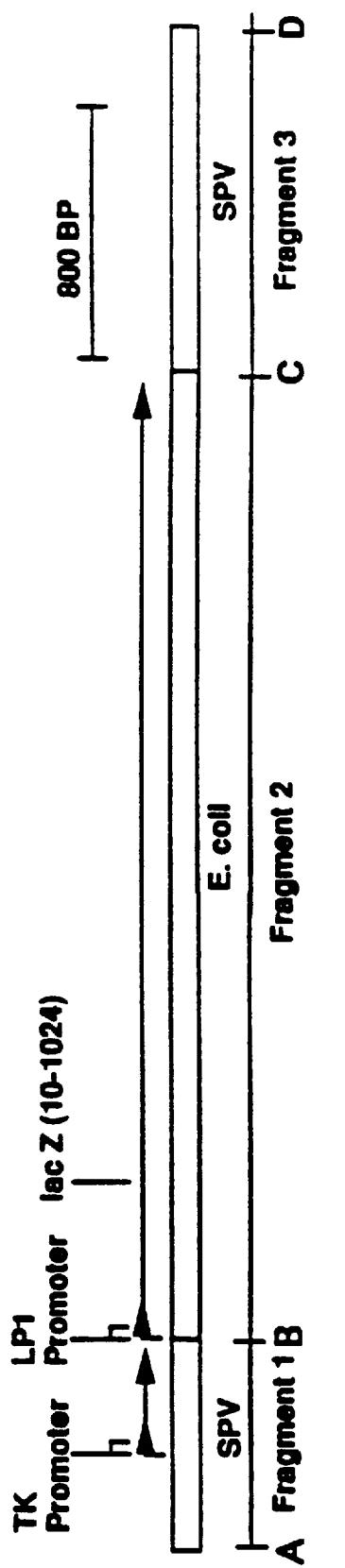
Figure 9B:
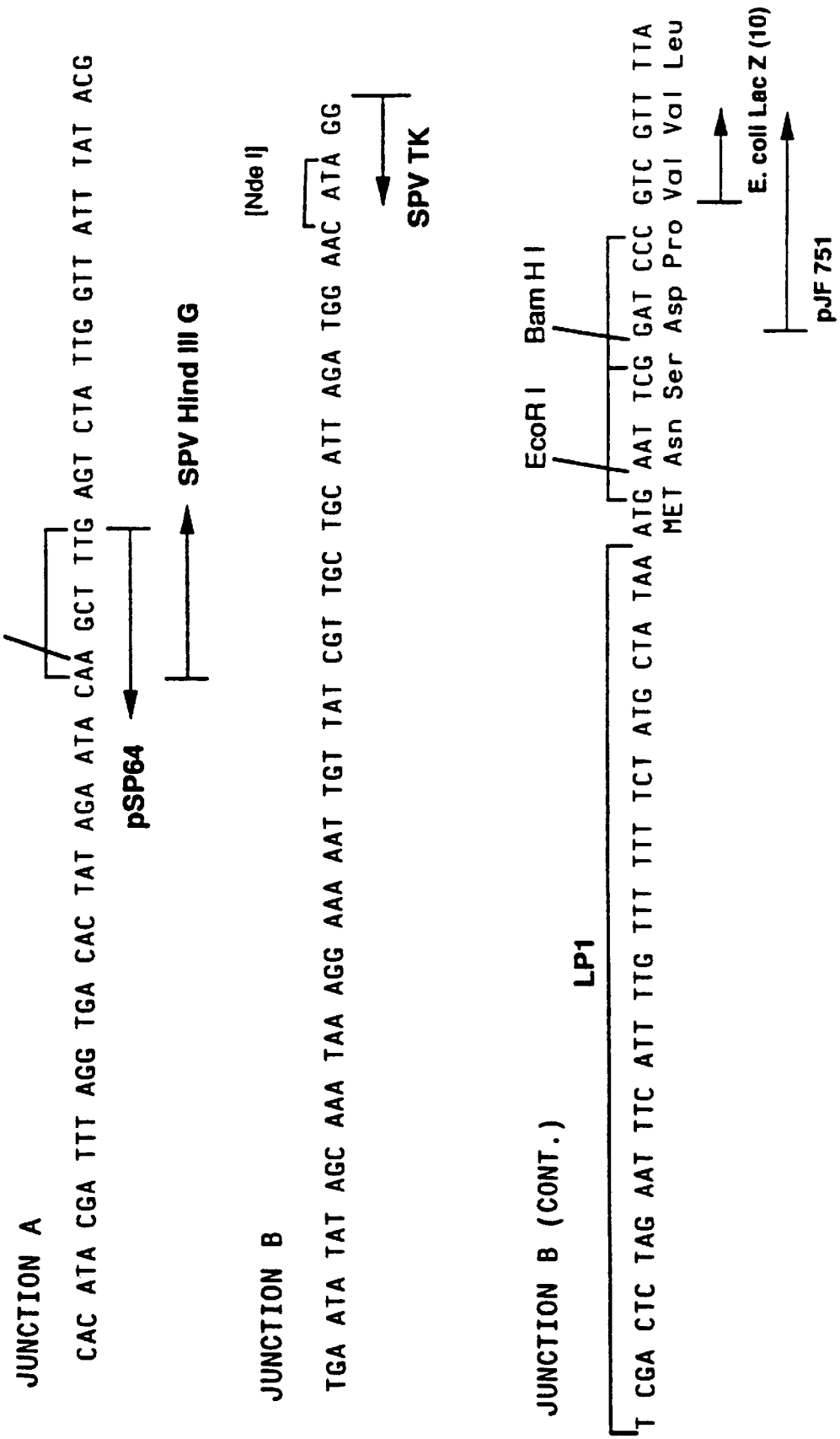
Figure 9C:
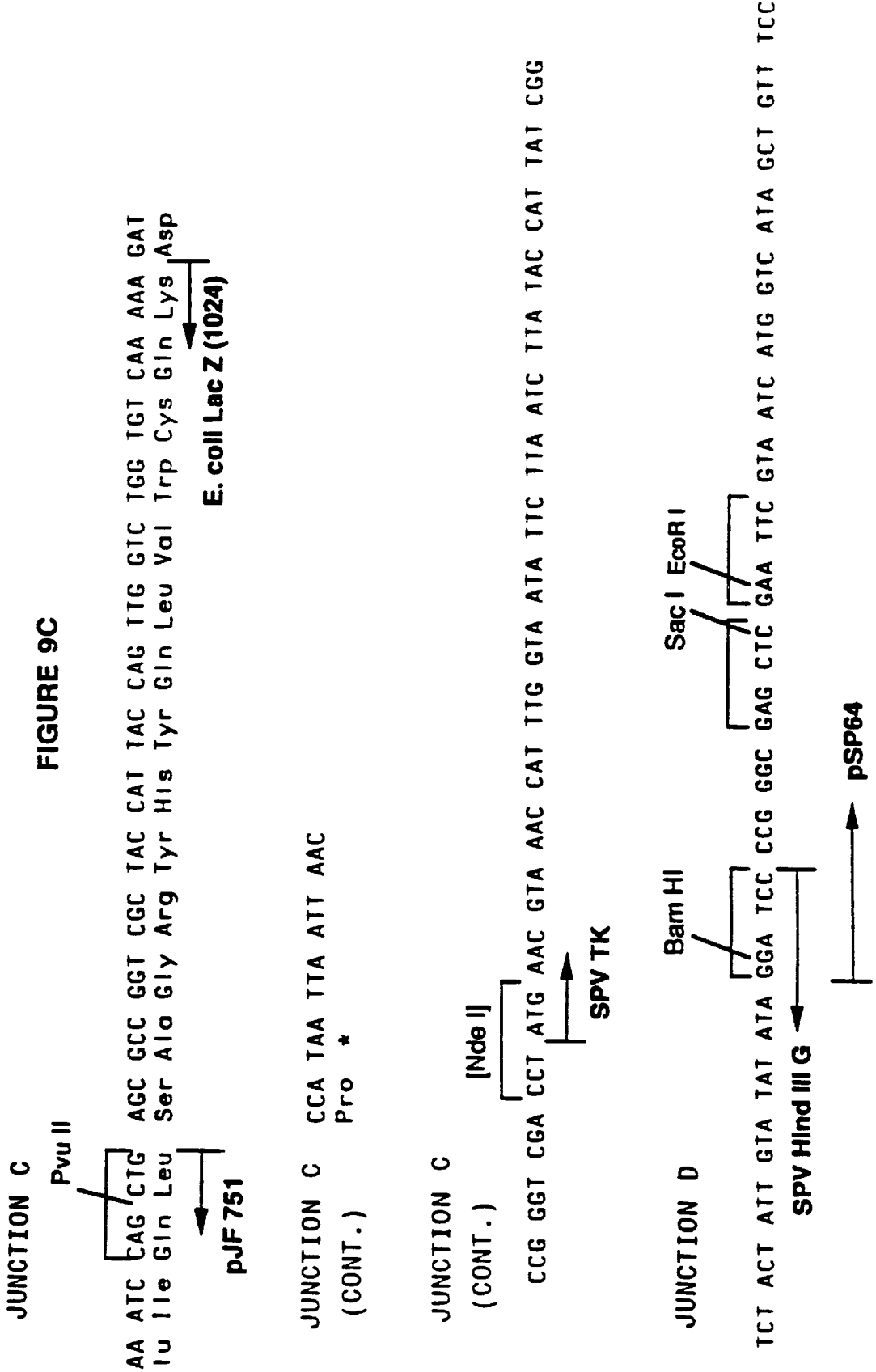

HOMOLOGY VECTOR 538-46.16. The plasmid 538-46.16 was constructed for the purpose of inserting foreign DNA into SPV. It incorporates an *E. coli* β-galactosidase (lacZ) marker gene and the PRV g50 (gpD) gene flanked by SPV DNA. Upstream of the foreign genes is an approximately 2149 base pair fragment of SPV DNA. Downstream of the foreign genes is an approximately 1484 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter (LP1) and the g50 (gpD) gene is under the control of a synthetic early/late pox promoter (EP1LP2). A detailed description of the plasmid is given in FIG. 5. It may be constructed utilizing standard recombinant DNA techniques (22 and 30), by joining restriction fragments from the following sources with the synthetic DNA sequences indicated in FIG. 5. The plasmid vector is derived from an approximately 2972 base pair HindIII to BamHI restriction fragment of pSP64 (Promega). Fragment 1 is an approximately 2149 base pair HindIII to AccI restriction sub-fragment of the SPV HindIII restriction fragment M (23). Fragment 2 is an approximately 3006 base pair BamHI to PvuII restriction fragment of plasmid pJF751 (11). Fragment 3 is an approximately 1571 base pair EcoRI to StuI restriction sub-fragment of the PRV BamHI fragment 7 (21). Note that the EcoRI site was introduced into this fragment by PCR cloning. In this procedure the primers described below were used along with a template consisting of a PRV BamHI #7 fragment subcloned into pSP64. The first primer 87.03 (5'-CGCGAATTCGCTCG CAGCGCTATTGGC-3') (SEQ ID NO:41) sits down on the PRV g50 (gpD) sequence (26) at approximately amino acid 3 priming toward the 3' end of the gene. The second primer 87.06 (5'-GTAGGAGTGGCTGCTGAAG-3') (SEQ ID NO:42) sits down on the opposite strand at approximately amino acid 174 priming toward the 5' end of the gene. The PCR product may be digested with EcoRI and SalI to produce an approximately 509 base pair fragment. The approximately 1049 base pair SalI to StuI sub-fragment of PRV BamHI #7 may then be ligated to the approximately 509 base pair EcoRI to SalI fragment to generate the approximately 1558 base pair EcoRI to StuI fragment 3. Fragment 4 is an approximately 1484 base pair AccI to BglII restriction sub-fragment of the SPV HindIII fragment M (23).

Figure 10A:
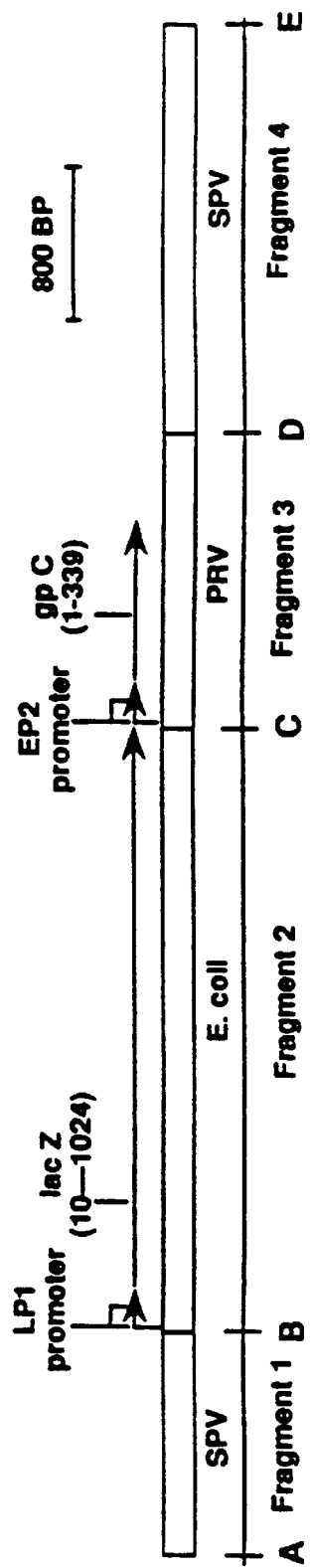
FIG. 10B show the sequences located at Junctions A and B between fragments.
FIG. 10C shows the sequences located at Junction C, and FIG. 10D shows the sequences located at Junctions 10D and 10E (SEQ ID NO: 51, 52, 53, 54, 55). The restriction sites used to generate each fragment as well as synthetic linker sequences which are used to join the fragments are described for each junction in FIGS. 10B to 10D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), Escherichia coli (*E. coli*), pox synthetic late promoter 1 (LP1), pox synthetic early promoter 2 (EP2) (SEQ ID NO: 45), gIII (gpC), base pairs (BP).
Figure 10C:
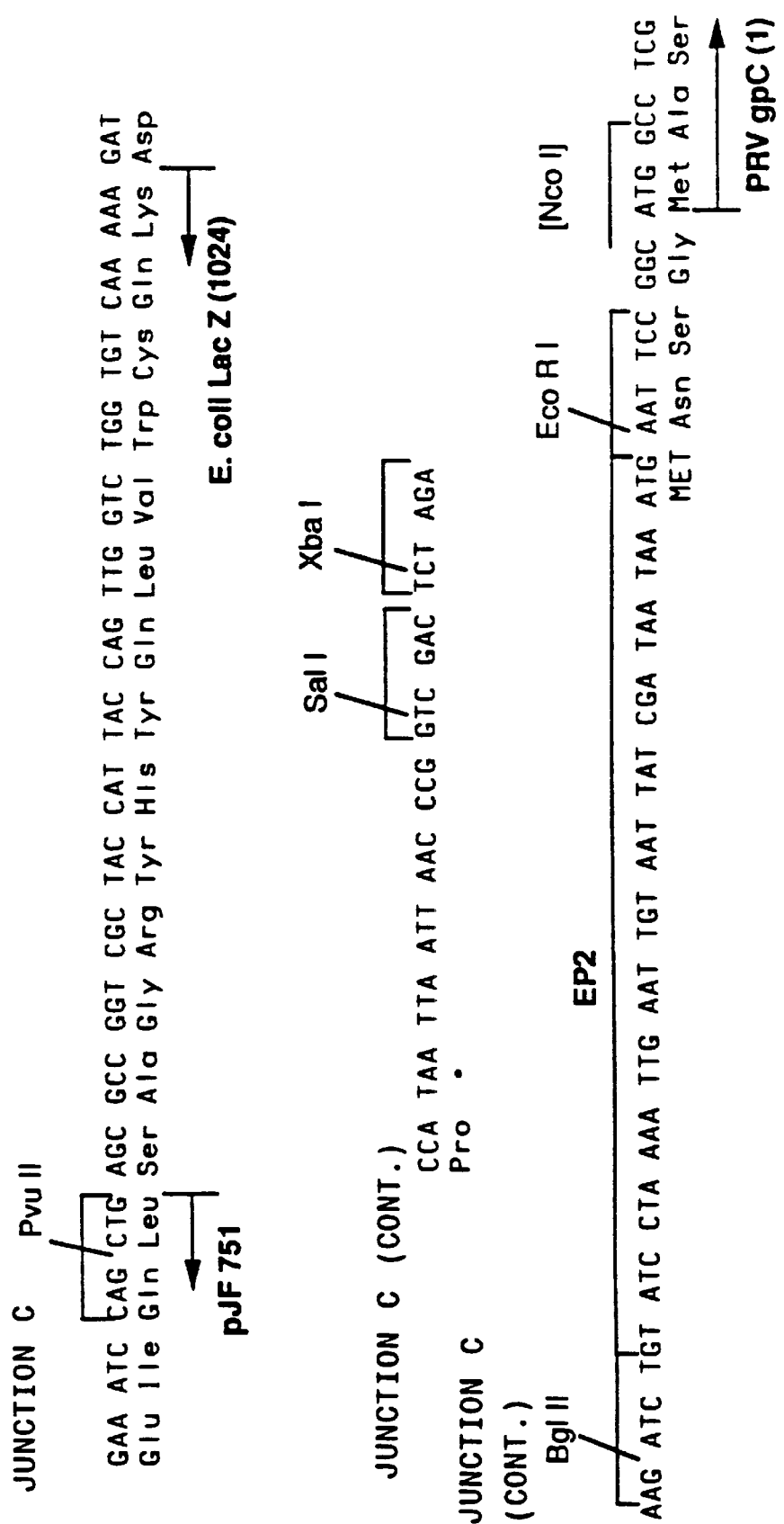

HOMOLOGY VECTOR 570-91.21. The plasmid 570-91.21 was constructed for the purpose of inserting foreign DNA into SPV. It incorporates an *E. coli* B-galactosidase (lacZ) marker gene and the PRV gIII (gpC) gene flanked by SPV DNA. Upstream of the foreign DNA genes is an approximately 1484 base pair fragment of SPV DNA. Downstream of the foreign genes is an approximately 2149 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gpC) gene is under the control of a synthetic early pox promoter (EP2). A detailed description of the plasmid is given in FIG. 10. It may be constructed utilizing standard recombinant DNA techniques (22 and 30), by joining restriction fragments from the following sources with the synthetic DNA sequences indicated in FIG. 10. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2149 base pair AccI to HindIII restriction sub-fragment of the SPV HindIII fragment M (23). The AccI sites in fragments 1 and 4 have been converted to PstI sites using synthetic DNA linkers.

Figure 11A:
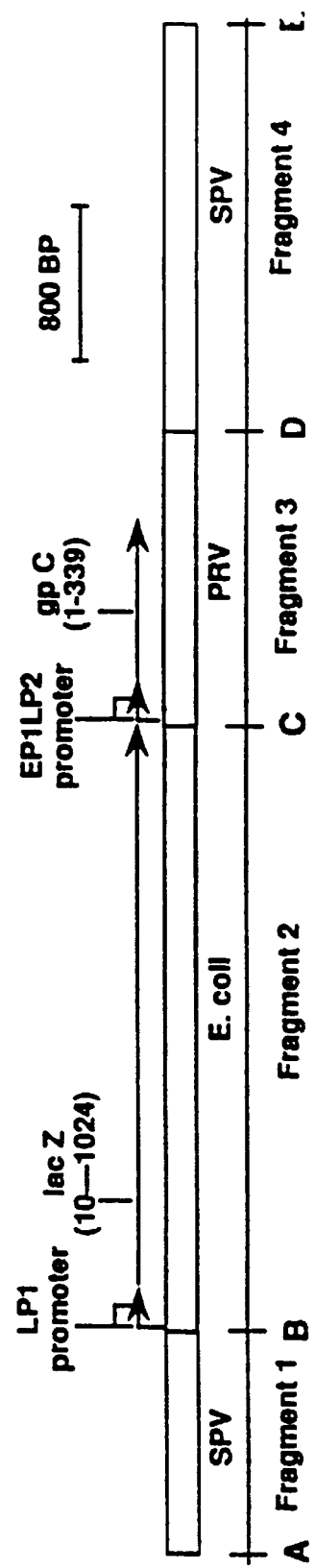
FIG. 11A contains a diagram showing the orientation of DNA fragments assembled in plasmid 570-91.41 and a table indicating the origin of each fragment.
Figure 11C:
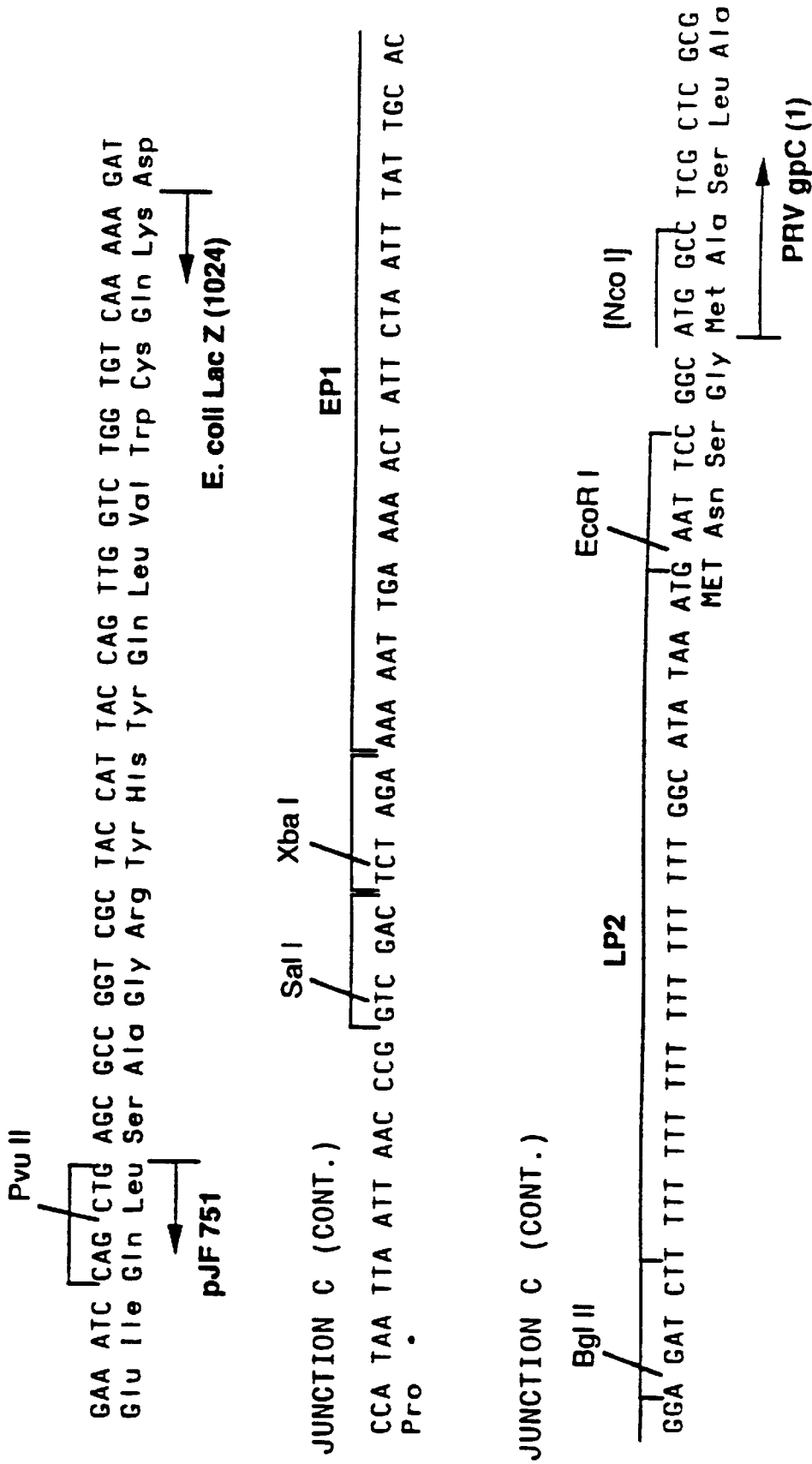
Figure 12A:
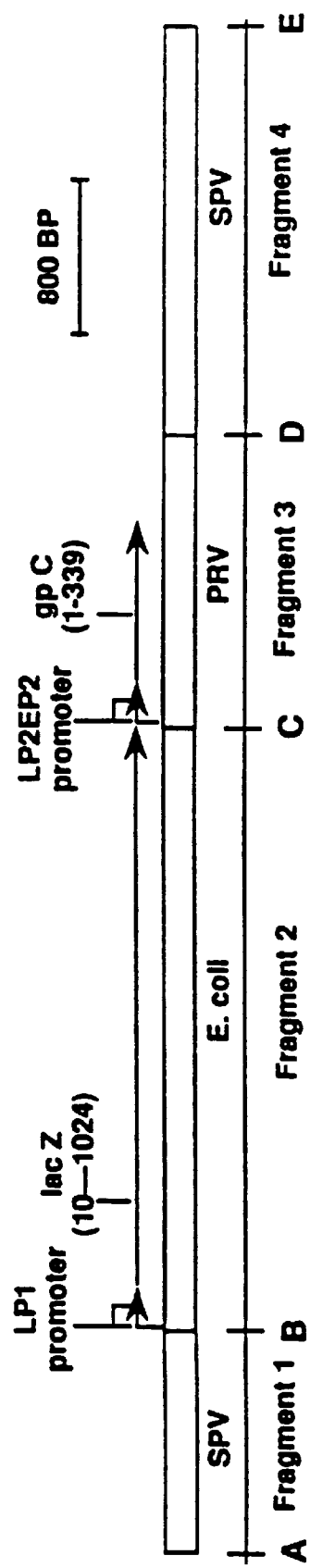
FIG. 12A contains a diagram showing the orientation of DNA fragments assembled in plasmid 570-91.64 and a table indicating the origin of each fragment.
Figure 12B:
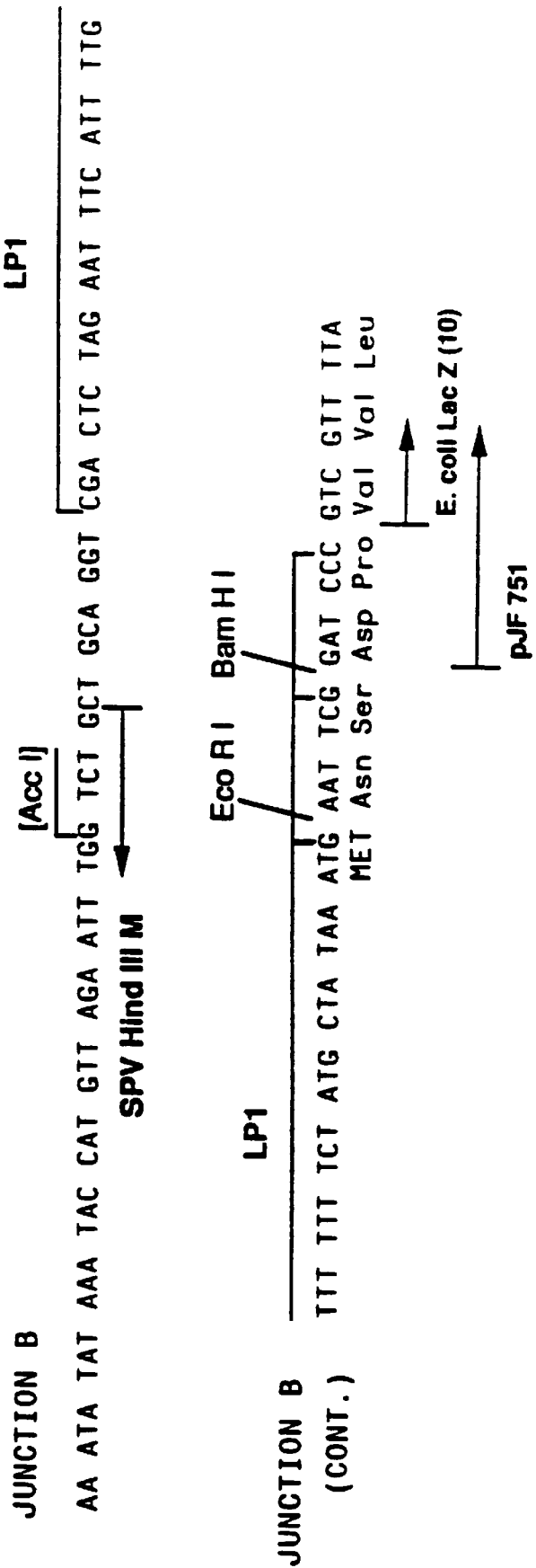
Figure 13A:
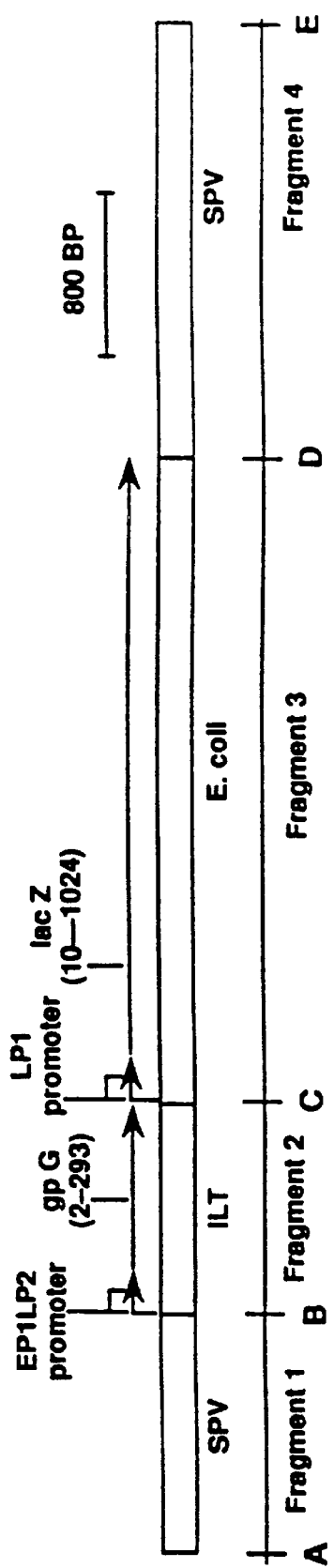
FIGS. 13A, 13B, 13C and 13D show a detailed description of Swinepox Virus S-PRV-014 and the DNA insertion in Homology Vector 599-65.25.
Figure 13B:
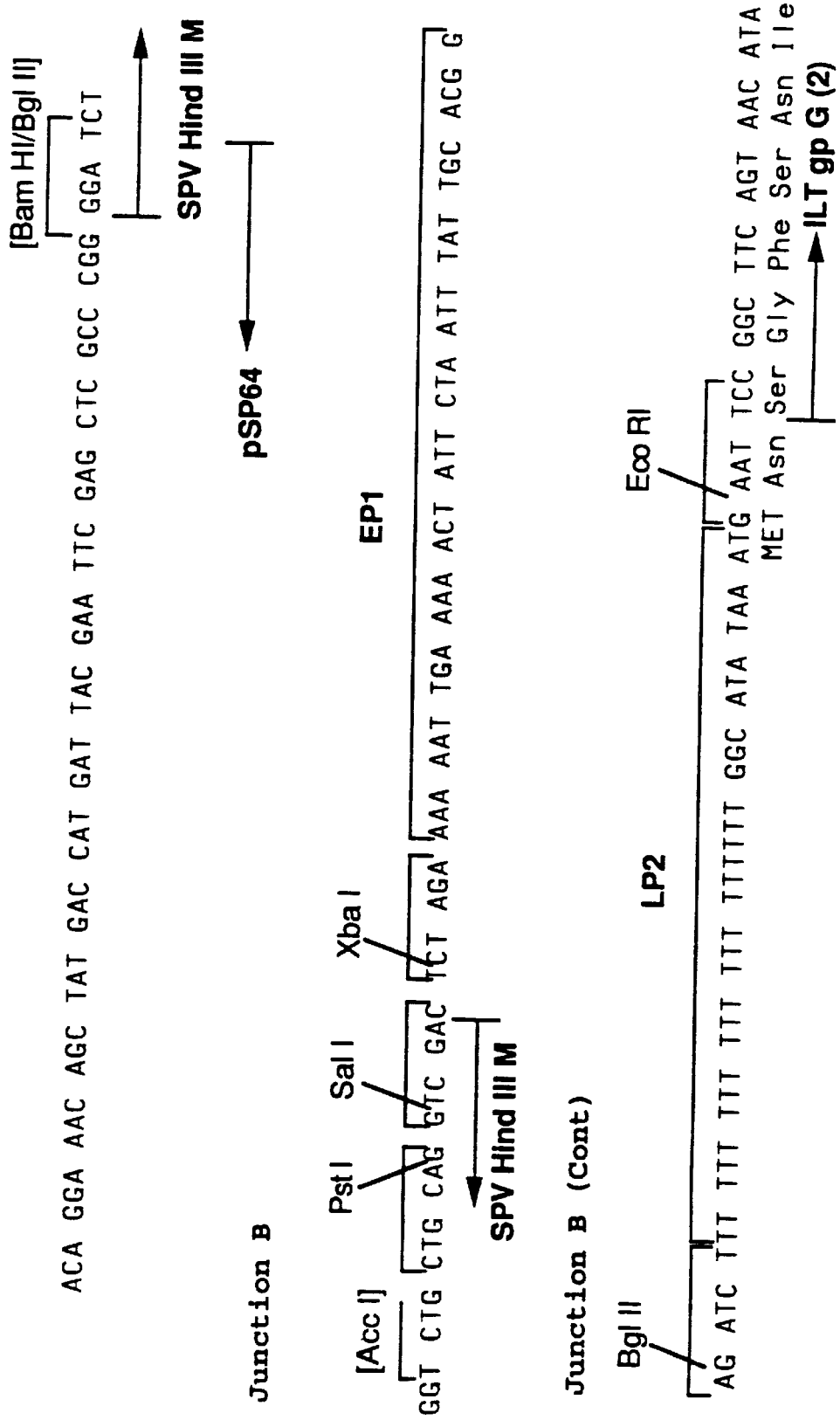
Figure 13C:
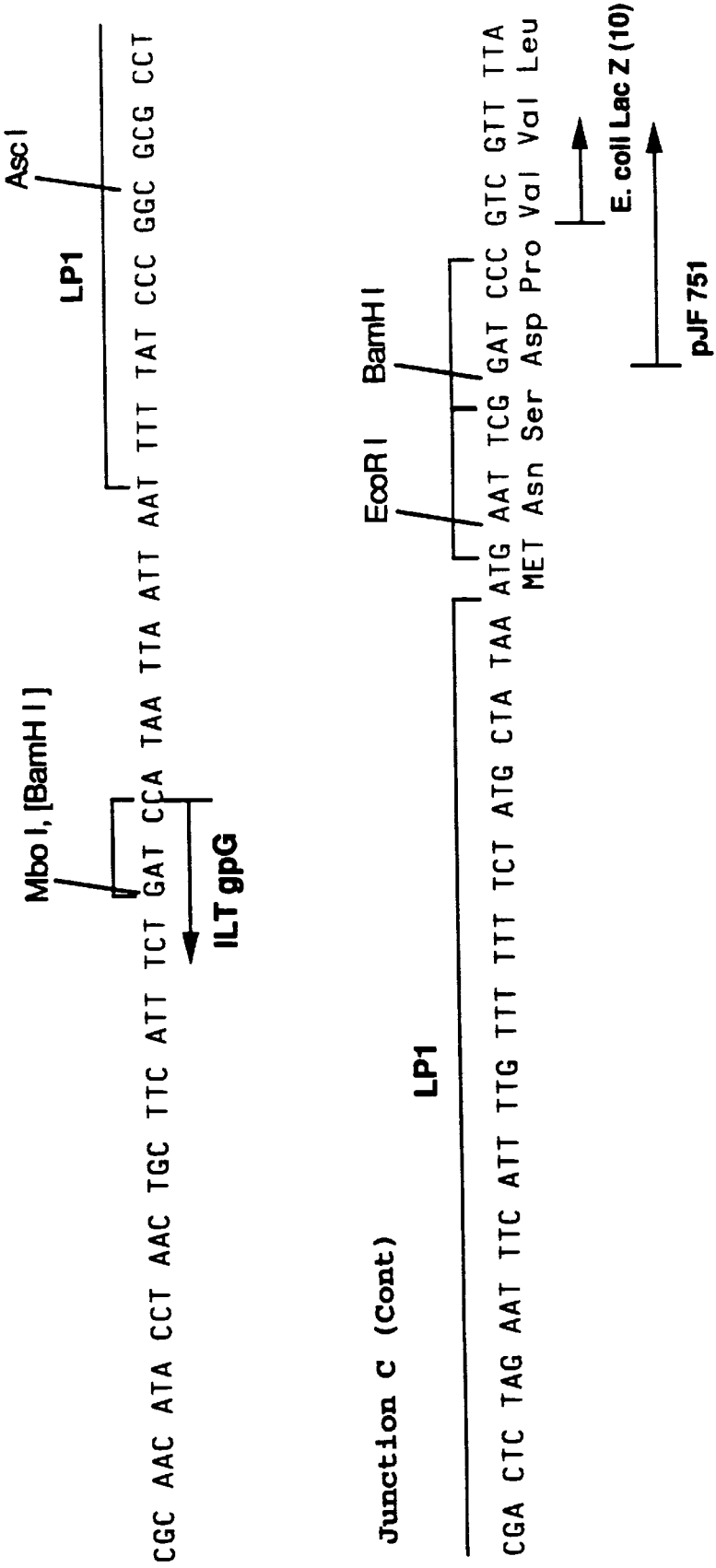
Figure 13D:
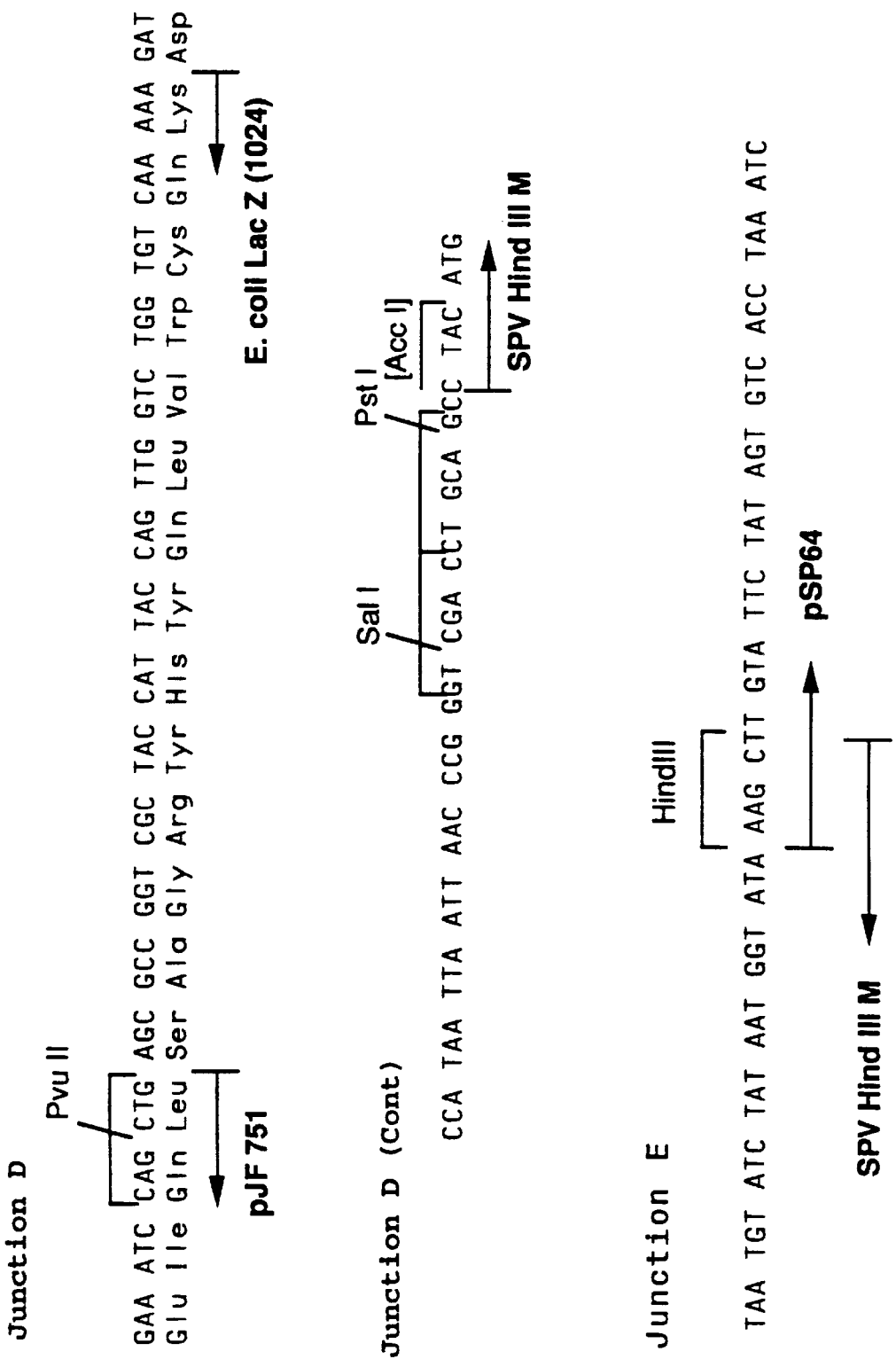

HOMOLOGY VECTOR 570-91.41. The plasmid 570-91.41 was constructed for the purpose of inserting foreign DNA into SPV. It incorporates an *E. coli* B-galactosidase (lacz) marker gene and the PRV gIII (gpC) gene flanked by SPV DNA. Upstream of the foreign DNA genes is an approximately 2149 base pair fragment of SPV DNA. Downstream of the foreign genes is an approximately 1484 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gpC) gene is under the control of a synthetic early late pox promoter (EP1LP2). A detailed description of the plasmid is given in FIG. 11. It may be constructed utilizing standard recombinant DNA techniques (22 and 30), by joining restriction fragments from the following sources with the synthetic DNA sequences indicated in FIG. 11. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2149 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 570-91.64. The plasmid 570-91.64 was constructed for the purpose of inserting foreign DNA into SPV. It incorporates an *E. coli* B-galactosidase (lacZ) marker gene and the PRV gIII (gpC) gene flanked by SPV DNA. Upstream of the foreign DNA genes is an approximately 1484 base pair fragment of SPV DNA. Downstream of the foreign genes is an approximately 2149 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gpC) gene is under the control of a synthetic late early pox promoter (LP2EP2). A detailed description of the plasmid is given in FIG. 12. It may be constructed utilizing standard recombinant DNA techniques (22 and 30), by joining restriction fragments from the following sources with the synthetic DNA sequences indicated in FIG. 12. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2149 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 538-46.26. The plasmid 538-46.26 was constructed for the purpose of inserting foreign DNA into SPV. It incorporates an *E.coli* β-galactosidase (lacZ) marker gene and the Newcastle Disease Virus (NDV) hemagglutinin-Neuraminidase (HN) gene flanked by SPV DNA. Upstream of the foreign genes is an approximately 2149 base pair fragment of SPV DNA. Downstream of the foreign genes is an approximately 1484 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter (LP1) and the HN gene is under the control of a synthetic early/late pox promoter (EP1LP2). A detailed description of the plasmid is given in FIG. 8. It may be constructed utilizing standard recombinant DNA techniques (22 and 30), by joining restriction fragments from the following sources with the synthetic DNA sequences indicated in FIG. 8. The plasmid vector is derived from an approximately 2972 base pair HindIII to BamHI restriction fragment of pSP64 (Promega). Fragment 1 is an approximately 2149 base pair HindIII to AccI restriction sub-fragment of the SPV HindIII restriction fragment M (23). Fragment 2 is an approximately 1810 base pair AvaII to NaeI restriction fragment of a NDV HN cDNA clone. The sequence of the HN cDNA clone is given in FIG. 7. The cDNA clone was generated from the Bi strain of NDV using standard cDNA cloning techniques (14). Fragment 3 is an approximately 3006 base pair BamHI to PvuII restriction fragment of plasmid pJF751 (11). Fragment 4 is an approximately 1484 base pair AccI to BglII restriction sub-fragment of the SPV HindIII fragment M (23).

HOMOLOGY VECTOR 599-65.25. The plasmid 599-65.25 was constructed for the purpose of inserting foreign DNA into SPV. It incorporates an *E. coli* B-galactosidase (lacZ) marker gene and the ILT gpG gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the B-galactosidase (lacZ) marker gene is under the control of a synthetic late pox promoter (LP1), and the ILT gpG gene is under the control of a synthetic early/late pox promoter (EP1LP2). A detailed description of the plasmid is given in FIG. 13. It may be constructed utilizing standard recombinant DNA techniques (22, 30), by joining restriction fragments from the following sources with the synthetic DNA sequences indicated in FIG. 13. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1073 base pair EcoRI to MboI fragment. Note that the EcoRI site was introduced by PCR cloning. In this procedure, the primers described below were used with a template consisting of a 2.6 kb Sst I to Asp718I subfragment of a 5.1 kbAsp718I fragment of ILT virus genome. The first primer 91.13 (5'-CCGAATTCCGGCTTCAGTAACATAGGATCG-3') (SEQ ID NO: 81) sits down on the ILT gpG sequence at amino acid 2. It adds an additional asparagine residue between amino acids 1 and 2 and also introduces an EcoRI restriction site. The second primer 91.14 (5'-GTACCCATAC-TGGTCGTGGC-3') (SEQ ID NO: 82) sits down on the opposite strand at approximately amino acid 196 priming toward the 5' end of the gene. The PCR product is digested with EcoRI and BamHI to produce an approximately 454 base pair fragment. The approximately 485 base pair MboI sub-fragment of ILT Asp718I (5.1 kb) fragment is ligated to the approximately 454 base pair EcoRI to BamHI fragment to generate fragment 2 from EcoRI to MboI which is approximately 939 base pairs (293 amino acids) in length. Fragment 3 is an approximately 3002 base pair BamHI to PvuII restriction fragment of plasmid pJF751 (11). Fragment 4 is an approximately 2149 base pair AccI to HindIII subfragment of the SPV HindIII fragment M. The AccI sites of fragments 1 and 4 have been converted to PstI sites using synthetic DNA linkers.

HOMOLOGY VECTOR 624-20.1C. The plasmid 624-20.lC was constructed for the purpose of inserting foreign DNA into SPV. It incorporates an *E. coli* B-galactosidase (lacZ) marker gene and the ILT gpI gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the B-galactosidase (lacZ) marker gene is under the control of a synthetic late pox promoter (LP1), and the ILT gpI gene is under the control of a synthetic late/early pox promoter (LP2EP2). A detailed description of the plasmid is given in FIG. 14. It may be constructed utilizing standard recombinant DNA techniques (22, 30), by joining restriction fragments from the following sources with the synthetic DNA sequences indicated in FIG. 14. The plasmid vector is derived from an approximately 2972 base pair HindIII to BamHI restriction fragment of pSP64 (Promega). Fragment 1 is an approximately 1484 base pair Bgl II to AccI restriction sub-fragment of the SPV HindIII restriction fragment M (23). Fragment 2 is an approximately 1090 base pair fragment with EcoRI and BamHI restriction sites at the ends synthesized by PCR cloning and containing the entire amino acid coding sequence of the ILT gpI gene. The ILT gpI gene was synthesized in two separate PCR reactions. In this procedure, the primers described below were used with a template consisting the 8.0 kb ILT Asp 7181 fragment. The first primer 103.6 (5'-CCGGAATTCGCTACTT GGAACTCTGG-3') (SEQ ID NO 83) sits down on the ILT gpI sequence at amino acid number 2 and introduces an EcoRI site at the 5' end of the ILT gpI gene, The second primer 103.3 (5'-CATTGTCCCGAGACGGACAG-3') (SEQ ID NO. 84) sits down on the ILT gpI sequence at approximately amino acid 269 on the opposite strand to primer 103.6 and primes toward the 5' end of the gene. The PCR product was digested with EcoRI and BglI (BglI is located approximately at amino acid 209 which is 179 base pairs 5' to primer 2) to yield a fragment 625 base pairs in length corresponding to the 5' end of the ILT gpI gene. The third primer 103.4 (5'-CGCGATCCAACTATCGGTG-3') (SEQ ID NO. 85) sits down on the ILT gpI gene at approximately amino acid 153 priming toward the 3' end of the gene. The fourth primer 103.5 (5'GCGGATCCACATTCAG ACTTAATCAC-3') (SEQ ID NO. 86) sits down at the 3' end of the ILT gpI gene 14 base pairs beyond the UGA stop codon, introducing a BamHI restriction site and priming toward the 5' end of the gene. The PCR product is digested with Bgl I (at amino acid 209) and BamHI to yield a fragment 476 base pairs in length corresponding to the 3' end of the ILT gpI gene. Fragment 2 consists of the products of the two PCR reactions ligated together to yield an ILT gpI gene which is a EcoRI to BamHI fragment approximately 1101 base pairs (361 amino acids) in length. Fragment 3 is an approximately 3002 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 614-83.18. The plasmid 614-83.18 was constructed for the purpose of inserting foreign DNA into SPV. It incorporates an *E. coli* B-galactosidase (lacZ) marker gene and the IBR gpG gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the B-galactosidase (lacZ) marker gene is under the control of a synthetic late pox promoter (LP1), and the IBR gG gene is under the control of a synthetic late/early pox promoter (LP2EP2). A detailed description of the plasmid is given in FIG. 15. It may be constructed utilizing standard recombinant DNA techniques (22, 30), by joining restriction fragments from the following sources with the synthetic DNA sequences indicated in FIG. 15. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1085 base pair fragment synthesized by PCR cloning with EcoRI and BamHI restriction sites at the ends and containing the amino acid coding sequence from amino acids 2 to 362 of the IBR gpG gene. In the PCR cloning procedure, the primers described below were used with a template consisting of the IBR-000 virus (Cooper strain). The first primer 106.9 (5'-ATGAATTCCCCTGCCGCCCGGACCGGCACC-3') (SEQ ID NO. 87) sits down on the IBR gpG sequence at amino acid number 1 and introduces an EcoRI site at the 5' end of the IBR gpG gene and two additional amino acids between amino acids 1 and 2. The second primer 106.8 (5'-CATGGATCCCGCTCGAGGCGAGCGGGCTCC-3') (SEQ ID NO. 88) sits down on the IBR gpG sequence at approximately amino acid 362 on the Opposite strand to primer 1 and primes synthesis toward the 5' end of the IBR gpG gene. Fragment 2 was generated by digesting the PCR product with EcoRI and BamHI to yield a fragment 1085 base pairs in length corresponding to the amino terminal 362 amino acids (approximately 80%) of the IBR gpG gene. Fragment 3 is an approximately 3002 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

Homology Vector for Constructing S-SPV-019
(LacZ/IBR gpE Homology Vector)

This lacZ/IBR gpE homology vector is used to insert foreign DNA into SPV. It incorporates an *E. coli* B-galactosidase (lacZ) marker gene and the IBR gpE gene flanked by SPV DNA. When this plasmid is used according to the HOMOLOGOUS RECOMBINATION PROCEDURE FOR GENERATING RECOMBINANT SPV a virus containing DNA coding for the foreign genes will result. Note that the B-galactosidase (lacZ) marker gene is under the control of a synthetic late pox promoter and the gpE gene is under the control of a synthetic late/early pox promoter. The homology vector may be constructed utilizing standard recombinant DNA techniques (22 and 30), by joining restriction fragments from the following sources with the appropriate synthetic DNA sequences. The plasmid vector is derived from an approximately 2972 base pair HindIII to BamHI restriction fragment of pSP64 (Promega). The upstream SPV homology is an approximately 1146 base pair BglIII to AccI restriction sub-fragment of the SPV HindIII fragment M (23). The IBR gE gene is an approximately 1888 base pair fragment synthesized by PCR cloning with EcoRI and BamHI ends. In the PCR cloning procedure, the primers described below were used with a template consisting of the IBR-000 VIRUS (Cooper strain). The first primer 4/93.17DR (5'-CTGGTTCGGCCCAGAATTCTATGGG-TCTCGCGCGGCTCGTGG-3' (SEQ ID NO. 89) sits down on the IBR gpE gene at amino acid number 1 and introduces an EcoRI site at the 5' end of the IBR gpE gene and adds two additional amino acids at the amino terminus of the protein. The second primer 4/93.18DR (5'-CTCGCT-CGCCCAGGATCCCTAGCGGAGGATGGACTTGAGT-CG-3') (SEQ ID NO. 90) sits down on the IBR gpE sequence at approximately amino acid 648 on the opposite strand to primer 1 and primes synthesis toward the 5' end of the IBR gpE gene. The lacZ promoter and marker gene is identical to the one used in plasmid 520-17.5. The downstream SPV homology is an approximately 2156 base pair AccI to HindIII restriction sub-fragment of the SPV HindIII restriction fragment M (23). The AccI site in the SPV homology vector is converted to a unique XbaI site.

Homology Vector for Constructing S-SPV-018
(LacZ/PRV gpE Homology Vector)

This homology vector is constructed for the purpose of inserting foreign DNA into SPV. It incorporates an *E. coli*

B-galactosidase (lacZ) marker gene and the PRV gpE gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing the DNA coding for the foreign genes results. Note that the B- galactosidase (lacz) marker gene is under the control of a synthetic late pox promoter (LP1), and the PRV gpE gene is under the control of a synthetic early/late pox promoter (EP1LP2). The homology vector is constructed utilizing standard recombinant DNA techniques (22, 30), by joining restriction fragments from the following sources with synthetic DNA sequences. The first plasmid vector is derived from an approximately 2972 base pair HindIII to BamHI restriction fragment pSP64 (Promega). Fragment 1 is an approximately 1484 base pair BglII to AccI restriction sub-fragment of the SPV HindIII restriction fragment M (23). Fragment 2 is the lacZ promoter and marker gene which is identical to the one used in plasmid 520-17.5. Fragment 3 is an approximately 2484 base pair DraI to MluI sub-fragment of PRV derived from the PRV BamHI #7 DNA fragment. The DraI site is converted to an EcoRI site through the use of a synthetic DNA linker. The DraI site sits 45 base pairs upstream of the natural gpE start codon and extends the open reading frame at the amino terminus of the protein for 15 amino acids. The synthetic pox promoter/EcoRI DNA linker contributes another 4 amino acids. Therefore, the engineered gpE gene contains 19 additional amino acids fused to the amino terminus of gpE. The nineteen amino acids are Met-Asn-Ser-Gly-Asn-Leu-Gly-Thr-Pro-Ala-Ser-Leu-Ala-His-Thr-Gly-Val-Glu-Thr. Fragment 4 is an approximately 2149 base pair AccI to HindIII sub-fragment of the SPV HindIII fragment M (23). The AccI sites of fragments 1 and 4 are converted to PstI sites using synthetic DNA linkers.

HOMOLOGY VECTOR 520-90.15. The plasmid 520-90.15 was constructed for the purpose of inserting foreign DNA into SPV. It contains a unique NdeI restriction enzyme site into which foreign DNA may be inserted. When a plasmid, containing a foreign DNA insert at the NdeI site, is used according to the HOMOLOGOUS RECOMBINATION PROCEDURE FOR GENERATING RECOMBINANT SPV a virus containing the foreign DNA will result. Plasmid 520-90.15 was constructed utilizing standard recombinant DNA techniques (22 and 30), by joining two restriction fragments from the following sources. The first fragment is an approximately 2972 base pair HindIII to BamHI restriction fragment of pSP64 (Promega). The second fragment is an approximately 1700 base pair HindIII to BamHI restriction subfragment of the SPV HindIII restriction fragment G (23).

HOMOLOGY VECTOR 708-78.9. The plasmid 708-78.9 was constructed for the purpose of inserting foreign DNA into SPV. It incorporates an *E. coli* β-galactosidase (lacZ) marker gene and the infectious bovine rhinotracheitis virus (IBRV) gE gene flanked by SPV DNA. Upstream of the foreign genes is an approximately 1484 base pair fragment of SPV DNA. Downstream of the foreign genes is an approximately 2149 base pair fragment of SPV DNA. When the plasmid is used is according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the IBRV gE gene is under the control of a synthetic late/early pox promoter (LP2EP2). It may be constructed utilizing standard recombinant DNA techniques (22, 30), by joining restriction fragments from the following sources. The plasmid vector is derived from an approximately 2972 base pair HindIII to BamHI restriction fragment of pSP64 (Promega). Fragment 1 is an approximately 1484 base pair Bgl II to AccI restriction sub-fragment of the SPV HindIII restriction fragment M (23). Fragment 2 is an approximately 475 base pair fragment with EcoRI and BamHI restriction sites at the ends. The EcoRI and BamHI sites are synthesized by PCR cloning. The PCR product contains the entire amino acid coding sequence of the IBRV gE gene. In the PCR cloning procedure, the primers described below were used with a template consisting of the IBR-000 virus (Cooper strain) (44). The first primer 2/94.5DR (5'-CTGGTTCGGCCC-AGAATTCGATGCAACCCACCGCGCCGCCCCG-3') (SEQ ID NO. 116) sits down on the IBR gpE gene at amino acid number 1 and introduces an EcoRI site at the 5' end of the IBRV gE gene and adds two additional amino acids at the amino terminus of the protein. The second primer 4/93.18DR (5'-CTCGCTCGCCCAGGATCCCTAGCGG-AGGATGGACTTGAGTCG-3,) (SEQ ID NO. 117) sits down on the IBRV gE sequence (44) at approximately amino acid 648 on the opposite strand to the first primer and primes synthesis toward the 5' end of the IBRV gE gene. The PCR product was digested with EcoRI and BamHI to yield a fragment approximately 1950 base pairs in length corresponding to the IBRV gE gene. Fragment 3 is an approximately 3002 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 723-59A9.22. The plasmid 723-59A9.22 was used to insert foreign DNA into SPV. It incorporates an E. coli β-galactosidase (lacZ) marker gene and the equine influenza virus NA PR/56 gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β-galactosidase (lacZ) marker gene is under the control of a synthetic late pox promoter (LP1) and the EIV PR/56 NA gene is under the control of a synthetic late/early pox promoter (LP2EP2). A detailed description of the plasmid is given in FIGS. 18A, 18B, 18C and 18D. The homology vector was constructed utilizing standard recombinant DNA techniques (22 and 30), by joining restriction fragments from the following sources with the appropriate synthetic DNA sequences. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 2 is the NA gene coding region from the equine Influenza A/Prague/56 (serotype 1 (N7) virus) cloned as an approximately 1450 base pair BamHI fragment-utilizing the following primers 5'-G<u>GGATCC</u>ATGAATCCTAATCAAAAACTCTTT-3' (SEQ ID NO: 118) for cDNA priming and combined with 5'-G<u>GGATCC</u>TTACGAAAAGTATTTAATTTGTGC-3' (SEQ ID NO: 119) for PCR. (see CLONING OF EQUINE INFLUENZA VIRUS HEMAGGLUTININ AND NEURAMINIDASE GENES). Fragment 3 is an approximately 3010 base pair BamHI to PvuII restriction fragment of plasmid pJF751 (11). Fragment 4 is an approximately 2149 base pair AccI to HindIII restriction sub-fragment of the SPV HindIII restriction fragment M (23). The AccI site in the SPV homology vector is converted to a unique NotI site.

HOMOLOGY VECTOR 727-54.60. The plasmid 727-54.60 was constructed for the purpose of inserting foreign DNA into SPV. It incorporates an E. coli β-galactosidase (lacz) marker gene and the pseudorabies virus (PRV) gII (gpB) gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the PRV gB gene is under the control of a synthetic late/early pox promoter (LP2EP2). A detailed description of the plasmid is given in FIGS. 19A, 19B, 19C, and 19D. It may be constructed utilizing standard recombinant DNA techniques (22, 30), by joining restriction fragments from the following sources with the synthetic DNA sequences indicated in FIGS. 19A to 19D. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3500 base pair fragment which contains the coding sequence for the PRV gB gene within the KpnI C fragment of genomic PRV DNA(21). Fragment 2 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M (23). The AccI sites in fragments 1 and 4 were-converted to unique NotI sites using NotI linkers.

HOMOLOGY VECTOR 727-67.18. The plasmid 727-67.18 was constructed for the purpose of inserting foreign DNA into SPV. It incorporates an E. coli β-galactosidase (lacZ) marker gene and the hepatitis B virus core antigen gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the hepatitis B core antigen gene is under the control of a synthetic early/late pox promoter (EP1LP2). A detailed description of the plasmid is given in FIGS. 20A, 20B, 20C and 20D. It may be constructed utilizing standard recombinant DNA techniques (22, 30), by joining restriction fragments from the following sources with the synthetic DNA sequences indicated in FIGS. 20A to 20D. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 589 base pair fragment with BamHI and EcoRI restriction sites at the ends. This fragment contains the hepatitis B core antigen coding sequences (amino acids 25–212) (Ref. 45, 50). Fragment 4 is an approximately 2149 base pair AccI to HindIII subfragment of the SPV HindIII fragment M. The AccI sites in fragments 1 and 4 were converted to unique NotI sites using NotI linkers.

CLONING OF EQUINE INFLUENZA VIRUS HEMAGGLUTININ AND NEURAMINIDASE GENES. The equine influenza virus hemagglutinin (HA) and Neuraminidase (NA) genes may be cloned essentially as described by Katz et al. (42) for the HA gene of human influenza virus. Viral RNA prepared from virus grown in MDBK cells (for Influenza A/equine/Alaska/91 and Influenza A/equine/Miami/63) and MDCK cells (for Influenza A/equine/Prague/56 and Influenza A/equine/Kentucky/81) is first converted to cDNA utilizing an oligo nucleotide primer specific for the target gene. The cDNA is then used as a template for PCR cloning (51) of the targeted gene region. The PCR primers are designed to incorporate restriction sites which permit the cloning of the amplified coding regions into vectors containing the appropriate signals for expression in EHV. One pair of oligo nucleotide primers will be required for each coding region. The HA gene coding regions from the serotype 2 (H3) viruses (Influenza A/equine/Miami/63, Influenza A/equine/Kentucky/81, and Influenza A/equine/Alaska/91) would be cloned utilizing the following primers 5'-GGAGGCCTTCATG-ACAGACAACCATTATTTTGATACTACTGA-3' (SEQ ID NO: 120) for cDNA priming and combined with 5'-GAAGGCCTTCTCAAATGCAAATGTTGCATCTGA-TGTTGCC-3' (SEQ ID NO: 121) for PCR. The HA gene coding region from the serotype 1 (H7) virus (Influenza A/equine/Prague/56) would be cloned utilizing the following primers 5'-GGGATCCATGAACACTCAAATT-CTAATATTAG-3' (SEQ ID NO: 122) for cDNA priming and combined with 5'-GGGATCCTTATAT-ACAAATAGTGCACCGCA-3' (SEQ ID NO: 123) for PCR. The NA gene coding regions from the serotype 2 (N8) viruses (Influenza A/equine/Miami/63, Influenza A/equine/ Kentucky/81, and Influenza A/equine/Alaska/91) would be cloned utilizing the following primers 5'-GGGTCGACATGAATCCAAATCAAAAGATAA-3' (SEQ ID NO: 124) for cDNA priming and combined with 5'-GGGTCGACTTACATCTTATCGATGTCAAA-3' (SEQ ID NO: 125) for PCR. The NA gene coding region from the serotype 1 (N7) virus (Influenza/A/equine/Prague/56) would be cloned utilizing the following primers 5'-GGGATCCATGAATCCTAATCAAAAACTCTTT-3' (SEQ ID NO: 118) for cDNA priming and combined with 5'-GGGATCCTTACGAAAAGTATTTAATTTGTGC-3' (SEQ ID NO: 119) for PCR. Note that this general strategy may be used to clone the coding regions of HA and NA genes from other strains of equine influenza A virus. The EIV HA or NA genes are cloned as a blunt ended SalI or BamHI fragment into a blunt ended EcoRI site behind the LP2EP2 promoter of the SPV homology vector.

HOMOLOGY VECTOR 732-18.4. The plasmid 732-18.4 was used to insert foreign DNA into SPV. It incorporates an E. coli β-galactosidase (lacZ) marker gene and the equine influenza virus AK/91 NA gene flanked by SPV DNA. When this plasmic was used according to the HOMOLOGOUS RECOMBINATION PROCEDURE FOR GENERATING RECOMBINANT SPV a virus containing DNA coding for the foreign genes results. Note that the β-galactosidase (lacZ) marker gene is under the control of a synthetic late pox promoter (LP1) and the EIV AK/91 NA gene is under the control of a synthetic late/early pox promoter (LP2EP2). A detail description of the plasmid is given in FIGS. 21A, 21B, 21C and 21D. The homology vector was constructed utilizing standard recombinant DNA techniques (22 and 30), by joining restriction fragments from the following sources with the appropriate synthetic DNA sequences. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 2 is the NA gene coding region from the equine Influenza A/Alaska/91 (serotype 2 (N8) virus) cloned as an approximately 1450 base pair SalI fragment utilizing the following primers 5'-G GGTCGACATGAATCCAAATCAAAAGATAA-3' (SEQ ID NO: 124) for cDNA priming and combined with 5'-GG GTCGACTTACATCTTATCGATGTCAAA-3' (SEQ ID NO: 125) for PCR (see CLONING OF EQUINE INFLUENZA VIRUS HEMAGGLUTININ AND NEURAMINIDASE GENES). Fragment 3 is an approximately 3010 base pair BamHI to PvuII restriction fragment of plasmid pJF751 (11). Fragment 4 is an approximately 2149 base pair AccI to HindIII restriction sub-fragment of the SPV HindIII restriction fragment M (23). The AccI site in the SPV homology vector is converted to a unique NotI site.

Figure 22A:
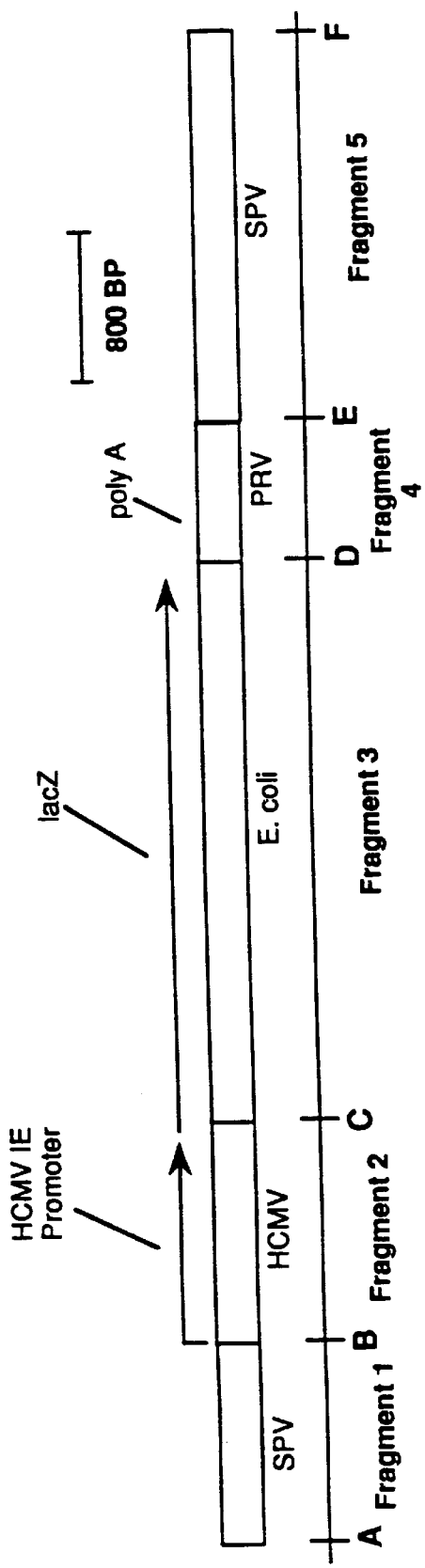
Figure 22B:
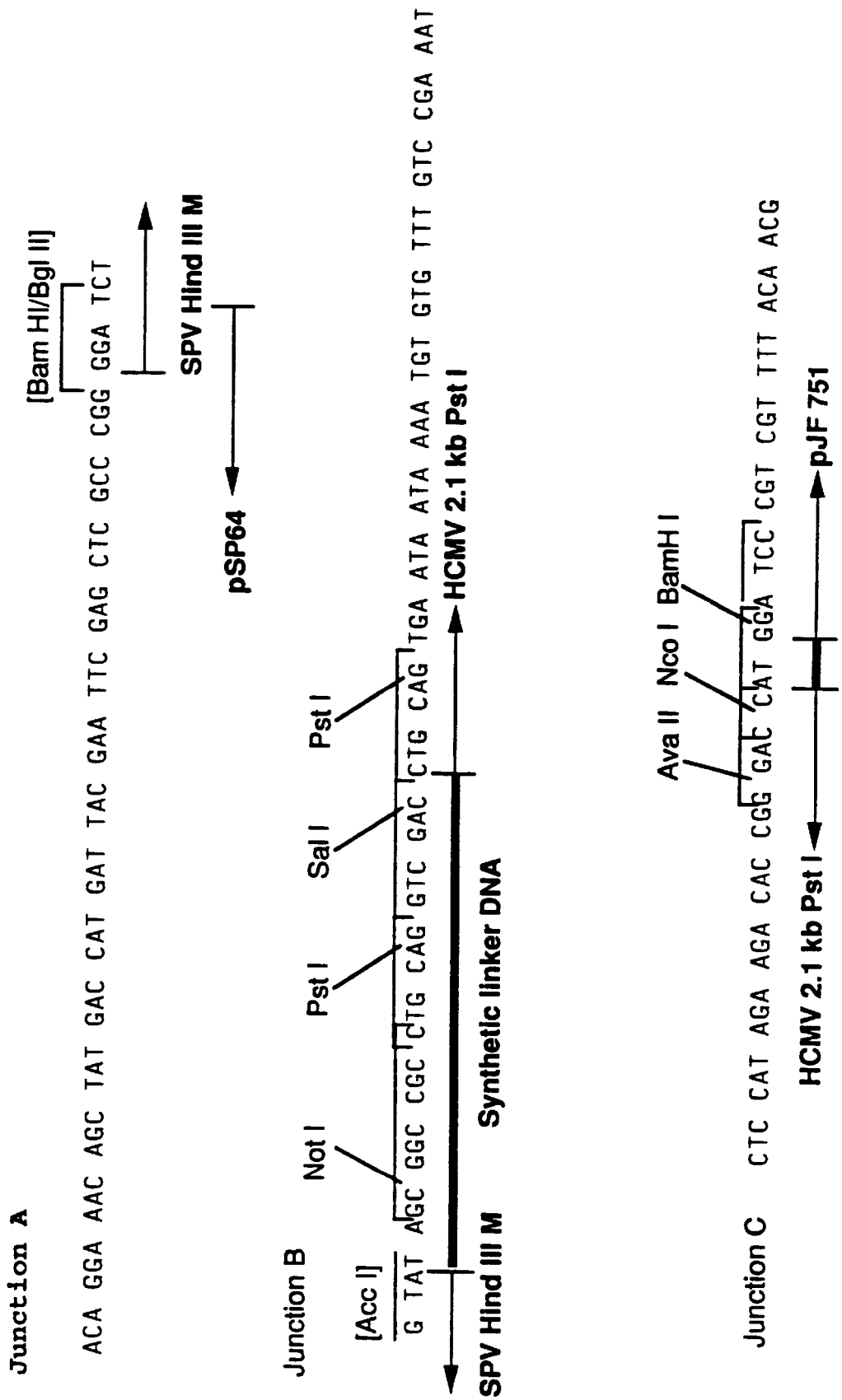

HOMOLOGY VECTOR 741-80.3 The plasmid 741-80.3 was constructed for the purpose of inserting foreign DNA into SPV. It incorporates an *E. coli* β-galactosidase (lacZ) marker gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a human cytomegalovirus immediate early (HCMV IE) promoter. A detailed description of the plasmid is given in FIGS. 22A, 22B and 22C. It may be constructed utilizing standard recombinant DNA techniques (22, 30), by joining restriction fragments from the following sources with the synthetic DNA sequences indicated in FIGS. 22A to 22C. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23) Fragment 2 is a 1154 base pair PstI to AvaII fragment derived from a HCMV 2.1 kb PstI fragment containing the HCMV IE promoter (46). Fragment 3 is a 3010 base pair BamHI to PvuII fragment derived from plasmid pJF751 (49) containing the *E. coli* lacZ gene. Fragment 4 is an approximately 750 base pair NdeI to SalI fragment derived from PRV BamHI #7 which contains the carboxy-terminal 19 amino acids and the polyadenylation signal of the PRV gX gene. Fragment 5 is an approximately 2149 base pair AccI to HindIII subfragment of the SPV HindIII fragment M. The AccI sites in fragments 1 and 5 were converted to unique NotI sites using NotI linkers.

HOMOLOGY VECTOR 741-84.14. The plasmid 741-84.14 was constructed for the purpose of inserting foreign DNA into SPV. It incorporates an *E. coli* β-galactosidase (lacZ) marker gene and the human interleukin-2 (IL-2) gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the human IL-2 gene is under the control of a synthetic late/early pox promoter (LP2EP2). The coding sequence for the human IL-2 protein is fused at the amino terminus to the PRV gX signal sequence for membrane transport. A detailed description of the plasmid is given in FIGS. 23A, 23B, 23C, and 23D. It may be constructed utilizing standard recombinant DNA techniques (22, 30), by joining restriction fragments from the following sources with the synthetic DNA sequences indicated in FIGS. 23A to 23D. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 475 base pair fragment with EcoRI and BglII restriction sites at the ends. The EcoRI site is synthesized by PCR cloning and the BglII site is at the 3' end of the human IL-2 cDNA (43, 47). The PCR product contains the entire amino acid coding sequence of the PRV gX signal sequence-human IL-2 gene. In this procedure, the primers described below were used with a template consisting of the cDNA for PRV gX signal sequence-human IL-2 (43). The first primer 5/94.23 (5'-CTCGAATTCGAAGTGGGCAACGTGGATCCTCGC-3') (SEQ ID NO 126) sits down on the PRV gX signal sequence at amino acid number 1 and introduces an EcoRI site at the 5' end of the gene. The second primer 5/94.24 (5'-CAGTTAGCCTCCCCCATCTCCCCA-3') (SEQ ID NO. 127) sits down on the human IL-2 gene sequence within the 3' untranslated region on the opposite strand to primer 5/94.23 and primes toward the 5 end of the gene. The PCR product was digested with EcoRI and BglII (BglII is located approximately 3 nucleotides beyond the stop codon for the human IL-2 gene, to yield a fragment 475 base pairs in length corresponding to the PRV gX signal sequence-human IL-2 gene. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 744-34. The plasmid 744-34 was constructed for the purpose of inserting foreign DNA into SPV. It incorporates an *E. coli* β-galactosidase (lacZ) marker gene and the equine herpesvirus type 1 gB gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the EHV-1 gB gene is under the control of a synthetic late/early pox promoter (LP2EP2). A detailed description of the plasmid is given in FIGS. 24A, 24B, 24C and 24D. It may be constructed utilizing standard recombinant DNA techniques (22, 30), by joining restriction fragments from the following sources with the synthetic DNA sequences indicated in FIGS. 24A to 24D The plasmid vector is derived from an approximately 2972 base pair HindIII to BamHI restriction fragment of pSP64 (Promega). Fragment 1 is an approximately 1484 base pair Bgl II to AccI restriction sub-fragment of the SPV HindIII restriction fragment M (23). Fragment 2 is an approximately 2941 base pair fragment with EcoRI and PmeI restriction sites at the ends. Fragment 2 is an approximately 2941 base pair EcoRI to PmeI fragment. Fragment 2 was synthesized as an approximately 429 base pair PCR fragment at the 5' end of the gene having a synthetic EcoRI site and a natural BamHI site within the BamHI "a" fragment of EHV-1 genomic DNA and an approximately 2512 base pair restriction fragment at the 3' end of the gene from BamHI to PmeI within the BamHI "i" fragment of EHV-1 genomic DNA (48). In the procedure to produce the 5' end PCR fragment, the primers described below were used with a template consisting of the EHV-1 BamHI "a" and "i" fragments. The first primer 5/94.3 (5'-CGGAATTCCTCTGGTTGCCGT-3') (SEQ ID NO 128) sits down on the EHV-1 gB sequence at amino acid number 2 and introduces an EcoRI site at the 5' end of the EHV-1 gB gene and an ATG start codon. The second primer 5/94.4 (5'-GACGGTGGATCCGGTAGGCGGT-3') (SEQ ID NO. 129) sits down on the EHV-1 gB sequence at approximately amino acid 144 on the opposite strand to primer 5/94.3 and primes toward the 5' end of the gene. The PCR product was digested with EcoRI and BamHI to yield a fragment 429 base pairs in length corresponding to the 5' end of the EHV-1 gB gene. Fragment 2 consists of the products of the PCR reaction (EcoRI to BamHI) and the restriction fragment (BamHI to PmeI) ligated together to yield an EHV-1 gB gene which is an EcoRI to PmeI fragment approximately 2941 base pairs (979 amino acids) in length. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 744-38. The plasmid 744-38 was constructed for the purpose of inserting foreign DNA into SPV. It incorporates an E. coli β-galactosidase (lacZ) marker gene and the equine herpesvirus type 1 gD gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the EHV-1 gD gene is under the control of a synthetic late/early pox promoter (LP2EP2). A detailed description of the plasmid is given in FIGS. 25A, 25B, 25C and 25D. It may be constructed utilizing standard recombinant DNA techniques (22, 30), by joining restriction fragments from the following sources with the synthetic DNA sequences indicated in FIGS. 25A to 25D. The plasmid vector is derived from an approximately 2972 base pair HindIII to BamHI restriction fragment of pSP64 (Promega). Fragment 1 is an approximately 1484 base pair Bgl II to AccI restriction sub-fragment of the SPV HindIII restriction fragment M (23). Fragment 2 is an approximately 1240 base pair HindIII fragment within the BamHI "d" fragment of EHV-1 (48). Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

CLONING OF PARAINFLUENZA-3 VIRUS FUSION AND HEMAGGLUTININ GENES. The parainfluenza-3 virus fusion (F) and hemagglutinin (HN) genes were cloned by a PCR CLONING procedure essentially as described by Katz et al. (42) for the HA gene of human influenza. Viral RNA prepared from bovine PI-3 virus grown in Madin-Darby bovine kidney (MDBK) cells was first converted to cDNA utilizing an oligonucleotide primer specific for the target gene. The cDNA was then used as a template for polymerase chain reaction (PCR) cloning (15) of the targeted region. The PCR primers were designed to incorporate restriction sites which permit the cloning of the amplified coding regions into vectors containing the appropriate signals for expression in SPV. One pair of oligonucleotides were required for each coding region. The F gene coding region from the PI-3 strain SF-4 (VR-281) was cloned using the following primers: 5'-TTATGGATCCTGC-TGCTGTGTTGAACAACTTTGT-3' (SEQ ID NO: 130) for cDNA priming and combined with 5'-CCG-CGGATCCCATGACCATCACAACCATAATCATAGCC-3' (SEQ ID NO: 131) for PCR. The HN gene coding region from PI-3 strain SF-4 (VR-281) was cloned utilizing the following primers: 5'-CGTCGGATCCCTT-AGCTGCAGTTTTTTGGAACTTCTGTTTTGA-3' (SEQ ID NO: 132) for cDNA priming and combined with 5'-CATAGGATCCCATGGAATATTGGAAACACACAA-ACAGCAC-3' (SEQ ID NO: 133) for PCR. Note that this general strategy is used to clone the coding region of F and HN genes from other strains of PI-3. The DNA fragment for PI-3 HN or F was digested with BamHI to yield an 1730 bp or 1620 bp fragment, respectively. The PI-3 HN fragment is cloned into the BamHI site next to the LP2EP2 promoter of the SPV homology vector. The PI-3 F fragment is cloned into the BamHI site next to the LP2EP2 promoter of the SPV homology vector to yield homology vector 713-55.10.

CLONING OF BOVINE VIRAL DIARRHEA VIRUS gp48 and gp53 GENES. The bovine viral diarrhea gp48 and gp53 genes were cloned by a PCR CLONING procedure essentially as described by Katz et al. (42) for the HA gene of human influenza. Viral RNA prepared from BVD virus Singer strain grown in Madin-Darby bovine kidney (MDBK) cells was first converted to cDNA utilizing an oligonucleotide primer specific for the target gene. The cDNA was then used as a template for polymerase chain reaction (PCR) cloning (15) of the targeted region. The PCR primers were designed to incorporate restriction sites which permit the cloning of the amplified coding regions into vectors containing the appropriate signals for expression in SPV. One pair of oligonucleotides were required for each coding region. The gp48 gene coding region from the BVDV Singer strain (49) was cloned using the following primers: 5'-ACGTCGGATCCCTTACCAAACCACG-TCTTACTCTTGTTTTCC-3' (SEQ ID NO: 134) for cDNA priming and combined with 5'-ACATAGGA-TCCCATGGGAGAAAACATAACACAGTGGAACC-3' (SEQ ID NO: 135) for PCR. The gp53 gene coding region from the BVDV Singer strain (49) was cloned using the following primers: 5'-CGTGGATCCTCAATTACAA-GAGGTATCGTCTAC-3' (SEQ ID NO: 136) for cDNA priming and combined with 5'-CATAGATCTT-GTGGTGCTGTCCGACTTCGCA-3' (SEQ ID NO: 137) for PCR. Note that this general strategy is used to clone the coding region of gp48 and gp53 genes from other strains of BVDV. The DNA fragment for BVDV gp 48 was digested with BamHI to yield an 678 bp fragment. The DNA fragment for BVDV gp 53 was digested with BglII and BamHI to yield an 1187 bp fragment. The BVDV gp48 or gp53 DNA fragments were cloned into the BamHI site next to the LP2EP2 promoter of the SPV homology vector to yield homology vectors, 727-78.1 and 738-96, respectively.

CLONING OF BOVINE RESPIRATORY SYNCYTIAL VIRUS FUSION, NUCLEOCAPSID AND GLYCOPROTEIN GENES. The bovine respiratory syncytial virus fusion (F), nucleocapsid (N), and glycoprotein (G) genes were cloned by a PCR CLONING procedure essentially as described by Katz et al. (42) for the HA gene of human influenza. Viral RNA prepared from BRSV virus grown in bovine nasal turbinate (BT) cells was first converted to cDNA utilizing an oligonucleotide primer specific for the target gene. The cDNA was then used as a template for polymerase chain reaction (PCR) cloning (15) of the targeted region. The PCR primers were designed to incorporate restriction sites which permit the cloning of the amplified coding regions into vectors containing the appropriate signals for expression in SPV. One pair of oligonucleotides were required for each coding region. The F gene coding region from the BRSV strain 375 (VR-1339) was cloned using the following primers: 5'-TGCAGG-ATCCTCATTTACTAAAGGAAAGATTGTTGAT-3' (SEQ ID NO: 138) for cDNA priming and combined with 5'-CTCTGGATCCTACAGCCATGAGGATGATCATCA-GC-3' (SEQ ID NO: 139) for PCR. The N gene coding region from BRSV strain 375 (VR-1339) was cloned utilizing the following primers: 5'-CGTCGG-ATCCCTCACAGTTCCACATCATTGTCTTTGGGAT-3' (SEQ ID NO: 140) for cDNA priming and combined with 5'-CTTAGGATCCCATGGCTCTTAGCAAGGTCAAAC-TAAATGAC-3' (SEQ ID NO: 141) for PCR. The G gene coding region from BRSV strain 375 (VR-1339) was cloned utilizing the following primers: 5'-CGTT-GGATCCCTAGATCTGTGTAGTTGATTGATTTGTGT-GA-3' (SEQ ID NO: 142) for cDNA priming and combined with 5'-CTCTGGATCCTCATACCCATCATCTTAAATTC-AAGACATTA-3' (SEQ ID NO: 143) for PCR. Note that this general strategy is used to clone the coding region of F, N and G genes from other strains of BRSV. The DNA fragments for BRSV F, N, or G were digested with BamHI to yield 1722 bp, 1173 bp, or 771 bp fragments, respectively. The BRSV F, N, and G DNA fragments were cloned into the BamHI site next to the LP2EP2 promoter of the SPV homology vector to yield homology vectors, 727-20.10, 713-55.37 and 727-20.5, respectively.

HOMOLOGY VECTOR 689-50.4 The plasmid 689-50.4 was constructed for the purpose of inserting foreign DNA into SPV. It incorporates an *E. coli* β-galactosidase (lacz) marker gene and the infectious bursal disease virus (IBDV) polyprotein gene flanked by SPV DNA. Upstream of the foreign genes is an approximately 1484 base pair fragment of SPV DNA. Downstream of the foreign genes is ar. approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the IBDV polyprotein gene is under the control of a synthetic late/early pox promoter (LP2EP2). It may be constructed utilizing standard recombinant DNA techniques (22, 30), by joining restriction fragments from the following sources. The plasmid vector is derived from an approximately 2972 base pair Hind III to BamHI restriction fragment of pSP64 (Promega). Fragment 1 is an approximately 1484 base pair BglII to AccI restriction subfragment of the SPV HindIII restriction fragment M (23). Fragment 2 is an approximately 3400 base pair fragment with SmaI and HpaI restriction sites at the ends from plasmid 2-84/2-40 (51). This fragment contains the IBDV polyprotein coding sequences. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 689-50.7. The plasmid 689-50.7 was constructed for the purpose of inserting foreign DNA into SPV. It incorporates an *E. coli* β-galactosidase (lacZ) marker gene and the infectious bursal disease virus (IBDV) VP2 gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the IBDV VP2 gene is under the control of a synthetic late/early pox promoter (LP2EP2). It may be constructed utilizing standard recombinant DNA techniques (22, 30), by joining restriction fragments from the following sources. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1081 base pair fragment with BclI and BamHI restriction sites at the ends. This fragment codes for the IBDV VP2 protein and is derived from a full length IBDV cDNA clone (51). Fragment 3 is an approximately 3010 base pair BamHI to PvuII restriction fragment of plasmid pJF751 (11). Fragment 4 is an approximately 2149 base pair AccI to HindIII sub-fragment of the SPV HindIII fragment M. The AccI sites in fragments 1 and 4 were converted to unique NotI sites using NotI linkers.

EXAMPLES

Example 1

Homology Vector 515-85.1. The homology vector 515-85.1 is a plasmid useful for the insertion of foreign DNA into SPV. Plasmid 515-85.1 contains a unique AccI restriction site into which foreign DNA may be cloned. A plasmid containing such a foreign DNA insert may be used according to the HOMOLOGOUS RECOMBINATION PROCEDURE FOR GENERATING RECOMBINANT SPV to generate a SPV containing the foreign DNA. For this procedure to be successful it is important that the insertion site (AccI) be in a region non-essential to the replication of the SPV and that the site be flanked with swinepox virus DNA appropriate for mediating homologous recombination between virus and plasmid DNAs. We have demonstrated that the AccI site in homology vector 515-85.1 may be used to insert foreign DNA into at least three recombinant SPV (see examples 2-4).

Figure 1B:
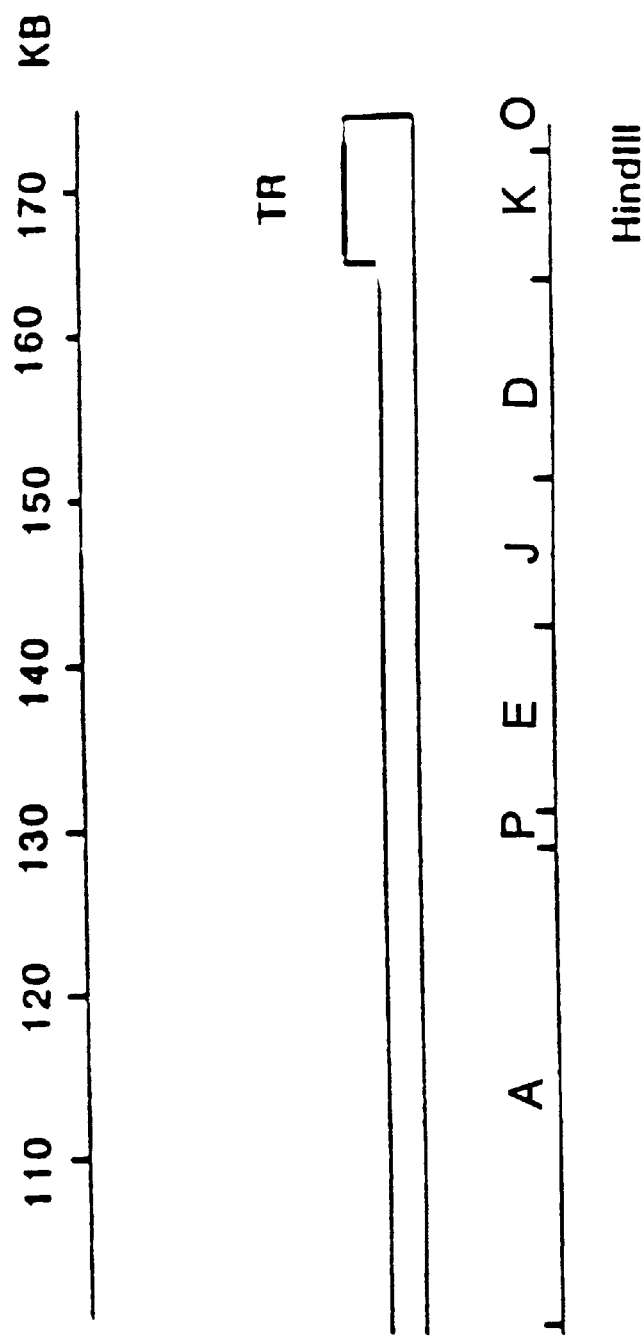

In order to define an appropriate insertion site, a library of SPV HindIII restriction fragments was generated. Several of these restriction fragments (HindIII fragments G, J, and M see FIGS. 1A and 1B) were subjected to restriction mapping analysis. Two restriction sites were identified in each fragment as potential insertion sites. These sites included HpaI and NruI in fragment G, BalI and XbaI in fragment J, and AccI and PstI in fragment M. A β-galactosidase (lacZ) marker gene was inserted in each of the potential sites. The resulting plasmids were utilized in the HOMOLOGOUS RECOMBINATION PROCEDURE FOR GENERATING RECOMBINANT SPV. The generation of recombinant virus was determined by the SCREEN FOR RECOMBINANT SPV EXPRESSING β-GALACTOSIDASE ASSAYS. Four of the six sites were found to generate recombinant virus, however the ability of each of these viruses to be purified away from the parental SPV varied greatly. In one case virus could not be purified above the level of 1%, in another case virus could not be purified above the level of 50%, and in a third case virus could not be purified above the level of 90%. The inability to purify these viruses indicates instability at the insertion site. This makes the corresponding sites inappropriate for insertion of foreign DNA. However the insertion at one site, the AccI site of Homology vector 515-85.1, resulted in a virus which was easily purified to 100% (see example 2), clearly defining an appropriate site for the insertion of foreign DNA.

Figure 3A:
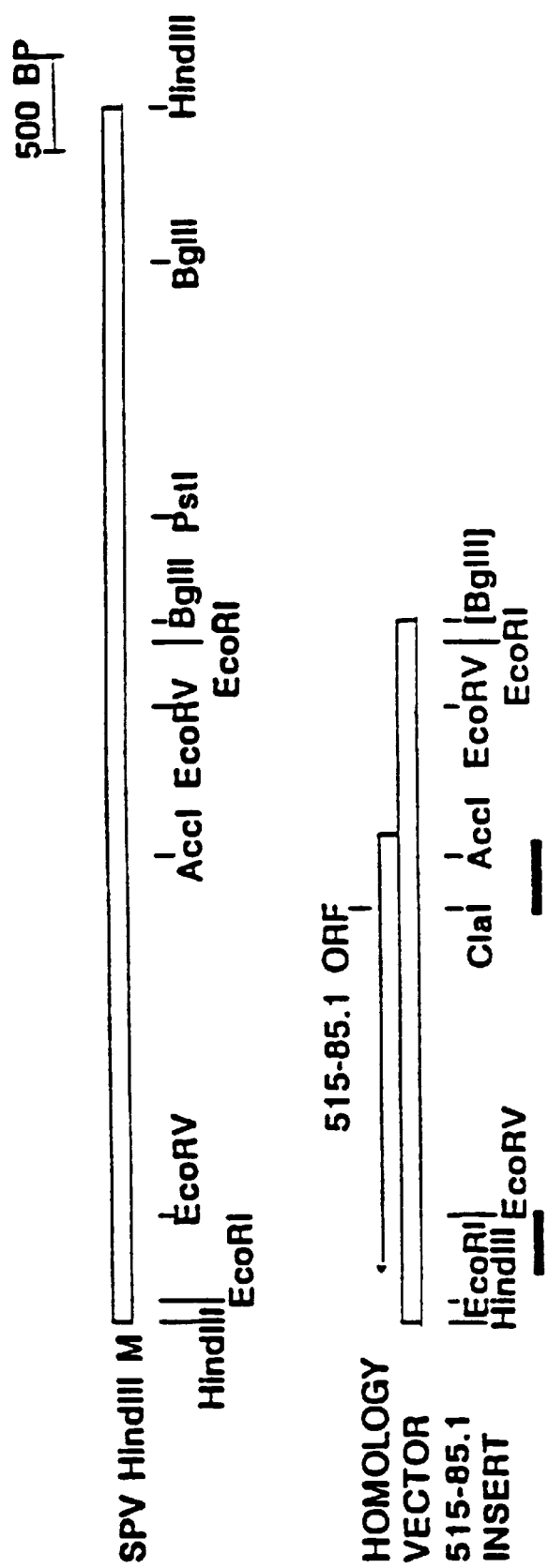
Figure 3C:
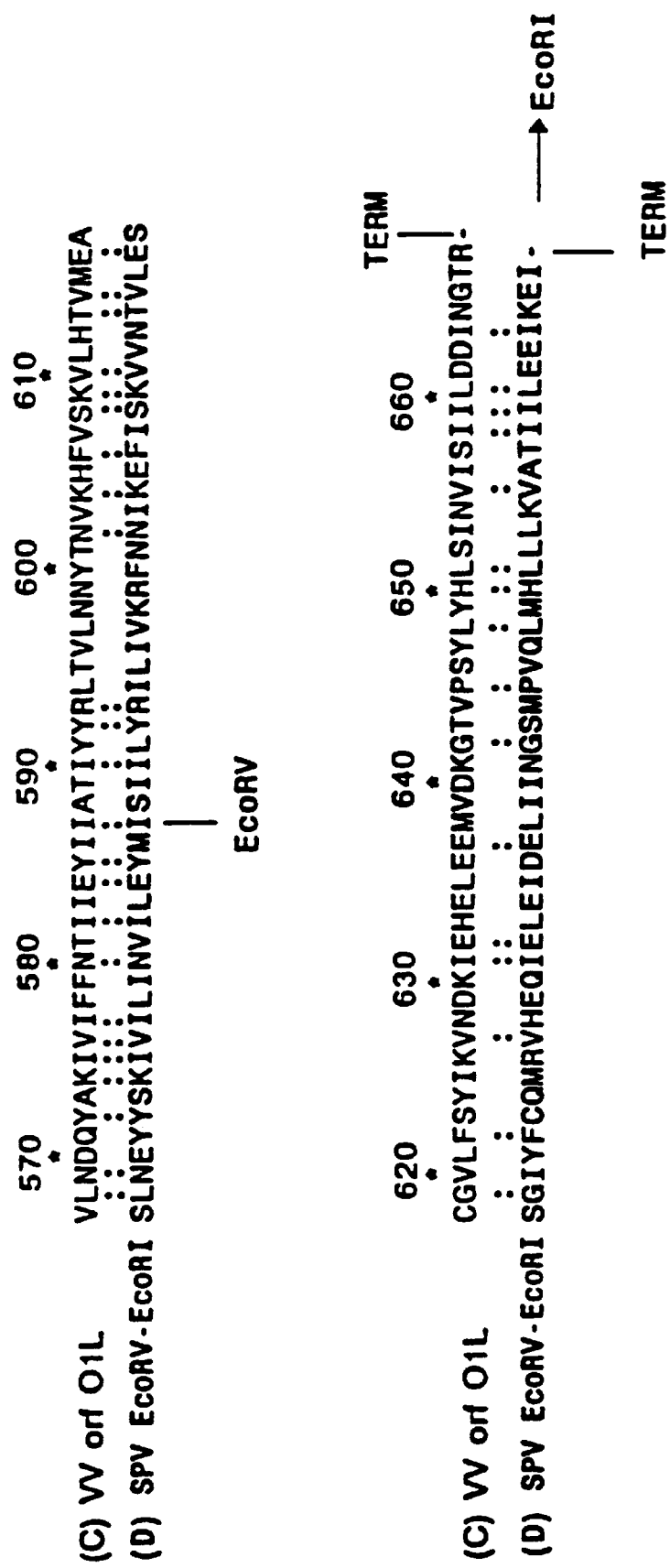

The homology vector 515-85.1 was further characterized by DNA sequence analysis. Two regions of the homology vector were sequenced. The first region covers a 599 base pair sequence which flanks the unique AccI site (see FIGS. 2A and 2B). The second region covers the 899 base pairs upstream of the unique HindIII site (see FIGS. 2A and 2B). The sequence of the first region codes for an open reading frame (ORF) which shows homology to amino acids 1 to 115 of the vaccinia virus (VV) O1L open reading frame identified by Goebel et al, 1990 (see FIGS. 3A, 3B and 3C). The sequence of the second region codes for an open reading frame which shows homology to amino acids 568 to 666 of the same vaccinia virus O1L open reading frame (see FIGS. 3A, 3B and 3C). These data suggest that the AccI site interrupts the presumptive VV O1L-like ORF at approximately amino acid 41, suggesting that this ORF codes for a gene non-essential for SPV replication. Goebel et al. suggest that the VV O1L ORF contains a leucine zipper motif characteristic of certain eukaryotic transcriptional regulatory proteins, however they indicate that it is not known whether this gene is essential for virus replication. The DNA sequence located upstream of the VV 01L-like ORF (see FIG. 2A) would be expected to contain a swinepox viral promoter. This swinepox viral promoter will be useful as the control element of foreign DNA introduced into the swinepox genome.

Example 2

S-SPV-003

S-SPV-003 is a swinepox virus that expresses a foreign gene. The gene for E.coli β-galactosidase (lacZ gene) was inserted into the SPV 515-85.1 ORF. The foreign gene (lacz) is under the control of a synthetic early/late promoter (EP1LP2).

S-SPV-003 was derived from S-SPV-001 (Kasza strain). This was accomplished utilizing the homology vector 520-17.5 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-003. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable and expressing the foreign gene. The assays described here were carried out in VERO cells as well as EMSK cells, indicating that VERO cells would be a suitable substrate for the production of SPV recombinant vaccines. S-SPV-003 has been deposited with the ATCC under Accession No. VR 2335.

Example 3

S-SPV-008

S-SPV-008 is a swinepox virus that expresses at least two foreign genes. The gene for E. coli β-galactosidase (lacz gene) and the gene for pseudorabies virus (PRV) g50 (gpD) (26) were inserted into the SPV 515-85.1 ORF. The lacZ gene is under the control of a synthetic late promoter (LP1) and the g50 (gp)D gene is under the control of a synthetic early/late promoter (EP1LP2).

S-SPV-008 was derived from S-SPV-001 (Kasza strain). This was accomplished utilizing the homology vector 538-46.16 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-008. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable and expressing the marker gene.

S-SPV-008 was assayed for expression of PRV specific antigens using the BLACK PLAQUE SCREEN FOR FOREIGN GENE EXPRESSION IN RECOMBINANT SPV. Swine anti-PRV serum was shown to react specifically with S-SPV-008 plaques and not with S-SPV-009 negative control plaques. All S-SPV-008 observed plaques reacted with the swine antiserum indicating that the virus was stably expressing the PRV foreign gene. The black plaque assay was also performed on unfixed monolayers. The SPV plaques on the unfixed monolayers also exhibited specific reactivity with swine anti-PRV serum indicating that the PRV antigen is expressed on the infected cell surface.

To confirm the expression of the PRV g50 (gpD) gene product, cells were infected with SPV and samples of infected cell lysates were subjected to SDS-polyacrylamide gel electrophoresis. The gel was blotted and analyzed using the WESTERN BLOTTING PROCEDURE. The swine anti-PRV serum was used to detect expression of PRV specific proteins. As shown in FIG. 6, the lysate from S-SPV-008 infected cells exhibits a specific band of approximately 48 kd, the reported size of PRV g50 (gpD) (35).

PRV g50 (gpD) is the g50 (gpD) homologue of HSV-1 (26). Several investigators have shown that VV expressing HSV-1 g50 (gpD) will protect mice against challenge with HSV-1 (6 and 34). Therefore the S-SPV-008 should be valuable as a vaccine to protect swine against PRV disease.

It is anticipated that several other PRV glycoproteins will be useful in the creation of recombinant swinepox vaccines to protect against PRV disease. These PRV glycoproteins include gpII (28), gpIII (27), and gpH (19). The PRV gpIII coding region has been engineered behind several synthetic pox promoters. The techniques utilized for the creation of S-SPV-008 will be used to create recombinant swinepox viruses expressing all four of these PRV glycoprotein genes. Such recombinant swinepox viruses will be useful as vaccines against PRV disease. Since the PRV vaccines described here do not express PRV gpX or gpI, they would be compatible with current PRV diagnostic tests (gX HerdChek®, gI HerdChek® and ClinEase®) which are utilized to distinguish vaccinated animals from infected animals. S-SPV-008 has been deposited with the ATCC under Accession No. VR 2339.

Example 4

S-SPV- 011

S-SPV-011 is a swinepox virus that expresses at least two foreign genes. The gene for E. coli B-galactosidase (lacZ) and the gene for pseudorabies virus gIII (gpC) were inserted into the unique PstI restriction site (PstI linkers inserted into a unique AccI site) of the homology vector 570-33.32. The lac Z gene is under the control of the synthetic late promoter (LP1) and the PRV gIII (gpC) gene is under the control of the synthetic early promoter (EP2).

S-SPV-011 was derived from S-SPV-001 (Kasza Strain). This was accomplished utilizing the homology vector 570-91.21 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-011. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-011 was assayed for expression of PRV specific antigens using the BLACK PLAQUE SCREEN FOR FOREIGN GENE EXPRESSION IN RECOMBINANT SPV. Polyclonal goat anti-PRV gIII (gpC) antibody was shown to react specifically with S-SPV- 011 plaques and not with S-SPV-001 negative control plaques. All S-SPV-011 observed plaques reacted with the swine anti-PRV serum indicating that the virus was stably expressing the PRV foreign gene. The assays described here were carried out in EMSK cells, indicating that EMSK cells would be a suitable substrate for the production of SPV recombinant vaccines.

To confirm the expression of the PRV gIII (gpC) gene product, cells were infected with SPV and samples of infected cell lysates were subjected to SDS-polyacrylamide gel electrophoresis. The gel was blotted and analyzed using the WESTERN BLOTTING PROCEDURE. Polyclonal goat anti-PRV gIII (gpC) antibody was used to detect expression of PRV specific proteins. As shown in FIG. 16, the lysate from S-SPV-011 infected cells exhibits a specific band of approximately 92 kd, the reported size of PRV gIII (gpC) (37).

Recombinant-expressed PRV gIII (gpC) has been shown to elicit a significant immune response in mice and swine (37, 38). Furthermore, when gIII (gpC) is coexpressed with gII (gpB) or g50 (gpD), significant protection from challenge with virulent PRV is obtained (39). Therefore S-SPV-011 should be valuable as a vaccine to protect swine against PRV disease. Since the PRV vaccines described here do not express PRV gpX or gpI, they would be compatible with current PRV diagnostic tests (gX HerdChek®, gI HerdChek® and ClinEase®) which are utilized to distinguish vaccinated animals from infected animals.

Example 5

S-SPV-012

S-SPV-012 is a swinepox virus that expresses at least two foreign genes. The gene for E. coli B-galactosidase (lacz) and the gene for pseudorabies virus gIII (gpC) were inserted into the unique PstI restriction site (PstI linkers inserted into a unique AccI site) of the homology vector 570-33.32. The lacZ gene is under the control of the synthetic late promoter (LP1) and the PRV gIII (gpC) gene is under the control of the synthetic early late promoter (EP1LP2).

S-SPV-012 was derived from S-SPV-001 (Kasza Strain). This was accomplished utilizing the homology vector 570-91.41 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-012. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-012 was assayed for expression of PRV specific antigens using the BLACK PLAQUE SCREEN FOR FOREIGN GENE EXPRESSION IN RECOMBINANT SPV. Polyclonal goat anti-PRV gIII (gpC) antibody was shown to react specifically with S-SPV-012 plaques and not with S-SPV-001 negative control plaques. All S-SPV-012 observed plaques reacted with the swine anti-PRV serum, indicating that the virus was stably expressing the PRV foreign gene. The assays described here were carried out in EMSK and VERO cells, indicating that EMSK cells would be a suitable substrate for the production of SPV recombinant vaccines.

To confirm the expression of the PRV gIII (gpC) gene product, cells were infected with S-SPV-012 and samples of infected cell lysates were subjected to SDS-polyacrylamide gel electrophoresis. The gel was blotted and analyzed using the WESTERN BLOTTING PROCEDURE. Polyclonal goat anti-PRV gIII (gpC) antibody was used to detect expression of PRV specific proteins. As shown in FIG. 16, the lysate from S-SPV-012 infected cells exhibits two specific bands which are the reported size of PRV gIII (gpC) (37)—a 92 kd mature form and a 74 kd pre-golgi form.

Recombinant-expressed PRV gIII (gpC) has been shown to elicit a significant immune response in mice and swine (37, 38). Furthermore, when gIII (gpC) is coexpressed with gII (gpB) or g50 (gpD), significant protection from challenge with virulent PRV is obtained (39). Therefore S-SPV-012 should be valuable as a vaccine to protect swine against PRV disease. Since the PRV vaccines described here do not express PRV gpX or gpI, they would be compatible with current PRV diagnostic tests (gX HerdChek®, gI HerdChek® and ClinEase®) which are utilized to distinguish vaccinated animals from infected animals.

Example 6

S-SPV-013

S-SPV-013 is a swinepox virus that expresses at least two foreign genes. The gene for E. coli B-galactosidase (lacZ) and the gene for pseudorabies virus gill (gpC) were inserted into the unique PstI restriction site (PstI linkers inserted into a unique AccI site) of the homology vector 570-33.32. The lacZ gene is under the control of the synthetic late promoter (LP1) and the PRV gIII (gpC) gene is under the control of the synthetic late early promoter (LP2EP2).

S-SPV-013 was derived from S-SPV-001 (Kasza Strain). This was accomplished utilizing the homology vector 570-91.64 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-013. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-013 was assayed for expression of PRV specific antigens using the BLACK PLAQUE SCREEN FOR FOREIGN GENE EXPRESSION IN RECOMBINANT SPV. Polyclonal goat anti-PRV gIII (gpC) antibody was shown to react specifically with S-SPV-013 plaques and not with S-SPV-001 negative control plaques. All S-SPV-013 observed plaques reacted with the swine anti-PRV serum indicating that the virus was stably expressing the PRV foreign gene. The assays described here were carried out in EMSK and VERO cells, indicating that EMSK cells would be a suitable substrate for the production of SPV recombinant vaccines.

To confirm the expression of the PRV gIII (gpC) gene product, cells were infected with SPV and samples of infected cell lysates were subjected to SDS-polyacrylamide gel electrophoresis. The gel was blotted and analyzed using the WESTERN BLOTTING PROCEDURE. Polyclonal goat anti-PRV gIII (gpC) antibody was used to detect expression of PRV specific proteins. As shown in FIG. 16, the lysate from S-SPV-013 infected cells exhibits two specific bands which are the reported size of PRV gIII (gpC) (37)—a 92 kd mature form and a 74 kd pre-Golgi form.

Recombinant-expressed PRV gIII (gpC) has been shown to elicit a significant immune response in mice and swine (37, 38). Furthermore, when gIII (gpC) is coexpressed with gII (gpB) or g50 (gpD), significant protection from challenge with virulent PRV is obtained. (39) Therefore S-SPV-013 should be valuable as a vaccine to protect swine against PRV disease. Since the PRV vaccines described here do not express PRV gpX or gpI, they would be compatible with current PRV diagnostic tests (gX HerdChek®, gI HerdChek® and ClinEase®) which are utilized to distinguish vaccinated animals from infected animals. S-SPV-013 has been deposited with the ATCC.

Protection against Aujeszky's disease using recombinant swinepox virus vaccines S-SPV-008 and S-SPV-013.

A vaccine containing S-SPV-008 and S-SPV-013 (1 x 106PFU/ml) (2 ml of a 1:1 mixture of the two viruses) was given to two groups of pigs (5 pigs per group) by intradermal inoculation or by oral/pharyngeal spray. A control group of 5 pigs received S-SPV-001 by both intradermal and oral/pharyngeal inoculation. Pigs were challenged three weeks post-vaccination with virulent PRV, strain 4892, by intranasal inoculation. The table presents a summary of clinical responses. The data support an increase in protection against Aujeszky's disease in the S-SPV-008/S-SPV-013 vaccinates compared to the S-SPV-001 vaccinate controls.

| Vaccine | Route of inoculation | Post-challenge Respiratory Signs: (# with signs/total number) | Post-challenge CNS signs: (# with signs/total number) | Post-challenge Group average: (Days of clinical signs) |
|---|---|---|---|---|
| S-SPV-008 + S-SPV-013 | Intradermal | 3/5 | 0/5 | 2.6 |
| S-SPV-008 + S-SPV-013 | Oral/pharyngeal | 3/5 | 0/5 | 2.2 |
| S-SPV-001 (Control) | Intradermal + Oral/Pharyngeal | 5/5 | 2/5 | 7.8 |

Example 7

S-SPV-015

S-SPV-015 is a swinepox virus that expresses at least two foreign genes. The gene for E. coli β-galactosidase (lacZ) and the gene for pseudorabies virus (PRV) gII (gpB) were inserted into the SPV 617-48.1 ORF (a unique NotI restriction site has replaced a unique AccI restrict ion site). The lacZ gene is under the control of the synthetic late promoter (LP1), and the PRV gB gene is under the control of the synthetic late/early promoter (LP2EP2).

S-SPV-015 was derived from S-SPV-001 (Kasza Strain). This was accomplished utilizing the homology vector 727-54.60 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-015. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-015 was assayed for expression of PRV-specific antigens using the BLACK PLAQUE SCREEN FOR FOREIGN GENE EXPRESSION IN RECOMBINANT SPV. Polyclonal swine anti-PRV serum was shown to react specifically with S-SPV-015 plaques and not with S-SPV-001 negative control plaques. All S-SPV-015 observed plaques reacted with the antiserum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gII gene product, cells were infected with SPV-015 and samples of infected cell lysates were subjected to SDS-polyacrylamide gel electrophoresis. The gel was blotted and analyzed using the WESTERN BLOTTING PROCEDURE. Polyclonal swine anti-PRV serum was used to detect expression of PRV specific proteins. The lysate from S-SPV-015 infected cells exhibited bands corresponding to 120 kd, 67 kd and 58 kd, which are the expected size of the PRV gII glycoprotein.

S-SPV-015 is useful as a vaccine in swine against pseudorabies virus. A superior vaccine is formulated by combining S-SPV-008 (PRV g50), S-SPV-013 (PRV gIII), and S-SPV-015 for protection against pseudorabies in swine.

Therefore S-SPV-015 should be valuable as a vaccine to protect swine against PRV disease. Since the PRV vaccines described here do not express PRV gpX or gpI, they would be compatible with current PRV diagnostic tests (gX HerdChek®, gI HerdChek® and ClinEase®) which are utilized to distinguish vaccinated animals from infected animals. S-SPV-015 has been deposited with the ATCC.

Example 8

Recombinant swinepox virus expressing more than one pseudorabies virus (PRV) glycoproteins, which can elicit production of neutralizing antibodies against pseudorabies virus, is constructed in order to obtain a recombinant swinepox virus with enhanced ability to protect against PRV infection than that which can be obtained by using a recombinant swinepox virus expressing only one of those PRV glycoproteins.

There are several examples of such recombinant swinepox virus expressing more than one PRV glycoproteins: a recombinant swinepox virus expressing PRV g50 (gpD) and gIII (gpC), a recombinant swinepox virus expressing PRV g50 (gpD) and gII (gpB); a recombinant swinepox virus expressing PRV gII (gpB) and gIII (gpC); and a recombinant swinepox virus expressing PRV g50 (gpD), gIII (gpC) and gII (gpB). Each of the viruses cited above is also engineered to contain and express E. coli B-galactosidase (lac Z) gene, which will facilitate the cloning of the recombinant swinepox virus.

Listed below are three examples of a recombinant swinepox virus expressing PRV g50 (gpD), PRV gIII (gpC), PRV gII (gpB) and E. coli B-galactosidase (lacZ):

a) Recombinant swinepox virus containing and expressing PRV g50 (gpD) gene, PRV gIII (gpC) gene, PRV gII (gpB) gene and lacZ gene. All four genes are inserted into the unique AccI restriction endonuclease site within the HindIII M fragment of the swinepox virus genome. PRV g50 (gpD) gene is under the control of a synthetic early/late promoter (EP1LP2), PRV gIII (gpC) gene is under the control of a synthetic early promoter (EP2), PRV gII (gpB) gene is under the control of a synthetic late/early promoter (LP2EP2) and lacZ gene is under the control of a synthetic late promoter (LP1).

b) Recombinant swinepox virus containing and expressing PRV g50 (gpD) gene, PRV gIII (gpC) gene, PRV gII (gpB) gene and lacz gene. All four genes are inserted into the unique AccI restriction endonuclease site within the HindIII M fragment of the swinepox virus genome. PRV g50 (gpD) gene is under the control of a synthetic early/late promoter (EP1LP2), PRV gIII (gpC) gene is under the control of a synthetic early/late promoter (EP1LP2), PRV gII (gpB) gene is under the control of a synthetic late/early promoter (LP2EP2) and lacZ gene is under the control of a synthetic late promoter (LP1).

c) Recombinant swinepox virus containing and expressing PRV g50 (gpD) gene, PRV gIII (gpC) gene, PRV gII (gpB) gene and lacZ gene. All four genes are inserted into the unique AccI restriction endonuclease site within the HindIII M fragment of the swinepox virus genome. PRV g50 (gpD) gene is under the control of a synthetic early/late promoter (EP1LP2), PRV gIII (gpC) gene is under the control of a synthetic late/early promoter (LP2EP2), PRV gII (gpB) gene is under the control of a synthetic late/early promoter (LP2EP2) and lacZ gene is under the control of a synthetic late promoter (LP1).

Example 9

S-SPV-009

S-SPV-009 is a swinepox virus that expresses at least two foreign genes. The gene for E. coli β-galactosidase (lacZ gene) and the gene for Newcastle's Disease virus hemagglutinin (HN) gene were inserted into the SPV 515-85.1 ORF. The lacZ gene is under the control of a synthetic late promoter (LP1) and the HN gene is under the control of an synthetic early/late promoter (EP1LP2).

S-SPV-009 was derived from S-SPV-001 (Kasza strain). This was accomplished utilizing the homology vector 538-46.26 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-009. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable and expressing the marker gene.

S-SPV-009 was assayed for expression of PRV specific antigens using the BLACK PLAQUE SCREEN FOR FOREIGN GENE EXPRESSION IN RECOMBINANT SPV. Rabbit anti-NDV HN serum was shown to react specifically with S-SPV-009 plaques and not with S-SPV-008 negative control plaques. All S-SPV-009 observed plaques reacted with the swine antiserum indicating that the virus was stably expressing the NDV foreign gene. S-SPV-009 has been deposited with the ATCC under Accession No. VR 2344).

To confirm the expression of the NDV HN gene product, cells were infected with SPV and samples of infected cell lysates were subjected to SDS-polyacrylamide gel electrophoresis. The gel was blotted and analyzed using the WESTERN BLOTTING PROCEDURE. The rabbit anti-NDV HN serum was used to detect expression of the HN protein. The lysate from S-SPV-009 infected cells exhibited a specific band of approximately 74 kd, the reported size of NDV HN (29).

Example 10

S-SPV-014

S-SPV-014 is a swinepox virus that expresses at least two foreign genes. The gene for E. coli B-galactosidase (lacZ) and the gene for infectious laryngotracheitis virus glycoprotein G (ILT gpG) were inserted into the SPV 570-33.32 ORF (a unique PstI site has replaced the unique AccI site). The lacZ gene is under the control of the synthetic late promoter (LP1), and the ILT gpG gene is under the control of the synthetic early/late promoter (EP1LP2).

S-SPV-014 was derived from S-SPV-001 (Kasza Strain). This was accomplished utilizing the homology vector 599-65.25 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-014. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. The assays described here were carried out in ESK-4 cells, indicating that ESK-4 cells would be a suitable substrate for the production of SPV recombinant vaccines.

To confirm the expression of the ILT gpG gene product, cells were infected with SPV-014 and samples of infected cell lysates were subjected to SDS-polyacrylamide gel electrophoresis. The gel was blotted and analyzed using the WESTERN BLOTTING PROCEDURE. Peptide antisera to ILT gG was used to detect expression of ILT specific proteins. The lysate from S-SPV-014 infected cells exhibited a band at 43 kd which is the expected size of the ILT gpG protein and additional bands of higher molecular weight which represent glycosylated forms of the protein which are absent in deletion mutants for ILT gpG.

This virus is used as an expression vector for expressing ILT glycoprotein G (gpG). Such ILT gpG is used as an antigen to identify antibodies directed against the wild-type ILT virus as opposed to antibodies directed against gpG deleted ILT viruses. This virus is also used as an antigen for the production of ILT gpG specific monoclonal antibodies. Such antibodies are useful in the development of diagnostic tests specific for the ILT gpG protein. Monoclonal antibodies are generated in mice utilizing this virus according to the PROCEDURE FOR PURIFICATION OF VIRAL GLYCOPROTEINS FOR USE AS DIAGNOSTICS (Materials & Methods).

Example 11

S-SPV-016

S-SPV-016 is a swinepox virus that expresses at least two foreign genes. The gene for E. coli B-galactosidase (lacZ) and the gene for infectious laryngotracheitis virus glycoproteinI (ILT gpI) were inserted into the SPV 617-48.1 ORF (a unique NotI restriction site has replaced a unique AccI restriction site). The lacZ gene is under the control of the synthetic late promoter (LP1), and the ILT gpI gene is under the control of the synthetic late/early promoter (LP2EP2).

S-SPV-016 was derived from S-SPV-001 (Kasza Strain). This was accomplished utilizing the homology vector 624-20.1C (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-016. This virus was assayed for B-galactosidase expression, purity, and insert stability by multiple passages monitored by the blue plaque assay as described in Materials and Methods. After the initial three rounds of purification, al; plaques observed were blue indicating that the virus was pure, stable, and expressing the foreign gene.

S-SPV-016 was assayed for expression of ILT gpI- and B-galactosidase-specific antigens using the BLACK PLAQUE SCREEN FOR FOREIGN GENE EXPRESSION IN RECOMBINANT SPV. Polyclonal chicken anti-ILT antibody was shown to react specifically with S-SPV-016 plaques and not with S-SPV-017 negative control plaques.

All S-SPV-016 observed plaques reacted with the chicken antiserum indicating that the virus was stably expressing the ILT foreign gene. The assays described here were carried out in ESK-4 cells, indicating that ESK-4 cells would be a suitable substrate for the production of SPV recombinant vaccines.

To confirm the expression of the ILT gpI gene product, cells were infected with SPV-016 and samples of infected cell lysates were subjected to SDS-polyacrylamide gel electrophoresis. The gel was blotted and analyzed using the WESTERN BLOTTING PROCEDURE. Polyclonal chicken anti-ILT antibody was used to detect expression of ILT specific proteins. The lysate from S-SPV-016 infected cells exhibits a range of bands reactive to the anti-ILT antibody from 40 to 200 kd indicating that the ILT gpI may be heavily modified.

This virus is used as an expression vector for expressing ILT glycoprotein I (gpI). Such ILT gpI is used as an antigen to identify antibodies directed against the wild-type ILT virus as opposed to antibodies directed against gpI deleted ILT viruses. This virus is also used as an antigen for the production of ILT gpI specific monoclonal antibodies. Such antibodies are useful in the development of diagnostic tests specific for the ILT gpI protein. Monoclonal antibodies are generated in mice utilizing this virus according to the PROCEDURE FOR PURIFICATION OF VIRAL GLYCOPROTEINS FOR USE AS DIAGNOSTICS (Materials & Methods)

Example 12

S-SPV-017

S-SPV-017 is a swinepox virus that expresses at least two foreign genes. The gene for E. coli B-galactosidase (lacZ) and the gene for infectious bovine rhinotracheitis virus glycoprotein G (IBR gpG) were inserted into the SPV 617-48.1 ORF (a unique NotI restriction site has replaced a unique AccI restriction site). The lacz gene is under the control of the synthetic late promoter (LP1), and the IBR gpG gene is under the control of the synthetic late/early promoter (LP2EP2).

S-SPV-017 was derived from S-SPV-001 (Kasza Strain). This was accomplished utilizing the homology vector 614-83.18 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-017. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-017 was assayed for expression of IBR-specific antigens using the BLACK PLAQUE SCREEN FOR FOREIGN GENE EXPRESSION IN RECOMBINANT SPV. Monoclonal antibodies and peptide antisera to IBR gpG were shown to react specifically with S-SPV-017 plaques and not with S-SPV-016 negative control plaques. All S-SPV-017 observed plaques reacted with the antiserum indicating that the virus was stably expressing the IBR foreign gene. The assays described here were carried out in ESK-4 cells, indicating that ESK-4 cells would be a suitable substrate for the production of SPV recombinant vaccines.

To confirm the expression of the IBR gpG gene product, cells were infected with SPV-017 and samples of infected cell lysates were subjected to SDS-polyacrylamide gel electrophoresis. The gel was blotted and analyzed using the WESTERN BLOTTING PROCEDURE. Antisera to IBR gpG was used to detect expression of IBR specific proteins. The lysate from S-SPV-017 infected cells exhibited a band at 43 kd which is the expected size of the IBR gpG protein and additional bands of higher molecular weight which represent glycosylated forms of the protein which are absent in deletion mutants for IBR gpG.

This virus is used as an expression vector for expressing IBR glycoprotein G (gpG). Such IBR gpG is used as an antigen to identify antibodies directed against the wild-type IBR virus as opposed to antibodies directed against gpG deleted IBR viruses. This virus is also used as an antigen for the production of IBR gpG specific monoclonal antibodies. Such antibodies are useful in the development of diagnostic tests specific for the IBR gpG protein. Monoclonal antibodies are generated in mice utilizing this virus according to the PROCEDURE FOR PURIFICATION OF VIRAL GLYCOPROTEINS FOR USE AS DIAGNOSTICS (Materials & Methods).

Example 13
S-SPV-019

S-SPV-019 is a swinepox virus that expresses at least two foreign genes. The gene for *E. coli* β-galactosidase (lacZ) and the gene for infectious bovine rhinotracheitis virus (IBRV) gE were inserted into the SPV 617-48.1 ORF (a unique NotI restriction site has replaced a unique AccI restriction site). The lacZ gene is under the control of the synthetic late promoter (LP1), and the IBRV gE gene is under the control of the synthetic late/early promoter (LP2EP2).

S-SPV-019 was derived from S-SPV-001 (Kasza Strain). This was accomplished utilizing the homology vector 708-78.9 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-019. This virus was assayed for β-galactosidase expression, purity and insert stability by multiple passages monitored by the blue plaque assay as described in Materials and Methods. After the initial three rounds of purification, all plaques observed were blue indicating that the virus was pure, stable, and expressing the foreign gene.

This virus is used as an expression vector for expressing IBR glycoprotein E (gpE). Such IBR gpE is used as an antigen to identify antibodies directed against the wild-type IBR virus as opposed to antibodies directed against gpE deleted IBR viruses. This virus is also used as an antigen for the production of IBR gpE specific monoclonal antibodies. Such antibodies are useful in the development of diagnostic tests specific for the IBR gpE protein. Monoclonal antibodies are generated in mice utilizing this virus according to the PROCEDURE FOR PURIFICATION OF VIRAL GLYCOPROTEINS FOR USE AS DIAGNOSTICS (Materials & Methods).

Example 14
S-SPV-018

S-SPV-018 is a swinepox virus that expresses at least two foreign genes. The gene for *E. coli* B-galactosidase (lacZ) and the gene for pseudorabies virus glycoprotein E (PRV gpE) are inserted into the SPV 570-33.32 ORF (a unique PstI site has replaced the unique AccI site). The lacZ gene is under the control of the synthetic late promoter (LP1), and the PRV gpE gene is under the control of the synthetic early/late promoter (EP1LP2).

S-SPV-018 is derived from the S-SPV-001 (Kasza Strain). This is accomplished utilizing the final homology vector and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING B-GALACTOSIDASE (BLUOGAL AND CPRG ASSAYS). Red plaque purification of the recombinant virus is designated S-SPV-018. This virus is assayed for B-galactosidase expression, purity, and insert stability by multiple passages monitored by the blue plaque assay described in Materials and Methods. After the initial three rounds of purification, all plaques observed are blue indicating that the virus is pure, stable, and expressing the foreign gene.

This virus is used as an expression vector for expressing PRV glycoprotein E (gpE). Such PRV gpE is used as an antigen to identify antibodies directed against the wild-type PRV virus as opposed to antibodies directed against gpE deleted PRV viruses. This virus is also used as an antigen for the production of PRV gpE specific monoclonal antibodies. Such antibodies are useful in the development of diagnostic tests specific for the PRV gpE protein. Monoclonal antibodies are generated in mice utilizing this virus according to the PROCEDURE FOR PURIFICATION OF VIRAL GLYCOPROTEINS FOR USE AS DIAGNOSTICS (Materials & Methods).

Example 15
Homology Vector 520-90.15

The homology vector 520-90.15 is a plasmid useful for the insertion of foreign DNA into SPV. Plasmid 520-90.15 contains a unique NdeI restriction site into which foreign DNA may be cloned. A plasmid containing such a foreign DNA insert has been used according to the HOMOLOGOUS RECOMBINATION PROCEDURE FOR GENERATING RECOMBINANT SPV to generate a SPV containing the foreign DNA. For this procedure to be successful, it is important that the insertion site be in a region nonessential to the replication of the SPV and that the site be flanked with swinepox virus DNA appropriate for mediating homologous recombination between virus and plasmid DNAs. The unique NdeI restriction site in plasmid 520-90.15 is located within the coding region of the SPV thymidine kinase gene (32). Therefore, we have shown that the thymidine kinase gene of swinepox virus is non-essential for DNA replication and is an appropriate insertion site.

Example 16
S-PRV-010

S-SPV-010 is a swinepox virus that expresses a foreign gene. The *E. coli* B-galactosidase (lacz) gene is inserted into a unique NdeI restriction site within the thymidine kinase gene. The foreign gene (lacZ) is under the control of the synthetic late promoter, LP1. We have shown that the swinepox virus thymidine kinase gene is non-essential for replication of the virus and is an appropriate insertion site.

A 1739 base pair HindIII-BamHI fragment subcloned from the HindIII G fragment contains the swinepox virus thymidine kinase gene and is designated homology vector 520-90.15. The homology vector 520-90.15 was digested with Nde I, and AscI linkers were inserted at this unique site within the thymidine kinase gene. The LP1 promoter-lac Z cassette with AscI linkers was ligated into the Asc I site within the thymidine kinase gene. The recombinant homology vector 561-36.26 was cotransfected with virus S-SPV-001 by the HOMOLOGOUS RECOMBINATION PROCEDURE FOR GENERATING RECOMBINANT SPV and virus plaques expressing B-galactosidase were selected by SCREEN FOR RECOMBINANT SPV EXPRESSING B-GALACTOSIDASE (BLUOGAL AND CPRG ASSAY). The final result of blue and red plaque purification was the recombinant virus designated S-SPV-010. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable and expressing the foreign gene. The assays described here were carried out in ESK-4 cells, indicating that ESK-4 cells would be a suitable substrate for the production of SPV recombinant vaccines.

Example 17

The development of vaccines utilizing the swinepox virus to express antigens from various disease causing microorganisms can be engineered.

Transmissible Gastroenteritis Virus

The major neutralizing antigen of the transmissible gastroenteritis virus (TGE), glycoprotein 195, for use in the swinepox virus vector has been cloned. The clone of the neutralizing antigen is disclosed in U.S. Ser. No. 078,519, filed Jul. 27, 1987. It is contemplated that the procedures that have been used to express PRV g50 (gpD) in SPV and are disclosed herein are applicable to TGE.

Porcine Parvovirus

We have cloned the major capsid protein of the porcine (swine) parvovirus (PPV) for use in the swinepox virus vector. The clone of the capsid protein is disclosed in U.S. Pat. No. 5,068,192 issued Nov. 26, 1991. It is contemplated that the procedures that have been used to express PRV g50 (gpD) in SPV and are disclosed herein are applicable to PPV.

Swine Rotavirus

We have cloned the major neutralizing antigen of the swine rotavirus, glycoprotein 38, for use in the swinepox virus vector. The clone of glycoprotein 38 is disclosed in U.S. Pat. No. 5,068,192 issued Nov. 26, 1991. It is contemplated that the procedures that have been used to express PRV g50 (gpD) in SPV and are disclosed herein are applicable to SRV.

Hog Cholera Virus

The major neutralizing antigen of the bovine viral diarrhea (BVD) virus was cloned as disclosed in U.S. Ser. No. 225,032, filed Jul. 27, 1988. Since the BVD and hog cholera viruses are cross protective (31), the BVD virus antigen has been targeted for use in the swinepox virus vector. It is contemplated that the procedures that have been used to express PRV g50 (gpD) in SPV and are disclosed herein are applicable to BVD virus.

*Serpulina hyodysenteriae*

A protective antigen of *Serpulina hyodysenteriae* (3), for use in the swinepox virus vector has been cloned. It is contemplated that the procedures that have been used to express PRV gp50 in SPV and are disclosed herein are also applicable to *Serpulina hyodysenteriae*.

Antigens from the following microorganisms may also be utilized to develop animal vaccines: swine influenza virus, foot and mouth disease virus, African swine fever virus, hog cholera virus, *Mycoplasma hyopneumoniae*, porcine reproductive and respiratory syndrome/swine infertility and respiratory syndrome (PRRS/SIRS).

Antigens from the following microorganisms may also be utilized to develop animal vaccines: feline leukemia virus, feline immunodeficiency virus, feline herpesvirus, feline infectious peritonitis virus, canine herpesvirus, canine coronavirus, canine parvovirus, parasitic diseases in animals (including *Dirofilaria immitis* in dogs and cats), equine infectious anemia, *Streptococcus equi*, coccidia, emeria, chicken anemia virus, *Borrelia bergdorferi*, bovine coronavirus, pasteurella, haemolytica.

Example 18

Recombinant swinepox viruses express equine influenza virus type A/Alaska 91, equine influenza virus type A/Prague 56, equine herpesvirus type 1 gB, or equine herpesvirus type 1 gD genes. S-SPV-033 and S-SPV-034 are useful as vaccines against equine influenza infection, and S-SPV-038 and S-SPV-039 are useful as a vaccine against equine herpesvirus infection which causes equine rhinotracheitis and equine abortion. These equine influenza and equine herpesvirus antigens are key to raising a protective immune response in the animal. The recombinant viruses are useful alone or in combination as an effective vaccine. The swinepox virus is useful for cloning other subtypes of equine influenza virus (including EIVA/Miami/63 and EIVA/Kentucky/81) to protect against rapidly evolving variants in this disease. S-SPV-033, S-SPV-034, S-SPV-038, and S-SPV-039 are also useful as an expression vector for expressing equine influenza or equine herpesvirus antigens. Such equine influenza or equine herpesvirus antigens are useful to identify antibodies directed against the wild-type equine influenza virus or equine herpesvirus. The viruses are also useful to in producing antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

Example 18A

S-SPV-033:

S-SPV-033 is a recombinant swinepox virus that expresses at least two foreign genes. The gene for *E. coli* β-galactosidase (lacZ) and the gene for equine influenza virus type A/Alaska 91 neuraminidase were inserted into the SPV 617-48.1 ORF (a unique NotI restriction site has replaced a unique AccI restriction site). The lacZ gene is under the control of the synthetic late promoter (LP1), and the EIV AK/91 NA gene is under the control of the synthetic late/early promoter (LP2EP2).

S-SPV-033 was derived from S-SPV-001 (Kasza Strain). This was accomplished utilizing the homology vector 732-18.4 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-033. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

Example 18B

S-SPV-034:

S-SPV-034 is a swinepox virus that expresses at least two foreign genes. The gene for E. coli β-galactosidase (lacZ) and the gene for equine influenza virus type A/Prague 56 neuraminidase were inserted into the SPV 617-48.1 ORF (a unique NotI restriction site has replaced a unique AccI restriction site). The lacZ gene is under the control of the synthetic late promoter (LP1), and the EIV PR/56 NA gene is under the control of the synthetic late/early promoter (LP2EP2).

S-SPV-034 was derived from S-SPV-001 (Kasza Strain). This was accomplished utilizing the homology vector 723-59A9.22 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-034. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-034 was assayed for expression of EIV-specific antigens using the BLACK PLAQUE SCREEN FOR FOREIGN GENE EXPRESSION IN RECOMBINANT SPV. Monospecific polyclonal antibodies to EIV PR/56 NA were shown to react specifically with S-SPV-034 plaques and not with S-SPV-001 negative control plaques. All S-SPV-034 observed plaques reacted with the antiserum indicating that the virus was stably expressing the EIV PR/56 NA gene. The assays described here were carried out in ESK-4 cells, indicating that ESK-4 cells would be a suitable substrate for the production of SPV recombinant vaccines.

Example 18C

S-SPV-038:

S-SPV-038 is a swinepox virus that expresses at least two foreign genes. The gene for E. coli β-galactosidase (lacZ) and the gene for equine herpesvirus type 1 glycoprotein B are inserted into the SPV 617-48.1 ORF (a unique NotI restriction site has replaced a unique AccI restriction site). The lacZ gene is under the control of the synthetic late promoter (LP1), and the EHV-1 gB gene is under the control of the synthetic late/early promoter (LP2EP2).

S-SPV-038 is derived from S-SPV-001 (Kasza Strain). This is accomplished utilizing the homology vector 744-34 (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV-038. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

Example 18D

S-SPV-039:

S-SPV-039 is a swinepox virus that expresses at least two foreign genes. The gene for E. coli β-galactosidase (lacZ) and the gene for equine herpesvirus type 1 glycoprotein D are inserted into the SPV 617-48.1 ORF (a unique NotI restriction site has replaced a unique AccI restriction site). The lacZ gene is under the control of the synthetic late promoter (LP1), and the EHV-1 gD gene is under the control of the synthetic late/early promoter (LP2EP2).

S-SPV-039 is derived from S-SPV-001 (Kasza Strain). This is accomplished utilizing the homology vector 744-38 (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV-039. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

Example 19

Recombinant swinepox viruses express bovine respiratory syncytial virus attachment protein (BRSV G), BRSV Fusion protein (BRSV F), BRSV nucleocapsid protein (BRSV N), bovine viral diarrhea virus (BVDV) gp48, BVDV gp53, bovine parainfluenza virus type 3 (BPI-3) F, or BPI-3 HN. S-SPV-020, S-SPV-029, S-SPV-030, and S-SPV-032, S-SPV-028 are useful as vaccines against bovine disease. These BRSV, BVDV, and BPI-3 antigens are key to raising a protective immune response in the animal. The recombinant viruses are useful alone or in combination as an effective vaccine. The swinepox virus is useful for cloning other subtypes of BRSV, BVDV, and BPI-3 to protect against rapidly evolving variants in this disease. S-SPV-020, S-SPV-029, S-SPV-030, and S-SPV-032, S-SPV-028 are also useful as an expression vector for expressing BRSV, BVDV, and BPI-3 antigens. Such BRSV, BVDV, and BPI-3 antigens are useful to identify antibodies directed against the wild-type BRSV, BVDV, and BPI-3. The viruses are also useful as antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

Example 19A

S-SPV-020:

S-SPV-020 is a swinepox virus that expresses at least two foreign genes. The gene for E. coli β-galactosidase (lacZ) and the gene for bovine respiratory syncytial virus (BRSV) G were inserted into the SPV 617-48.1 ORF (a unique NotI restriction site has replaced a unique AccI restriction site). The lacz gene is under the control of the synthetic late promoter (LP1), and the BRSV G gene is under the control of the synthetic late/early promoter (LP2EP2).

S-SPV-020 was derived from S-SPV-001 (Kasza Strain). This was accomplished utilizing the homology vector 727-20.5 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-020. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-020 was assayed for expression of BRSV-specific antigens using the BLACK PLAQUE SCREEN FOR FOREIGN GENE EXPRESSION IN RECOMBINANT SPV. Bovine anti-BRSV FITC (Accurate Chemicals) was shown to react specifically with S-SPV-020 plaques and not with S-SPV-003 negative control plaques. All S-SPV-020 observed plaques reacted with the antiserum indicating that the virus was stably expressing the BRSV foreign gene. The assays described here were carried out in ESK-4 cells, indicating that ESK-4 cells would be a suitable substrate for the production of SPV recombinant vaccines.

To confirm the expression of the BRSV G gene product, cells were infected with S-SPV-020 and samples of infected cell lysates were subjected to SDS-polyacrylamide gel electrophoresis. The gel was blotted and analyzed using the WESTERN BLOTTING PROCEDURE. Bovine anti-BRSV FITC (Accurate Chemicals) was used to detect expression of BRSV specific proteins. The lysate from S-SPV-020 infected cells exhibited a band at 36 kd which is the expected size of the non-glycosylated form of BRSV G protein and bands at 43 to 45 kd and 80 to 90 kd which are the expected size of glycosylated forms of the BRSV G protein.

Example 19B
S-SPV-029:

S-SPV-029 is a swinepox virus that expresses at least two foreign genes. The gene for E. coli β-galactosidase (lacZ) and the gene for bovine respiratory syncytial virus (BRSV) F were inserted into the SPV 617-48.1 ORF (a unique NotI restriction site has replaced a unique AccI restriction site). The lacZ gene is under the control of the synthetic late promoter (LP1), and the BRSV F gene is under the control of the synthetic late/early promoter (LP2EP2).

S-SPV-029 was derived from S-SPV-O01 (Kasza Strain). This was accomplished utilizing the homology vector 727-20.10 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-029.

This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-029 was assayed for expression of BRSV-specific antigens using the BLACK PLAQUE SCREEN FOR FOREIGN GENE EXPRESSION IN RECOMBINANT SPV. Bovine anti-BRSV FITC (Accurate Chemicals) was shown to react specifically with S-SPV-029 plaques and not with S-SPV-003 negative control plaques. All S-SPV-029 observed plaques reacted with the antiserum indicating that the virus was stably expressing the BRSV foreign gene. The assays described here were carried out in ESK-4 cells, indicating that ESK-4 cells would be a suitable substrate for the production of SPV recombinant vaccines.

Example 19C
S-SPV-030:

S-SPV-030 is a swinepox virus that expresses at least two foreign genes. The gene for E. coli β-galactosidase (lacZ) and the gene for bovine respiratory syncytial virus (BRSV) N were inserted into the SPV 617-48.1 ORF (a unique NotI restriction site has replaced a unique AccI restriction site). The lacZ gene is under the control of the synthetic late promoter (LP1), and the BRSV N gene is under the control of the synthetic late/early promoter (LP2EP2).

S-SPV-030 was derived from S-SPV-001 (Kasza Strain). This was accomplished utilizing the homology vector 713-55.37 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-030. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-030 was assayed for expression of BRSV-specific antigens using the BLACK PLAQUE SCREEN FOR FOREIGN GENE EXPRESSION IN RECOMBINANT SPV. Bovine anti-BRSV FITC (Accurate Chemicals) was shown to react specifically wit h S-SPV-030 plaques and not with S-SPV-003 negative control plaques. All S-SPV-030 observed plaques reacted with the antiserum indicating that the virus was stably expressing the BRSV foreign gene. The assays described here were carried out in ESK-4 cells, indicating that ESK-4 cells would be a suitable substrate for the production of SPV recombinant vaccines.

To confirm the expression of the BRSV N gene product, cells were infected with SPV-030 and samples of infected cell lysates were subjected to SDS-polyacrylamide gel electrophoresis. The gel was blotted and analyzed using the WESTERN BLOTTING PROCEDURE. Bovine anti-BRSV FITC (Accurate Chemicals) was used to detect expression of BRSV specific proteins. The lysate from S-SPV-030 infected cells exhibited a band at 43 kd which is the expected size of the BRSV N protein.

Example 19D
S-SPV-028:

S-SPV-028 is a swinepox virus that expresses at least two foreign genes. The gene for E. coli β-galactosidase (lacZ) and the gene for bovine parainfluenza virus type 3 (BPI-3) F were inserted into the SPV 617-48.1 ORF (a unique NotI restriction site has replaced a unique AccI restriction site). The lacz gene is under the control of the synthetic late promoter (LP1), and the BPI-3 F gene is under the control of the synthetic late/early promoter (LP2EP2).

S-SPV-028 was derived from S-SPV-001 (Kasza Strain). This was accomplished utilizing the homology vector 713-55.10 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-028. This virus was assayed for β-galactosidase expression, purity, and insert stability by multiple passages monitored by the blue plaque assay as described in Materials and Methods.

After the initial three rounds of purification, all plaques observed were blue indicating that the virus was pure, stable, and expressing the foreign gene.

S-SPV-028 was assayed for expression of BPI-3-specific antigens using the BLACK PLAQUE SCREEN FOR FOREIGN GENE EXPRESSION IN RECOMBINANT SPV. Bovine anti-BPI-3 FITC (Accurate Chemicals) was shown to react specifically with S-SPV-028 plaques and not with S-SPV-003 negative control plaques. All S-SPV-028 observed plaques reacted with the antiserum indicating that the virus was stably expressing the BPI-3 foreign gene. The assays described here were carried out in ESK-4 cells, indicating that ESK-4 cells would be a suitable substrate for the production of SPV recombinant vaccines. To confirm the expression of the BPI-3 F gene product, cells were infected with SPV-028 and samples of infected cell lysates were subjected to SDS-polyacrylamide gel electrophoresis. The gel was blotted and analyzed using the WESTERN BLOTTING PROCEDURE. Bovine anti-BPI-3 FITC (Accurate Chemicals) was used to detect expression of BPI-3 specific proteins. The lysate from S-SPV-028 infected cells exhibited bands at 43, and 70 kd which is the expected size of the BPI-3 F protein.

Example 19E

S-SPV-032:

S-SPV-032 is a swinepox virus that expresses at least two foreign genes. The gene for E. coli β-galactosidase (lacZ) and the gene for bovine viral diarrhea virus (BVDV) gp48 were inserted into the SPV 617-48.1 ORF (a unique NotI restriction site has replaced a unique AccI restriction site). The lacZ gene is under the control of the synthetic late promoter (LP1), and the BVDV gp48 gene is under the control of the synthetic late/early promoter (LP2EP2).

S-SPV-032 was derived from S-SPV-001 (Kasza Strain). This was accomplished utilizing the homology vector 727-78.1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-032. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

Example 19F

S-SPV-040:

S-SPV-040 is a swinepox virus that expresses at least two foreign genes. The gene for E. coli β-galactosidase (lacZ) and the gene for bovine viral diarrhea virus (BVDV) gp53 were inserted into the SPV 617-48.1 ORF (a unique NotI restriction site has replaced a unique AccI restriction site). The lacZ gene is under the control of the synthetic late promoter (LP1), and the BVDV gp53 gene is under the control of the synthetic late/early promoter (LP2EP2).

S-SPV-040 is derived from S-SPV-001 (Kasza Strain). This is accomplished utilizing the homology vector 738-96 (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV-040. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

Example 19G

Shipping Fever Vaccine

Shipping fever or bovine respiratory disease (BRD) complex is manifested as the result of a combination of infectious diseases of cattle and additional stress related factors (52). Respiratory virus infections augmented by pathophysiological effects of stress, alter the susceptibility of cattle to Pasteurella organisms by a number of mechanisms. Control of the viral infections that initiate BRD is essential to preventing the disease syndrome (53).

The major infectious disease pathogens that contribute to BRD include but are not limited to infectious bovine rhinotracheitis virus (IBRV), parainfluenza virus type 3 (PI-3), bovine respiratory syncytial virus (BRSV), and Pasteurella haemolytica (53). Recombinant swinepox virus expressing protective antigens to organisms causing BRD is useful as a vaccine. S-SPV-020, S-SPV-029, S-SPV-030, S-SPV-032, and S-SPV-028 are useful components of such a vaccine.

Example 20

Recombinant swinepox viruses S-SPV-031 and S-SPV-035 are useful as a vaccine against human disease. S-SPV-031 expresses the core antigen of hepatitis B virus. S-SPV-031 is useful against hepatitis B infection in humans. S-SPV-035 expresses the cytokine, interleukin-2, and is useful as an immune modulator to enhance an immune response in humans. When S-SPV-031 and S-SPV-035 are combined, a superior vaccine against hepatitis B is produced.

Example 20A

S-SPV-031:

S-SPV-031 is a swinepox virus that expresses at least two foreign genes. The gene for E. coli β-galactosidase (lacZ) and the gene for Hepatitis B Core antigen were inserted into the SPV 617-48.1 ORF (a unique NotI restriction site has replaced a unique AccI restriction site). The lacZ gene is under the control of the synthetic late promoter (LP1), and the Hepatitis B Core antigen gene is under the control of the synthetic early/late promoter (EP1LP2).

S-SPV-031 was derived from S-SPV-001 (Kasza Strain). This was accomplished utilizing the homology vector 727-67.18 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-031. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-031 was assayed for expression of Hepatitis B Core antigen-specific antigens using the BLACK PLAQUE SCREEN FOR FOREIGN GENE EXPRESSION IN RECOMBINANT SPV. Rabbit antisera to Hepatitis B Core antigen was shown to react specifically with S-SPV-031 plaques and not with S-SPV-001 negative control plaques. All S-SPV-031 observed plaques reacted with the antiserum indicating that the virus was stably expressing the Hepatitis B Core antigen gene. The assays described here were carried out in ESK-4 cells, indicating that ESK-4 cells would be a suitable substrate for the production of SPV recombinant vaccines.

To confirm the expression of the Hepatitis B Core antigen gene product, cells were infected with SPV-031 and samples of infected cell lysates were subjected to SDS-polyacrylamide gel electrophoresis. The gel was blotted and analyzed using the WESTERN BLOTTING PROCEDURE. Rabbit antisera to Hepatitis B Core antigen was used to detect expression of Hepatitis B specific proteins. The lysate from S-SPV-031 infected cells exhibited a band at 21 kd which is the expected size of the Hepatitis B Core antigen.

Example 20B

S-SPV-035:

S-SPV-035 is a swinepox virus that expresses at least two foreign genes. The gene for E. coli β-galactosidase (lacZ) and the gene for human IL-2 were inserted into the SPV 617-48.1 ORF (a unique NotI restriction site has replaced a unique AccI restriction site). The lacZ gene is under the control of the synthetic late promoter (LP1), and the human IL-2 gene is under the control of the synthetic late/early promoter (LP2EP2).

S-SPV-035 was derived from S-SPV-001 (Kasza Strain). This was accomplished utilizing the homology vector 741-84.14 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-035. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

Example 21

Human vaccines using recombinant swinepox virus as a vector

Recombinant swinepox virus is useful as a vaccine against human diseases. For example, human influenza virus is a rapidly evolving virus whose neutralizing viral epitopes rapidly change. A useful recombinant swinepox vaccine is one in which the influenza virus neutralizing epitopes are quickly adapted by recombinant DNA techniques to protect against new strains of influenza virus. Human influenza virus hemagglutinin (HN) and neuraminidase (NA) genes are cloned into the swinepox virus as described in CLONING OF EQUINE INFLUENZA VIRUS HEMAGGLUTININ AND NEURAMINIDASE GENES (See Materials and Methods and Example 17).

Recombinant swinepox virus is useful as a vaccine against other human diseases when foreign antigens from the following diseases or disease organisms are expressed in the swinepox virus vector: hepatitis B virus surface and core antigens, hepatitis C virus, human immunodeficiency virus, human herpesviruses, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirs, poliovirus, human respiratory syncytial virus, retrovirus, human T-cell leukemia virus, rabies virus, mumps virus, malaria (*Pasmodium falciparum*), *Bordetelia pertussis*, Diptheria, *Rickettsia prowazekii, Borrlia bergdorferi, Tetanus toxoid*, malignant tumor antigens.

Furthermore, S-SPV-035 (Example 20), when combined with swinepox virus interleukin-2 is useful in enhancing immune response in humans. Additional cytokines, including but not limited to, interleukin-2, interleukin-6, interleukin-12, interferons, granulocyte-macrophage colony stimulating factors, interleukin receptors from human and other animals when vectored into a non-essential site in the swinepox viral genome, and subsequently expressed, have immune stimulating effects.

Recombinant swinepox virus express foreign genes in a human cell line. We demonstrated that S-SPV-003 (EP1LP2 promoter expressing the lacZ gen) expressed the lacZ gene in THP human monocyte cell lines by measuring β-galactosidase activity. We did not observe any cytopathic effect of swinepox virus on the THP human monocyte cells, indicating that recombinant swinepox virus can express foreign genes in a human cell line, but will not productively infect or replicated in the human cell line. We have demonstrated that swinepox virus replicates well in ESK-4 cells (embryonic swine kidney) indicating that ESK-4 cells would be a suitable substrate for the production of SPV recombinant vaccines.

Example 22

Avian vaccines using recombinant swinepox virus as a vector

Example 22A

S-SPV-026

S-SPV-026 is a swinepox virus that expresses at least two foreign genes. The gene for E. coli β-galactosidase (lacZ) and the gene for infectious bursal disease virus (IBDV) polyprotein were inserted into the SPV 617-48.1 ORF (a unique NotI restriction site has replaced a unique AccI restriction site). The lacZ gene is under the control of the synthetic late promoter (LP1), and the IBDV polyprotein gene is under the control of the synthetic early/late promoter (EP1LP2).

S-SPV-026 was derived from S-SPV-001 (Kasza Strain). This was accomplished utilizing the homology vector 689-50.4 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-026. This virus was assayed for β-galactosidase expression, purity, and insert stability by multiple passages monitored by the blue plaque assay as described in Materials and Methods. After the initial three rounds of purification, all plaques observed were blue indication that the virus was pure, stable, and expressing the foreign gene.

S-SPV-026 was assayed for expression of IBDV polyprotein-specific antigens using the BLACK PLAQUE SCREEN FOR FOREIGN GENE EXPRESSION IN RECOMBINANT SPV. Rat antisera to IBDV polyprotein were shown to react specifically with S-SPV-026 plaques and not with S-SPV-001 negative control plaques. All S-SPV-026 observed plaques reacted with the antiserum indicating that the virus was stably expressing the IBDV polyprotein gene. The assays described here were carried out in ESK-4 cells, indicating that ESK-4 cells would be a suitable substrate for the production of SPV recombinant vaccines.

To confirm the expression of the IBDV polyprotein gene product, cells were infected with SPV-026 and samples of infected cell lysates were subjected to SDS-polyacrylamide gel electrophoresis. The gel was blotted and analyzed using the WESTERN BLOTTING PROCEDURE. Rat antisera to IBDV proteins VP2, VP3, and VP4 and monoclonal antibody R63 to IBDV VP2 were used to detect expression of IBDV proteins. The lysate from S-SPV-026 infected cells exhibited bands at 32 to 40 kd which is the expected size of the IBDV proteins.

Example 22B

S-SPV-027

S-SPV-027 is a swinepox virus that expresses at least two foreign genes. The gene for *E. coli* β-galactosidase (lacZ) and the gene for infectious bursal disease virus (IBDV) VP2 (40 kd) were inserted into the SPV 617-48.1 ORF (a unique NotI restriction site has replaced a unique AccI restriction site). The lacZ gene is under the control of the synthetic late promoter (LP1), and the IBDV VP2 gene is under the control of the synthetic early/late promoter (EP1LP2).

S-SPV-027 was derived from S-SPV-001 (Kasza Strain). This was accomplished utilizing the homology vector 689-50.7 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-027. This virus is assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-027 was assayed for expression of IBDV VP2-specific antigens using the BLACK PLAQUE SCREEN FOR FOREIGN GENE EXPRESSION IN RECOMBINANT SPV. Rat antisera to IBDV protein was shown to react specifically with S-SPV-027 plaques and not with S-SPV-001 negative control plaques. All S-SPV-027 observed plaques reacted with the antiserum indicating that the virus was stably expressing the IBDV VP2 gene. The assays described here were carried out in ESK-4 cells, indicating that ESK-4 cells would be a suitable substrate for the production of SPV recombinant vaccines.

To confirm the expression of the IBDV VP2 gene product, cells were infected with S-SPV-027 and samples of infected cell lysates were subjected to SDS-polyacrylamide gel electrophoresis. The gel was blotted and analyzed using the WESTERN BLOTTING PROCEDURE. Rat antisera to IBDV protein and monoclonal antibody R63 to IBDV VP2 were used to detect expression of IBDV VP2 protein. The lysate from S-SPV-027 infected cells exhibited a band at 40 kd which is the expected size of the IBDV VP2 protein.

S-SPV-026 and S-SPV-027 are useful as vaccines against infectious bursal disease in chickens and also as expression vectors for IBDV proteins. Recombinant swinepox virus is useful as a vaccine against other avian disease when foreign antigens from the following diseases or disease organisms are expressed in the swinepox virus vector: Marek's disease virus, infectious laryngotracheitis virus, Newcastle disease virus, infectious bronchitis virus, and chicken anemia virus.

Example 23

SPV-036:

S-SPV-036 is a swinepox virus that expresses at one foreign gene. The gene for *E. coli* β-galactosidase (lacZ) was inserted into the SPV 617-48.1 ORF (a unique NotI restriction site has replaced a unique AccI restriction site). The lacZ gene is under the control of the human cytomegalovirus immediate early (HCMV IE) promoter.

S-SPV-036 was derived from S-SPV-001 (Kasza Strain). This was accomplished utilizing the homology vector 741-80.3 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-036. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

The expression of lacZ from the HCMV IE promoter provides a strong promoter for expression of foreign genes in swinepox. S-SPV-036 is a novel and unexpected demonstration of a herpesvirus promoter driving expression of a foreign gene in a poxvirus. S-SPV-036 is useful in formulating human vaccines, and recombinant swinepox virus is useful for the expression of neutralizing antigens from human pathogens. Recombinant swinepox virus expressed foreign genes in a human cell line as demonstrated by S-SPV-003 (EP1LP2) promoter expressing the lacZ gene) expressed β-galactosidase in THP human monocyte cell lines.

Recombinant swinepox virus expressed foreign genes in a human cell line as demonstrated by s-SPV-003 (EP1LP2 promoter expressing the lacz gene) expressed β-galactosidase in THP human monocyte cell lines. THP human monocyte cells are useful for the production of recombinant swinepox virus as a human vaccine. Other cell lines in which swinepox virus will replicate include, but are not limited to, Vero cells (monkey), ST cells (swine testicle), PK-15 (porcine kidney), and ESK-4 cells (embryonic swine kidney).

Example 24

Homology Vector 738-94.5

Figure 17:
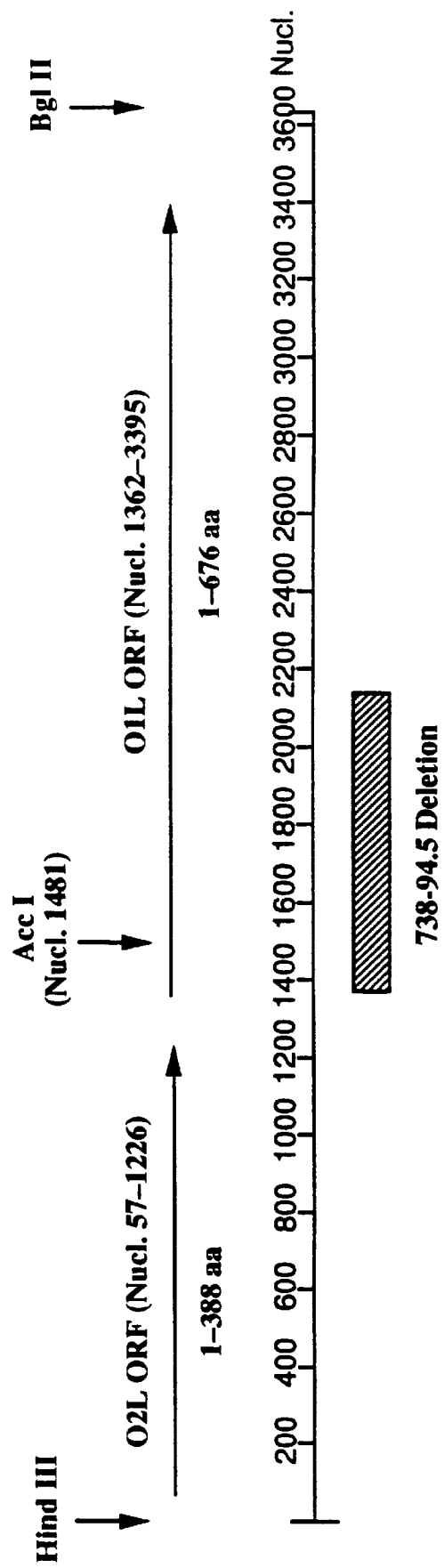
Figure 18A:
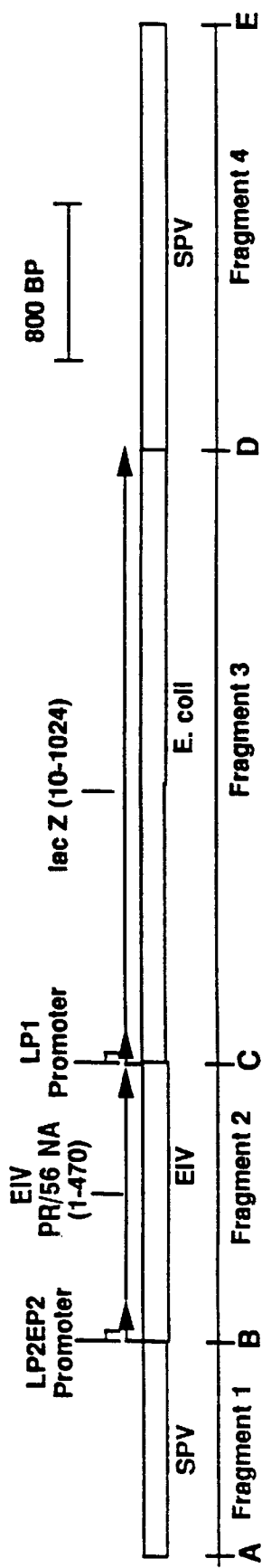
Figure 18B:
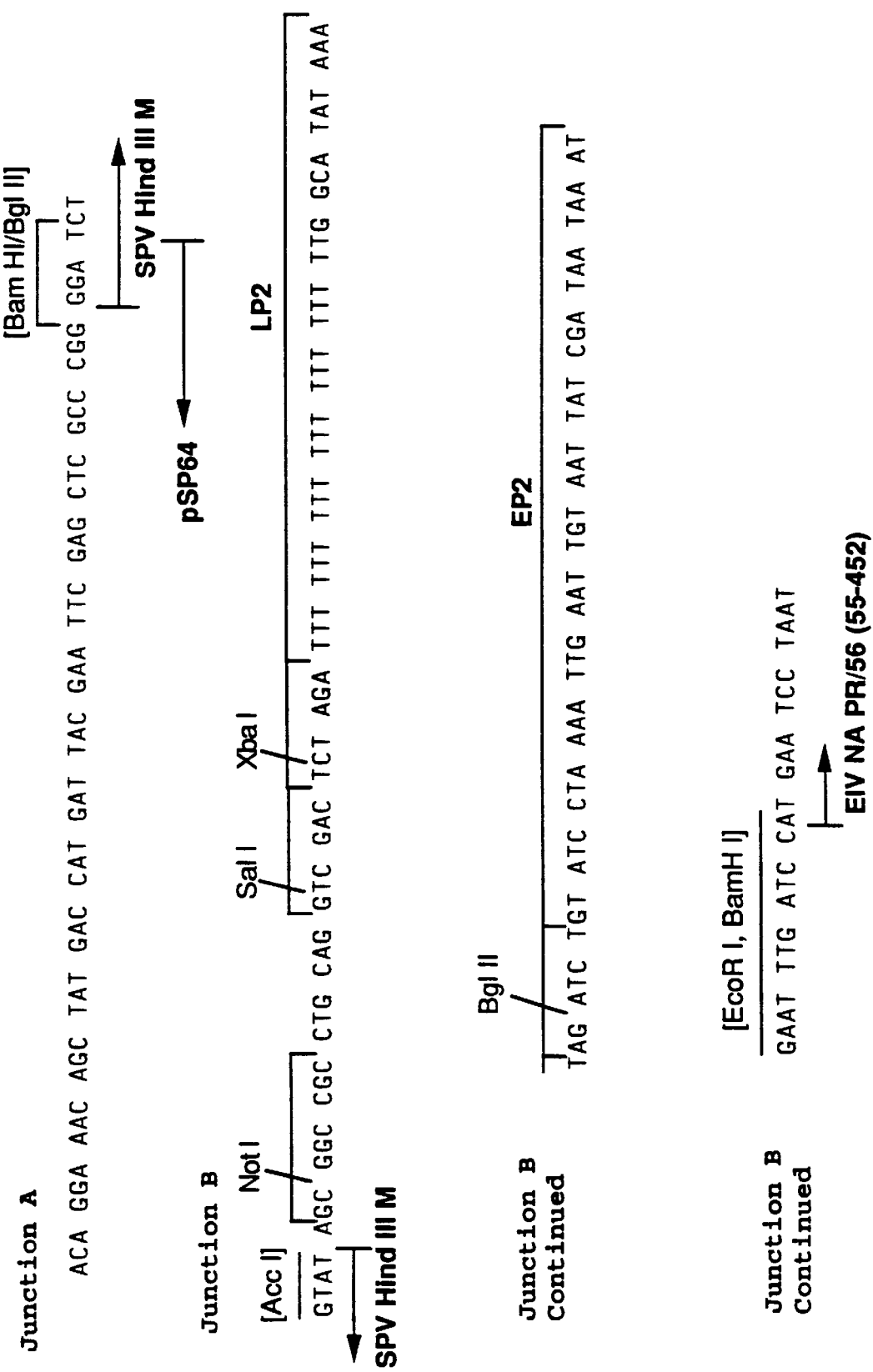
Figure 18C:
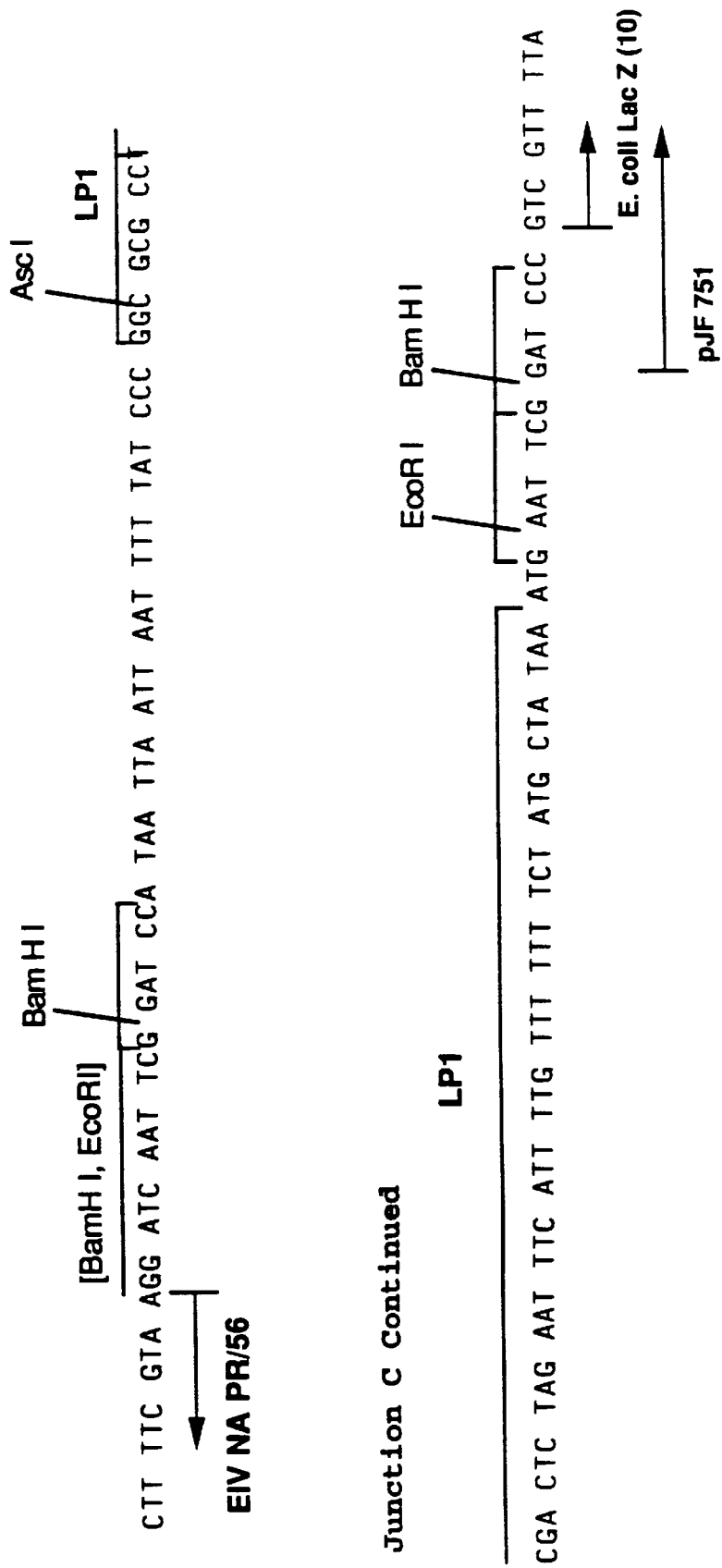
Figure 18D:
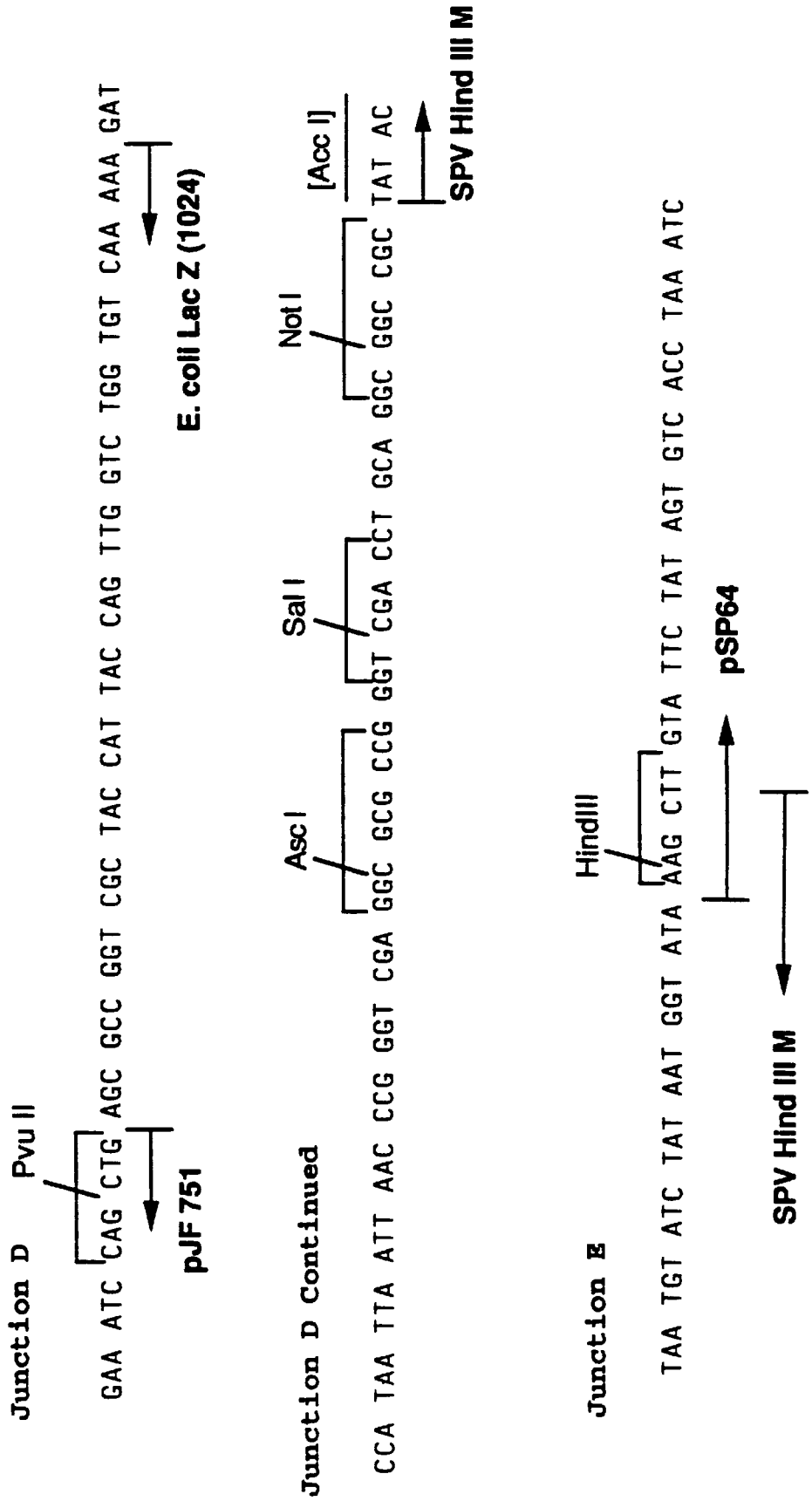
Figure 19A:
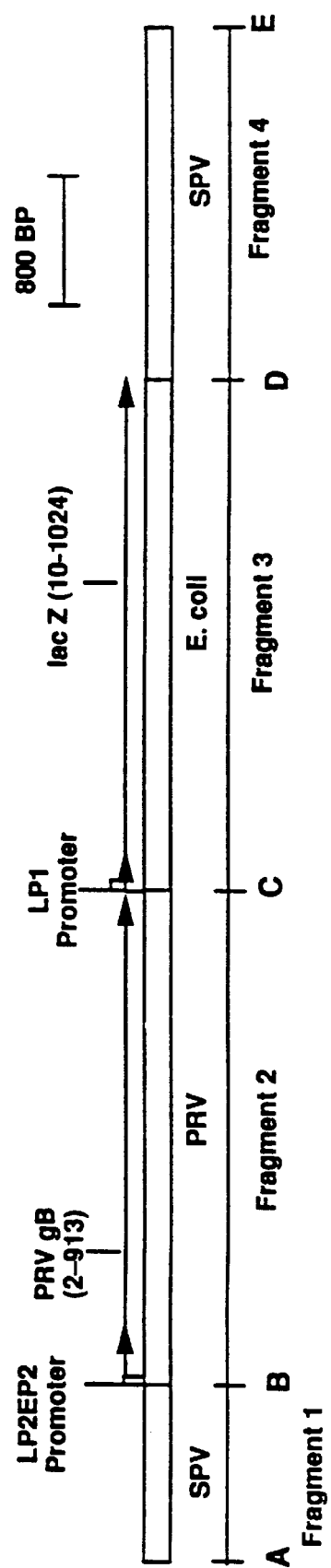
Figure 19D:
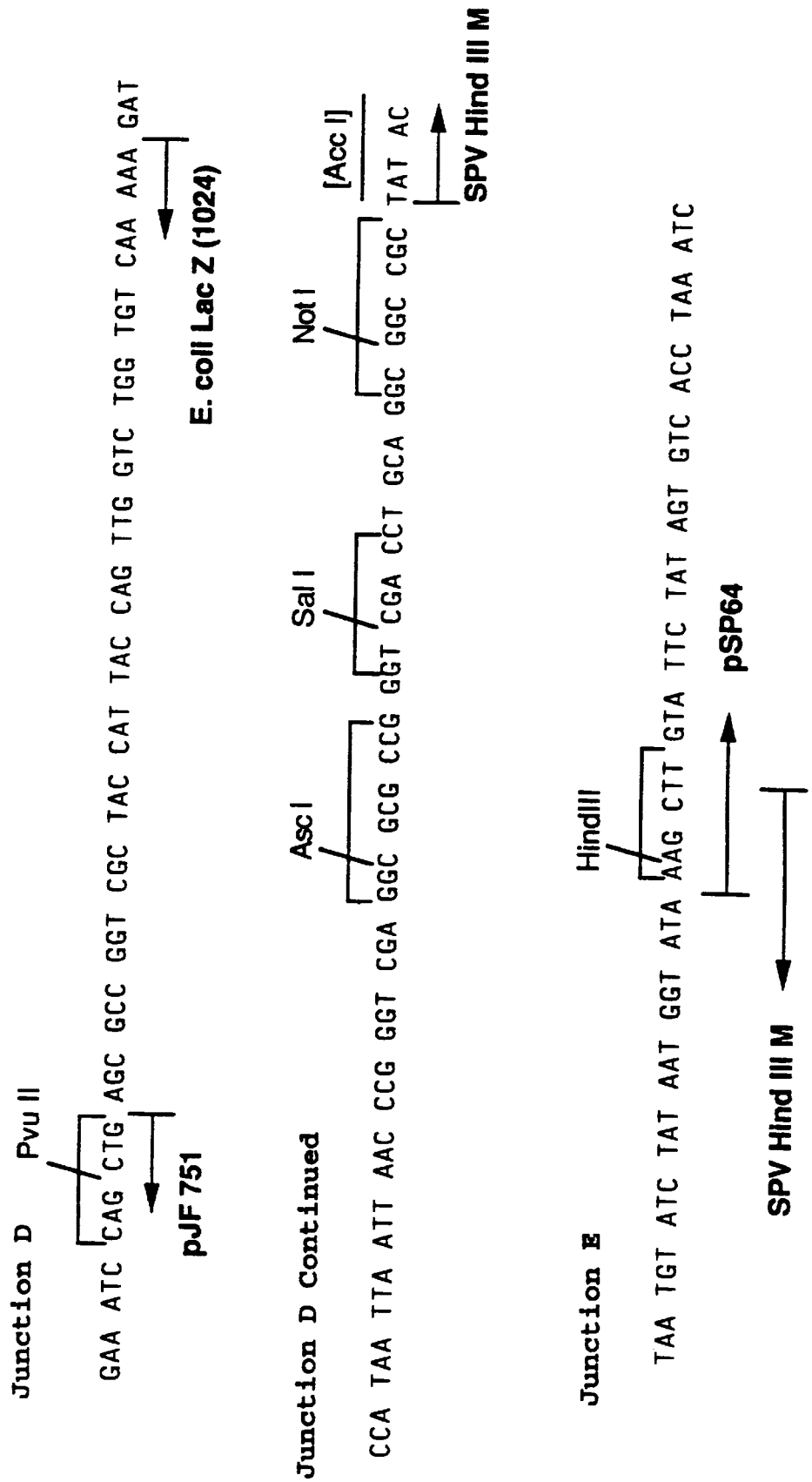
Figure 20A:
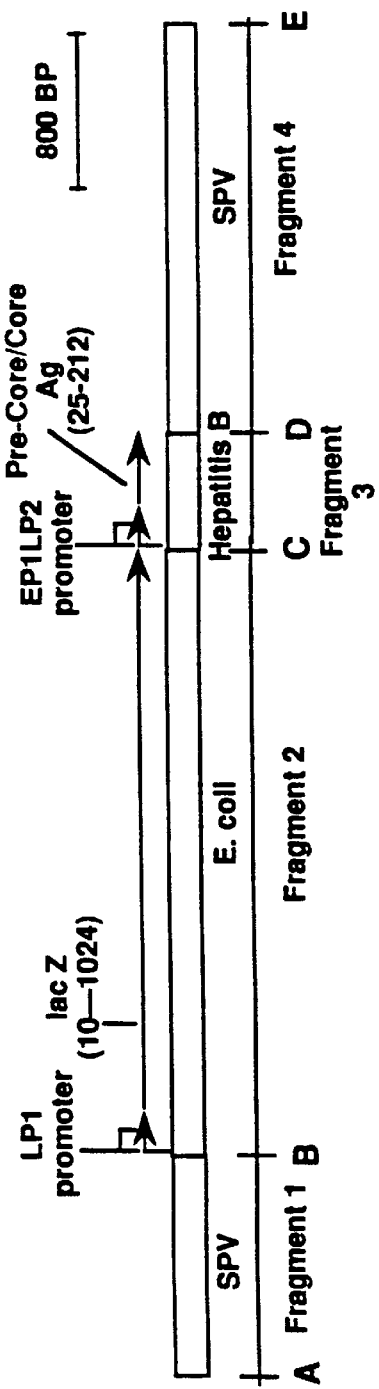
Figure 20B:
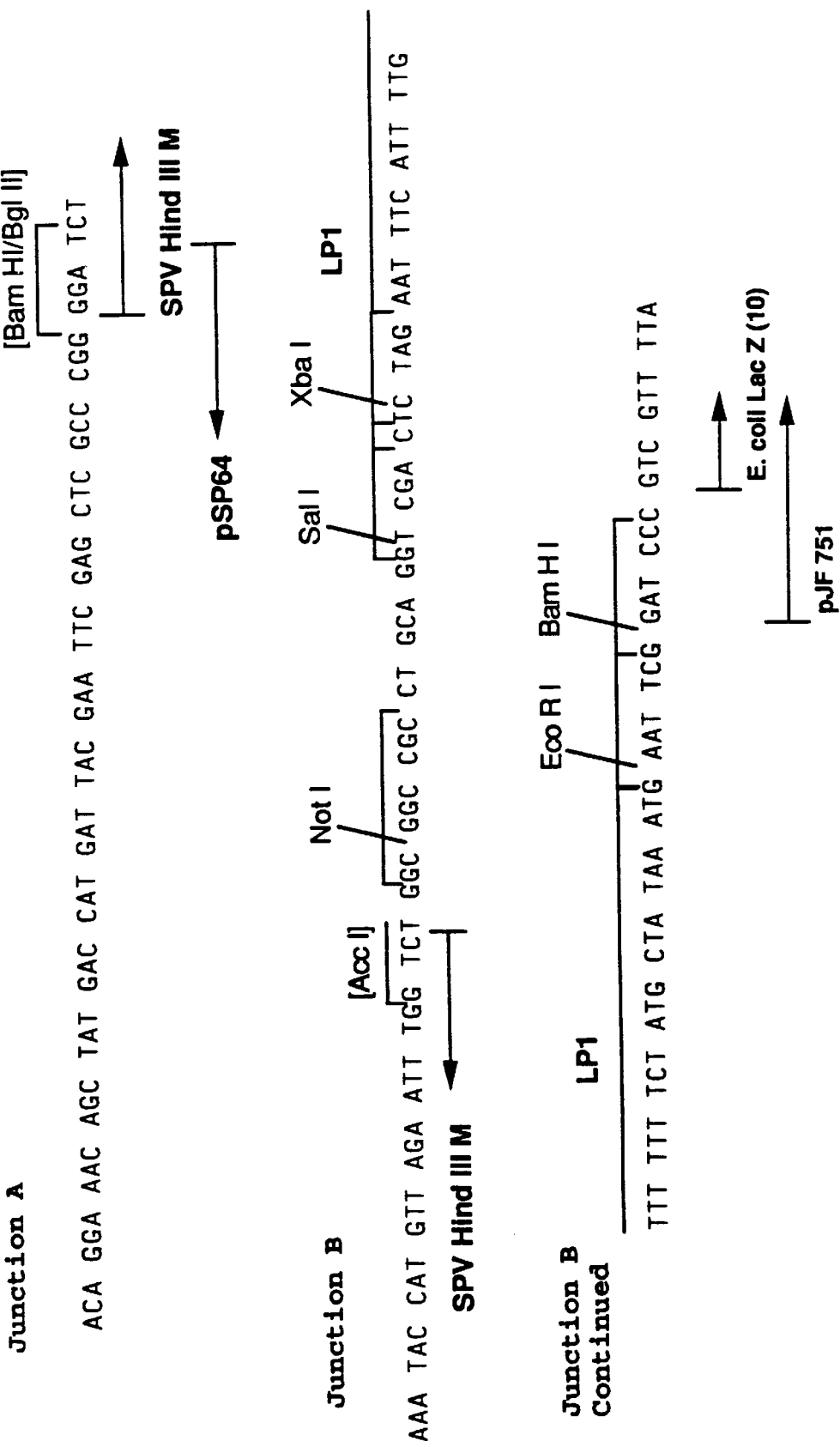
Figure 20C:
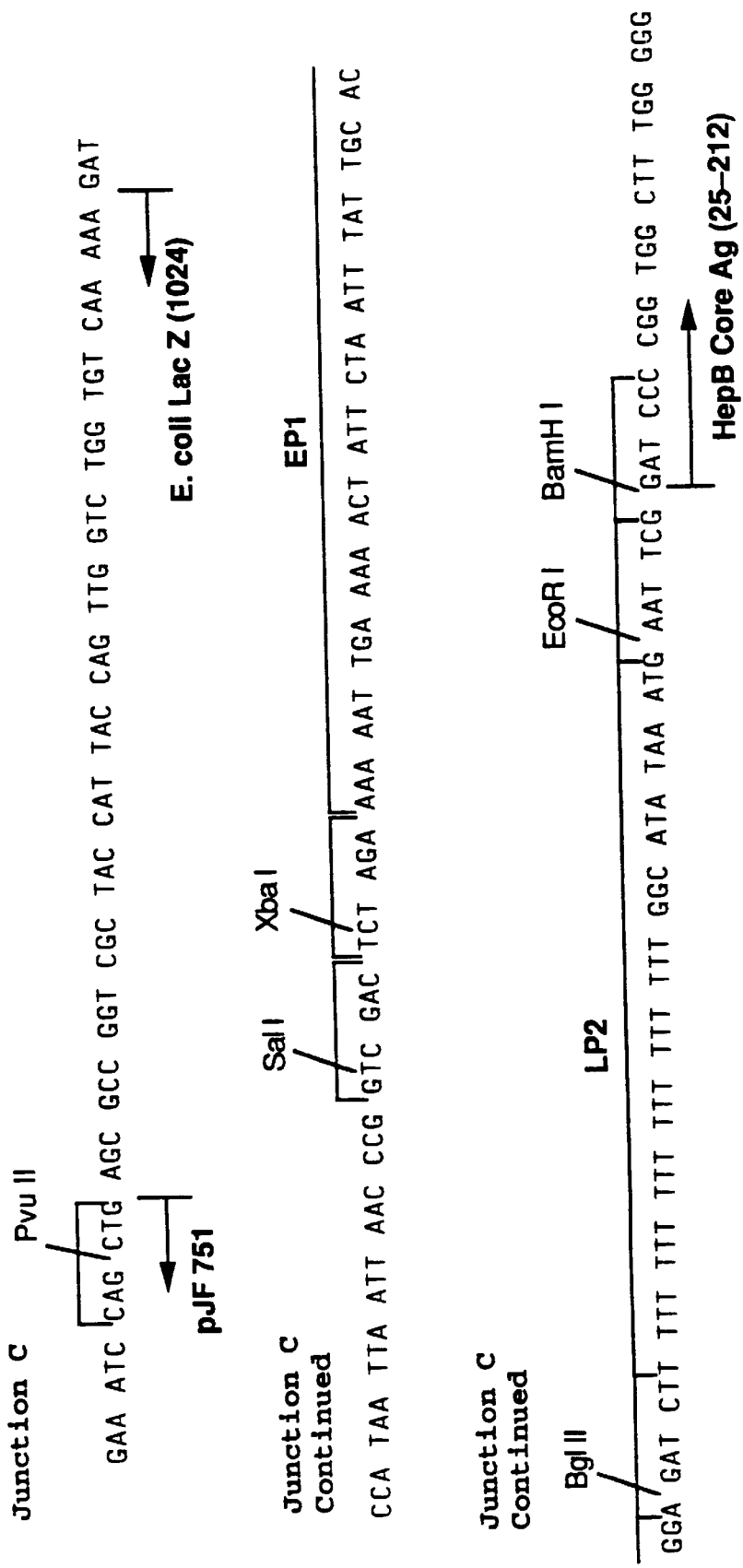
Figure 21A:
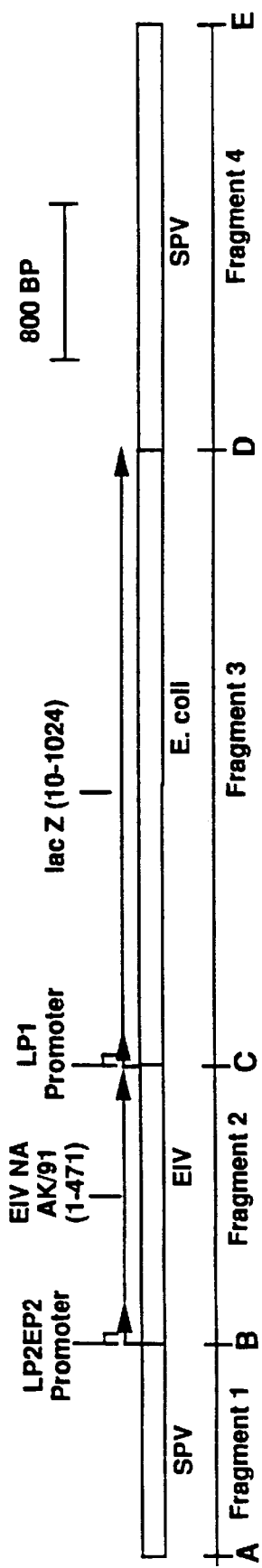
Figure 21B:
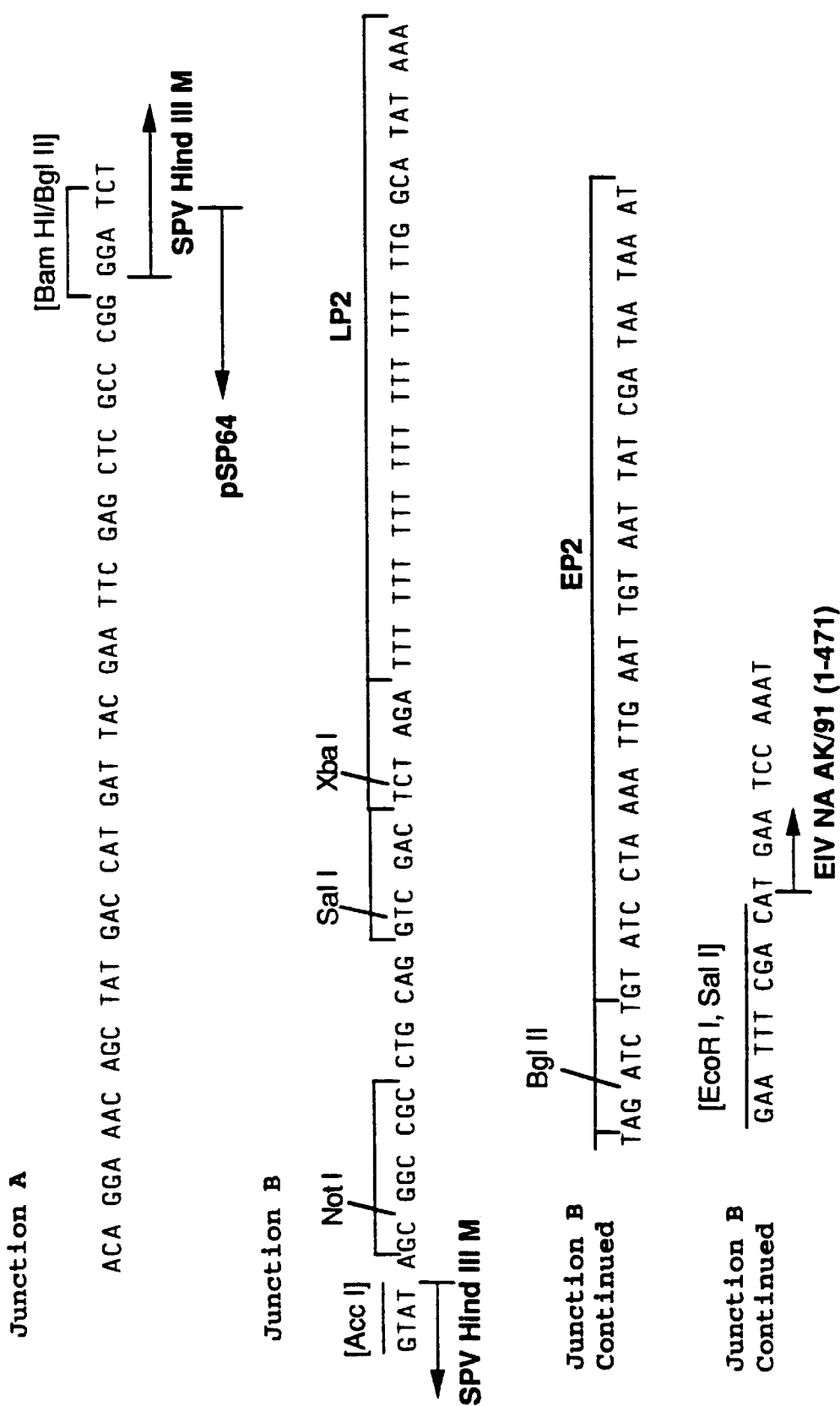
Figure 21C:
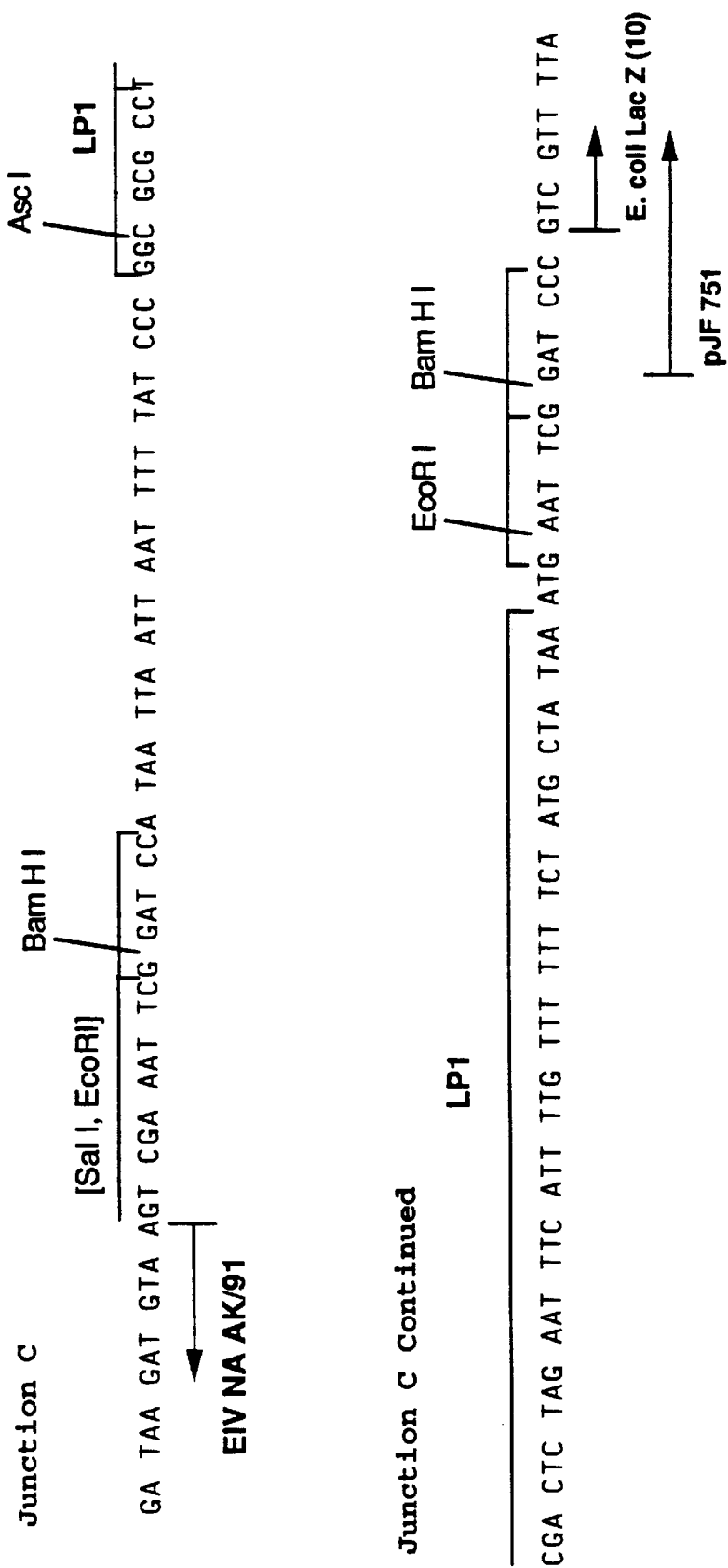
Figure 21D:
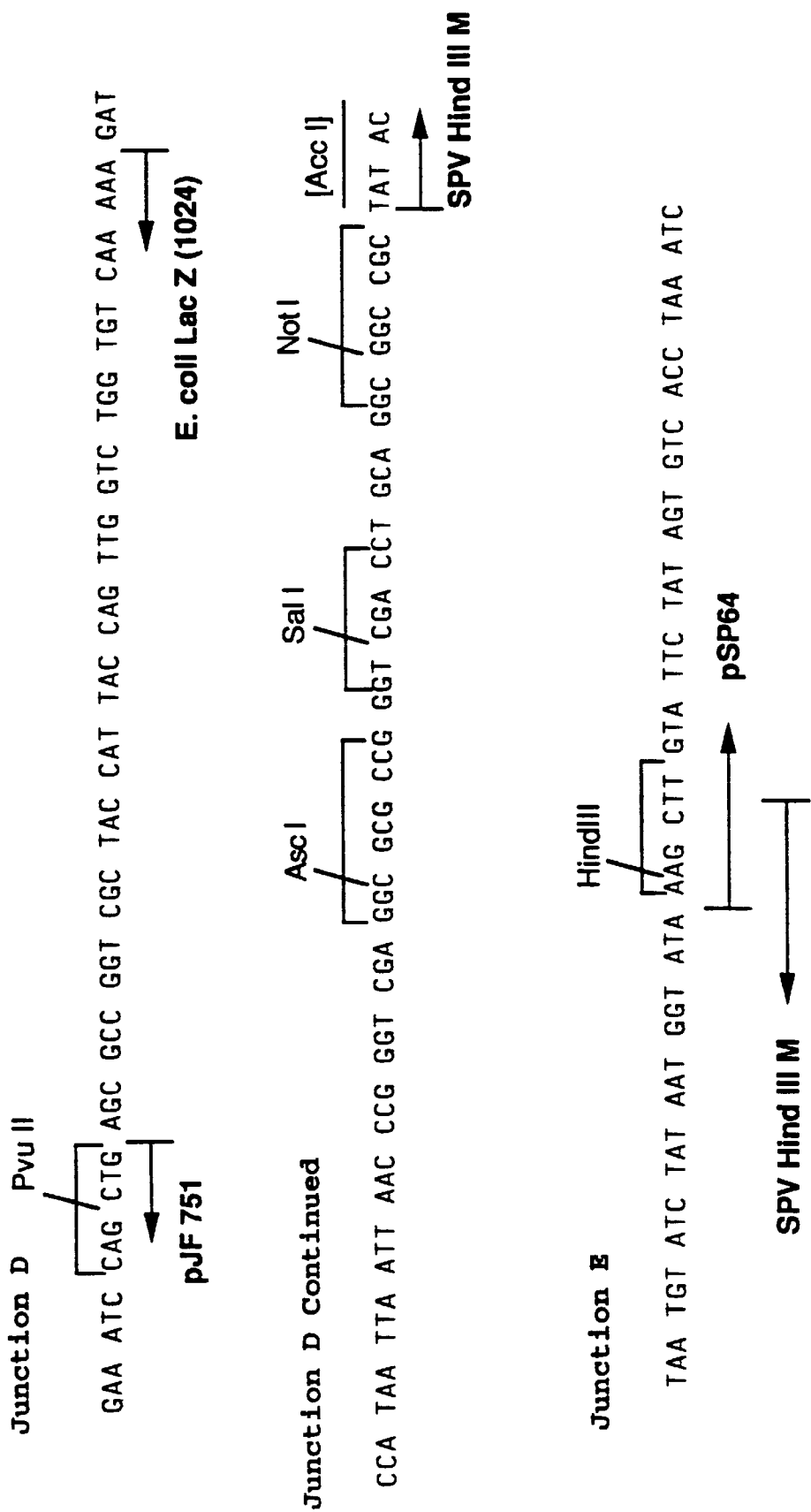

Homology Vector 738-94.5 is a swinepox virus vector that expresses one foreign gene. The gene for *E. coli* β-galactosidase (lacZ) was inserted into the the O1L open reading frame (SEQ ID NO. 115). The lacZ gene is under the control of the O1L promoter. The homology vector 738-94.5 contains a deletion of SPV DNA from nucleotides 1381 to 2133 (SEQ ID NO. 113; FIG. 17) which deletes part of the O1L ORF.

The upstream SPV sequences were synthesized by polymerase chain reaction using DNA primers 5'-GAAGCATGCCCGTTCTTATCAATAGTTTAGTCGA-AAATA-3' (SEQ ID NO. 185) and 5'-CATAA-GATCTGGCATTGTGTTATTATACTAACAAAAATAAG-3' (SEQ ID NO. 186) to produce an 871 base pair fragment with BglII and SphI ends. The O1L promoter is present on this fragment. The downstream SPV sequences were synthesized by polymerase chain reaction using DNA primers 5'-CCGTAGTCGACAAAGATCGACTTATTAATATGTA-TGGGATT-3' (SEQ ID NO. 187) and 5'-GCCT-GAAGCTTCTAGTACAGTATTTACGACTTTTGAAAT-3' (SEQ ID NO. 188) to produce an 1123 base pair fragment with SalI and HindIII ends. A recombinant swinepox virus was derived utilizing homology vector 738-94.5 and S-SPV-001 (Kasza strain) in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification is the recombinant virus. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene. Recombinant swinepox viruses derived from homology vector 738-94.5 are utilized as an expression vector to express foreign antigens and as a vaccine to raise a protective immune response in animals to foreign genes expressed by the recombinant swinepox virus. Other promoters in addition to the O1L promoter are inserted into the deleted region including LP1, EP1LP2, LP2EP2, HCMV immediate early, and one or more forei gn genes are expressed from these promoters.

REFERENCES

1. C. Bertholet, et al., *EMBO Journal* 5, 1951–1957 (1986).
2. R. A. Bhat, et al., *Nucleic Acids Research* 17, 1159–1176 (1989).
3. D. A. Boyden, et al., *Infection and Immunity* 57, 3808–3815 (1989).
4. D. B. Boyle and B. E. H. Coupar, *Virus Research* 10, 343–356 (1988).
5. R. M. Buller, et al., *Nature* 317, 813–815 (1985).
6. K. J. Cremer, et al., *Science* 228, 737–739 (1985).
7. A. J. Davidson and B. Moss, *J. Mol. Biol.* 210, 749–769 (1989).
8. A. J. Davidson and B. Moss, *J. Mol. Biol.* 210, 771–784 (1989).
9. P. L. Earl, et al., *Journal of Virology* 64, 2448–2451 (1990).
10. J. J. Esposito, et al., Virology 165, 313 (1988).
11. F. A. Ferrari, et al., *J. of Bacteriology* 161, 556–562 (1985).
12. C. Flexner, et al., Vaccine 8, 17–21 (1990).
13. S. J. Goebel, et al., *Virology* 179, 247–266 (1990).
14. U. Gubler and B. J. Hoffman, *Gene* 25, 263–269 (1983).
15. M. A. Innis, et al., *PCR Protocols A Guide to Methods and Applications,* 84–91, Academic Press, Inc., San Diego (1990).
16. S. Joshi, et al., Journal of Virology. 65, 5524–5530 (1991).
17. L. Kasza, et al., *Am. J. Vet. Res.* 21, 269–273 (1960).
18. L. Kasza, Diseases of Swine, 254–260, Ed. A. D. Leman, et al., The Iowa State University Press, Ames, Iowa (1981).
19. B. G. Klupp and T. C. Mettenleiter, *Virology* 182, 732–741 (1991).
20. U. K. Laemnli, *Nature* 227, 680–685 (1970).
21. B. Lominiczi, et al., *Journal of Virology* 49, 970–979 (1984).
22. T. Maniatis, et al., *Molecular Cloning: A Laboratory Manual*, Cold Spring Harbor Press, Cold Spring Harbor, N.Y. (1982).
23. R. F. Massung, and R. W. Moyer, Virology 180, 347–354 (1991).
24. R. F. Massung, and R. W. Moyer, *Virology* 180, 355–364 (1991).
25. B. Moss, *Science* 252, 1662–1667 (1991).
26. E. A. Petrovskis, et al., *Journal of Virology* 59, 216–223 (1986).
27. A. K. Robbins et al., *Journal of Virology* 58, 339–347 (1986).
28. A. K. Robbins et al., *Journal of Virology* 61, 2691–2701 (1987).
29. A. C. R. Samson, *Journal of Virology* 67, 1199–1203 (1986).
30. J. Sambrook, et al., *Molecular Cloning A Laboratory Manual Second Edition*, Cold Spring Harbor Press, Cold Spring Harbor, N.Y. (1989).
31. Sheffy, et al., *Proceedings 65th Annual Meeting of the United States Livestock Association* 65, 347–353 (1961).
32. W. M. Schnitzlein and D. N. Tripathy, *Virology* 181, 727–732, (1991).
33. J. Taylor, et al., *Vaccine* 9, 190–193, (1991).
34. M. Wachsman, et al., *Journal of General Virology* 70, 2513–2520 (1989).
35. M. W. Wathen, et al., *Journal of Virology* 51, 57–62 (1984).
36. M. Weerasinge, *Journal of Virology* 65, 5531–5534 (1991).
37. T. Ben-Porat, et al., *Journal of Virology*, volume 154, 325–334 (1986).
38. F. Zuckerman, et al., Vaccination and Control of Adjesky's Disease, J. T. Van Oirchot (ed.). Kluwer Academic Publishers, London, pp. 107–117 (1989).
39. Paolette, et al., *Journal of Virology*, volume 66, pp. 3424–3434 (June, 1992).
40. M. W. Mellencamp, et al., *Journal of Clinical Microbiology*, volume 27, pp. 2208–2213 (1989).
41. L. A. Herzenberg, et al., Selected Methods in Cellular Immunology, Freeman Publ. Co., San Francisco, 351–372 (1980).
42. Katz et al., Journal of Virology 64, 1808–1811 (1990).
43. Maeda et al., Biochem. Biophys. Res. Commun. 115 1040–1047 (1983).
44. Cochran, M. D. and Macdonald, R. D., WO 93/02104, published Feb. 4, 1993.
45. Galibert, F., et al., Nature 281, 646–650 (1979).
46. Thomsen, D. R., et al., Proc. Natl. Acad. Sci. USA 81, 659–663 (1984).
47. Catalog Number 267402, Beckman Instruments, Inc., Fullerton Calif.
48. Whalley, J. M., et al., Journal of General Virology 57 307–323 (1981).
49. Collett, M. S., et al., Virology 165 200–208 (1988).
50. Schodel, F. et al., Journal of Virology 66, 106–114 (1992).
51. Cochran, M.D., WO 93/25665, published Dec. 23, 1993.
52. C. A. Hjerpe, The bovine Respiratory Disease Complex. Ed. by J. L. Howard, Philadelphia, W. B. Saunders Co., 670–680 (1986).
53. F. Fenner, et al., Veterinary Virology. Academic Press, Inc., Orlando Fla., 183–202 (1987).

```
                    SEQUENCE LISTING (1) GENERAL INFORMATION:

(iii) NUMBER OF SEQUENCES: 188

(2) INFORMATION FOR SEQ ID NO:1:

(i) SEQUENCE CHARACTERISTICS:
          (A) LENGTH: 599 base pairs
```

-continued

```
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swinepox virus
         (B) STRAIN: Kasza
         (C) INDIVIDUAL ISOLATE: S-SPV-001

(vii) IMMEDIATE SOURCE:
         (B) CLONE: 515-85.1

(viii) POSITION IN GENOME:
         (B) MAP POSITION: []23.2
         (C) UNITS: %G (ix) FEATURE:
         (A) NAME/KEY: CDS
         (B) LOCATION: 202..597
         (D) OTHER INFORMATION: /partial
              /codon_start= 202
              /function= "Potential eukaryotic transcriptional
              regulatory protein"
              /standard_name= "515-85.1 ORF"

(xi) SEQUENCE DESCRIPTION: SEQ ID NO:1:

AATGTATCCA GAGTTGTTGA ATGCCTTATC GTACCTAATA TTAATATAGA GTTATTAACT     60

GAATAAGTAT ATATAAATGA TTGTTTTTAT AATGTTTGTT ATCGCATTTA GTTTTGCTGT    120

ATGGTTATCA TATACATTTT TAAGGCCGTA TATGATAAAT GAAAATATAT AAGCACTTAT    180

TTTTGTTAGT ATAATAACAC A ATG CCG TCG TAT ATG TAT CCG AAG AAC GCA      231
                        Met Pro Ser Tyr Met Tyr Pro Lys Asn Ala
                          1               5                  10

AGA AAA GTA ATT TCA AAG ATT ATA TCA TTA CAA CTT GAT ATT AAA AAA      279
Arg Lys Val Ile Ser Lys Ile Ile Ser Leu Gln Leu Asp Ile Lys Lys
                 15                  20                  25

CTT CCT AAA AAA TAT ATA AAT ACC ATG TTA GAA TTT GGT CTA CAT GGA     327
Leu Pro Lys Lys Tyr Ile Asn Thr Met Leu Glu Phe Gly Leu His Gly
             30                  35                  40

AAT CTA CCA GCT TGT ATG TAT AAA GAT GCC GTA TCA TAT GAT ATA AAT      375
Asn Leu Pro Ala Cys Met Tyr Lys Asp Ala Val Ser Tyr Asp Ile Asn
        45                  50                  55

AAT ATA AGA TTT TTA CCT TAT AAT TGT GTT ATG GTT AAA GAT TTA ATA      423
Asn Ile Arg Phe Leu Pro Tyr Asn Cys Val Met Val Lys Asp Leu Ile
     60                  65                  70

AAT GTT ATA AAA TCA TCA TCT GTA ATA GAT ACT AGA TTA CAT CAA TCT      471
Asn Val Ile Lys Ser Ser Ser Val Ile Asp Thr Arg Leu His Gln Ser
 75                  80                  85                  90

GTA TTA AAA CAT CGT AGA GCG TTA ATA GAT TAC GGC GAT CAA GAC ATT      519
Val Leu Lys His Arg Arg Ala Leu Ile Asp Tyr Gly Asp Gln Asp Ile
                 95                 100                 105

ATC ACT TTA ATG ATC ATT AAT AAG TTA CTA TCG ATA GAT GAT ATA TCC      567
Ile Thr Leu Met Ile Ile Asn Lys Leu Leu Ser Ile Asp Asp Ile Ser
            110                 115                 120

TAT ATA TTA GAT AAA AAA ATA ATT CAT GTA AC                           599
Tyr Ile Leu Asp Lys Lys Ile Ile His Val
        125                 130

(2) INFORMATION FOR SEQ ID NO:2:

(i) SEQUENCE CHARACTERISTICS:
         (A) LENGTH: 132 amino acids
```

(B) TYPE: amino acid
            (D) TOPOLOGY: linear (ii) MOLECULE TYPE: protein (xi) SEQUENCE DESCRIPTION: SEQ ID NO:2:

Met Pro Ser Tyr Met Tyr Pro Lys Asn Ala Arg Lys Val Ile Ser Lys
 1               5                  10                  15

Ile Ile Ser Leu Gln Leu Asp Ile Lys Lys Leu Pro Lys Lys Tyr Ile
             20                  25                  30

Asn Thr Met Leu Glu Phe Gly Leu His Gly Asn Leu Pro Ala Cys Met
         35                  40                  45

Tyr Lys Asp Ala Val Ser Tyr Asp Ile Asn Asn Ile Arg Phe Leu Pro
     50                  55                  60

Tyr Asn Cys Val Met Val Lys Asp Leu Ile Asn Val Ile Lys Ser Ser
 65                  70                  75                  80

Ser Val Ile Asp Thr Arg Leu His Gln Ser Val Leu Lys His Arg Arg
                 85                  90                  95

Ala Leu Ile Asp Tyr Gly Asp Gln Asp Ile Ile Thr Leu Met Ile Ile
            100                 105                 110

Asn Lys Leu Leu Ser Ile Asp Asp Ile Ser Tyr Ile Leu Asp Lys Lys
        115                 120                 125

Ile Ile His Val
    130

(2) INFORMATION FOR SEQ ID NO:3:

(i) SEQUENCE CHARACTERISTICS:
        (A) LENGTH: 899 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 3..662
        (D) OTHER INFORMATION: /partial
            /codon_start= 3
            /function= "Potential eukaryotic transcriptional
            regulatory protein"
            /standard_name= "515-85.1 ORF"

(xi) SEQUENCE DESCRIPTION: SEQ ID NO:3:

GA GAT ATT AAA TCA TGT AAA TGC TCG ATA TGT TCC GAC TCT ATA ACA         47
   Asp Ile Lys Ser Cys Lys Cys Ser Ile Cys Ser Asp Ser Ile Thr
    1               5                  10                  15

CAT CAT ATA TAT GAA ACA ACA TCA TGT ATA AAT TAT AAA TCT ACC GAT        95
His His Ile Tyr Glu Thr Thr Ser Cys Ile Asn Tyr Lys Ser Thr Asp
             20                  25                  30

```
AAT GAT CTT ATG ATA GTA TTG TTC AAT CTA ACT AGA TAT TTA ATG CAT      143
Asn Asp Leu Met Ile Val Leu Phe Asn Leu Thr Arg Tyr Leu Met His
             35                  40                  45

GGG ATG ATA CAT CCT AAT CTT ATA AGC GTA AAA GGA TGG GGT CCC CTT      191
Gly Met Ile His Pro Asn Leu Ile Ser Val Lys Gly Trp Gly Pro Leu
     50                  55                  60

ATT GGA TTA TTA ACG GGT GAT ATA GGT ATT AAT TTA AAA CTA TAT TCC      239
Ile Gly Leu Leu Thr Gly Asp Ile Gly Ile Asn Leu Lys Leu Tyr Ser
 65                  70                  75

ACC ATG AAT ATA AAT GGG CTA CGG TAT GGA GAT ATT ACG TTA TCT TCA      287
Thr Met Asn Ile Asn Gly Leu Arg Tyr Gly Asp Ile Thr Leu Ser Ser
 80                  85                  90                  95

TAC GAT ATG AGT AAT AAA TTA GTC TCT ATT ATT AAT ACA CCC ATA TAT      335
Tyr Asp Met Ser Asn Lys Leu Val Ser Ile Ile Asn Thr Pro Ile Tyr
                100                 105                 110

GAG TTA ATA CCG TTT ACT ACA TGT TGT TCA CTC AAT GAA TAT TAT TCA      383
Glu Leu Ile Pro Phe Thr Thr Cys Cys Ser Leu Asn Glu Tyr Tyr Ser
            115                 120                 125

AAA ATT GTG ATT TTA ATA AAT GTT ATT TTA GAA TAT ATG ATA TCT ATT      431
Lys Ile Val Ile Leu Ile Asn Val Ile Leu Glu Tyr Met Ile Ser Ile
        130                 135                 140

ATA TTA TAT AGA ATA TTG ATC GTA AAA AGA TTT AAT AAC ATT AAA GAA      479
Ile Leu Tyr Arg Ile Leu Ile Val Lys Arg Phe Asn Asn Ile Lys Glu
    145                 150                 155

TTT ATT TCA AAA GTC GTA AAT ACT GTA CTA GAA TCA TCA GGC ATA TAT      527
Phe Ile Ser Lys Val Val Asn Thr Val Leu Glu Ser Ser Gly Ile Tyr
160                 165                 170                 175

TTT TGT CAG ATG CGT GTA CAT GAA CAA ATT GAA TTG GAA ATA GAT GAG      575
Phe Cys Gln Met Arg Val His Glu Gln Ile Glu Leu Glu Ile Asp Glu
                180                 185                 190

CTC ATT ATT AAT GGA TCT ATG CCT GTA CAG CTT ATG CAT TTA CTT CTA      623
Leu Ile Ile Asn Gly Ser Met Pro Val Gln Leu Met His Leu Leu Leu
            195                 200                 205

AAG GTA GCT ACC ATA ATA TTA GAG GAA ATC AAA GAA ATA TAACGTATTT      672
Lys Val Ala Thr Ile Ile Leu Glu Glu Ile Lys Glu Ile
        210                 215                 220

TTTCTTTTAA ATAAATAAAA ATACTTTTTT TTTTAAACAA GGGGTGCTAC CTTGTCTAAT   732

TGTATCTTGT ATTTTGGATC TGATGCAAGA TTATTAAATA ATCGTATGAA AAAGTAGTAG   792

ATATAGTTTA TATCGTTACT GGACATGATA TTATGTTTAG TTAATTCTTC TTTGGCATGA   852

ATTCTACACG TCGGANAAGG TAATGTATCT ATAATGGTAT AAAGCTT                 899

(2) INFORMATION FOR SEQ ID NO:4:

(i) SEQUENCE CHARACTERISTICS:
        (A) LENGTH: 220 amino acids
        (B) TYPE: amino acid
        (D) TOPOLOGY: linear (ii) MOLECULE TYPE: protein (xi) SEQUENCE DESCRIPTION: SEQ ID NO:4:

Asp Ile Lys Ser Cys Lys Cys Ser Ile Cys Ser Asp Ser Ile Thr His
 1               5                  10                  15

His Ile Tyr Glu Thr Thr Ser Cys Ile Asn Tyr Lys Ser Thr Asp Asn
                20                  25                  30

Asp Leu Met Ile Val Leu Phe Asn Leu Thr Arg Tyr Leu Met His Gly
         35                  40                  45

Met Ile His Pro Asn Leu Ile Ser Val Lys Gly Trp Gly Pro Leu Ile
 50                  55                  60
```

```
Gly Leu Leu Thr Gly Asp Ile Gly Ile Asn Leu Lys Leu Tyr Ser Thr
 65                  70                  75                  80

Met Asn Ile Asn Gly Leu Arg Tyr Gly Asp Ile Thr Leu Ser Ser Tyr
                 85                  90                  95

Asp Met Ser Asn Lys Leu Val Ser Ile Ile Asn Thr Pro Ile Tyr Glu
            100                 105                 110

Leu Ile Pro Phe Thr Thr Cys Cys Ser Leu Asn Glu Tyr Tyr Ser Lys
        115                 120                 125

Ile Val Ile Leu Ile Asn Val Ile Leu Glu Tyr Met Ile Ser Ile Ile
    130                 135                 140

Leu Tyr Arg Ile Leu Ile Val Lys Arg Phe Asn Asn Ile Lys Glu Phe
145                 150                 155                 160

Ile Ser Lys Val Val Asn Thr Val Leu Glu Ser Ser Gly Ile Tyr Phe
                165                 170                 175

Cys Gln Met Arg Val His Glu Gln Ile Glu Leu Glu Ile Asp Glu Leu
            180                 185                 190

Ile Ile Asn Gly Ser Met Pro Val Gln Leu Met His Leu Leu Leu Lys
        195                 200                 205

Val Ala Thr Ile Ile Leu Glu Glu Ile Lys Glu Ile
    210                 215                 220

(2) INFORMATION FOR SEQ ID NO:5:

(i) SEQUENCE CHARACTERISTICS:
        (A) LENGTH: 129 amino acids
        (B) TYPE: amino acid
        (C) STRANDEDNESS: double
        (D) TOPOLOGY: linear (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Vaccinia virus
        (B) STRAIN: Copenhagen (viii) POSITION IN GENOME:
        (B) MAP POSITION: []23.2
        (C) UNITS: %G (xi) SEQUENCE DESCRIPTION: SEQ ID NO:5:

Met Phe Met Tyr Pro Glu Phe Ala Arg Lys Ala Leu Ser Lys Leu Ile
  1               5                  10                  15

Ser Lys Lys Leu Asn Ile Glu Lys Val Ser Ser Lys His Gln Leu Val
                 20                  25                  30

Leu Leu Asp Tyr Gly Leu His Gly Leu Leu Pro Lys Ser Leu Tyr Leu
            35                  40                  45

Glu Ala Ile Asn Ser Asp Ile Leu Asn Val Arg Phe Phe Pro Pro Glu
 50                  55                  60

Ile Ile Asn Val Thr Asp Ile Val Lys Ala Leu Gln Asn Ser Cys Arg
 65                  70                  75                  80

Val Asp Glu Tyr Leu Lys Ala Val Ser Leu Tyr His Lys Asn Ser Leu
                 85                  90                  95

Met Val Ser Gly Pro Asn Val Val Lys Leu Met Ile Glu Tyr Asn Leu
            100                 105                 110

Leu Thr His Ser Asp Leu Glu Trp Leu Ile Asn Glu Asn Val Val Lys
        115                 120                 125
```

Ala (2) INFORMATION FOR SEQ ID NO:6:

(i) SEQUENCE CHARACTERISTICS:
        (A) LENGTH: 132 amino acids
        (B) TYPE: amino acid
        (C) STRANDEDNESS: double
        (D) TOPOLOGY: linear (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Swinepox virus
        (B) STRAIN: Kasza (viii) POSITION IN GENOME:
        (B) MAP POSITION: []23.2
        (C) UNITS: %G (xi) SEQUENCE DESCRIPTION: SEQ ID NO:6:

```
Met Pro Ser Tyr Met Tyr Pro Lys Asn Ala Arg Lys Val Ile Ser Lys
1               5                   10                  15

Ile Ile Ser Leu Gln Leu Asp Ile Lys Lys Leu Pro Lys Lys Tyr Ile
            20                  25                  30

Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
50                  55                  60

Tyr Asn Cys Val Met Val Lys Asp Leu Ile Asn Val Ile Lys Ser Ser
65                  70                  75                  80

Ser Val Ile Asp Thr Arg Leu His Gln Ser Val Leu Lys His Arg Arg
            85                  90                  95

Ala Leu Ile Asp Tyr Gly Asp Gln Asp Ile Ile Thr Leu Met Ile Ile
            100                 105                 110

Asn Lys Leu Leu Ser Ile Asp Asp Ile Ser Tyr Ile Leu Asp Lys Lys
            115                 120                 125

Ile Ile His Val
        130
```

(2) INFORMATION FOR SEQ ID NO:7:

(i) SEQUENCE CHARACTERISTICS:
        (A) LENGTH: 101 amino acids
        (B) TYPE: amino acid
        (C) STRANDEDNESS: double
        (D) TOPOLOGY: linear (ii) MOLECULE TYPE: peptide (iii) HYPOTHETICAL: YES (iv) ANTI-SENSE: NO (v) FRAGMENT TYPE: C-terminal (vi) ORIGINAL SOURCE:
        (A) ORGANISM: Vaccinia virus
        (B) STRAIN: Copenhagen (viii) POSITION IN GENOME:
        (B) MAP POSITION: []23.2

(C) UNITS: %G (xi) SEQUENCE DESCRIPTION: SEQ ID NO:7:

Val Leu Asn Asp Gln Tyr Ala Lys Ile Val Ile Phe Phe Asn Thr Ile
1               5                   10                  15

Ile Glu Tyr Ile Ile Ala Thr Ile Tyr Tyr Arg Leu Thr Val Leu Asn
                20                  25                  30

Asn Tyr Thr Asn Val Lys His Phe Val Ser Lys Val Leu His Thr Val
            35                  40                  45

Met Glu Ala Cys Gly Val Leu Phe Ser Tyr Ile Lys Val Asn Asp Lys
50                  55                  60

Ile Glu His Glu Leu Glu Met Val Asp Lys Gly Thr Val Pro Ser
65                  70                  75                  80

Tyr Leu Tyr His Leu Ser Ile Asn Val Ile Ser Ile Leu Asp Asp
                85                  90                  95

Ile Asn Gly Thr Arg
            100

(2) INFORMATION FOR SEQ ID NO:8:

(i) SEQUENCE CHARACTERISTICS:
        (A) LENGTH: 100 amino acids
        (B) TYPE: amino acid
        (C) STRANDEDNESS: double
        (D) TOPOLOGY: linear (ii) MOLECULE TYPE: peptide (iii) HYPOTHETICAL: YES (iv) ANTI-SENSE: NO (v) FRAGMENT TYPE: C-terminal (vi) ORIGINAL SOURCE:
        (A) ORGANISM: Swinepox virus
        (B) STRAIN: Kasza (viii) POSITION IN GENOME:
        (B) MAP POSITION: []23.2
        (C) UNITS: %G (xi) SEQUENCE DESCRIPTION: SEQ ID NO:8:

Ser Leu Asn Glu Tyr Tyr Ser Lys Ile Val Ile Leu Ile Asn Val Ile
1               5                   10                  15

Leu Glu Tyr Met Ile Ser Ile Ile Leu Tyr Arg Ile Leu Ile Val Lys
                20                  25                  30

Arg Phe Asn Asn Ile Lys Glu Phe Ile Ser Lys Val Val Asn Thr Val
            35                  40                  45

Leu Glu Ser Ser Gly Ile Tyr Phe Cys Gln Met Arg Val His Glu Gln
50                  55                  60

Ile Glu Leu Glu Ile Asp Glu Leu Ile Ile Asn Gly Ser Met Pro Val
65                  70                  75                  80

Gln Leu Met His Leu Leu Leu Lys Val Ala Thr Ile Ile Leu Glu Glu
                85                  90                  95

Ile Lys Glu Ile
            100

(2) INFORMATION FOR SEQ ID NO:9:

(i) SEQUENCE CHARACTERISTICS:
        (A) LENGTH: 102 base pairs
        (B) TYPE: nucleic acid
        (C) STRANDEDNESS: double (D) TOPOLOGY: circular (ii) MOLECULE TYPE: DNA (genomic)

(iii) HYPOTHETICAL: NO (iv) ANTI-SENSE: NO (vi) ORIGINAL SOURCE:
          (A) ORGANISM: Plasmid (vii) IMMEDIATE SOURCE:
          (B) CLONE: 520-17.5 (Junction A)

(x) PUBLICATION INFORMATION:
          (A) AUTHORS: Ferrari, Franco A
                Trach, Kathleen
                Hoch, James A
          (B) TITLE: Sequence Analysis of the spo0B Locus Revels a
                Polycistronic Transcription Unit
          (C) JOURNAL: J. Bacteriol.
          (D) VOLUME: 161
          (E) ISSUE: 2
          (F) PAGES: 556-562
          (G) DATE: Feb.-1985

(xi) SEQUENCE DESCRIPTION: SEQ ID NO:9:

CACATACGAT TTAGGTGACA CTATAGAATA CAAGCTTTAT ACCATTATAG ATACATTACC        60

TTGTCCGACG TGTAGAATTC ATGCCAAAGA AGAATTAACT AA                         102

(2) INFORMATION FOR SEQ ID NO:10:

(i) SEQUENCE CHARACTERISTICS:
          (A) LENGTH: 102 base pairs
          (B) TYPE: nucleic acid
          (C) STRANDEDNESS: double
          (D) TOPOLOGY: circular (ii) MOLECULE TYPE: DNA (genomic)

(iii) HYPOTHETICAL: NO (iv) ANTI-SENSE: NO (vi) ORIGINAL SOURCE:
          (A) ORGANISM: Plasmid (vii) IMMEDIATE SOURCE:
          (B) CLONE: 520-17.5 (Junction B)

(ix) FEATURE:
          (A) NAME/KEY: CDS
          (B) LOCATION: 85..99
          (D) OTHER INFORMATION: /codon_start= 85
                /function= "Translational start of hybrid protein"
                /product= "N-terminal peptide"
                /number= 1
                /standard_name= "Translation of synthetic DNA
                sequence"

(ix) FEATURE:
          (A) NAME/KEY: CDS
          (B) LOCATION: 100..102
          (C) IDENTIFICATION METHOD: experimental
          (D) OTHER INFORMATION: /partial
                /codon_start= 100
                /function= "marker enzyme"
                /product= "Beta-Galactosidase"
                /evidence= EXPERIMENTAL
                /gene= "lacZ"
                /number= 2
                /citation= ([1])

(x) PUBLICATION INFORMATION:
          (A) AUTHORS: Ferrari, Franco A
                Trach, Kathleen
                Hoch, James A (B) TITLE: Seqquence Analysis of the spo0B Locus Reveals
            a Polycistronic Transcription Unit
        (C) JOURNAL: J. Bacteriol.
        (D) VOLUME: 161
        (E) ISSUE: 2
        (F) PAGES: 556-562
        (G) DATE: Feb.-1985

(xi) SEQUENCE DESCRIPTION: SEQ ID NO:10:

GTAGTCGACT CTAGAAAAAA TTGAAAAACT ATTCTAATTT ATTGCACGGA GATCTTTTTT         60

TTTTTTTTTT TTTTTGGCAT ATAA ATG AAT TCG GAT CCC GTC                      102
                          Met Asn Ser Asp Pro Val
                           1               5   1

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:11:

Met Asn Ser Asp Pro
 1               5

(2) INFORMATION FOR SEQ ID NO:12:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO:12:

Val
 1

(2) INFORMATION FOR SEQ ID NO:13:

(i) SEQUENCE CHARACTERISTICS:
        (A) LENGTH: 103 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 520-17.5 (Junction C)

(ix) FEATURE:
        (A) NAME/KEY: CDS
        (B) LOCATION: 1..72
        (C) IDENTIFICATION METHOD: experimental
        (D) OTHER INFORMATION: /partial
            /codon_start= 1
            /function= "marker enzyme"
            /product= "Beta-galactosidase"
            /evidence= EXPERIMENTAL
            /gene= "lacZ"
            /number= 1
            /citation= ([1])

```
    (ix) FEATURE:
          (A) NAME/KEY: CDS
          (B) LOCATION: 73..78
          (C) IDENTIFICATION METHOD: experimental
          (D) OTHER INFORMATION: /codon_start= 73
              /function= "Translational finish of hybrid
              protein"
              /product= "C-terminal peptide"
              /evidence= EXPERIMENTAL
              /number= 2
              /standard_name= "Translation of synthetic DNA
              sequence"

(x) PUBLICATION INFORMATION:
          (A) AUTHORS: Ferrari, Franco A
                       Trach, Kathleen
                       Hoch, James A
          (B) TITLE: Seqquence Analysis of the spo0B Locus Reveals
              a Polycistronic Transcription Unit
          (C) JOURNAL: J. Bacteriol.
          (D) VOLUME: 161
          (E) ISSUE: 2
          (F) PAGES: 556-562
          (G) DATE: Feb.-1985

(xi) SEQUENCE DESCRIPTION: SEQ ID NO:13:

AGC CCG TCA GTA TCG GCG GAA ATC CAG CTG AGC GCC GGT CGC TAC CAT        48
Ser Pro Ser Val Ser Ala Glu Ile Gln Leu Ser Ala Gly Arg Tyr His
 1               5                  10                  15

TAC CAG TTG GTC TGG TGT CAA AAA GAT CCA TAATTAATTA ACCCGGGTCG         98
Tyr Gln Leu Val Trp Cys Gln Lys Asp Pro
             20                   1

AAGAC                                                                 103

(2) INFORMATION FOR SEQ ID NO:14:

(i) SEQUENCE CHARACTERISTICS:
          (A) LENGTH: 24 amino acids
          (B) TYPE: amino acid
          (D) TOPOLOGY: linear (ii) MOLECULE TYPE: protein (xi) SEQUENCE DESCRIPTION: SEQ ID NO:14:

Ser Pro Ser Val Ser Ala Glu Ile Gln Leu Ser Ala Gly Arg Tyr His
 1               5                  10                  15

Tyr Gln Leu Val Trp Cys Gln Lys
             20

(2) INFORMATION FOR SEQ ID NO:15:

(i) SEQUENCE CHARACTERISTICS:
          (A) LENGTH: 2 amino acids
          (B) TYPE: amino acid
          (D) TOPOLOGY: linear (ii) MOLECULE TYPE: protein (xi) SEQUENCE DESCRIPTION: SEQ ID NO:15:

Asp Pro
 1

(2) INFORMATION FOR SEQ ID NO:16:

(i) SEQUENCE CHARACTERISTICS:
          (A) LENGTH: 48 base pairs
          (B) TYPE: nucleic acid
          (C) STRANDEDNESS: double
          (D) TOPOLOGY: circular (ii) MOLECULE TYPE: DNA (genomic)
```

(iii) HYPOTHETICAL: NO (iv) ANTI-SENSE: NO (vi) ORIGINAL SOURCE:
            (A) ORGANISM: Plasmid (vii) IMMEDIATE SOURCE:
             (B) CLONE: 520-17.5 (Junction D)

(xi) SEQUENCE DESCRIPTION: SEQ ID NO:16:

AGATCCCCGG GCGAGCTCGA ATTCGTAATC ATGGTCATAG CTGTTTCC                48

(2) INFORMATION FOR SEQ ID NO:17:

(i) SEQUENCE CHARACTERISTICS:
           (A) LENGTH: 57 base pairs
           (B) TYPE: nucleic acid
           (C) STRANDEDNESS: double
           (D) TOPOLOGY: circular (ii) MOLECULE TYPE: DNA (genomic)

(iii) HYPOTHETICAL: NO (iv) ANTI-SENSE: NO (vi) ORIGINAL SOURCE:
            (A) ORGANISM: Plasmid (vii) IMMEDIATE SOURCE:
             (B) CLONE: 538-46.26 (Junction A)

(xi) SEQUENCE DESCRIPTION: SEQ ID NO:17:

CACATACGAT TTAGGTGACA CTATAGAATA CAAGCTTTAT ACCATTATAG ATACATT       57

(2) INFORMATION FOR SEQ ID NO:18:

(i) SEQUENCE CHARACTERISTICS:
           (A) LENGTH: 102 base pairs
           (B) TYPE: nucleic acid
           (C) STRANDEDNESS: double
           (D) TOPOLOGY: circular (ii) MOLECULE TYPE: DNA (genomic)

(iii) HYPOTHETICAL: NO (iv) ANTI-SENSE: NO (vi) ORIGINAL SOURCE:
            (A) ORGANISM: Plasmid (vii) IMMEDIATE SOURCE:
             (B) CLONE: 538-46.16 (Junction B)

(ix) FEATURE:
            (A) NAME/KEY: CDS
            (B) LOCATION: 91..102
            (C) IDENTIFICATION METHOD: experimental
            (D) OTHER INFORMATION: /partial
                /codon_start= 91
                /function= "marker enzyme"
                /product= "Beta-Galactosidase"
                /evidence= EXPERIMENTAL
                /gene= "lacZ"
                /number= 2
                /citation= ([1])

(ix) FEATURE:
            (A) NAME/KEY: CDS
            (B) LOCATION: 76..90
            (D) OTHER INFORMATION: /partial
                /codon_start= 76
                /function= "Translational start of hybrid protein"

```
            /product= "N-terminal peptide"
            /number= 1
            /standard_name= "Translation of synthetic DNA
            sequence"

(x) PUBLICATION INFORMATION:
        (A) AUTHORS: Ferrari, Franco A
            Trach, Kathleen
            Hoch, James A
        (B) TITLE: Seqquence Analysis of the spo0B Locus Reveals
            a Polycistronic Transcription Unit
        (C) JOURNAL: J. Bacteriol.
        (D) VOLUME: 161
        (E) ISSUE: 2
        (F) PAGES: 556-562
        (G) DATE: Feb.-1985

(xi) SEQUENCE DESCRIPTION: SEQ ID NO:18:

AAGCTGGTAG ATTTCCATGT AGGGCCGCCT GCAGGTCGAC TCTAGAATTT CATTTTGTTT      60

TTTTCTATGC TATAA ATG AAT TCG GAT CCC GTC GTT TTA CAA                 102
               Met Asn Ser Asp Pro Val Val Leu Gln
                 1           5           1

(2) INFORMATION FOR SEQ ID NO:19:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:19:

Met Asn Ser Asp Pro
  1               5

(2) INFORMATION FOR SEQ ID NO:20:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:20:

Val Val Leu Gln
  1

(2) INFORMATION FOR SEQ ID NO:21:

(i) SEQUENCE CHARACTERISTICS:
        (A) LENGTH: 206 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.16 (Junction C)

(ix) FEATURE:
        (A) NAME/KEY: CDS
        (B) LOCATION: 1..63
        (C) IDENTIFICATION METHOD: experimental
```

(D) OTHER INFORMATION: /partial
                  /codon_start= 1
                  /function= "marker enzyme"
                  /product= "Beta-galactosidase"
                  /evidence= EXPERIMENTAL
                  /number= 1
                  /citation= ([1])

(ix) FEATURE:
              (A) NAME/KEY: CDS
              (B) LOCATION: 64..69
              (C) IDENTIFICATION METHOD: experimental
              (D) OTHER INFORMATION: /codon_start= 64
                  /function= "Translational finish of hybrid
                  protein"
                  /product= "C-terminal peptide"
                  /evidence= EXPERIMENTAL
                  /standard_name= "Translation of synthetic DNA
                  sequence"

(ix) FEATURE:
              (A) NAME/KEY: CDS
              (B) LOCATION: 177..185
              (C) IDENTIFICATION METHOD: experimental
              (D) OTHER INFORMATION: /codon_start= 177
                  /function= "Translational start of hybrid protein"
                  /product= "N-terminal peptide"
                  /evidence= EXPERIMENTAL
                  /standard_name= "Translation of synthetic DNA
                  sequence"

(ix) FEATURE:
              (A) NAME/KEY: CDS
              (B) LOCATION: 186..206
              (C) IDENTIFICATION METHOD: experimental
              (D) OTHER INFORMATION: /partial
                  /codon_start= 186
                  /function= "glycoprotein"
                  /product= "PRV gp50"
                  /evidence= EXPERIMENTAL
                  /gene= "gp50"
                  /number= 3
                  /citation= ([2])

(x) PUBLICATION INFORMATION:
              (A) AUTHORS: Ferrari, Franco A
                  Trach, Kathleen
                  Hoch, James A
              (B) TITLE: Seqquence Analysis of the spo0B Locus Reveals
                  a Polycistronic Transcription Unit
              (C) JOURNAL: J. Bacteriol.
              (D) VOLUME: 161
              (E) ISSUE: 2
              (F) PAGES: 556-562
              (G) DATE: Feb.-1985

(x) PUBLICATION INFORMATION:
              (A) AUTHORS: Petrovskis, Erik A
                  Timmins, James G
                  Armentrout, Marty A
                  Marchioli, Carmine C
                  Jr. Yancy, Robert J
                  Post, Leonard E
              (B) TITLE: DNA Sequence of the Gene for Pseudorabies
                  Virus gp50, a Glycoprotein without N-Linked
                  Glycosylation
              (C) JOURNAL: J. Virol.
              (D) VOLUME: 59
              (E) ISSUE: 2
              (F) PAGES: 216-223
              (G) DATE: Aug.-1986

(xi) SEQUENCE DESCRIPTION: SEQ ID NO:21:

```
GTA TCG GCG GAA ATC CAG CTG AGC GCC GGT CGC TAC CAT TAC CAG TTG        48
Val Ser Ala Glu Ile Gln Leu Ser Ala Gly Arg Tyr His Tyr Gln Leu
 1               5                  10                  15

GTC TGG TGT CAA AAA GAT CCA TAATTAATTA ACCCGGCCGC CTGCAGGTCG           99
Val Trp Cys Gln Lys Asp Pro
```

```
                      20              1
ACTCTAGAAA AAATTGAAAA ACTATTCTAA TTTATTGCAC GGAGATCTTT TTTTTTTTTT      159

TTTTTTTTGG CATATAA ATG AAT TCG CTC GCA GCG CTA TTG GCG GCG             206
                   Met Asn Ser Leu Ala Ala Leu Leu Ala Ala
                     1           1               5
```

(2) INFORMATION FOR SEQ ID NO:22:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:22:

```
Val Ser Ala Glu Ile Gln Leu Ser Ala Gly Arg Tyr His Tyr Gln Leu
 1               5                  10                  15
Val Trp Cys Gln Lys
            20
```

(2) INFORMATION FOR SEQ ID NO:23:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO:23:

```
Asp Pro
 1
```

(2) INFORMATION FOR SEQ ID NO:24:

(i) SEQUENCE CHARACTERISTICS:
        (A) LENGTH: 3 amino acids
        (B) TYPE: amino acid
        (D) TOPOLOGY: linear (ii) MOLECULE TYPE: protein (xi) SEQUENCE DESCRIPTION: SEQ ID NO:24:

```
Met Asn Ser
 1
```

(2) INFORMATION FOR SEQ ID NO:25:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:25:

```
Leu Ala Ala Leu Leu Ala Ala
 1               5
```

(2) INFORMATION FOR SEQ ID NO:26:

(i) SEQUENCE CHARACTERISTICS:
        (A) LENGTH: 101 base pairs
        (B) TYPE: nucleic acid
        (C) STRANDEDNESS: double
        (D) TOPOLOGY: circular

```
    (ii) MOLECULE TYPE: DNA (genomic)

(iii) HYPOTHETICAL: NO (iv) ANTI-SENSE: NO (vi) ORIGINAL SOURCE:
         (A) ORGANISM: Plasmid (vii) IMMEDIATE SOURCE:
         (B) CLONE: 538-46.16 (Junction D)

(ix) FEATURE:
         (A) NAME/KEY: CDS
         (B) LOCATION: 1..15
         (D) OTHER INFORMATION: /partial
             /codon_start= 1
             /function= "glycoprotein"
             /product= "PRV gp63"
             /gene= "gp63"
             /number= 1
             /citation= ([1])

(x) PUBLICATION INFORMATION:
         (A) AUTHORS: Petrovskis, Erik A
             Timmins, James G
             Post, Lenoard E
         (B) TITLE: Use of Lambda-gt11 To Isolate Genes for two
             Pseudorabies Virus Glycoproteins with homology to
             Herpes Simplex Virus and Varicella-Zoster Virus
             Glycoproteins
         (C) JOURNAL: J. Virol.
         (D) VOLUME: 60
         (E) ISSUE: 1
         (F) PAGES: 185-193
         (G) DATE: Oct.-1986

(xi) SEQUENCE DESCRIPTION: SEQ ID NO:26:

CGC GTG CAC CAC GAG GGACTCTAGA GGATCCATAA TTAATTAATT AATTTTTATC        55
Arg Val His His Glu
 1               5

CCGGGTCGAC CTGCAGGCGG CCGGGTCGAC CTGCAGGCGG CCAGAC                    101

(2) INFORMATION FOR SEQ ID NO:27:

(i) SEQUENCE CHARACTERISTICS:
         (A) LENGTH: 5 amino acids
         (B) TYPE: amino acid
         (D) TOPOLOGY: linear (ii) MOLECULE TYPE: protein (xi) SEQUENCE DESCRIPTION: SEQ ID NO:27:

Arg Val His His Glu
 1               5

(2) INFORMATION FOR SEQ ID NO:28:

(i) SEQUENCE CHARACTERISTICS:
         (A) LENGTH: 57 base pairs
         (B) TYPE: nucleic acid
         (C) STRANDEDNESS: double
         (D) TOPOLOGY: circular (ii) MOLECULE TYPE: DNA (genomic)

(iii) HYPOTHETICAL: NO (iv) ANTI-SENSE: NO (vi) ORIGINAL SOURCE:
         (A) ORGANISM: Plasmid (vii) IMMEDIATE SOURCE:
         (B) CLONE: 538-46.16 (Junction E)
```

(xi) SEQUENCE DESCRIPTION: SEQ ID NO:28:

| | |
|---|---|
| AGATCCCCGG GCGAGCTCGA ATTCGTAATC ATGGTCATAG CTGTTTCCTG TGTGAAA | 57 |

(2) INFORMATION FOR SEQ ID NO:29:

(i) SEQUENCE CHARACTERISTICS:
        (A) LENGTH: 1907 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Newcastle disease virus
        (B) STRAIN: B1

(vii) IMMEDIATE SOURCE:
        (B) CLONE: 137-23.803 (PSY1142)

(viii) POSITION IN GENOME:
        (B) MAP POSITION: []50%
        (C) UNITS: %G (ix) FEATURE:
        (A) NAME/KEY: CDS
        (B) LOCATION: 92..1822
        (D) OTHER INFORMATION: /codon_start= 92
            /product= "NDV heamagglutinin-Neuraminidase"
            /gene= "HN"
            /number= 1

(xi) SEQUENCE DESCRIPTION: SEQ ID NO:29:

```
ACGGGTAGAA CGGTAAGAGA GGCCGCCCCT CAATTGCGAG CCAGACTTCA CAACCTCCGT         60

TCTACCGCTT CACCGACAAC AGTCCTCAAT C ATG GAC CGC GCC GTT AGC CAA          112
                                  Met Asp Arg Ala Val Ser Gln
                                    1               5

GTT GCG TTA GAG AAT GAT GAA AGA GAG GCA AAA AAT ACA TGG CGC TTG         160
Val Ala Leu Glu Asn Asp Glu Arg Glu Ala Lys Asn Thr Trp Arg Leu
         10                  15                  20

ATA TTC CGG ATT GCA ATC TTA TTC TTA ACA GTA GTG ACC TTG GCT ATA         208
Ile Phe Arg Ile Ala Ile Leu Phe Leu Thr Val Val Thr Leu Ala Ile
     25                  30                  35

TCT GTA GCC TCC CTT TTA TAT AGC ATG GGG GCT AGC ACA CCT AGC GAT         256
Ser Val Ala Ser Leu Leu Tyr Ser Met Gly Ala Ser Thr Pro Ser Asp
 40                  45                  50                  55

CTT GTA GGC ATA CCG ACT AGG ATT TCC AGG GCA GAA GAA AAG ATT ACA         304
Leu Val Gly Ile Pro Thr Arg Ile Ser Arg Ala Glu Glu Lys Ile Thr
                 60                  65                  70

TCT ACA CTT GGT TCC AAT CAA GAT GTA GTA GAT AGG ATA TAT AAG CAA         352
Ser Thr Leu Gly Ser Asn Gln Asp Val Val Asp Arg Ile Tyr Lys Gln
             75                  80                  85

GTG GCC CTT GAG TCT CCA TTG GCA TTG TTA AAT ACT GAG ACC ACA ATT         400
Val Ala Leu Glu Ser Pro Leu Ala Leu Leu Asn Thr Glu Thr Thr Ile
         90                  95                 100

ATG AAC GCA ATA ACA TCT CTC TCT TAT CAG ATT AAT GGA GCT GCA AAC         448
Met Asn Ala Ile Thr Ser Leu Ser Tyr Gln Ile Asn Gly Ala Ala Asn
    105                 110                 115

AAC AGC GGG TGG GGG GCA CCT ATT CAT GAC CCA GAT TAT ATA GGG GGG         496
Asn Ser Gly Trp Gly Ala Pro Ile His Asp Pro Asp Tyr Ile Gly Gly
120                 125                 130                 135

ATA GGC AAA GAA CTC ATT GTA GAT GAT GCT AGT GAT GTC ACA TCA TTC         544
```

-continued

```
           Ile Gly Lys Glu Leu Ile Val Asp Asp Ala Ser Asp Val Thr Ser Phe
                           140                 145                 150

TAT CCC TCT GCA TTT CAA GAA CAT CTG AAT TTT ATC CCG GCG CCT ACT       592
Tyr Pro Ser Ala Phe Gln Glu His Leu Asn Phe Ile Pro Ala Pro Thr
            155                 160                 165

ACA GGA TCA GGT TGC ACT CGA ATA CCC TCA TTT GAC ATG AGT GCT ACC       640
Thr Gly Ser Gly Cys Thr Arg Ile Pro Ser Phe Asp Met Ser Ala Thr
170                 175                 180

CAT TAC TGC TAC ACC CAT AAT GTA ATA TTG TCT GGA TGC AGA GAT CAC       688
His Tyr Cys Tyr Thr His Asn Val Ile Leu Ser Gly Cys Arg Asp His
    185                 190                 195

TCA CAC TCA CAT CAG TAT TTA GCA CTT GGT GTG CTC CGG ACA TCT GCA       736
Ser His Ser His Gln Tyr Leu Ala Leu Gly Val Leu Arg Thr Ser Ala
200                 205                 210                 215

ACA GGG AGG GTA TTC TTT TCT ACT CTG CGT TCC ATC AAC CTG GAC GAC       784
Thr Gly Arg Val Phe Phe Ser Thr Leu Arg Ser Ile Asn Leu Asp Asp
                220                 225                 230

ACC CAA AAT CGG AAG TCT TGC AGT GTG AGT GCA ACT CCC CTG GGT TGT       832
Thr Gln Asn Arg Lys Ser Cys Ser Val Ser Ala Thr Pro Leu Gly Cys
            235                 240                 245

GAT ATG CTG TGC TCG AAA GCC ACG GAG ACA GAG GAA GAA GAT TAT AAC       880
Asp Met Leu Cys Ser Lys Ala Thr Glu Thr Glu Glu Glu Asp Tyr Asn
                250                 255                 260

TCA GCT GTC CCT ACG CGG ATG GTA CAT GGG AGG TTA GGG TTC GAC GGC       928
Ser Ala Val Pro Thr Arg Met Val His Gly Arg Leu Gly Phe Asp Gly
        265                 270                 275

CAA TAT CAC GAA AAG GAC CTA GAT GTC ACA ACA TTA TTC GGG GAC TGG       976
Gln Tyr His Glu Lys Asp Leu Asp Val Thr Thr Leu Phe Gly Asp Trp
280                 285                 290                 295

GTG GCC AAC TAC CCA GGA GTA GGG GGT GGA TCT TTT ATT GAC AGC CGC       1024
Val Ala Asn Tyr Pro Gly Val Gly Gly Gly Ser Phe Ile Asp Ser Arg
                300                 305                 310

GTG TGG TTC TCA GTC TAC GGA GGG TTA AAA CCC AAT ACA CCC AGT GAC       1072
Val Trp Phe Ser Val Tyr Gly Gly Leu Lys Pro Asn Thr Pro Ser Asp
            315                 320                 325

ACT GTA CAG GAA GGG AAA TAT GTG ATA TAC AAG CGA TAC AAT GAC ACA       1120
Thr Val Gln Glu Gly Lys Tyr Val Ile Tyr Lys Arg Tyr Asn Asp Thr
        330                 335                 340

TGC CCA GAT GAG CAA GAC TAC CAG ATT CGA ATG GCC AAG TCT TCG TAT       1168
Cys Pro Asp Glu Gln Asp Tyr Gln Ile Arg Met Ala Lys Ser Ser Tyr
345                 350                 355

AAG CCT GGA CGG TTT GGT GGG AAA CGC ATA CAG CAG GCT ATC TTA TCT       1216
Lys Pro Gly Arg Phe Gly Gly Lys Arg Ile Gln Gln Ala Ile Leu Ser
                360                 365                 370                 375

ATC AAA GTG TCA ACA TCC TTA GGC GAA GAC CCG GTA CTG ACT GTA CCG       1264
 Ile Lys Val Ser Thr Ser Leu Gly Glu Asp Pro Val Leu Thr Val Pro
            380                 385                 390

CCC AAC ACA GTC ACA CTC ATG GGG GCC GAA GGC AGA ATT CTC ACA GTA       1312
Pro Asn Thr Val Thr Leu Met Gly Ala Glu Gly Arg Ile Leu Thr Val
        395                 400                 405

GGG ACA TCC CAT TTC TTG TAT CAG CGA GGG TCA TCA TAC TTC TCT CCC       1360
Gly Thr Ser His Phe Leu Tyr Gln Arg Gly Ser Ser Tyr Phe Ser Pro
                410                 415                 420

GCG TTA TTA TAT CCT ATG ACA GTC AGC AAC AAA ACA GCC ACT CTT CAT       1408
Ala Leu Leu Tyr Pro Met Thr Val Ser Asn Lys Thr Ala Thr Leu His
            425                 430                 435

AGT CCT TAT ACA TTC AAT GCC TTC ACT CGG CCA GGT AGT ATC CCT TGC       1456
Ser Pro Tyr Thr Phe Asn Ala Phe Thr Arg Pro Gly Ser Ile Pro Cys
440                 445                 450                 455

CAG GCT TCA GCA AGA TGC CCC AAC TCA TGT GTT ACT GGA GTC TAT ACA       1504
```

```
Gln Ala Ser Ala Arg Cys Pro Asn Ser Cys Val Thr Gly Val Tyr Thr
                460                 465                 470

GAT CCA TAT CCC CTA ATC TTC TAT AGA AAC CAC ACC TTG CGA GGG GTA    1552
Asp Pro Tyr Pro Leu Ile Phe Tyr Arg Asn His Thr Leu Arg Gly Val
            475                 480                 485

TTC GGG ACA ATG CTT GAT GGT GAA CAA GCA AGA CTT AAC CCT GCG TCT    1600
Phe Gly Thr Met Leu Asp Gly Glu Gln Ala Arg Leu Asn Pro Ala Ser
        490                 495                 500

GCA GTA TTC GAT AGC ACA TCC CGC AGT CGC ATA ACT CGA GTG AGT TCA    1648
Ala Val Phe Asp Ser Thr Ser Arg Ser Arg Ile Thr Arg Val Ser Ser
    505                 510                 515

AGC AGC ATC AAA GCA GCA TAC ACA ACA TCA ACT TGT TTT AAA GTG GTC    1696
Ser Ser Ile Lys Ala Ala Tyr Thr Thr Ser Thr Cys Phe Lys Val Val
520                 525                 530                 535

AAG ACC AAT AAG ACC TAT TGT CTC AGC ATT GCT GAA ATA TCT AAT ACT    1744
Lys Thr Asn Lys Thr Tyr Cys Leu Ser Ile Ala Glu Ile Ser Asn Thr
                540                 545                 550

CTC TTC GGA GAA TTC AGA ATC GTC CCG TTA CTA GTT GAG ATC CTC AAA    1792
Leu Phe Gly Glu Phe Arg Ile Val Pro Leu Leu Val Glu Ile Leu Lys
            555                 560                 565

GAT GAC GGG GTT AGA GAA GCC AGG TCT GGC TAGTTGAGTC AACTATGAAA      1842
Asp Asp Gly Val Arg Glu Ala Arg Ser Gly
        570                 575

GAGTTGGAAA GATGGCATTG TATCACCTAT CTTCTGCGAC ATCAAGAATC AAACCGAATG  1902

CCGGC                                                              1907

(2) INFORMATION FOR SEQ ID NO:30:

(i) SEQUENCE CHARACTERISTICS:
        (A) LENGTH: 577 amino acids
        (B) TYPE: amino acid
        (D) TOPOLOGY: linear (ii) MOLECULE TYPE: protein (xi) SEQUENCE DESCRIPTION: SEQ ID NO:30:

Met Asp Arg Ala Val Ser Gln Val Ala Leu Glu Asn Asp Glu Arg Glu
 1               5                  10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175
```

```
Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Ala Thr Glu
                245                 250                 255

Thr Glu Glu Glu Asp Tyr Asn Ser Ala Val Pro Thr Arg Met Val His
            260                 265                 270

Gly Arg Leu Gly Phe Asp Gly Gln Tyr His Glu Lys Asp Leu Asp Val
        275                 280                 285

Thr Thr Leu Phe Gly Asp Trp Val Ala Asn Tyr Pro Gly Val Gly Gly
    290                 295                 300

Gly Ser Phe Ile Asp Ser Arg Val Trp Phe Ser Val Tyr Gly Gly Leu
305                 310                 315                 320

Lys Pro Asn Thr Pro Ser Asp Thr Val Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asn Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Ser
450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Glu Gln
                485                 490                 495

Ala Arg Leu Asn Pro Ala Ser Ala Val Phe Asp Ser Thr Ser Arg Ser
            500                 505                 510

Arg Ile Thr Arg Val Ser Ser Ser Ile Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly (2) INFORMATION FOR SEQ ID NO:31:
```

-continued

```
     (i) SEQUENCE CHARACTERISTICS:
          (A) LENGTH: 57 base pairs
          (B) TYPE: nucleic acid
          (C) STRANDEDNESS: double
          (D) TOPOLOGY: circular (ii) MOLECULE TYPE: DNA (genomic)

(iii) HYPOTHETICAL: NO (iv) ANTI-SENSE: NO (vi) ORIGINAL SOURCE:
          (A) ORGANISM: Plasmid (vii) IMMEDIATE SOURCE:
          (B) CLONE: 538-46.26 (Junction A)

(xi) SEQUENCE DESCRIPTION: SEQ ID NO:31:

CACATACGAT TTAGGTGACA CTATAGAATA CAAGCTTTAT ACCATTATAG ATACATT        57

(2) INFORMATION FOR SEQ ID NO:32:

(i) SEQUENCE CHARACTERISTICS:
          (A) LENGTH: 108 base pairs
          (B) TYPE: nucleic acid
          (C) STRANDEDNESS: double
          (D) TOPOLOGY: circular (ii) MOLECULE TYPE: DNA (genomic)

(iii) HYPOTHETICAL: NO (iv) ANTI-SENSE: NO (vi) ORIGINAL SOURCE:
          (A) ORGANISM: Plasmid (vii) IMMEDIATE SOURCE:
          (B) CLONE: 538-46.26 (Junction B)

(ix) FEATURE:
          (A) NAME/KEY: exon
          (B) LOCATION: 88..102
          (D) OTHER INFORMATION: /codon_start= 88
               /function= "Translational start of hybrid protein"
               /product= "N-terminal peptide"
               /number= 1
               /standard_name= "Translation of synthetic DNA
               sequence"

(ix) FEATURE:
          (A) NAME/KEY: CDS
          (B) LOCATION: 103..108
          (C) IDENTIFICATION METHOD: experimental
          (D) OTHER INFORMATION: /partial
               /codon_start= 103
               /product= "NDV Heamagglutinin-Neuraminidase"
               /evidence= EXPERIMENTAL
               /gene= "HN"
               /number= 2

(xi) SEQUENCE DESCRIPTION: SEQ ID NO:32:

CATGTAGTCG ACTCTAGAAA AAATTGAAAA ACTATTCTAA TTTATTGCAC GGAGATCTTT     60

TTTTTTTTTT TTTTTTTTGG CATATAAATG AATTCGGATC CG GAC CGC               108
                                               Asp Arg
                                                 1

(2) INFORMATION FOR SEQ ID NO:33:

(i) SEQUENCE CHARACTERISTICS:
          (A) LENGTH: 2 amino acids
          (B) TYPE: amino acid
          (D) TOPOLOGY: linear
```

(ii) MOLECULE TYPE: protein (xi) SEQUENCE DESCRIPTION: SEQ ID NO:33:

Asp Arg
 1

(2) INFORMATION FOR SEQ ID NO:34:

(i) SEQUENCE CHARACTERISTICS:
       (A) LENGTH: 108 base pairs
       (B) TYPE: nucleic acid
       (C) STRANDEDNESS: double
       (D) TOPOLOGY: circular (ii) MOLECULE TYPE: DNA (genomic)

(iii) HYPOTHETICAL: NO (iv) ANTI-SENSE: NO (vi) ORIGINAL SOURCE:
       (A) ORGANISM: Plasmid (vii) IMMEDIATE SOURCE:
       (B) CLONE: 538-46.26 (Junction C)

(ix) FEATURE:
       (A) NAME/KEY: CDS
       (B) LOCATION: 70..84
       (D) OTHER INFORMATION: /codon_start= 70
          /function= "Translational start of hybrid protein"
          /product= "N-terminal peptide"
          /number= 1
          /standard_name= "Translation of synthetic DNA
          sequence"

(ix) FEATURE:
       (A) NAME/KEY: CDS
       (B) LOCATION: 85..108
       (C) IDENTIFICATION METHOD: experimental
       (D) OTHER INFORMATION: /partial
          /codon_start= 85
          /function= "marker enzyme"
          /product= "Beta-galactosidase"
          /evidence= EXPERIMENTAL
          /gene= "lacZ"
          /number= 2
          /citation= ([1])

(x) PUBLICATION INFORMATION:
       (A) AUTHORS: Ferrari, Franco A
          Trach, Kathleen
          Hoch, James A
       (B) TITLE: Sequence Analysis of the spo0B Locus Reveals
          a Polycistronic Transcription Unit
       (C) JOURNAL: J. Bacteriol.
       (D) VOLUME: 161
       (E) ISSUE: 2
       (F) PAGES: 556-562
       (G) DATE: Feb.-1985

(xi) SEQUENCE DESCRIPTION: SEQ ID NO:34:

```
TGCGACATCA AGAATCAAAC CGAATGCCCT CGACTCTAGA ATTTCATTTT GTTTTTTCT      60

ATGCTATAA ATG AAT TCG GAT CCC GTC GTT TTA CAA CGT CGT GAC TGG        108
          Met Asn Ser Asp Pro Val Val Leu Gln Arg Arg Asp Trp
            1               5   1                   5
```

(2) INFORMATION FOR SEQ ID NO:35:

(i) SEQUENCE CHARACTERISTICS:
       (A) LENGTH: 5 amino acids
       (B) TYPE: amino acid
       (D) TOPOLOGY: linear (ii) MOLECULE TYPE: protein (xi) SEQUENCE DESCRIPTION: SEQ ID NO:35:

Met Asn Ser Asp Pro
 1               5

(2) INFORMATION FOR SEQ ID NO:36:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:36:

Val Val Leu Gln Arg Arg Asp Trp
 1               5

(2) INFORMATION FOR SEQ ID NO:37:

(i) SEQUENCE CHARACTERISTICS:
        (A) LENGTH: 108 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.26

(ix) FEATURE:
        (A) NAME/KEY: CDS
        (B) LOCATION: 1..54
        (C) IDENTIFICATION METHOD: experimental
        (D) OTHER INFORMATION: /partial
           /codon_start= 1
           /function= "marker enzyme"
           /product= "Beta-galactosidase"
           /evidence= EXPERIMENTAL
           /gene= "lacZ"
           /number= 1
           /citation= ([1])

(ix) FEATURE:
        (A) NAME/KEY: CDS
        (B) LOCATION: 55..63
        (C) IDENTIFICATION METHOD: experimental
        (D) OTHER INFORMATION: /codon_start= 55
           /function= "Translational finish of hybrid
           protein"
           /product= "C-terminal peptide"
           /evidence= EXPERIMENTAL
           /number= 2
           /standard_name= "Translation of synthetic DNA
           sequence"

(xi) SEQUENCE DESCRIPTION: SEQ ID NO:37:

```
GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG AGGGTCGAAG ACCAAATTCT           100
Gln Lys Asp Pro
             1

AACATGGT                                                              108
```

(2) INFORMATION FOR SEQ ID NO:38:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:38:

```
Glu Ile Gln Leu Ser Ala Gly Arg Tyr His Tyr Gln Leu Val Trp Cys
 1               5                  10                  15
Gln Lys
```

(2) INFORMATION FOR SEQ ID NO:39:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO:39:

```
Asp Pro
 1
```

(2) INFORMATION FOR SEQ ID NO:40:

(i) SEQUENCE CHARACTERISTICS:
        (A) LENGTH: 57 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.26 (Junction E)

(xi) SEQUENCE DESCRIPTION: SEQ ID NO:40:

```
AGATCCCCGG GCGAGCTCGA ATTCGTAATC ATGGTCATAG CTGTTTCCTG TGTGAAA        57
```

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (vi) ORIGINAL SOURCE:
        (A) ORGANISM: Pseudorabies virus [\]mSynthetic oligonucleotide
            primer (xi) SEQUENCE DESCRIPTION: SEQ ID NO:41:

```
CGCGAATTCG CTCGCAGCGC TATTGGC                                          27
```

(2) INFORMATION FOR SEQ ID NO:42:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (vi) ORIGINAL SOURCE:
        (A) ORGANISM: Pseudorabies virus [\]mSynthetic oligonucleotide
&

(B) MAP POSITION: []23.2
            (C) UNITS: %G (xi) SEQUENCE DESCRIPTION: SEQ ID NO:44:

TTTTTTTTTT TTTTTTTTTT GGCATATAAA TAGATCTGTA TCCTAAAATT GAATTGTAAT    60

TATCGATAAT AAAT    74

(2) INFORMATION FOR SEQ ID NO:45:

(i) SEQUENCE CHARACTERISTICS:
            (A) LENGTH: 37 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (xi) SEQUENCE DESCRIPTION: SEQ ID NO:45:

GTATCCTAAA ATTGAATTGT AATTATCGAT AATAAAT    37

(2) INFORMATION FOR SEQ ID NO:46:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (xi) SEQUENCE DESCRIPTION: SEQ ID NO:46:

CGACTCTAGA ATTTCATTTT GTTTTTTTCT ATGCTATAAA T    41

(2) INFORMATION FOR SEQ ID NO:47:

(i) SEQUENCE CHARACTERISTICS:
            (A) LENGTH: 60 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Swinepox virus
             (B) STRAIN: Kasza
             (C) INDIVIDUAL ISOLATE: S-SPV-001

(vii) IMMEDIATE SOURCE:
             (B) CLONE: 515-85.1

(viii) POSITION IN GENOME:
             (B) MAP POSITION: []23.2
             (C) UNITS: %G (xi) SEQUENCE DESCRIPTION: SEQ ID NO:47:

```
CACATACGAT TTAGGTGACA CTATAGAATA CAAGCTTTGA GTCTATTGGT TATTTATACG     60
```

(2) INFORMATION FOR SEQ ID NO:48:

(i) SEQUENCE CHARACTERISTICS:
(A) LENGTH: 123 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Swinepox virus
(B) STRAIN: Kasza
(C) INDIVIDUAL ISOLATE: S-SPV-001

(vii) IMMEDIATE SOURCE:
(B) CLONE: 515-85.1

(viii) POSITION IN GENOME:
(B) MAP POSITION: []23.2
(C) UNITS: %G (ix) FEATURE:
(A) NAME/KEY: CDS
(B) LOCATION: 100..123

(xi) SEQUENCE DESCRIPTION: SEQ ID NO:48:

```
TGAATATATA GCAAATAAAG GAAAAATTGT TATCGTTGCT GCATTAGATG GAACATAGGT     60

CGACTCTAGA ATTTCATTTT GTTTTTTTCT ATGCTATAA ATG AAT TCG GAT CCC       114
                                          Met Asn Ser Asp Pro
                                            1               5

GTC GTT TTA                                                         123
Val Val Leu
```

(2) INFORMATION FOR SEQ ID NO:49:

(i) SEQUENCE CHARACTERISTICS:
(A) LENGTH: 8 amino acids
(B) TYPE: amino acid
(D) TOPOLOGY: linear (ii) MOLECULE TYPE: protein (xi) SEQUENCE DESCRIPTION: SEQ ID NO:49:

```
Met Asn Ser Asp Pro Val Val Leu
  1               5
```

(2) INFORMATION FOR SEQ ID NO:50:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 1..63

(xi) SEQUENCE DESCRIPTION: SEQ ID NO:50:

```
GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG ACCTATGAAC GTAAACCATT           100
Gln Lys Asp Pro
            20

TGGTAATATT CTTAATCTTA TACCATTATC GG                                   132
```

(2) INFORMATION FOR SEQ ID NO:51:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:51:

```
Glu Ile Gln Leu Ser Ala Gly Arg Tyr His Tyr Gln Leu Val Trp Cys
 1               5                  10                  15

Gln Lys Asp Pro
            20
```

(2) INFORMATION FOR SEQ ID NO:52:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO:52:

TCTACTATTG TATATATAGG ATCCCCGGGC GAGCTCGAAT TCGTAATCAT GGTCATAGCT      60

GTTTCC                                                                66

(2) INFORMATION FOR SEQ ID NO:53:

(i) SEQUENCE CHARACTERISTICS:
              (A) LENGTH: 51 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO:53:

ACAGGAAACA GCTATGACCA TGATTACGAA TTCGAGCTCG CCCGGGGATC T              51

(2) INFORMATION FOR SEQ ID NO:54:

(i) SEQUENCE CHARACTERISTICS:
              (A) LENGTH: 104 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (ix) FEATURE:
              (A) NAME/KEY: CDS
              (B) LOCATION: 81..104

(xi) SEQUENCE DESCRIPTION: SEQ ID NO:54:

AAATATATAA ATACCATGTT AGAATTTGGT CTGCTGCAGG TCGACTCTAG AATTTCATTT     60

TGTTTTTTTC TATGCTATAA ATG AAT TCG GAT CCC GTC GTT TTA                104

Met Asn Ser Asp Pro Val Val Leu
 1               5

(2) INFORMATION FOR SEQ ID NO:55:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:55:

Met Asn Ser Asp Pro Val Val Leu
 1               5

(2) INFORMATION FOR SEQ ID NO:56:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 1..63

(ix) FEATURE:
        (A) NAME/KEY: CDS
        (B) LOCATION: 130..150

(xi) SEQUENCE DESCRIPTION: SEQ ID NO:56:

GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
 1               5                  10                  15

CAA AAA GAT CCA TAATTAATTA ACCCGGTCGA CTCTAGAAAG ATCTGTATCC            100
Gln Lys Asp Pro
            20

TAAAATTGAA TTGTAATTAT CGATAATAA ATG AAT TCC GGC ATG GCC TCG            150
                                Met Asn Ser Gly Met Ala Ser
                                 1               5

(2) INFORMATION FOR SEQ ID NO:57:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:57:

Glu Ile Gln Leu Ser Ala Gly Arg Tyr His Tyr Gln Leu Val Trp Cys

-continued 1 5 10 15

Gln Lys Asp Pro
20

(2) INFORMATION FOR SEQ ID NO:58:

(i) SEQUENCE CHARACTERISTICS:
(A) LENGTH: 7 amino acids
(B) TYPE: amino acid
(D) TOPOLOGY: linear (ii) MOLECULE TYPE: protein (xi) SEQUENCE DESCRIPTION: SEQ ID NO:58:

Met Asn Ser Gly Met Ala Ser
1 5

(2) INFORMATION FOR SEQ ID NO:59:

(i) SEQUENCE CHARACTERISTICS:
(A) LENGTH: 109 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Swinepox virus
(B) STRAIN: Kasza
(C) INDIVIDUAL ISOLATE: S-SPV-001

(vii) IMMEDIATE SOURCE:
(B) CLONE: 515-85.1

(viii) POSITION IN GENOME:
(B) MAP POSITION: []23.2
(C) UNITS: %G (xi) SEQUENCE DESCRIPTION: SEQ ID NO:59:

CCATGCTCTA GAGGATCCCC GGGCGAGCTC GAATTCGGAT CCATAATTAA TTAATTAATT 60

TTTATCCCGG GTCGACCGGG TCGACCTGCA GCCTACATGG AAATCTACC 109

(2) INFORMATION FOR SEQ ID NO:60:

(i) SEQUENCE CHARACTERISTICS:
(A) LENGTH: 51 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Swinepox virus
(B) STRAIN: Kasza
(C) INDIVIDUAL ISOLATE: S-SPV-001

(vii) IMMEDIATE SOURCE:
(B) CLONE: 515-85.1

(viii) POSITION IN GENOME:
(B) MAP POSITION: []23.2
(C) UNITS: %G (xi) SEQUENCE DESCRIPTION: SEQ ID NO:60:

TAATGTATCT ATAATGGTAT AAAGCTTGTA TTCTATAGTG TCACCTAAAT C          51

(2) INFORMATION FOR SEQ ID NO:61:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:61:

ACAGGAAACA GCTATGACCA TGATTACGAA TTCGAGCTCG CCCGGGGATC T          51

(2) INFORMATION FOR SEQ ID NO:62:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 81..104

(xi) SEQUENCE DESCRIPTION: SEQ ID NO:62:

AAATATATAA ATACCATGTT AGAATTTGGT CTGCTGCAGG TCGACTCTAG AATTTCATTT          60

TGTTTTTTTC TATGCTATAA ATG AAT TCG GAT CCC GTC GTT TTA                    104
               Met Asn Ser Asp Pro Val Val Leu
                 1               5

(2) INFORMATION FOR SEQ ID NO:63:

(i) SEQUENCE CHARACTERISTICS:
        (A) LENGTH: 8 amino acids
        (B) TYPE: amino acid (D) TOPOLOGY: linear (ii) MOLECULE TYPE: protein (xi) SEQUENCE DESCRIPTION: SEQ ID NO:63:

Met Asn Ser Asp Pro Val Val Leu
 1               5

(2) INFORMATION FOR SEQ ID NO:64:

(i) SEQUENCE CHARACTERISTICS:
            (A) LENGTH: 182 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (ix) FEATURE:
            (A) NAME/KEY: CDS
            (B) LOCATION: 1..63

(ix) FEATURE:
            (A) NAME/KEY: CDS
            (B) LOCATION: 156..182

(xi) SEQUENCE DESCRIPTION: SEQ ID NO:64:

```
GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
 1               5                  10                  15

CAA AAA GAT CCA TAATTAATTA ACCCGGTCGA CTCTAGAAAA AATTGAAAAA           100
Gln Lys Asp Pro
            20

CTATTCTAAT TTATTGCACG GAGATCTTTT TTTTTTTTTT TTTTTTGGCA TATAA ATG      158
                                                             Met
                                                              1

AAT TCC GGC ATG GCC TCG CTC GCG                                       182
Asn Ser Gly Met Ala Ser Leu Ala
            5
```

(2) INFORMATION FOR SEQ ID NO:65:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO:65:

Glu Ile Gln Leu Ser Ala Gly Arg Tyr His Tyr Gln Leu Val Trp Cys
 1               5                  10                  15

Gln Lys Asp Pro
            20

(2) INFORMATION FOR SEQ ID NO:66:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:66:

```
Met Asn Ser Gly Met Ala Ser Leu Ala
 1               5
```

(2) INFORMATION FOR SEQ ID NO:67:

(i) SEQUENCE CHARACTERISTICS:
        (A) LENGTH: 109 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:67:

```
CCATGCTCTA GAGGATCCCC GGGCGAGCTC GAATTCGGAT CCATAATTAA TTAATTAATT      60

TTTATCCCGG GTCGACCGGG TCGACCTGCA GCCTACATGG AAATCTACC                 109
```

(2) INFORMATION FOR SEQ ID NO:68:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:68:

```
TAATGTATCT ATAATGGTAT AAAGCTTGTA TTCTATAGTG TCACCTAAAT C              51
```

(2) INFORMATION FOR SEQ ID NO:69:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:69:

ACAGGAAACA GCTATGACCA TGATTACGAA TTCGAGCTCG CCCGGGGATC T          51

(2) INFORMATION FOR SEQ ID NO:70:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 81..104

(xi) SEQUENCE DESCRIPTION: SEQ ID NO:70:

AAATATATAA ATACCATGTT AGAATTTGGT CTGCTGCAGG TCGACTCTAG AATTTCATTT          60

TGTTTTTTTC TATGCTATAA ATG AAT TCG GAT CCC GTC GTT TTA          104

(2) INFORMATION FOR SEQ ID NO:71:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:71:

Met Asn Ser Asp Pro Val Val Leu (2) INFORMATION FOR SEQ ID NO:72:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 1..63

(ix) FEATURE:
        (A) NAME/KEY: CDS
        (B) LOCATION: 160..180

(xi) SEQUENCE DESCRIPTION: SEQ ID NO:72:

```
GAA ATC CAG CTG AGC GCC GGT CGC TAC CAT TAC CAG TTG GTC TGG TGT      48
Glu Ile Gln Leu Ser Ala Gly Arg Tyr His Tyr Gln Leu Val Trp Cys
 1               5                  10                  15

CAA AAA GAT CCA TAATTAATTA ACCCGGTCGA CTCTAGATTT TTTTTTTTT          100
Gln Lys Asp Pro
            20

TTTTTTTGGC ATATAAATAG ATCTGTATCC TAAAATTGAA TTGTAATTAT CGATAATAA    159

ATG AAT TCC GGC ATG GCC TCG                                         180
Met Asn Ser Gly Met Ala Ser
 1               5
```

(2) INFORMATION FOR SEQ ID NO:73:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:73:

```
Glu Ile Gln Leu Ser Ala Gly Arg Tyr His Tyr Gln Leu Val Trp Cys
 1               5                  10                  15

Gln Lys Asp Pro
            20
```

(2) INFORMATION FOR SEQ ID NO:74:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:74:

Met Asn Ser Gly Met Ala Ser
 1               5

(2) INFORMATION FOR SEQ ID NO:75:

(i) SEQUENCE CHARACTERISTICS:
         (A) LENGTH: 109 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swinepox virus
         (B) STRAIN: Kasza
         (C) INDIVIDUAL ISOLATE: S-SPV-001

(vii) IMMEDIATE SOURCE:
         (B) CLONE: 515-85.1

(viii) POSITION IN GENOME:
         (B) MAP POSITION: []23.2
         (C) UNITS: %G (xi) SEQUENCE DESCRIPTION: SEQ ID NO:75:

CCATGCTCTA GAGGATCCCC GGGCGAGCTC GAATTCGGAT CCATAATTAA TTAATTAATT    60

TTTATCCCGG GTCGACCGGG TCGACCTGCA GCCTACATGG AAATCTACC              109

(2) INFORMATION FOR SEQ ID NO:76:

(i) SEQUENCE CHARACTERISTICS:
         (A) LENGTH: 51 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swinepox virus
         (B) STRAIN: Kasza
         (C) INDIVIDUAL ISOLATE: S-SPV-001

(vii) IMMEDIATE SOURCE:
         (B) CLONE: 515-85.1

(viii) POSITION IN GENOME:
         (B) MAP POSITION: []23.2
         (C) UNITS: %G (xi) SEQUENCE DESCRIPTION: SEQ ID NO:76:

TAATGTATCT ATAATGGTAT AAAGCTTGTA TTCTATAGTG TCACCTAAAT C             51

(2) INFORMATION FOR SEQ ID NO:77:

(i) SEQUENCE CHARACTERISTICS:
         (A) LENGTH: 51 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swinepox virus
         (B) STRAIN: Kasza
         (C) INDIVIDUAL ISOLATE: S-SPV-001

(vii) IMMEDIATE SOURCE:
         (B) CLONE: 515-85

(B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (ix) FEATURE:
            (A) NAME/KEY: CDS
            (B) LOCATION: 103..126

(xi) SEQUENCE DESCRIPTION: SEQ ID NO:80:

CGCAACATAC CTAACTGCTT CATTTCTGAT CCATAATTAA TTAATTTTTA TCCCGGCGCG      60

CCTCGACTCT AGAATTTCAT TTTGTTTTTT TCTATGCTAT AA ATG AAT TCG GAT       114
                                                 Met Asn Ser Asp
                                                  1

CCC GTC GTT TTA                                                     126
Pro Val Val Leu
 5

(2) INFORMATION FOR SEQ ID NO:81:

(i) SEQUENCE CHARACTERISTICS:
            (A) LENGTH: 8 amino acids
            (B) TYPE: amino acid
            (D) TOPOLOGY: linear (ii) MOLECULE TYPE: protein (xi) SEQUENCE DESCRIPTION: SEQ ID NO:81:

Met Asn Ser Asp Pro Val Val Leu
 1               5

(2) INFORMATION FOR SEQ ID NO:82:

(i) SEQUENCE CHARACTERISTICS:
            (A) LENGTH: 96 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (ix) FEATURE:
        (A) NAME/KEY: CDS
        (B) LOCATION: 1..63

(xi) SEQUENCE DESCRIPTION: SEQ ID NO:82:

GAA AT (B) STRAIN: Kasza
            (C) INDIVIDUAL ISOLATE: S-SPV-001

(v (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
(B) MAP POSITION: []23.2
(C) UNITS: %G (ix) FEATURE:
(A) NAME/KEY: CDS
(B) LOCATION: 1..12

(ix) FEATURE:
(A) NAME/KEY: CDS
(B) LOCATION: 103..126

(xi) SEQUENCE DESCRIPTION: SEQ ID NO:88:

```
ATA AAA ATG TGATTAAGTC TGAATGTGGA TCCATAATTA ATTAATTTTT              49
Ile Lys Met
  1

ATCCCGGCGC GCCTCGACTC TAGAATTTCA TTTTGTTTTT TTCTATGCTA TAA ATG      105
                                                           Met
                                                             1

AAT TCG GAT CCC GTC GTT TTA                                         126
Asn Ser Asp Pro Val Val Leu
              5
```

(2) INFORMATION FOR SEQ ID NO:89:

(i) SEQUENCE CHARACTERISTICS:
(A) LENGTH: 3 amino acids
(B) TYPE: amino acid
(D) TOPOLOGY: linear (ii) MOLECULE TYPE: protein (xi) SEQUENCE DESCRIPTION: SEQ ID NO:89:

```
Ile Lys Met
  1
```

(2) INFORMATION FOR SEQ ID NO:90:

(i) SEQUENCE CHARACTERISTICS:
(A) LENGTH: 8 amino acids
(B) TYPE: amino acid
(D) TOPOLOGY: linear (ii) MOLECULE TYPE: protein (xi) SEQUENCE DESCRIPTION: SEQ ID NO:90:

```
Met Asn Ser Asp Pro Val Val Leu
  1               5
```

(2) INFORMATION FOR SEQ ID NO:91:

(i) SEQUENCE CHARACTERISTICS:
(A) LENGTH: 116 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (ix) FEATURE:
              (A) NAME/KEY: CDS
              (B) LOCATION: 1..63

(xi) SEQUENCE DESCRIPTION: SEQ ID NO:91:

```
GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG AGGCGCGCCG GGTCGACCTG           100
Gln Lys Asp Pro
                20

CAGGCGGCCG CTATAC                                                     116
```

(2) INFORMATION FOR SEQ ID NO:92:

(i) SEQUENCE CHARACTERISTICS:
              (A) LENGTH: 20 amino acids
              (B) TYPE: amino acid
              (D) TOPOLOGY: linear (ii) MOLECULE TYPE: protein (xi) SEQUENCE DESCRIPTION: SEQ ID NO:92:

```
Glu Ile Gln Leu Ser Ala Gly Arg Tyr His Tyr Gln Leu Val Trp Cys
 1               5                  10                  15

Gln Lys Asp Pro
                20
```

(2) INFORMATION FOR SEQ ID NO:93:

(i) SEQUENCE CHARACTERISTICS:
              (A) LENGTH: 51 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO:93:

147                                                                              148
-continued

```
TAATGTATCT ATAATGGTAT AAAGCTTGTA TTCTATAGTG TCACCTAAAT C              51

(2) INFORMATION FOR SEQ ID NO:94:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:94:

ACAGGAAACA GCTATGACCA TGATTACGAA TTCGAGCTCG CCCGGGGATC T              51

(2) INFORMATION FOR SEQ ID NO:95:

(i) SEQUENCE CHARACTERISTICS:
        (A) LENGTH: 124 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 104..124

(xi) SEQUENCE DESCRIPTION: SEQ ID NO:95:

GTATAGCGGC CGCCTGCAGG TCGACTCTAG ATTTTTTTTT TTTTTTTTTT TGGCATATAA      60

ATAGATCTGT ATCCTAAAAT TGAATTGTAA TTATCGATAA TAA ATG AAT TCC CCT GCC  118
                                              Met Asn Ser Pro Ala
                                                1               5

GCC CGG                                                              124
Ala Arg (2) INFORMATION FOR SEQ ID NO:96:

(i) SEQUENCE CHARACTERISTICS:
        (A) LENGTH: 7 amino acids
```

```
            (B) TYPE: amino acid
            (D) TOPOLOGY: linear (ii) MOLECULE TYPE: protein (xi) SEQUENCE DESCRIPTION: SEQ ID NO:96:

Met Asn Ser Pro Ala Ala Arg
 1               5

(2) INFORMATION FOR SEQ ID NO:97:

(i) SEQUENCE CHARACTERISTICS:
            (A) LENGTH: 126 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (ix) FEATURE:
            (A) NAME/KEY: CDS
            (B) LOCATION: 1..36

(ix) FEATURE:
            (A) NAME/KEY: CDS
            (B) LOCATION: 103..126

(xi) SEQUENCE DESCRIPTION: SEQ ID NO:97:

CTC CAG GAG CCC GCT CGC CTC GAG CGG GAT CCA TAATTAATTA ATTTTTATCC      53
Leu Gln Glu Pro Ala Arg Leu Glu Arg Asp Pro
 1               5                  10

CGGCGCGCCT CGACTCTAGA ATTTCATTTT GTTTTTTTCT ATGCTATAA ATG AAT       108
                                                      Met Asn
                                                       1

TCG GAT CCC GTC GTT TTA                                            126
Ser Asp Pro Val Val Leu
         5

(2) INFORMATION FOR SEQ ID NO:98:

(i) SEQUENCE CHARACTERISTICS:
            (A) LENGTH: 11 amino acids
            (B) TYPE: amino acid
            (D) TOPOLOGY: linear (ii) MOLECULE TYPE: protein (xi) SEQUENCE DESCRIPTION: SEQ ID NO:98:

Leu Gln Glu Pro Ala Arg Leu Glu Arg Asp Pro
 1               5                  10

(2) INFORMATION FOR SEQ ID NO:99:

(i) SEQUENCE CHARACTERISTICS:
            (A) LENGTH: 8 amino acids
            (B) TYPE: amino acid
```

(D) TOPOLOGY: linear (ii) MOLECULE TYPE: protein (xi) SEQUENCE DESCRIPTION: SEQ ID NO:99:

Met Asn Ser Asp Pro Val Val Leu
 1               5

(2) INFORMATION FOR SEQ ID NO:100:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 1..63

(xi) SEQUENCE DESCRIPTION: SEQ ID NO:100:

GAA ATC CAG CTG AGC GCC GGT CGC TAC CAT TAC CAG TTG GTC TGG TGT         48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG AGGCGCGCCG GGTCGACCTG            100
Gln Lys Asp Pro
            20

CAGGCGGCCG CTATAC                                                       116

(2) INFORMATION FOR SEQ ID NO:101:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:101:

Glu Ile Gln Leu Ser Ala Gly Arg Tyr His Tyr Gln Leu Val Trp Cys
 1               5                  10                  15

Gln Lys Asp Pro
            20

(2) INFORMATION FOR SEQ ID NO:102:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Swinepox virus
             (B) STRAIN: Kasza
             (C) INDIVIDUAL ISOLATE: S-SPV-001

(vii) IMMEDIATE SOURCE:
              (B) CLONE: 515-85.1

(viii) POSITION IN GENOME:
               (B) MAP POSITION: []23.2
               (C) UNITS: %G (xi) SEQUENCE DESCRIPTION: SEQ ID NO:102:

TAATGTATCT ATAATGGTAT AAAGCTTGTA TTCTATAGTG TCACCTAAAT C         51

(2) INFORMATION FOR SEQ ID NO:103:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Swinepox virus
             (B) STRAIN: Kasza
             (C) INDIVIDUAL ISOLATE: S-SPV-001

(vii) IMMEDIATE SOURCE:
              (B) CLONE: 515-85.1

(viii) POSITION IN GENOME:
               (B) MAP POSITION: []23.2
               (C) UNITS: %G (xi) SEQUENCE DESCRIPTION: SEQ ID NO:103:

CCGAATTCCG GCTTCAGTAA CATAGGATCG                                 30

(2) INFORMATION FOR SEQ ID NO:104:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Swinepox virus
             (B) STRAIN: Kasza
             (C) INDIVIDUAL ISOLATE: S-SPV-001

(vii) IMMEDIATE SOURCE:
              (B) CLONE: 515-85.1

(viii) POSITION IN GENOME:
               (B) MAP POSITION: []23.2
               (C) UNITS: %G (xi) SEQUENCE DESCRIPTION: SEQ ID NO:104:

GTACCCATAC TGGTCGTGGC                                                       20

(2) INFORMATION FOR SEQ ID NO:105:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:105:

CCGGAATTCG CTACTTGGAA CTCTGG                                                26

(2) INFORMATION FOR SEQ ID NO:106:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:106:

CATTGTCCCG AGACGGACAG                                                       20

(2) INFORMATION FOR SEQ ID NO:107:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:107:

CGCGATCCAA CTATCGGTG                                                  19

(2) INFORMATION FOR SEQ ID NO:108:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:108:

GCGGATCCAC ATTCAGACTT AATCAC                                          26

(2) INFORMATION FOR SEQ ID NO:109:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:109:

ATGAATTCCC CTGCCGCCCG GACCGGCACC                                      30

(2) INFORMATION FOR SEQ ID NO:110:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:110:

CATGGATCCC GCTCGAGGCG AGCGGGCTCC                                    30

(2) INFORMATION FOR SEQ ID NO:111:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:111:

CTGGTTCGGC CCAGAATTCT ATGGGTCTCG CGCGGCTCGT GG                      42

(2) INFORMATION FOR SEQ ID NO:112:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO:112:

CTCGCTCGCC CAGGATCCCT AGCGGAGGAT GGACTTGAGT CG                            42

(2) INFORMATION FOR SEQ ID NO:113:

(i) SEQUENCE CHARACTERISTICS:
              (A) LENGTH: 3628 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (ix) FEATURE:
              (A) NAME/KEY: CDS
              (B) LOCATION: 57..1226

(ix) FEATURE:
              (A) NAME/KEY: CDS
              (B) LOCATION: 1362..3395

(xi) SEQUENCE DESCRIPTION: SEQ ID NO:113:

TTGAAGATGA ATGCATAGAG GAAGATGATG TCGANACGTC ATTATTTAAT GTATAAATGG         60

ATAAATTGTA TGCGGCAATA TTCGGCGTTT TTATGCACATC TAAAGATGAT GATTTTAATA       120

ACTTTATAGA AGTTGTAAAA TCTGTATTAA CAGATACATC ANCTAATCAT ACAATATCGT        180

CGTCCAATAA TAATACATGG ATATATATAT TTCTAGCGAT ATTATTTGGT GTTATGGNAT        240

TATTAGTTTT TANTTTGTAT GTAGAAGTTC CTAAACCNAC TTANATGGAG GAAGCAGATA        300

ACCNACTCGT TNTAAATAGT ATTAGTGCTA GAGCATTGGN GGCATTTTTT GTATCTAAAA        360

NTANTGATAT GGTCGNTGAA NTAGTTNCCC AAAAATNTCC NCCAAAGAAG ANATCACAAA        420

TAAAACGCAT AGATACACGA ATTCCTATTG ATCTTATTAA TCAACAATTC GTTAAAAGAT        480

TTAAACTAGA AAATTATAAA AATGGAATTT TATCCGTTCT TATCAATAGT TTAGTCGAAA        540

ATAATTACTT TGAACAAGAT GGTAAACTTA ATAGCAGTGA TATTGATGAA TTAGTGCTCA        600

CAGACATAGA GAAAAAGATT TTATCGTTGA TTCCTAGATG TTCTCCTCTT TATATAGATA        660

TCAGTGACGT TAAAGTTCTC GCATCTAGGT TAANNAAAAG TGCTAAATCA TTTACGTTTA        720

ATGATCATGA ATATATTATA CAATCTGATA AAATAGAGGA ATTAATAAAT AGTTTATCTA        780

GAAACCATGA TATTATACTA GATGAAAAAA GTTCTATTAA AGACAGCATA TATATACTAT        840

CTGATGATCT TTTGAATATA CTTCGTGAAA GATTATTTAG ATGTCCACAG GTTAAAGATA        900

ATACTATTTC TAGAACACGT CTATATGATT ATTTTACTAG AGTGTCAAAG AAAGAAGAAG        960

-continued

```
CGAAAATATA CGTTATATTG AAAGATTTAA AGATTGCTGA TATACTCGGT ATCGAAACAG   1020

TAACGATAGG ATCATTTGTA TATACGAAAT ATAGCATGTT GATTAATTCA ATTTCGTCTA   1080

ATGTTGATAG ATATTCAAAA AGGTTCCATG ACTCTTTTTA TGAAGATATT GCGGAATTTA   1140

TAAAGGATAA TGAAAAAATT AATGTATCCA GAGTTGTTGA ATGCCTTATC GTACCTAATA   1200

TTAATATAGA GTTATTAACT GAATAAGTAT ATATAAATGA TTGTTTTTAT AATGTTTGTT   1260

ATCGCATTTA GTTTTGCTGT ATGGTTATCA TATACATTTT TAAGGCCGTA TATGATAAAT   1320

GAAAATATAT AAGCACTTAT TTTTGTTAGT ATAATAACAC AATGCCGTCG TATATGTATC   1380

CGAAGAACGC AAGAAAAGTA ATTTCAAAGA TTATATCATT ACAACTTGAT ATTAAAAAAC   1440

TTCCTAAAAA ATATATAAAT ACCATGTTAG AATTTGGTCT ACATGGAAAT CTACCAGCTT   1500

GTATGTATAA AGATGCCGTA TCATATGATA TAAATAATAT AAGATTTTTA CCTTATAATT   1560

GTGTTATGGT TAAAGATTTA ATAAATGTTA TAAAATCATC ATCTGTAATA GATACTAGAT   1620

TACATCAATC TGTATTAAAA CATCGTAGAG CGTTAATAGA TTACGGCGAT CAAGACATTA   1680

TCACTTTAAT GATCATTAAT AAGTTACTAT CGATAGATGA TATATCCTAT ATATTAGATA   1740

AAAAAATAAT TCATGTAACA AAAATATTAA AAATAGACCC TACAGTAGCC AATTCAAACA   1800

TGAAACTGAA TAAGATAGAG CTTGTAGATG TAATAACATC AATACCTAAG TCTTCCTATA   1860

CATATTTATA TAATAATATG ATCATTGATC TCGATACATT ATTATATTTA TCCGATGCAT   1920

TCCACATACC CCCCACACAT ATATCATTAC GTTCACTTAG AGATATAAAC AGGATTATTG   1980

AATTGCTTAA AAAATATCCG AATAATAATA TTATTGATTA TATATCCGAT AGCATAAAAT   2040

CAAATAGTTC ATTCATTCAC ATACTTCATA TGATAATATC AAATATGTTT CCTGCTATAA   2100

TCCCTAGTGT AAACGATTTT ATATCTACCG TAGTTGATAA AGATCGACTT ATTAATATGT   2160

ATGGGATTAA GTGTGTTGCT ATGTTTTCGT ACGATATAAA CATGATCGAT TTAGAGTCAT   2220

TAGATGACTC AGATTACATA TTTATAGAAA AAAATATATC TATATACGAC GTTAAATGTA   2280

GAGATTTTGC GAATATGATT AGAGATAAGG TTAAAAGAGA AAAGAATAGA ATATTAACTA   2340

CGAAATGTGA AGATATTATA AGATATATAA AATTATTCAG TAAAAATAGA ATAAACGATG   2400

AAAATAATAA GGTGGAGGAG GTGTTGATAC ATATTGATAA TGTATCTAAA AATAATAAAT   2460

TATCACTGTC TGATATATCA TCTTTAATGG ATCAATTTCG TTTAAATCCA TGTACCATAA   2520

GAAATATATT ATTATCTTCA GCAACTATAA AATCAAAACT ATTAGCGTTA CGGGCAGTAA   2580

AAAACTGGAA ATGTTATTCA TTGACAAATG TATCAATGTA TAAAAAAATA AAGGGTGTTA   2640

TCGTAATGGA TATGGTTGAT TATATATCTA CTAACATTCT TAAATACCAT AAACAATTAT   2700

ATGATAAAAT GAGTACGTTT GAATATAAAC GAGATATTAA ATCATGTAAA TGCTCGATAT   2760

GTTCCGACTC TATAACACAT CATATATATG AAACAACATC ATGTATAAAT TATAAATCTA   2820

CCGATAATGA TCTTATGATA GTATTGTTCA ATCTAACTAG ATATTTAATG CATGGGATGA   2880

TACATCCTAA TCTTATAAGC GTAAAAGGAT GGGGTCCCCT TATTGGATTA TTAACGGGTG   2940

ATATAGGTAT TAATTTAAAA CTATATTCCA CCATGAATAT AAATGGGCTA CGGTATGGAG   3000

ATATTACGTT ATCTTCATAC GATATGAGTA ATAAATTAGT CTCTATTATT AATACACCCA   3060

TATATGAGTT AATACCGTTT ACTACATGTT GTTCACTCAA TGAATATTAT TCAAAAATTG   3120

TGATTTTAAT AAATGTTATT TTAGAATATA TGATATCTAT TATATTATAT AGAATATTGA   3180

TCGTAAAAAG ATTTAATAAC ATTAAAGAAT TTATTTCAAA AGTCGTAAAT ACTGTACTAG   3240

AATCATCAGG CATATATTTT TGTCAGATGC GTGTACATGA ACAAATTGAA TTGGAAATAG   3300

ATGAGCTCAT TATTAATGGA TCTATGCCTG TACAGCTTAT GCATTTACTT CTAAAGGTAG   3360
```

-continued

```
CTACCATAAT ATTAGAGGAA ATCAAAGAAA TATAACGTAT TTTTTCTTTT AAATAAATAA      3420

AAATACTTTT TTTTTAAAC AAGGGGTGCT ACCTTGTCTA ATTGTATCTT GTATTTTGGA       3480

TCTGATGCAA GATTATTAAA TAATCGTATG AAAAAGTAGT AGATATAGTT TATATCGTTA     3540

CTGGACATGA TATTATGTTT AGTTAATTCT TCTTTGGCAT GAATTCTACA CGTCGGANAA    3600

GGTAATGTAT CTATAATGGT ATAAAGCT                                        3628
```

(2) INFORMATION FOR SEQ ID NO:114:

(i) SEQUENCE CHARACTERISTICS:
        (A) LENGTH: 389 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:114:

```
Met Asp Lys Leu Tyr Ala Ala Ile Phe Gly Val Phe Met Thr Ser Lys
  1               5                  10                  15

Asp Asp Asp Phe Asn Asn Phe Ile Glu Val Val Lys Ser Val Leu Thr
             20                  25                  30

Asp Thr Ser Xaa Asn His Thr Ile Ser Ser Ser Asn Asn Asn Thr Trp
         35                  40                  45

Ile Tyr Ile Phe Leu Ala Ile Leu Phe Gly Val Met Xaa Leu Leu Val
     50                  55                  60

Phe Xaa Leu Tyr Val Glu Val Pro Lys Pro Thr Xaa Met Glu Glu Ala
 65                  70                  75                  80

Asp Asn Xaa Leu Val Xaa Asn Ser Ile Ser Ala Arg Ala Leu Xaa Ala
             85                  90                  95

Phe Phe Val Ser Lys Xaa Xaa Asp Met Val Xaa Glu Xaa Val Xaa Gln
            100                 105                 110

Lys Xaa Pro Pro Lys Lys Xaa Ser Gln Ile Lys Arg Ile Asp Thr Arg
        115                 120                 125

Ile Pro Ile Asp Leu Ile Asn Gln Gln Phe Val Lys Arg Phe Lys Leu
    130                 135                 140

Glu Asn Tyr Lys Asn Gly Ile Leu Ser Val Leu Ile Asn Ser Leu Val
145                 150                 155                 160

Glu Asn Asn Tyr Phe Glu Gln Asp Gly Lys Leu Asn Ser Ser Asp Ile
                165                 170                 175

Asp Glu Leu Val Leu Thr Asp Ile Glu Lys Ile Leu Ser Leu Ile
            180                 185                 190

Pro Arg Cys Ser Pro Leu Tyr Ile Asp Ile Ser Asp Val Lys Val Leu
        195                 200                 205

Ala Ser Arg Leu Xaa Lys Ser Ala Lys Ser Phe Thr Phe Asn Asp His
    210                 215                 220
```

-continued

```
Glu Tyr Ile Ile Gln Ser Asp Lys Ile Glu Glu Leu Ile Asn Ser Leu
225                 230                 235                 240

Ser Arg Asn His Asp Ile Ile Leu Asp Glu Lys Ser Ser Ile Lys Asp
                    245                 250                 255

Ser Ile Tyr Ile Leu Ser Asp Asp Leu Leu Asn Ile Leu Arg Glu Arg
                260                 265                 270

Leu Phe Arg Cys Pro Gln Val Lys Asp Asn Thr Ile Ser Arg Thr Arg
            275                 280                 285

Leu Tyr Asp Tyr Phe Thr Arg Val Ser Lys Glu Glu Ala Lys Ile
290                 295                 300

Tyr Val Ile Leu Lys Asp Leu Lys Ile Ala Asp Ile Leu Gly Ile Glu
305                 310                 315                 320

Thr Val Thr Ile Gly Ser Phe Val Tyr Thr Lys Tyr Ser Met Leu Ile
                325                 330                 335

Asn Ser Ile Ser Ser Asn Val Asp Arg Tyr Ser Lys Arg Phe His Asp
                340                 345                 350

Ser Phe Tyr Glu Asp Ile Ala Glu Phe Ile Lys Asp Asn Glu Lys Ile
            355                 360                 365

Asn Val Ser Arg Val Val Glu Cys Leu Ile Val Pro Asn Ile Asn Ile
370                 375                 380

Glu Leu Leu Thr Glu
385
```

(2) INFORMATION FOR SEQ ID NO:115:

(i) SEQUENCE CHARACTERISTICS:
        (A) LENGTH: 677 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO:115:

```
Met Pro Ser Tyr Met Tyr Pro Lys Asn Ala Arg Lys Val Ile Ser Lys
1               5                   10                  15

Ile Ile Ser Leu Gln Leu Asp Ile Lys Lys Leu Pro Lys Lys Tyr Ile
            20                  25                  30

Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
    50                  55                  60

Tyr Asn Cys Val Met Val Lys Asp Leu Ile Asn Val Ile Lys Ser Ser
65                  70                  75                  80

Ser Val Ile Asp Thr Arg Leu His Gln Ser Val Leu Lys His Arg Arg
                85                  90                  95
```

-continued

Ala Leu Ile Asp Tyr Gly Asp Gln Asp Ile Thr Leu Met Ile Ile
            100                 105                 110

Asn Lys Leu Leu Ser Ile Asp Asp Ile Ser Tyr Ile Leu Asp Lys Lys
            115                 120                 125

Ile Ile His Val Thr Lys Ile Leu Lys Ile Asp Pro Thr Val Ala Asn
            130                 135                 140

Ser Asn Met Lys Leu Asn Lys Ile Glu Leu Val Asp Val Ile Thr Ser
145                 150                 155                 160

Ile Pro Lys Ser Ser Tyr Thr Tyr Leu Tyr Asn Asn Met Ile Ile Asp
                165                 170                 175

Leu Asp Thr Leu Leu Tyr Leu Ser Asp Ala Phe His Ile Pro Pro Thr
            180                 185                 190

His Ile Ser Leu Arg Ser Leu Arg Asp Ile Asn Arg Ile Ile Glu Leu
            195                 200                 205

Leu Lys Lys Tyr Pro Asn Asn Asn Ile Ile Asp Tyr Ile Ser Asp Ser
            210                 215                 220

Ile Lys Ser Asn Ser Ser Phe Ile His Ile Leu His Met Ile Ile Ser
225                 230                 235                 240

Asn Met Phe Pro Ala Ile Ile Pro Ser Val Asn Asp Phe Ile Ser Thr
                245                 250                 255

Val Val Asp Lys Asp Arg Leu Ile Asn Met Tyr Gly Ile Lys Cys Val
            260                 265                 270

Ala Met Phe Ser Tyr Asp Ile Asn Met Ile Asp Leu Glu Ser Leu Asp
            275                 280                 285

Asp Ser Asp Tyr Ile Phe Ile Glu Lys Asn Ile Ser Ile Tyr Asp Val
            290                 295                 300

Lys Cys Arg Asp Phe Ala Asn Met Ile Arg Asp Lys Val Lys Arg Glu
305                 310                 315                 320

Lys Asn Arg Ile Leu Thr Thr Lys Cys Glu Asp Ile Ile Arg Tyr Ile
                325                 330                 335

Lys Leu Phe Ser Lys Asn Arg Ile Asn Asp Glu Asn Asn Lys Val Glu
            340                 345                 350

Glu Val Leu Ile His Ile Asp Asn Val Ser Lys Asn Asn Lys Leu Ser
            355                 360                 365

Leu Ser Asp Ile Ser Ser Leu Met Asp Gln Phe Arg Leu Asn Pro Cys
370                 375                 380

Thr Ile Arg Asn Ile Leu Leu Ser Ser Ala Thr Ile Lys Ser Lys Leu
385                 390                 395                 400

Leu Ala Leu Arg Ala Val Lys Asn Trp Lys Cys Tyr Ser Leu Thr Asn
            405                 410                 415

Val Ser Met Tyr Lys Lys Ile Lys Gly Val Ile Val Met Asp Met Val
                420                 425                 430

Asp Tyr Ile Ser Thr Asn Ile Leu Lys Tyr His Lys Gln Leu Tyr Asp
            435                 440                 445

Lys Met Ser Thr Phe Glu Tyr Lys Arg Asp Ile Lys Ser Cys Lys Cys
            450                 455                 460

Ser Ile Cys Ser Asp Ser Ile Thr His His Ile Tyr Glu Thr Thr Ser
465                 470                 475                 480

Cys Ile Asn Tyr Lys Ser Thr Asp Asn Asp Leu Met Ile Val Leu Phe
                485                 490                 495

Asn Leu Thr Arg Tyr Leu Met His Gly Met Ile His Pro Asn Leu Ile
            500                 505                 510

Ser Val Lys Gly Trp Gly Pro Leu Ile Gly Leu Leu Thr Gly Asp Ile

```
                515                 520                 525

Gly Ile Asn Leu Lys Leu Tyr Ser Thr Met Asn Ile Asn Gly Leu Arg
    530                 535                 540

Tyr Gly Asp Ile Thr Leu Ser Ser Tyr Asp Met Ser Asn Lys Leu Val
545                 550                 555                 560

Ser Ile Ile Asn Thr Pro Ile Tyr Glu Leu Ile Pro Phe Thr Thr Cys
                565                 570                 575

Cys Ser Leu Asn Glu Tyr Tyr Ser Lys Ile Val Ile Leu Ile Asn Val
             580                 585                 590

Ile Leu Glu Tyr Met Ile Ser Ile Ile Leu Tyr Arg Ile Leu Ile Val
    595                 600                 605

Lys Arg Phe Asn Asn Ile Lys Glu Phe Ile Ser Lys Val Val Asn Thr
    610                 615                 620

Val Leu Glu Ser Ser Gly Ile Tyr Phe Cys Gln Met Arg Val His Glu
625                 630                 635                 640

Gln Ile Glu Leu Glu Ile Asp Glu Leu Ile Ile Asn Gly Ser Met Pro
                645                 650                 655

Val Gln Leu Met His Leu Leu Leu Lys Val Ala Thr Ile Ile Leu Glu
            660                 665                 670

Glu Ile Lys Glu Ile
        675
```

(2) INFORMATION FOR SEQ ID NO:116:

(i) SEQUENCE CHARACTERISTICS:
        (A) LENGTH: 43 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Infectious bovine rhinotracheitis virus
        (B) STRAIN: Cooper Strain (xi) SEQUENCE DESCRIPTION: SEQ ID NO:116:

CTGGTTCGGC CCAGAATTCG ATGCAACCCA CCGCGCCGCC CCG              43

(2) INFORMATION FOR SEQ ID NO:117:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Infectious bovine rhinotracheitis virus
        (B) STRAIN: Cooper Strain (xi) SEQUENCE DESCRIPTION: SEQ ID NO:117:

CTCGCTCGCC CAGGATCCCT AGCGGAGGAT GGACTTGAGT CG               42

(2) INFORMATION FOR SEQ ID NO:118:

(i) SEQUENCE CHARACTERISTICS:
            (A) LENGTH: 31 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Equine Influenza A neuraminidase
            (B) STRAIN: Prague/56

(xi) SEQUENCE DESCRIPTION: SEQ ID NO:118:

GGGATCCATG AATCCTAATC AAAAACTCTT T                                  31

(2) INFORMATION FOR SEQ ID NO:119:

(i) SEQUENCE CHARACTERISTICS:
            (A) LENGTH: 31 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Equine Influenza A neuraminidase
            (B) STRAIN: Prague/56

(xi) SEQUENCE DESCRIPTION: SEQ ID NO:119:

GGGATCCTTA CGAAAAGTAT TTAATTTGTG C                                  31

(2) INFORMATION FOR SEQ ID NO:120:

(i) SEQUENCE CHARACTERISTICS:
            (A) LENGTH: 42 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Equine influenza A hemagglutinin (xi) SEQUENCE DESCRIPTION: SEQ ID NO:120:

GGAGGCCTTC ATGACAGACA ACCATTATTT TGATACTACT GA                      42

(2) INFORMATION FOR SEQ ID NO:121:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO

```
        (vi) ORIGINAL SOURCE:
             (A) ORGANISM: Equine influenza A hemagglutinin (xi) SEQUENCE DESCRIPTION: SEQ ID NO:121:

GAAGGCCTTC TCAAATGCAA ATGTTGCATC TGATGTTGCC                              40

(2) INFORMATION FOR SEQ ID NO:122:

(i) SEQUENCE CHARACTERISTICS:
             (A) LENGTH: 32 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Equine Influenza A hemagglutinin
             (B) STRAIN: Prague/56

(xi) SEQUENCE DESCRIPTION: SEQ ID NO:122:

GGGATCCATG AACACTCAAA TTCTAATATT AG                                     32

(2) INFORMATION FOR SEQ ID NO:123:

(i) SEQUENCE CHARACTERISTICS:
             (A) LENGTH: 30 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Equine Influenza A hemagglutinin
             (B) STRAIN: Prague/56

(xi) SEQUENCE DESCRIPTION: SEQ ID NO:123:

GGGATCCTTA TATACAAATA GTGCACCGCA                                        30

(2) INFORMATION FOR SEQ ID NO:124:

(i) SEQUENCE CHARACTERISTICS:
             (A) LENGTH: 30 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Equine Influenza A neuraminidase (xi) SEQUENCE DESCRIPTION: SEQ ID NO:124:

GGGTCGACAT GAATCCAAAT CAAAAGATAA                                        30

(2) INFORMATION FOR SEQ ID NO:125:

(i) SEQUENCE CHARACTERISTICS:
```

(A) LENGTH: 29 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Equine Influenza A neuraminidase (xi) SEQUENCE DESCRIPTION: SEQ ID NO:125:

GGGTCGACTT ACATCTTATC GATGTCAAA 29

(2) INFORMATION FOR SEQ ID NO:126:

(i) SEQUENCE CHARACTERISTICS:
(A) LENGTH: 33 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Human (xi) SEQUENCE DESCRIPTION: SEQ ID NO:126:

CTCGAATTCG AAGTGGGCAA CGTGGATCCT CGC 33

(2) INFORMATION FOR SEQ ID NO:127:

(i) SEQUENCE CHARACTERISTICS:
(A) LENGTH: 24 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Human (xi) SEQUENCE DESCRIPTION: SEQ ID NO:127:

CAGTTAGCCT CCCCCATCTC CCCA 24

(2) INFORMATION FOR SEQ ID NO:128:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Equine herpesvirus type 1

(xi) SEQUENCE DESCRIPTION: SEQ ID NO:128:

CGGAATTCCT CTGGTTGCCG T                                                21

(2) INFORMATION FOR SEQ ID NO:129:

(i) SEQUENCE CHARACTERISTICS:
         (A) LENGTH: 22 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Equine herpesvirus type 1

(xi) SEQUENCE DESCRIPTION: SEQ ID NO:129:

GACGGTGGAT CCGGTAGGCG GT                                               22

(2) INFORMATION FOR SEQ ID NO:130:

(i) SEQUENCE CHARACTERISTICS:
         (A) LENGTH: 34 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Bovine parainfluenza-3 virus (xi) SEQUENCE DESCRIPTION: SEQ ID NO:130:

TTATGGATCC TGCTGCTGTG TTGAACAACT TTGT                                  34

(2) INFORMATION FOR SEQ ID NO:131:

(i) SEQUENCE CHARACTERISTICS:
         (A) LENGTH: 38 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Bovine parainfluenza-3 virus (xi) SEQUENCE DESCRIPTION: SEQ ID NO:131:

CCGCGGATCC CATGACCATC ACAACCATAA TCATAGCC                              38

(2) INFORMATION FOR SEQ ID NO:132:

(i) SEQUENCE CHARACTERISTICS:
         (A) LENGTH: 43 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine parainfluenza-3 virus (xi) SEQUENCE DESCRIPTION: SEQ ID NO:132:

CGTCGGATCC CTTAGCTGCA GTTTTTTGGA ACTTCTGTTT TGA                              43

(2) INFORMATION FOR SEQ ID NO:133:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine parainfluenza-3 virus (xi) SEQUENCE DESCRIPTION: SEQ ID NO:133:

CATAGGATCC CATGGAATAT TGGAAACACA CAAACAGCAC                                  40

(2) INFORMATION FOR SEQ ID NO:134:

(i) SEQUENCE CHARACTERISTICS:
            (A) LENGTH: 42 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine viral diarrhea virus
            (B) STRAIN: Singer Strain (xi) SEQUENCE DESCRIPTION: SEQ ID NO:134:

ACGTCGGATC CCTTACCAAA CCACGTCTTA CTCTTGTTTT CC                               42

(2) INFORMATION FOR SEQ ID NO:135:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine viral diarrhea virus
            (B) STRAIN: Singer Strain (xi) SEQUENCE DESCRIPTION: SEQ ID NO:135:

ACATAGGATC CCATGGGAGA AAACATAACA CAGTGGAACC                                  40

-continued (2) INFORMATION FOR SEQ ID NO:136:

(i) SEQUENCE CHARACTERISTICS:
(A) LENGTH: 33 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bovine viral diarrhea virus
(B) STRAIN: Singer Strain (xi) SEQUENCE DESCRIPTION: SEQ ID NO:136:

CGTGGATCCT CAATTACAAG AGGTATCGTC TAC 33

(2) INFORMATION FOR SEQ ID NO:137:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bovine viral diarrhea virus
(B) STRAIN: Singer Strain (xi) SEQUENCE DESCRIPTION: SEQ ID NO:137:

CATAGATCTT GTGGTGCTGT CCGACTTCGC A 31

(2) INFORMATION FOR SEQ ID NO:138:

(i) SEQUENCE CHARACTERISTICS:
(A) LENGTH: 37 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bovine respiratory syncytial virus
(B) STRAIN: Strain 375

(xi) SEQUENCE DESCRIPTION: SEQ ID NO:138:

TGCAGGATCC TCATTTACTA AAGGAAAGAT TGTTGAT 37

(2) INFORMATION FOR SEQ ID NO:139:

(i) SEQUENCE CHARACTERISTICS:
(A) LENGTH: 35 base pairs
(B) TYPE: nucleic acid
(C) STRANDEDNESS: double
(D) TOPOLOGY: linear (ii) MOLECULE TYPE: DNA (genomic)

```
        (iii) HYPOTHETICAL: NO (iv) ANTI-SENSE: NO (vi) ORIGINAL SOURCE:
             (A) ORGANISM: Bovine respiratory syncytial virus
             (B) STRAIN: Strain 375

(xi) SEQUENCE DESCRIPTION: SEQ ID NO:139:

CTCTGGATCC TACAGCCATG AGGATGATCA TCAGC                                    35

(2) INFORMATION FOR SEQ ID NO:140:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Bovine respiratory syncytial virus
             (B) STRAIN: Strain 375

(xi) SEQUENCE DESCRIPTION: SEQ ID NO:140:

CGTCGGATCC CTCACAGTTC CACATCATTG TCTTTGGGAT                               40

(2) INFORMATION FOR SEQ ID NO:141:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Bovine respiratory syncytial virus
             (B) STRAIN: Strain 375

(xi) SEQUENCE DESCRIPTION: SEQ ID NO:141:

CTTAGGATCC CATGGCTCTT AGCAAGGTCA AACTAAATGA C                             41

(2) INFORMATION FOR SEQ ID NO:142:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Bovine respiratory syncytial virus
             (B) STRAIN: Strain 375

(xi) SEQUENCE DESCRIPTION: SEQ ID NO:142:

CGTTGGATCC CTAGATCTGT GTAGTTGATT GATTTGTGTG A                             41
```

(2) INFORMATION FOR SEQ ID NO:143:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine respiratory syncytial virus
        (B) STRAIN: Strain 375

(xi) SEQUENCE DESCRIPTION: SEQ ID NO:143:

```
CTCTGGATCC TCATACCCAT CATCTTAAAT TCAAGACATT A                    41
```

(2) INFORMATION FOR SEQ ID NO:144:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:144:

```
ACAGGAAACA GCTATGACCA TGATTACGAA TTCGAGCTCG CCCGGGGATC T         51
```

(2) INFORMATION FOR SEQ ID NO:145:

(i) SEQUENCE CHARACTERISTICS:
        (A) LENGTH: 128 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:145:

```
GTATAGCGGC CGCCTGCAGG TCGACTCTAG ATTTTTTTTT TTTTTTTTTT TGGCATATAA    60

ATAGATCTGT ATCCTAAAAT TGAATTGTAA TTATCGATAA TAAATGAATT TGATCCATGA   120

ATCCTAAT                                                           128
```

(2) INFORMATION FOR SEQ ID NO:146:

(i) SEQUENCE CHARACTERISTICS:
        (A) LENGTH: 120 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO 189                                                                                              190
-continued (xi) SEQUENCE DESCRIPTION: SEQ ID NO:146:

CTTTTCGTAA GGATCAATTC GGATCCATAA TTAATTAATT TTTATCCCGG CGCGCCTCGA     60

CTCTAGAATT TCATTTTGTT TTTTTCTATG CTATAAATGA ATTCGGATCC CGTCGTTTTA    120

(2) INFORMATION FOR SEQ ID NO:147:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:147:

GAAATCCAGC TGAGCGCCGG TCGCTACCAT TACCAGTTGG TCTGGTGTCA AAAAGATCCA     60

TAATTAATTA ACCCGGGTCG AGGCGCGCCG GGTCGACCTG CAGGCGGCCG CTATAC        116

(2) INFORMATION FOR SEQ ID NO:148:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:148:

TAATGTATCT ATAATGGTAT AAAGCTTGTA TTCTATAGTG TCACCTAAAT C              51

(2) INFORMATION FOR SEQ ID NO:149:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:149:

ACAGGAAACA GCTATGACCA TGATTACGAA TTCGAGCTCG CCCGGGGATC T              51

(2) INFORMATION FOR SEQ ID NO:150:

(i) SEQUENCE CHARACTERISTICS:
        (A) LENGTH: 168 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:150:

GTATTGCGGC CGCCTGCAGG TCGACTCTAG ATTTTTTTTT TTTTTTTTTT TGGCATATAA  60

ATAGATCTGT ATCCTAAAAT TGAATTGTAA TTATCGATAA TAAATGAATT CACCCGCTGG  120

TGGCGGTCTT TGGCGCGGGC CCCGTGGGCA TCGGCCCGGG CACCACGG  168

(2) INFORMATION FOR SEQ ID NO:151:

(i) SEQUENCE CHARACTERISTICS:
        (A) LENGTH: 112 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:151:

GAGCTCGAAT TCGGATCCAT AATTAATTAA TTTTTATCCC GGCGCGCCTC GACTCTAGAA  60

TTTCATTTTG TTTTTTTCTA TGCTATAAAT GAATTCGGAT CCCGTCGTTT TA  112

(2) INFORMATION FOR SEQ ID NO:152:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:152:

GAAATCCAGC TGAGCGCCGG TCGCTACCAT TACCAGTTGG TCTGGTGTCA AAAAGATCCA  60

TAATTAATTA ACCCGGGTCG AGGCGCGCCG GGTCGACCTG CAGGCGGCCG CTATAC  116

(2) INFORMATION FOR SEQ ID NO:153:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:153:

TAATGTATCT ATAATGGTAT AAAGCTTGTA TTCTATAGTG TCACCTAAAT C  51

(2) INFORMATION FOR SEQ ID NO:154:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:154:

ACAGGAAACA GCTATGACCA TGATTACGAA TTCGAGCTCG CCCGGGGATC T                51

(2) INFORMATION FOR SEQ ID NO:155:

(i) SEQUENCE CHARACTERISTICS:
            (A) LENGTH: 104 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:155:

AAATATATAA ATACCATGTT AGAATTTGGT CTGCTGCAGG TCGACTCTAG AATTTCATTT       60

TGTTTTTTTC TATGCTATAA ATGAATTCGG ATCCCGTCGT TTTA                      104

(2) INFORMATION FOR SEQ ID NO:156:

(i) SEQUENCE CHARACTERISTICS:
            (A) LENGTH: 185 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:156:

GAAATCCAGC TGAGCGCCGG TCGCTACCAT TACCAGTTGG TCTGGTGTCA AAAAGATCCA       60

TAATTAATTA ACCCGGTCGA CTCTAGAAAA AATTGAAAAA CTATTCTAAT TTATTGCACG      120

GAGATCTTTT TTTTTTTTTT TTTTTTGGCA TATAAATGAA TTCGGATCCC CGGTGGCTTT      180

GGGGG                                                                 185

(2) INFORMATION FOR SEQ ID NO:157:

(i) SEQUENCE CHARACTERISTICS:
            (A) LENGTH: 66 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:157:

CTCAATGTTA GGGTACCGAG CTCGAATTGG GTCGACCGGG TCGACCTGCA GCCTACATGG       60

AAATCT                                                                 66

(2) INFORMATION FOR SEQ ID NO:158:

(i) SEQUENCE CHARACTERISTICS:

(A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:158:

TAATGTATCT ATAATGGTAT AAAGCTTGTA TTCTATAGTG TCACCTAAAT C            51

(2) INFORMATION FOR SEQ ID NO:159:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:159:

ACAGGAAACA GCTATGACCA TGATTACGAA TTCGAGCTCG CCCGGGGATC T            51

(2) INFORMATION FOR SEQ ID NO:160:

(i) SEQUENCE CHARACTERISTICS:
        (A) LENGTH: 127 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:160:

GTATAGCGGC CGCCTGCAGG TCGACTCTAG ATTTTTTTTT TTTTTTTTTT TGGCATATAA    60

ATAGATCTGT ATCCTAAAAT TGAATTGTAA TTATCGATAA TAAATGAATT CGACATGAA   120

TCCAAAT                                                            127

(2) INFORMATION FOR SEQ ID NO:161:

(i) SEQUENCE CHARACTERISTICS:
        (A) LENGTH: 122 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:161:

GATAAGATGT AAGTCGAAAT TCGGATCCAT AATTAATTAA TTTTTATCCC GGCGCGCCTC    60

GACTCTAGAA TTTCATTTTG TTTTTTTCTA TGCTATAAAT GAATTCGGAT CCCGTCGTTT   120

TA                                                                 122

(2) INFORMATION FOR SEQ ID NO:162:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:162:

```
GAAATCCAGC TGAGCGCCGG TCGCTACCAT TACCAGTTGG TCTGGTGTCA AAAAGATCCA      60

TAATTAATTA ACCCGGGTCG AGGCGCGCCG GGTCGACCTG CAGGCGGCCG CTATAC         116
```

(2) INFORMATION FOR SEQ ID NO:163:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:163:

```
TAATGTATCT ATAATGGTAT AAAGCTTGTA TTCTATAGTG TCACCTAAAT C               51
```

(2) INFORMATION FOR SEQ ID NO:164:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:164:

```
ACAGGAAACA GCTATGACCA TGATTACGAA TTCGAGCTCG CCCGGGGATC T               51
```

(2) INFORMATION FOR SEQ ID NO:165:

(i) SEQUENCE CHARACTERISTICS:
        (A) LENGTH: 61 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:165:

```
GTATAGCGGC CGCCTGCAGG TCGACCTGCA GTGAATAATA AAATGTGTGT TTGTCCGAAA      60

T                                                                     61
```

(2) INFORMATION FOR SEQ ID NO:166:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:166:

```
CTCCATAGAA GACACCGGGA CCATGGATCC CGTCGTTTTA CAACG                45
```

(2) INFORMATION FOR SEQ ID NO:167:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:167:

```
TCGGCGGAAA TCCAGCTGAG CGCCGGTCGC TACCATTACC AGTTGGTCTG GTGTCAAAAA   60

GATCTAGAAT AAGCTAGAGG ATCGATCCCC TATGGCGATC ATCAG                 105
```

(2) INFORMATION FOR SEQ ID NO:168:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:168:

```
CTGCAGGTCG ACCTGCAGGC GGCCGCTATA C                               31
```

(2) INFORMATION FOR SEQ ID NO:169:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:169:

```
TAATGTATCT ATAATGGTAT AAAGCTTGTA TTCTATAGTG TCACCTAAAT C           51
```

(2) INFORMATION FOR SEQ ID NO:170:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:170:

ACAGGAAACA GCTATGACCA TGATTACGAA TTCGAGCTCG CCCGGGGATC T    51

(2) INFORMATION FOR SEQ ID NO:171:

(i) SEQUENCE CHARACTERISTICS:
        (A) LENGTH: 193 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:171:

GTATAGCGGC CGCCTGCAGG TCGACTCTAG ATTTTTTTTT TTTTTTTTTT TGGCATATAA    60

ATAGATCTGT ATCCTAAAAT TGAATTGTAA TTATCGATAA TAAATGAATT CCGAAGTGGG    120

CAACGTGGAT CCTCGCCCTC GGGCTCCTCG TGGTCCGCAC CGTCGTGGCC AGAAGTGCTC    180

CTACTAGCTC GAG    193

(2) INFORMATION FOR SEQ ID NO:172:

(i) SEQUENCE CHARACTERISTICS:
        (A) LENGTH: 123 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:172:

ATCATTAGCA CGTTAACTTA ATAAGATCCA TAATTAATTA ATTTTTATCC CGGCGCGCCT    60

CGACTCTAGA ATTTCATTTT GTTTTTTTCT ATGCTATAAA TGAATTCGGA TCCCGTCGTT    120

TTA    123

(2) INFORMATION FOR SEQ ID NO:173:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:173:

GAAATCCAGC TGAGCGCCGG TCGCTACCAT TACCAGTTGG TCTGGTGTCA AAAAGATCCA    60

TAATTAATTA ACCCGGGTCG AGGCGCGCCG GGTCGACCTG CAGGCGGCCG CTATAC    116

(2) INFORMATION FOR SEQ ID NO:174:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:174:

TAATGTATCT ATAATGGTAT AAAGCTTGTA TTCTATAGTG TCACCTAAAT C    51

(2) INFORMATION FOR SEQ ID NO:175:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:175:

ACAGGAAACA GCTATGACCA TGATTACGAA TTCGAGCTCG CCCGGGGATC T    51

(2) INFORMATION FOR SEQ ID NO:176:

(i) SEQUENCE CHARACTERISTICS:
        (A) LENGTH: 133 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:176:

GTATAGCGGC CGCCTGCAGG TCGACTCTAG ATTTTTTTTT TTTTTTTTTT TGGCATATAA    60

ATAGATCTGT ATCCTAAAAT TGAATTGTAA TTATCGATAA TAAATGAATT CCTCTGGTTG    120

CCGTTCTGTC GGC    133

(2) INFORMATION FOR SEQ ID NO:177:

(i) SEQUENCE CHARACTERISTICS:
        (A) LENGTH: 99 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO

-continued (iv) ANTI-SENSE: NO (xi) SEQUENCE DESCRIPTION: SEQ ID NO:177:

GAAAATGAAA AAATGGTTTA AACCGGGGGC GCGCCTCGAC TCTAGAATTT CATTTTGTTT      60

TTTTCTATGC TATAAATGAA TTCGGATCCC GTCGTTTTA                             99

(2) INFORMATION FOR SEQ ID NO:178:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:178:

GAAATCCAGC TGAGCGCCGG TCGCTACCAT TACCAGTTGG TCTGGTGTCA AAAAGATCCA      60

TAATTAATTA ACCCGGGTCG AGGCGCGCCG GGTCGACCTG CAGGCGGCCG CTATAC         116

(2) INFORMATION FOR SEQ ID NO:179:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:179:

TAATGTATCT ATAATGGTAT AAAGCTTGTA TTCTATAGTG TCACCTAAAT C               51

(2) INFORMATION FOR SEQ ID NO:180:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:180:

ACAGGAAACA GCTATGACCA TGATTACGAA TTCGAGCTCG CCCGGGGATC T               51

(2) INFORMATION FOR SEQ ID NO:181:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:181:

GTATAGCGGC CGCCTGCAGG TCGACTCTAG ATTTTTTTTT TTTTTTTTTT TGGCATATAA      60

ATAGATCTGT ATCCTAAAAT TGAATTGTAA TTATCGATAA TAAATGAATT CGGATCAGCT     120

TATGATGGAT GGACGTTTGG                                                 140

(2) INFORMATION FOR SEQ ID NO:182:

(i) SEQUENCE CHARACTERISTICS:
        (A) LENGTH: 123 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:182:

GGAGGTGTCC ACGGCCTTAA AGCTGATCCA TAATTAATTA ATTTTTATCC CGGCGCGCCT      60

CGACTCTAGA ATTTCATTTT GTTTTTTTCT ATGCTATAAA TGAATTCGGA TCCCGTCGTT     120

TTA                                                                   123

(2) INFORMATION FOR SEQ ID NO:183:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:183:

GAAATCCAGC TGAGCGCCGG TCGCTACCAT TACCAGTTGG TCTGGTGTCA AAAAGATCCA      60

TAATTAATTA ACCCGGGTCG AGGCGCGCCG GGTCGACCTG CAGGCGGCCG CTATAC         116

(2) INFORMATION FOR SEQ ID NO:184:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:184:

TAATGTATCT ATAATGGTAT AAAGCTTGTA TTCTATAGTG TCACCTAAAT C               51

(2) INFORMATION FOR SEQ ID NO:185:

(i) SEQUENCE CHARACTERISTICS:
        (A) LENGTH: 39 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:185:

GAAGCATGCC CGTTCTTATC AATAGTTTAG TCGAAAATA                                39

(2) INFORMATION FOR SEQ ID NO:186:

(i) SEQUENCE CHARACTERISTICS:
           (A) LENGTH: 41 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:186:

CATAAGATCT GGCATTGTGT TATTATACTA ACAAAAATAA G                             41

(2) INFORMATION FOR SEQ ID NO:187:

(i) SEQUENCE CHARACTERISTICS:
           (A) LENGTH: 41 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:187:

CCGTAGTCGA CAAAGATCGA CTTATTAATA TGTATGGGAT T                             41

(2) INFORMATION FOR SEQ ID NO:188:

(i) SEQUENCE CHARACTERISTICS:
           (A) LENGTH: 39 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:188:

GCCTGAAGCT TCTAGTACAG TATTTACGAC TTTTGAAAT                                39

What is claimed is:

1. A recombinant swinepox virus which comprises a foreign DNA which (a) is inserted into a non-essential site located in the HindIII M fragment of the swinepox genome, wherein the foreign DNA encodes a polypeptide derived from a human pathogen and (b) is expressed in a host cell infected by the recombinant swinepox virus.

2. The recombinant swinepox virus of claim 1, wherein the polypeptide is derived from the group consisting of human herpesvirus, herpes simplex virus-1, herpes simplex virus-2, human cytomegalovirus, Epstein-Barr virus, Varicell-Zoster virus, human herpesvirus-6, human herpesvirus- 7, human influenza, human immunodeficiency virus, rabies virus, measles virus, hepatitis B virus and hepatitis C virus.

3. The recombinant swinepox virus of claim 2, wherein the polypeptide is hepatitis B virus core protein or hepatitis B virus surface protein.

4. The recombinant swinepox virus of claim 3, designated S-SPV-031.

5. The recombinant swinepox virus of claim 1, wherein the polypeptide is associated with malaria.

6. The recombinant swinepox virus of claim 1, wherein the insertion site is present within the larger HindIII to BglII sub-fragment of the HindIII M fragment of the swinepox viral genome.

7. The recombinant swinepox virus of claim 6, wherein the insertion site is within an open reading frame contained in the HindIII to BglII sub-fragment.

8. The recombinant swinepox virus of claim 7, wherein the insertion site is the AccI restriction endonuclease site located in the HindIII to BglII sub-fragment.

9. The recombinant swinepox virus of claim 8, wherein the AccI restriction endonuclease site is replaced by a NotI restriction endonuclease site.

10. The recombinant swinepox virus of claim 8, wherein the AccI restriction endonuclease site is replaced by a PstI restriction endonuclease site.

11. The recombinant swinepox virus of claim 1, further comprising an insertion site within an open reading frame encoding swinepox virus thymidine kinase.

12. The recombinant swinepox virus of claim 11, wherein the insertion site is the NdeI restriction endonuclease site located within the open reading frame encoding the swinepox virus thymidine kinase.

13. The recombinant swinepox virus of claim 12, wherein the NdeI restriction site is replaced by a AscI restriction endonuclease site.

14. The recombinant swinepox virus of claim 1, wherein the expression of the foreign DNA is under the control of a promoter located upstream from the foreign DNA.

15. The recombinant swinepox virus of claim 14, wherein the promoter is an endogenous swinepox viral promoter or an exogenous promoter.

16. The recombinant swinepox virus of claim 15, wherein the exogenous promoter is a synthetic pox viral promoter.

17. The recombinant swinepox virus of claim 15, wherein the exogenous promoter is human cytomegalovirus immediately early gene promoter.

18. A recombinant swinepox virus which comprises a foreign DNA which (a) is inserted into a non-essential site located in the HindIII M fragment of the swinepox genome, wherein the foreign DNA encodes a cytokine capable of stimulating an immune response in a host infected by the recombinant swinepox virus and (b) is expressed in a host cell infected by the recombinant swinepox virus.

19. The recombinant swinepox virus of claim 18, wherein the cytokine is interleukin-2, interleukin-6, interleukin-12, an interferon, a granulocyte-macrophage colony stimulating factor, or an interleukin receptor.

20. The recombinant swinepox virus of claim 19, wherein the cytokine is human interleukin-2.

21. A recombinant swinepox virus which comprises a foreign DNA which (a) is inserted into a non-essential site of the swinepox genome, wherein the foreign DNA encodes a polypeptide derived from an equine pathogen and (b) is expressed in a host cell infected by the recombinant swinepox virus.

22. The recombinant swinepox virus of claim 21, wherein the polypeptide is derived from equine influenza virus or equine herpesvirus.

23. The recombinant swinepox virus of claim 22, wherein the polypeptide is equine influenza virus type A/Alaska 91 neuraminidase, equine influenza virus type A/Prague 56 neuraminidase, equine influenza virus type A/Miami 63 neuraminidase, equine influenza virus type A/Kentucky neuraminidase, equine herpesvirus type 1 glycoprotein B, or equine herpesvirus type 1 glycoprotein D.

24. The recombinant swinepox virus of claim 23, wherein the polypeptide is equine influenza virus type A/Alaska 91 neuraminidase.

25. The recombinant swinepox virus of claim 24, designated S-SPV-033.

26. The recombinant swinepox virus of claim 23, wherein the polypeptide is equine influenza virus type A/Prague 56 neuraminidase.

27. The recombinant swinepox virus of claim 26, designated S-SPV-034.

28. The recombinant swinepox virus of claim 23, wherein the polypeptide is equine herpesvirus type 1 glycoprotein B.

29. The recombinant swinepox virus of claim 28, designated S-SPV-038.

30. The recombinant swinepox virus of claim 23, wherein the polypeptide is equine herpesvirus type 1 glycoprotein D.

31. The recombinant swinepox virus of claim 30, designated S-SPV-039.

32. A recombinant swinepox virus which comprises a foreign DNA which (a) is inserted into a non-essential site located in the HindIII M fragment of the swinepox genome, wherein the foreign DNA encodes a polypeptide derived from bovine respiratory syncytial virus or bovine parainfluenza virus, and wherein the foreign DNA (b) is expressed in a host cell infected by the recombinant swinepox virus.

33. The recombinant swinepox virus of claim 32, wherein the polypeptide is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, or bovine parainfluenza virus type 3 hemagglutinin neuraminidase.

34. The recombinant swinepox virus of claim 33, wherein the polypeptide is bovine respiratory syncytial virus attachment protein (BRSV G).

35. The recombinant swinepox virus of claim 34, designated S-SPV-020.

36. The recombinant swinepox virus of claim 33, wherein the polypeptide is bovine respiratory syncytial virus fusion protein (BRSV F).

37. The recombinant swinepox virus of claim 36, designated S-SPV-029.

38. The recombinant swinepox virus of claim 33, wherein the polypeptide is bovine respiratory syncytial virus nucleocapsid protein (BRSV N).

39. The recombinant swinepox virus of claim 38, designated S-SPV-030.

40. The recombinant swinepox virus of claim 33, wherein the polypeptide is bovine parainfluenza virus type 3 fusion protein.

41. The recombinant swinepox virus of claim 40, designated S-SPV-028.

42. The recombinant swinepox virus of claim 32, wherein the polypeptide is bovine parainfluenza virus type 3 hemagglutinin neuraminidase.

43. A recombinant swinepox virus which comprises a foreign DNA which (a) is inserted into a non-essential site located in the HindIII M fragment of the swinepox genome wherein the foreign DNA encodes bovine viral diarrhea virus glycoprotein 48 or bovine viral diarrhea virus glycoprotein 53, and wherein the foreign DNA (b) is expressed in a host infected by the recombinant swinepox virus.

44. The recombinant swinepox virus of claim 43, designated S-SPV-032.

45. The recombinant swinepox virus of claim 43, designated S-SPV-040.

46. A recombinant swinepox virus which comprises a foreign DNA which (a) is inserted into a non-essential site located in the HindIII M fragment of the swinepox genome, wherein the foreign DNA encodes a polypeptide derived from infectious bursal disease virus and wherein the foreign DNA (b) is expressed in a host cell infected by the recombinant swinepox virus.

47. The recombinant swinepox virus of claim 46, wherein the polypeptide is infectious bursal disease virus polyprotein.

48. The recombinant swinepox virus of claim 46, wherein the polypeptide is infectious bursal disease virus VP2.

* * * * *